US008889385B2

(12) United States Patent
Donaldson et al.

(10) Patent No.: US 8,889,385 B2
(45) Date of Patent: Nov. 18, 2014

(54) FERMENTIVE PRODUCTION OF FOUR CARBON ALCOHOLS

(71) Applicant: Butamax(TM) Advanced Biofuels LLC, Wilmington, DE (US)

(72) Inventors: Gail K. Donaldson, Newark, DE (US); Andrew C. Eliot, Wilmington, DE (US); Dennis Flint, Newark, DE (US); Lori Ann Maggio-Hall, Wilmington, DE (US); Vasantha Nagarajan, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 13/838,949

(22) Filed: Mar. 15, 2013

(65) Prior Publication Data

US 2014/0051151 A1  Feb. 20, 2014

Related U.S. Application Data

(63) Continuation of application No. 13/646,097, filed on Oct. 5, 2012, which is a continuation of application No. 12/939,284, filed on Nov. 4, 2010, now Pat. No. 8,283,144, which is a continuation of application No. 11/586,315, filed on Oct. 25, 2006, now Pat. No. 7,851,188.

(60) Provisional application No. 60/730,290, filed on Oct. 26, 2005.

(51) Int. Cl.
| | | |
|---|---|---|
| *C12P 21/06* | (2006.01) | |
| *C12P 7/04* | (2006.01) | |
| *C12P 7/16* | (2006.01) | |
| *C12N 9/00* | (2006.01) | |
| *C12N 1/20* | (2006.01) | |
| *C12N 15/00* | (2006.01) | |
| *C07H 21/04* | (2006.01) | |
| *C12N 15/52* | (2006.01) | |
| *C12N 15/75* | (2006.01) | |
| *C12N 15/74* | (2006.01) | |
| *C12N 9/02* | (2006.01) | |
| *C12N 9/10* | (2006.01) | |
| *C12N 15/81* | (2006.01) | |
| *C12N 9/88* | (2006.01) | |
| *C12N 9/06* | (2006.01) | |
| *C12N 9/04* | (2006.01) | |
| *C12N 15/70* | (2006.01) | |

(52) U.S. Cl.
CPC ............ *C12N 15/81* (2013.01); *C12N 15/52* (2013.01); *C12N 15/75* (2013.01); *C12N 15/74* (2013.01); *Y02E 50/10* (2013.01); *C12N 9/0008* (2013.01); *Y02E 50/343* (2013.01); *C12N 9/1096* (2013.01); *C12N 9/88* (2013.01); *C12Y 202/01006* (2013.01); *C12P 7/16* (2013.01); *C12N 9/0016* (2013.01); *C12N 9/0006* (2013.01); *C12Y 102/04004* (2013.01); *C12N 15/70* (2013.01)

USPC .......... 435/160; 435/69.1; 435/157; 435/183; 435/252.3; 435/320.1; 536/23.2

(58) Field of Classification Search
None
See application file for complete search history.

(56) References Cited

U.S. PATENT DOCUMENTS

| | | |
|---|---|---|
| 4,424,275 A | 1/1984 | Levy |
| 4,568,643 A | 2/1986 | Levy |
| 5,210,032 A | 5/1993 | Kashket |
| 5,210,296 A | 5/1993 | Cockrem et al. |
| 5,686,276 A | 11/1997 | Laffend et al. |
| 6,013,494 A | 1/2000 | Nakamura et al. |
| 6,177,264 B1 | 1/2001 | Eggeling et al. |
| 6,358,717 B1 | 3/2002 | Blaschek et al. |
| 6,579,330 B2 | 6/2003 | Nakahama et al. |
| 6,660,507 B2 | 12/2003 | Cheng et al. |
| 6,787,334 B1 | 9/2004 | Elischweski et al. |
| 7,632,663 B1 | 12/2009 | Eggeling et al. |
| 7,851,188 B2 | 12/2010 | Donaldson et al. |
| 7,993,889 B1 | 8/2011 | Donaldson et al. |
| 8,017,375 B2 | 9/2011 | Feldman et al. |
| 8,178,328 B2 | 5/2012 | Donaldson et al. |
| 8,273,558 B2 | 9/2012 | Donaldson et al. |
| 8,283,144 B2 | 10/2012 | Donaldson et al. |
| 8,735,114 B2 | 5/2014 | Donaldson et al. |
| 2002/0028492 A1 | 3/2002 | Lenke et al. |
| 2004/0146996 A1 | 7/2004 | Yocum et al. |
| 2004/0157301 A1 | 8/2004 | Chotani et al. |
| 2009/0081746 A1 | 3/2009 | Liao et al. |
| 2009/0226991 A1 | 9/2009 | Feldman et al. |
| 2009/0305363 A1 | 12/2009 | Anthony et al. |
| 2010/0081182 A1 | 4/2010 | Paul et al. |
| 2010/0120105 A1 | 5/2010 | Anthony et al. |

(Continued)

FOREIGN PATENT DOCUMENTS

| | | |
|---|---|---|
| AU | 620802 B2 | 10/1988 |
| CA | 2039245 | 3/1991 |

(Continued)

OTHER PUBLICATIONS

Wynn et al. J Biol Chem. Jun. 25, 1992;267(18):12400-3.*

(Continued)

*Primary Examiner* — Christian Fronda

(57) ABSTRACT

Methods for the fermentative production of four carbon alcohols is provided. Specifically, butanol, preferably isobutanol is produced by the fermentative growth of a recombinant bacterium expressing an isobutanol biosynthetic pathway.

18 Claims, 1 Drawing Sheet

(56) References Cited

U.S. PATENT DOCUMENTS

| | | | |
|---|---|---|---|
| 2010/0129886 | A1 | 5/2010 | Anthony et al. |
| 2010/0151545 | A1 | 6/2010 | Roessler et al. |
| 2011/0053235 | A1 | 3/2011 | Festel et al. |
| 2011/0111472 | A1 | 5/2011 | Donaldson et al. |
| 2011/0112334 | A1 | 5/2011 | Donaldson et al. |
| 2011/0160442 | A1 | 6/2011 | Pietarinen et al. |
| 2011/0313206 | A1 | 12/2011 | Donaldson et al. |
| 2013/0171706 | A1 | 7/2013 | Donaldson et al. |
| 2013/0183731 | A1 | 7/2013 | Donaldson et al. |
| 2014/0030794 | A1 | 1/2014 | Donaldson et al. |

FOREIGN PATENT DOCUMENTS

| | | | |
|---|---|---|---|
| EP | 0 112 459 | A1 | 7/1984 |
| EP | 0 282 474 | A1 | 9/1988 |
| EP | 0 315 949 | A2 | 5/1989 |
| EP | 1 149 918 | A1 | 10/2001 |
| JP | 61-209594 | | 9/1986 |
| JP | 63-017695 | | 1/1988 |
| JP | 63-102687 | | 5/1988 |
| JP | 63-254986 | | 10/1988 |
| JP | 2000-41655 | A | 2/2000 |
| WO | WO 90/02193 | A1 | 3/1990 |
| WO | WO 98/51813 | A1 | 11/1998 |
| WO | WO 00/50624 | A1 | 8/2000 |
| WO | WO 01/21772 | A2 | 3/2001 |
| WO | WO 2008/072920 | A1 | 6/2008 |
| WO | WO 2008/072921 | A1 | 6/2008 |

OTHER PUBLICATIONS

Bussey, H. and Umbarger H.E., "Biosynthesis of Branched-Chain Amino Acids in Yeast: Regulation of Synthesis of the Enzymes of Isoleucine and Valine Biosynthesis," *Journal of Bacteriology* 98(2):623-628, American Society for Microbiology, United States (1969).

Lill, R. and Mühlenhoff, U., "Iron-sulfur-protein biogenesis in eukaryotes," *TRENDS in Biochemical Sciences* 30(3):133-141, Elsevier Ltd., England (2005).

Byrne, K.L. and Meacock, P.A., "Thiamin auxotrophy in yeast through altered cofactor dependence of the enzyme acetohydroxyacid synthase," *Microbiology* 147:2389-2398, SGM, Great Britain (2001).

Gray, M.W., et al., "Mitochondrial Evolution," *Science* 283: 1476-1481, American Association for the Advancement of Science, United States (1999).

Djaman, O., et al., "Repair of Oxidized Iron-Sulfur Clusters in *Escherichia coli*," *The Journal of Biological Chemistry* 279(43):44590-44599, American Society for Biochemistry and Molecular Biology, United States (2004).

Strain, J., et al., "Suppressors of Superoxide Dismutase (SODI) Deficiency in *Saccharomyces cerevisiae*," *The Journal of Biological Chemistry* 273(47):31138-31144, The American Society for Biochemistry and Molecular Biology, Inc., United States (1998).

"Top Value Added Chemicals from Biomass: vol. I—Results of Screening for Potential Candidates from Sugars and Synthesis Gas," U.S. Department of Energy—Energy Efficiency and Renewable Energy, Ed., Werpy, T. and Petersen, G., 76 Pages, National Renewable Energy Laboratory, United States (2004).

Causey, T.B., et al., "Engineering the metabolism of *Escherichia coli* W3110 for the conversion of sugar to redox-neutral and oxidized products: Homoacetate production," *PNAS* 100(3):825-832, National Academy of Sciences, United States (2003).

"Homegrown for the Homeland: Ethanol Industry Outlook 2005," 20 Pages, Renewable Fuels Association, Washington, DC, United States (2005).

"DuPont Receives U.S. EPA's Presidential Green Chemistry Award for New Innovation," Jun. 24, 2003, 2 Pages, accessed at http://www2/dupont.com/Media_Center/en_US/news_releases/2003/nr06_24_03a.htm.

Rai, M. and Padh, H., "Expression systems for production of heterologous proteins," *Current Science* 80(9):1121-1128, Academy of Sciences, United States (2001).

Schreier, H.J., et al., "Heterologous expression in the Archaea: transcription from *Pyrococcus furiosus* gdh and mlrA promoters in *Haloferax volcanii*," *Extremophiles* 3:11-19, Springer-Verlag, Germany (1999).

Martin, V.J.J., et al., "Engineering a mevalonate pathway in *Escherichia coli* for production of terpenoids," *Nature Biotechnology* 21(7):796-802, Nature Publishing Group, England (2003).

Christen, P., et al., "Ethanol Extraction by Supported Liquid Membrane During Fermentation," *Biotechnology and Bioengineering* 36:116-123, John Wiley & Sons, Inc., United States (1990).

Bryan, T., "Adsorbing It All," Biodiesel Magazine, Mar. 1, 2005, 3 Pages, accessed at http://www.biodieselmagazine.com/articles/239/adsorbing-it-all on May 17, 2014.

Palomares, L.A., et al., "Production of Recombinant Proteins: Challenges and Solutions," *Methods in Molecular Biology* 267:15-52, Humana Press Inc., United States (2004).

Chase, R., "DuPont, BP join to make butanol; they say it outperforms ethanol as a fuel additive," USA Today, Jun. 23, 2006, 2 Pages, accessed at http://usatoday30.usatoday.com/money/industries/energy/2006-06-20-butanol_x.htm on May 14, 2014.

"50 Disruptive Companies: Company Profile: Joule Unlimited," MIT Technology Review (2013), 2 Pages, accessed at http://www2.technologyreview.com/tr50/jouleunlimited/ on May 14, 2014.

Schwartz, D., "AIM Interview: Sapphire Energy's Tim Zenk," Algae Industry Magazine (2010), 11 Pages, accessed at http://www.algaeindustrymagazine.com/tim-zenk/ on May 15, 2014.

Singer, E., "A Better Biofuel: A California biotech company is engineering microbes to produce cheap biofuels that could outcompete ethanol," MIT Technology Review, Apr. 3, 2007, 2 Pages, accessed at http://www.technologyreview.com/news/407629/a-better-biofuel/ on May 19, 2014.

*Butamax™ Advanced Biofuels LLC* v. *Gevo, Inc.*, No. 13-1342, Joint Appendix vol. II of III, A10447-A10495, ECF No. 49, (2012).

Meinhold, P., et al., "Direct Conversion of Ethane to Ethanol by Engineered Cytochrome P450 BM3," *ChemBioChem* 6:1765-1768, Wiley-VCH Verlag GmbH & Co. KGaA, Germany (2005).

Gevo Investor Relations FAQs, Gevo, accessed at http://ir.gevo.com/phoenix.zhtml?c=238618&p=irol-faq on May 7, 2014.

Amendment No. 4 to Form S-1 Registration Statement, United States Securities and Exchange Commission, Registration No. 333-168792, filed Jan. 19, 2011, 303 Pages.

Burtis, P.R., et al., "California's Cleantech Industry: Annual Venture Capital Investment Update 2006," Environmental Entrepreneurs and Cleantech Venture Network LLC, 15 Pages.

Day, R., "Methanotech and Turtle Island Recycling," Cleantech Investing: Greentech Media, Aug. 30, 2005, accessed at http://www.greentechmedia.com/cleantech-investing/post/methanotech-and-turtle-island-recycling-151 on May 7, 2014.

Dijkhuizen, L., et al., "Methanol, a potential feedstock for biotechnological processes," *Trends in Biotechnology* 3(10):262-267, Elsevier Science Publishers B.V., Netherlands (1985).

Bekkaoui, F., et al., "Isolation and structure of an acetolactate synthase gene from *Schizosaccharomyces pombe* and complementation of the ilv2 mutation in *Saccharomyces cerevisiae*," *Current Genetics* 24:544-547, Springer-Verlag, Germany, 1993.

Card, J.C. and Farrell, L.M., "Separation of Alcohol-Water Mixtures Using Salts" in Technical Reports of Oak Ridge National Laboratory, Chemical Technology Division, Contract No. W-7405-eng-26, 1982.

Derrick, S. and Large, P., "Activities of the enzymes of the Ehrlich Pathway and formation of the branched-chain alcohols in *Saccharomyces cerevisiae* and *Candida utilis* grown in continuous culture on valine or ammonium as sole nitrogen source," *J. of General Microbiology* 139:2783-2792, Society for Chemical Microbiology, Great Britain, 1993.

Dickinson, J.R., et al., "An Investigation of the Metabolism of Valine to Isobutyl Alcohol in *Saccharomyces cerevisiae*," *J. Biol. Chem.* 273(40): 25751-25756, The American Society for Biochemistry and Molecular Biology, Inc., United States, 1998.

Dickinson, J.R., et al., "The Catabolism of Amino Acids to Long Chain and Complex Alcohols in *Saccharomyces cerevisiae*," *J. Biol.*

(56) References Cited

OTHER PUBLICATIONS

*Chem.* 278:8028-8034, The American Society for Biochemistry and Molecular Biology Inc., United States, 2003.

Hansen, J., et al., Topics in Current Genetics, Chapter, 5, vol. 2, J.H. de Winde (Ed.): *Functional Genetics of Industrial Yeasts*, Springer-Verlag Berlin Heidelberg, Germany, pp. 143-170, 2003.

Ishige, T., et al., "Whole organism biocatalysis," *Current Opinion in Chemical Biology* 9:174-180, Elsevier, The Netherlands, 2005.

Larroy, C., et al., "Characterization of the *Saccharomyces cerevisiae YMR318C (ADH6)* gene product as a broad specificity NADPH-dependent alcohol dehydrogenase: relevance in aldehyde reduction," *Biochem J.* 361:163-172, Biochemical Society, Great Britain, 2002.

Larroy, C., et al., "Properties and Functional Significance of *Saccharomyces cerevisiae* ADHVL," *Chemico-Biological Interactions 143-144*: 229-238, Elsevier, The Netherlands, 2003.

*Lehninger Principles of Biochemistry*, 3rd ed., David L. Nelson and Michael M. Cox, Eds., Worth Publishers, New York, NY, pp. 293-294, 2000.

Matak-Vinkovic, D., et al. "Crystal Structure of *Escherichia coli* Ketopantoate Reductase at 1.7 Å Resolution and Insight into the Enzyme Mechanism," *Biochemistry* 40:14493-14500, American Chemical Society, United States, 2001.

Petersen, J.G.L., et al. "The *ILV5* gene of *Saccharomyces cerevisiae* is highly expressed," *Nucl. Acids Res.* 14:9631-9651, IRL Press Limited, England, 1986.

Radmacher, E., et al., "Linking Central Metabolism with Increased Pathway Flux: L-Valine Accumulation by *Corynebacterium glutamicum*," *App. Environ. Micro.* 68:2246-2250, American Society for Microbiology, United States, 2002.

Renna, M.C., et al., "Regulation of the *Bacillus subtilis alsS, alsD*, and *alsR* Genes Involved in Post-Exponential-Phase Production of Acetoin," *J. Bacteriology* 175:3863-3875, American Society for Microbiology, United States, 1993.

Rosenfeld, E. and Beauvoit, B., "Role of the non-respiratory pathways in the utilization of molecular oxygen by *Saccharomyces cerevisiae*," *Yeast* 20:1115-1144, John Wiley & Sons, Inc., United States, 2003.

Screen capture of http://enzyme.expasy.org/EC/2.2.1.6, the ExPASy Bioformatics Resource Portal Enzyme Nomenclature Database for EC No. 2.2.1.6, ExPASy Proteomics Server [retrieved on Aug. 16, 2011].

Screen capture of http://www.chem.qmul.ac.uk/iubmb/enzyme/EC2/2/1/6.html, the IUBMB Enzyme Nomenclature Database for EC No. 2.2.1.6, [retrieved on Sep. 12, 2011].

Smit, Ph.D. Thesis, Wageningen Universiteit (Wageningen, The Netherlands), *Formation of Amino Acid Derived Cheese Flavour Compounds*, orally defended on Apr. 23, 2004, cataloged into the U.S.D.A. National Agricultural Library system on Oct. 3, 2004.

Catalog Receipt from U.S.D.A. National Agricultural Library of Smit, Ph.D. Thesis, Wageningen Universiteit (Wageningen, The Netherlands), *Formation of Amino Acid Derived Cheese Flavour Compounds*, MARC Record View, 2 pages, indicating date cataloged as Oct. 3, 2004 (i.e., Oct. 3, 2004) via MARC Code "005".

Re-examination Request Control No. 95/001,718, filed on Aug. 18, 2011.

Re-examination Request Control No. 95/001,735, filed on Sep. 1, 2011.

Complaint filed on Jan. 14, 2011 by Plaintiff Butamax™ Advanced Biofuels LLC against Defendant Gevo, Inc. in the United States District Court for the District of Delaware, Case 1:11-cv-00054-SRL-MPT.

Answer to Complaint filed on Mar. 25, 2011 by Defendant Gevo, Inc. in the United States District Court for the District of Delaware, Case 1:11-cv-00054-SRL-MPT.

Amended Complaint filed on Aug. 11, 2011 by Plaintiff Butamax™ against Defendant Gevo, Inc. in the United States District Court for the District of Delaware, Case 1:11-cv-00054-SRL-MPT.

Answer to Amended Complaint filed on Sep. 13, 2011 by Defendant Gevo, Inc. in the United States District Court for the District of Delaware, Case 1:11-cv-00054-SRL-MPT.

Plaintiff's Opening Brief in Support of Its Motion for a Preliminary Injuction (Redacted Version) filed on Sep. 30, 2011 in the United the District Court for the District of Delaware, Case 1:11-cv-00054-SRL-MPT.

Atsumi, S., et al., "Acetolactate synthase from *Bacillus subtilis* serves as a 2-ketoisovalerate decarboxylase for isobutanol biosynthesis in *Escherichia coli*," *Appl. Environ. Microbiol.* 75(19):6306-11, American Society for Microbiology, United States (Oct. 2009; Epub.: Aug. 2009).

Seffernick, J.L., et al., "Melamine deaminase and atrazine chlorohydrolase: 98 percent identical but functionally different," *J. Bacteriol.* 183(8):2405-2410, American Society for Microbiology, United States, Apr. 2001.

Yoshimoto, H., et al., "Genetic and physiological analysis of branched-chain alcohols and isoamyl acetate production in *Saccharomyces cervisiae*," *Appl. Microbiol. Biotechnol.* 59(4-5):501-8, Springer International, Germany (Aug. 2002; Epub.: Jun. 2002).

Peng, H.L., et al., "Cloning, sequencing and heterologous expression of a *Klebsiella pneumoniae* gene encoding an FAD-independent acetolactate synthase," *Gene* 117(1):125-130, Elsevier Science Publishers B.V., Netherlands, 1992.

De La Plaza, M., et al., "Biochemical and molecular characterization of alpha-ketoisovalerate decarboxylase, an enzyme involved in the formation of aldehydes from amino acids by *Lactococcus lactis*," *FEMS Microbiol. Lett.* 238(2):367-74, Elsevier/North Holland on behalf of the Federation of European Microbiological Societies, England, Sep. 2004.

Ullmann's Encyclopedia of Industrial Chemistry, $6^{th}$ Edition, 5:716-719, 2003.

Carlini et al., "Guerbet Condensation of Methanol with N-Propanol to Isobutanol Alcohol Over Heterogeneous Copper Chromite/Mg—Al Mixed Oxides Catalysts," *J. Mol. Catal. A: Chem.* 220:215-220, 2004.

Garcia et al., "Fusel Alcohols Biochemistry in Beer Fermentation Processes," *Process Biochemistry* 29:303-309, 1994.

Durre, "New Insights and Novel Developments in Clostridial Acetone/Butanol/Isopropanol Fermentation," *Applied Microbiology and Biotechnology* 49:639-648, 1998.

Harris et al., "Characterization of Recombinant Strains of the *Clostridium acetobutylicum* Butyrate Kinase Inactivation Mutant: Need for New Phenomenological Models for Solventogenesis and Butanol Inhibition," *Biotechnology and Bioengineering* 67:1-11, 2000.

International Search Report and Written Opinion of corresponding PCT/US2006/041602, European Patent Office, Rijswijk, Netherlands, mailed Apr. 11, 2007.

International Preliminary Report on Patentability of corresponding PCT/US2006/041602, European Patent Office, Rijswijk, Netherlands, mailed, May 8, 2008.

Chen, Thesis, McGill University (Montreal, Canada), "Formation and Analysis of Fusel Alcohols in Beer," submitted to the Faculty of Graduate Studies and Research, Department of Agricultural Chemistry (1978).

Oshita, K., et al., "Clarification of the relationship between fusel alcohol formation and amino acid assimilation by brewing yeast using $^{13}$C-labeled amino acid," *Proc. Eur. Brewery Convention Congr.* 387-394 (1995).

Order Denying Request for Inter Partes Reexamination of U.S. Patent No. 7,851,188, mailed Oct. 27, 2011, U.S. Control No. 95/001,718, filed Aug. 18, 2011.

Petition Under 37 CFR §§ 1.927 and 1.181 for Supervisory Review of Refusal to Order Reexamination for Claims 1-3, 13-15, 17-24, and 34-37, mailed Nov. 28, 2011, U.S. Control No. 95/001,718, filed Aug. 18, 2011.

Second Request for Reexamination of U.S. Patent No. 7,851,188, U.S. Control No. 95/001,857, filed Dec. 19, 2011.

Order Granting Request for Inter Partes Reexamination of U.S. Patent No. 7,851,188, mailed Mar. 5, 2012, U.S. Control No. 95/001,857, filed Dec. 19, 2011.

Office Action in Inter Partes Reexamination of U.S. Patent No. 7,851,188, mailed Mar. 5, 2012, U.S. Control No. 95/001,857, filed Dec. 19, 2011.

(56) References Cited

OTHER PUBLICATIONS

Petition of Patent Owner Under 37 CFR §§1.181 and/or 1.183 to Vacate the Order Granting Second Reexamination Request, mailed Mar. 19, 2012, U.S. Control No. 95/001,857, filed Dec. 19, 2011.

Opposition to Petition of Patent Owner Under 37 CFR §§1.181 and/or 1.183 to Vacate the Order Granting Second Reexamination Request, mailed Apr. 2, 2012, U.S. Control No. 95/001,857, filed Dec. 19, 2011.

Order Granting Request for Inter Partes Reexamination of U.S. Patent No. 7,993,889, mailed Nov. 25, 2011, U.S. Control No. 95/001,735, filed Sep. 1, 2011.

Office Action in Inter Partes Reexamination of U.S. Patent No. 7,993,889, mailed Nov. 25, 2011, U.S. Control No. 95/001,735, filed Sep. 1, 2011.

Response filed Feb. 24, 2012 in Inter Partes Reexamination of U.S. Patent No. 7,993,889,U.S. Control No. 95/001,735, filed Sep. 1, 2011.

Response filed Feb. 27, 2012 in Inter Partes Reexamination of U.S. Patent No. 7,993,889, U.S. Control No. 95/001,735, filed Sep. 1, 2011.

Third Party Requester Comments After Non-Final Office Action, filed Mar. 26, 2012 in Inter Partes Reexamination of U.S. Patent No. 7,993,889, U.S. Control No. 95/001,735, filed Sep. 1, 2011.

Request for Reexamination of U.S. Patent No. 8,178,328, U.S. Control No. 95/001,998, Submitted May 25, 2012, including its Appendices and Exhibits.

Memorandum Opinion of District Judge Robinson, in *Butamax™ Advanced Biofuels LLC* vs. *Gevo, Inc.*, Case 1:11-cv-00054-SLR, united States District Court for the District of Delaware, dated Jun. 19, 2012; 26 pages.

Alasfour, F.N., "$NO_x$ Emission from a Spark Ignition Engine using 30% Iso-Butanol-Gasoline Blend: Part 1—Preheating Inlet Air," *Appl. Thermal Eng'g 18*(5):245-56, Elsevier Science Ltd., England (1998).

Alasfour, F.N., "$NO_x$ Emission from a Spark Ignition Engine using 30% Iso-Butanol-Gasoline Blend: Part 2—Ignition Timing," *Appl. Thermal Eng'g 18*(8):609-18, Elsevier Science Ltd., England (1998).

Atsumi, S., et al., "Non-fermentative pathways for synthesis of branched-chain higher alcohols as biofuels," *Nature 451*(7174):86-89, Nature Publishing Group, England (2008).

Atsumi, S., et al., "Direct photosynthetic recycling of carbon dioxide to isobutyraldehyde," *Nat. Biotechnol. 27*(12):1177-80, Nature Publishing Group, England (2009).

Äyräpää, T., "Formation of Higher Alcohols From $^{14}$C-Labelled Valine and Leucine," *J. Inst. Brewing*, 73:17-30, W. Heffer & Sons, Ltd, England (1967).

Flint, D.H., et al., "The Inactivation of Dihydroxy-acid Dehydratase in *Escherichia coli* Treated with Hyperbaric Oxygen Occurs Because of the Destruction of Its Fe—S Cluster, but the Enzyme Remains in the Cell in a Form That Can Be Reactivated," *J. Biol. Chem. 268*(34):25547-25552, The American Society for Biochemistry and Molecular Biology, Inc., United States (1993).

Glick, B.R., "Metabolic Load and Heterologous Gene Expressions," *Biotechnol. Adv. 13*:247-261, Elsevier Science, Ltd., England (1995).

Jones, D.T. and Woods, D.R., "Acetone-Butanol Fermentation Revisited," *Microbiol. Rev. 50*(4):484-524, American Society for Microbiology, United States (1986).

Kispal, G., et al., "Mitochondrial and Cytosolic Branched-chain Amino Acid Transaminases from Yeast, Homologs of the *myc* Oncogene-regulated Eca39 Protein," *J. Biol. Chem. 271*(40):24458-24464, The American Society for Biochemistry and Molecular Biology, Inc., United States (1996).

Kohlhaw, G.B., "Leucine Biosynthesis in Fungi: Entering Metabolism through the Back Door," *Microbiol. Mol. Biol. Rev. 67*:1-15, American Society for Microbiology, United States (2003).

Lagier, M.J., et al., "Mitochondrial-type iron—sulfur cluster biosynthesis genes (*IscS* and *IscU*) in the apicomplexan *Cryptosporidium parvum*," *Microbiology 149*:3519-3530, SGM, England (2003).

Llopis, J., et al., "Measurement of cytosolic, mitochondrial, and Golgi pH in single living cells with green fluorescent proteins," *Proc. Natl. Acad. Sci. USA 95*:6803-6808, The National Academy of Sciences, United States (1998).

Marobbio, C.M.T., et al., "60 -Isopropylmalate, a Leucine Biosynthesis Intermediate in Yeast, is Transported by the Mitochondrial Oxalacetate Carrier," *J. Biol. Chem. 283*(42):28445-28453, The American Society for Biochemistry and Molecular Biology, Inc., United States (2008).

Outten, C.E. and Culotta, V.C., "Alternative Start Sites in the *Saccharomyces cerevisiae GLR1* Gene Are Responsible for Mitochondrial and Cytosolic Isoforms of Glutathione Reductase," *J. Biol. Chem. 279*(9):7785-7791, The American Society for Biochemistry and Molecular Biology, Inc., United States (2004).

Popuri, S.S.S. and Bata, R.M., "A Performance Study of Iso-Butanol-, Methanol-, and Ethanol-Gasoline Blends Using a Single Cylinder Engine," Truck Alternative Fuels and Exhaust Gas Emission, SP-1001, 932953, pp. 41-60, The Society of Automotive Engineers, Inc., United States (1993).

Ryan, E.D. and Kohlhaw, G.B., "Subcellular Localization of Isoleucine-Valine Biosynthetic Enzymes in Yeast," *J. Bacteriol. 120*(2):631-637, American Society for Microbiology, United States (1974).

Sarthy, A.V., et al., "Expression of the *Escherichia coli* Xylose Isomerase Gene in *Saccharomyces cerevisiae*," *Appl. Environ. Microbiol. 53*(9):1996-2000, American Society for Microbiology, United States (1987).

Stephanopoulos, G.A. et al., in *Metabolic Engineering Principles and Methodologies*, pp. 1-15 and 26-37, Academic Press, United States (1998).

Chin, M., "UCLA researchers develop method for production of more efficient biofuels," UCLA Newsroom, Jan. 2, 2008, available at http://newsroom.ucla.edu/portal/ucla/ucla-engineering-researchers-develop-42502.aspx, UC Regents, United States.

Petition Denial, mailed Mar. 5, 2012, U.S. Control No. 95/001,718, filed Aug. 18, 2011.

Decision on Petition Denied, Re-examination Request Terminated, mailed May 23, 2012, U.S. Control No. 95/001,718, filed Aug. 18, 2011.

The Presidential Green Chemistry Challenge Awards Program: Summary of 2010 Award Entries and Recipients, United States Environmental Protection Agency, 58 pages.

BRENDA Comprehensive Enzyme Information System entry for EC 1.1.1.2 alcohol dehydrogenase (NADP+) in *E. coli*, accessed at www.brenda-enzymes.org, accessed on Jun. 1, 2012, 8 pages.

Chen, E.C.-H., "Keto Acid Decarboxylase and Alcohol Dehydrogenase Activities of Yeast in Relation to the Formation of Fusel Alcohols," *Can. Inst. Food Sci. Technol. J. 10*:27-30, Canadian Institute of Food Science and Technology, Canada (1977).

Eden, A., et al., "Involvement of branched-chain amino acid aminotransferases in the production of fusel alcohols during fermentation in yeast," *Appl. Microbiol. Biotechnol. 55*:296-300, Springer-Verlag, Germany (2001).

Hansen, J. and Kielland-Brandt, M.C., "Modification of biochemical pathways in industrial yeasts," *J. Biotechnol. 49*:1-12 Elsevier Science B.V., Netherlands (1996).

Holmerg, S. and Litske Petersen, J.G., "Regulation of isoleucine-valine biosynthesis in *Saccharomyces cerevisiae*," *Curr. Genet. 13*:207-217, Springer-Verlag, Germany (1988).

Polaina, J., "Cloning of the *ILV2, ILV3*, and *ILV5* Genes of *Saccharomyces cerevisiae*," *Carlsberg Res. Commun. 49*:577-584, Springer-Verlag, Germany (1984).

Rainbow, C., in *The Yeasts*, vol. 3, Rose, A.H. and Harrison, J.S., eds., pp. 190-199, Academic Press, United States (1970).

Schulthess, D. and Ettlinger, L., "Influence of the Concentration of Branched Chain Amino Acids on the Formation of Fusel Alcohols," *J. Inst. Brew. 84*:240-243, W. Heffer & Sons, Ltd, England (1978).

Van Maris, A.J.A., et al., "Directed Evolution of Pyruvate Decarboxylase-Negative *Saccharomyces cerevisiae*, Yielding a $C_2$-Independent, Glucose-Tolerant, and Pyruvate-Hyperproducing Yeast," *Appl. Environ, Microbiol. 70*(1):159-166, American Society for Microbiology, United States (2004).

(56) References Cited

OTHER PUBLICATIONS

Velasco, J.A., et al., "Cloning of the dihydroxyacid dehydratase-encoding gene (ILV3) from Saccharomyces cerevisiae," Gene 137:179-185, Elsevier Science B.V., Netherlands (1993).
Webb, A.D. and Ingraham, J.L., "Fusel Oil" in Advances in Appl. Microbiol., vol. 5, pp. 317-353, Academic Press Inc., England (1963).
"Butamax Expands Early Adopters Group as Two New Ethanol Producers Join for Early Access to Biobutanol Production", available at http://www.butamax.com/_assets/pdf/butamax%20announces%202%20new%20eag%20may%201%202012.pdf, May 1, 2012.
Stephanopoulos Preliminary Injunction Hearing Transcript, pp. 114-117, Butamax™ Advanced Biofuels LLC v. Gevo, Inc., Case 11-054-SLR-MPT, U.S. District Court for the District of Delaware, Mar. 1, 2012.
Omura, F., "Targeting of mitochondrial Saccharomyces cerevisiae ILv5p to the cytosol and its effect on vicinal diketone formation in brewing," Appl. Microbiol. Biotechnol. 78:503-513, Springer-Verlag, Germany (2008).
Reazin, G., et al., "Mechanism of Major Congener Formation in Alcoholic Grain Fermentations," J. Agr. Food Chem. 18(4):585-589, American Chemical Society, United States (1970).
Magee, P.T. and De Robichon-Szulmajster, H., "The Regulation of Isoleucine-Valine Biosynthesis in Saccharomyces cerevisiae," European J. Biochem. FEBS 3:507-511, Federation of European Biochemical Societies, Germany (1968).
Glassner, D.A., "Hydrocarbon Fuels from Plant Biomass" available at http://www1.eere.energy.gov/biomass/pdfs/Biomass_2009_Adv_Biofuels_II_Glassner.pdf (2009).
Bayrock, D., "Fusel Oil Recycle—A Silent, Odorous Killer," Ethanol Producer Magazine, BBI International, United States, accessed at http://ethanolproducer.com/articles/8774/fusel-oil-recycleundefineda-silent-odorous-killer, May 10, 2012.
Atsumi, S. and Liao, J.C., "Metabolic engineering for advanced biofuels production from Escherichia coli," Curr. Op. Biotechnol. 19:414-419, Elsevier Ltd., England (2008).
Keasling, J.D. and Chou, H., "Metabolic engineering delivers next-generation biofuels," Nature Biotechnology 26(3):298-299, Nature Publishing Group, England (2008).
Boulton, et al, 2001. Brewing Yeast & Fermentation, Chapters 3-4, first ed., Blackwell Science Ltd, Oxford United Kingdom, pp. 69-259.
Response to Office Action filed Jun. 6, 2012 in Reexamination of U.S. Patent No. 7,851,188, U.S. Control No. 95/001,857, filed Dec. 19, 2011.
Declaration of Professor Alexander M. Klivanov, filed Jun. 5, 2012 in Re-examination of U.S. Patent 7,851,188, U.S. Control No. 95/001,857, filed Dec. 19, 2011.
Declaration of Larry C. Anthony, filed Jun. 5, 2012 in Reexamination of U.S. Patent 7,851,188, U.S. Control No. 95/001,857, filed Dec. 19, 2011.
Requester's Opposition Petition to Return or Expunge Patent Owner's Petition, filed Jun. 20, 2012, in Reexamination of U.S. Patent 7,851,188, U.S. Control No. 95/001,857, filed Dec. 19, 2011.
Petition of Patent Owner to Seek Supervisory Review of Dismissal of Petition to Vacate the Order Granting Third Party Requester's Second Reexamination Request, filed Jun. 11, 2012, in Reexamination of U.S. Patent 7,851,188, U.S. Control No. 95/001,857, filed Dec. 19, 2011.
"Boosting Biomass-to . . . Butanol?", Green Car Congress, Jul. 20, 2005, available at http://www.greencarcongress.com/2005/07/boosting_biomass.html.
Bailey, J.E., "Toward a Science of Metabolic Engineering," Science 252:1668-1675, American Association for the Advancement of Science, United States (1991).
Lee et al., 1999, Metabolic Engineering, First Ed., Lee, S.Y. and Papoutsakis, E.T, Eds., Marcel Dekker, United States, p. 292-293.
Walker, G.M., "Yeast Technology," in Yeast Physiology and Biotechnology, John Wiley & Sons, Ltd, Chichester, England, pp. 265-320 (1998).
Watanabe et al., "Mutants of bakers' yeasts producing a large amount of isobutyl alcohol or isoamyl alcohol, flavour components of bread," Applied Microbiology and Biotechnology 34:154-159, Springer-Verlag, Germany (1990).
Yoshizawa et al., "The Formation of Higher Alcohols in the Fermentation of Amino Acids by Yeast. The Formation of Isobutanol and Isoamyl Alcohol from Pyruvic Acid by Washed Yeats Cells," Agricultural and Biological Chemistry 29:672-677, Agricultural Chemical Society of Japan, Japan (1965).
English language abstract for JP 63-017695, File 347, Accession No. 2400795, Derwent WPI English language abstract for JP 63-017695, published Jan. 25, 1988.
English language abstract for JP 63-254986, File 347, Accession No. 2638086, Derwent WPI English language abstract for JP 63-254986, published Oct. 21, 1988.
English language abstract for JP 63-102687, File 347, Accession No. 2485787, Derwent WPI English language abstract for JP 63-102687, published May 7, 1988.
English language abstract for JP 61-209594, File 347, Accession No. 1995494, Derwent WPI English language abstract for JP 61-209594, published Sep. 17, 1986.
Third Party Requester Declaration of Dr. Stephanopoulos, filed Nov. 28, 2011, U.S. Control No. 95/001,718, filed Aug. 18, 2011.
Patent Owner Declaration of Professor Klibanov, filed Feb. 24, 2012, U.S. Control No. 95/001,735, filed Sep. 1, 2011.
Third Party Requester Declaration of Dr. Stephanopoulos After Non-Final Office Action, filed Mar. 26, 2012, U.S. Control No. 95/001,735, filed Sep. 1, 2011.
Third Party Requester Declaration of Dr. Porter-Scheinman After Non-Final Office Action, filed Mar. 26, 2012, U.S. Control No. 95/001,735, filed Sep. 1, 2011.
Third Party Requester Declaration of Dr. Stephanopoulos, filed May 25, 2012, U.S. Control No. 95/001,998, filed May 25, 2012.
Äyräpää, T., "The Formation of Phenethyl Alcohol from $^{14}$C-Labelled Phenylalanine," J. Inst. Brewing 71:341-347, W. Heffer & Sons, Ltd. England (1965).
Äyräpää, T., "Formation of Higher Alcohols by Various Yeasts," J. Inst. Brewing 74:169-178, W. Heffer & Sons, Ltd, England (1968).
Causton, H.C., et al., "Remodeling of Yeast Genome Expression in Response to Environmental Changes," Mol. Biol. Cell 12:323-337, The American Society for Cell Biology, United States (2001).
Trinh, C.T., et al., "Redesigning Escherichia coli Metabolism for Anaerobic Production of Isobutanol," Appl. Env. Microbiol. 77:4894-904, American Society for Microbiology, United States (2011).
Kolkman, A., et al., "Comparative Proteome Analysis of Saccharomyces cerevisiae Grown in Chemostat Cultures Limited for Glucose or Ethanol," Mol. Cell. Proteom 4:1-11, The American Society for Biochemistry and Molecular Biology, Inc., United States (2005).
Boer, V.M., et al., "The Genome-wide Transcriptional Responses of Saccharomyces cerevisiae Grown on Glucose in Aerobic Chemostat Cultures Limited for Carbon, Nitrogen, Phosphorus, or Sulfur," J. Biol. Chem. 278:3265-3274, The American Society for Biochemistry and Molecular Biology, Inc., United States (2003).
Frodyma, M.E. and Downs, D., "ApbA, the Ketopantoate Reductase Enzyme Salmonella typhimurium is Required for the Synthesis of Thiamine via the Alternative Pyrimidine Biosynthetic Pathway," J. Biol. Chem. 273:5572-76, The American Society for Biochemistry and Molecular Biology, Inc., United States (1998).
Inoue, T., "Mechanism of Higher Alcohol Formation During Wort Fermentation by Brewer's Yeast," Rept. Res. Lab. Kirin Brewery Co. 18:13-16, The Research Laboratories of Kirin Brewery Co., Ltd., Japan (1975).
Chen, E. C.-H., "The Relative contribution of Ehrlich and Biosynthetic Pathways to the Formation of Fusel Alcohols," J. Amer. Soc. Brewing Chem. 36(1):39-43, American Society of Brewing Chemists, Inc., United States (1978).
Norbeck, J. and Bloomberg, A., "Metabolic and regulatory changes associated with growth of Saccharomyces cerevisiae in 1.4 M NaCl: Evidence for osmotic induction of glycerol dissimilation via the

(56) References Cited

OTHER PUBLICATIONS dihydroxyacetone pathway," *J. Biol Chem.* 272(9):5544-54, The American Society for Biochemistry and Molecular Biology, Inc., United States (1997).

Unverified English language translation of Japanese Patent Application No. JP 2000-041655 A, publication date Feb. 15, 2000.

Kotula, L and Curtis, P.J., "Evaluation of Foreign Gene Codon Optimization in Yeast: Expression of a Mouse IG Kappa Chain," *Nature Biotechnology* 9:1386-1389, Nature Publishing Group, England (1991).

Kassow, A., Metabolic effects of deleting the region encoding the transit peptide in *Saccharomyces cerevisiae ILV5*, Thesis for the cand. scient. degree at Institute of Genetics, University of Copenhagen, Department of Yeast Genetics, 48 pages, Denmark (1992).

U.S. Appl. No. 61/016,483, Feldman et al., filed Dec. 23, 2007.

Blombach, B., et al., "*Corynebacterium glutamicum* Tailored for Efficient Isobutanol Production," *Appl. Environ. Microbiol.* 77(10):3300-3310, The American Society for Microbiology, United States (2011).

Hammond, J.R.M., "Brewer's Yeasts," in The Yeasts, vol. 5, 2$^{nd}$ Edition, Rose, A.H. and Harrison, J.S., eds., pp. 7-67, Academic Press, United States (1993).

Third Party Requester Comments After Patent Owner Response to Non-Final Office Action, filed Jul. 5, 2012, Inter Partes Reexamination of U.S. Patent No. 7,851 188, U.S. Control No. 95/001,857, filed Dec. 19, 2011.

Third Party Declaration of Dr. Glassner, filed Jul. 5, 2012, U.S. Control No. 95/001,857, filed Dec. 19, 2011.

Chen, et al., "Increased isobutanol production in *Saccharomyces cerevisiae* by overexpression of genes in valine metabolism," *Biotechnol. Biofuels* 4(21):1-12, BioMed Central Ltd., England (2011).

Hammond, J.R.M., "Genetically-modified brewing yeasts for the 21st century. Progress to date" *Yeast* 11(16):1613-27, John Wiley & Sons Ltd, United States (1995).

U.S. Appl. No. 60/900,477, Liao et al., filed Feb. 9, 2007.

U.S. Appl. No. 60/900,546, Liao et al., filed Feb. 9, 2007.

"Diet beer offers a slim hope," http://www.independent.co.uk/news/diet-beer-offers-a-slim-hope-1305762.html, The Independent Newspaper, Apr. 20, 1996.

Herman, R.G., "Advances in catalytic synthesis and utilization of higher alcohols," *Catalysis Today* 55(3):233-245, Elsevier B.V., Netherlands (2000).

Olson, E.S., et al., "Higher-alcohols biorefinery: Improvement of catalyst for ethanol conversion," *Appl. Biochem. Biotechnol.* 113-116:913-932, Humana Press, United States (2004).

Sheldon-Coulson, "Production of Levalinic Acid in Urban Biorefineries," M.S. Thesis., Sep. 12, 2011, 84 pp., Massachusetts Institute of Technology, United States.

Sequence Alignment SEQ ID No. 2 vs Peng's Accession No. P27696, provided with Third Party Requester Comments After Patent Owner Response to Non-Final Office Action, filed Jul. 5, 2012, Inter Partes Reexamination of U.S. Patent No. 7,851 188, U.S. Control No. 95/001,857, filed Dec. 19, 2011.

Presecan, E., "The *Bacillus subtilis* genome from *gerBC* (311°) to *licR* (334°)," *Microbiology* 143:3313-3328, SGM, England (1997).

Bolotin, A., "The Complete Genome Sequence of the Lactic Acid Bacterium *Lactococcus lactis* ssp. *lactis* IL1403," *Genome Res.* 11(5):731-753, Cold Spring Harbor Press, United States (2001).

Pretokius, I.S., et al., "Designer Yeasts for the Fermentation Industry of the 21st Century," *Food Technol. Biotechnol.* 41(1):3-10, Journal of the Faculty of Food Technology and Biotechnology, Croatia (2003).

Alberts, et al., "Chapter 3. Macromolecules: Structure, Shape and Information," in *Molecular Biology of the Cell*, 3$^{rd}$ Ed., pp. 134-135, Garland Publishing, United States (1994).

Third Party Requester Declaration of Dr. Stephanopoulos, filed Jul. 5, 2012, U.S. Control No. 95/001,857, filed Dec. 19, 2011.

"Gevo Announces Successful Startup of World's First Commercial Biobased Isobutanol Plant," Gevo Investor Relations News Release, May 24, 2012, 2 pages, accessed at http://ir.gevo.com/phoenix.zhtml?c=238618&p=irol-newsArticle&ID=1699401&highlight=.

De Kok, S., et al., "Energy coupling in *Saccharomyces cerevisiae*: selected opportunities for metabolic engineering," *Federation of European Microbiological Societies FEMS Yeast Re 12*:387-397, Blackwell Publishing Ltd., England (2012).

"Agricultural Futures" in The Wall Street Journal Online, U.S. Edition, Thursday, Jun. 28, 2012, 8 pages, accessed at http://online.wsj.com/mdc/public/page/2_3023-fut_agricultural-futures.html?mod=mdc_c, Dow Jones & Company, Inc., United States.

Zaworski, F., ed., "US Oxo-alcohols sinking lower," *ICISpricing Oxo-Alcohols*, Jun. 22, 2012, 2 pages, Reed Business Information Limited, England.

Kwiatkowski, J.R., et al., "Modeling the process and costs of fuel ethanol production by the corn dry-grind process," *Industrial Crops and Products* 23:288-296, Elsevier B.V., Netherlands (2006).

Natural Gas Weekly Update for Week Ending Jun. 27, 2012, Release Date Jun. 28, 2012, U.S. Energy Information Administration, 10 pages, accessed at http://205.254.135.7/naturalgas/weekly.

Bevill, K., et al., "Proposed Ethanol Plant List: 2008 United States & Canada Part 1," Ethanol Producer Magazine, EthanolProducer.com Apr. 1, 2008, 9 pages, accessed at http://www.ethanolproducer.com/articles/3851/proposed-ethanol-plant-list-2008-united-states-and-canada-part-1.

"Who Shall Dare: Biobutanol and the intrepid ethanol producer," Biofuelsdigest.com, Jun. 22, 2012, Biofuels Digest, Unites States, 4 pages, accessed at http://biofuelsdigest.com/bdigest/2012/06/22/who-shall-dare-biobutanol-and-the-intrepid-ethanol-producer/.

Eberhardt, I., et al., "Autoregulation of yeast pyruvate decarboxylase gene expression requires the enzyme but not its catalytic activity," *Eur. J. Biochem.* 262(1):191-201, Federation of European Biochemical Societies, England (1999).

Hohmann, S. and Cederberg, H., "Autoregulation may control the expression of yeast pyruvate decarboxylase structural genes *PDC1* and *PDC5*," *Eur. J. Biochem.* 188(3):615-621, Federation of European Biochemical Societies, England (1990).

Møller, K., et al., "Pyruvate decarboxylase from the petite-negative yeast *Saccharomyces kluyveri*," *Mol. Genet. Genomics* 270(6):558-568, Springer-Verlag, Germany (2004).

Ter Schure, E.g., et al., "Pyruvate Decarboxylase Catalyzes Decarboxylation of Branched-Chain 2-Oxo Acids But Is Not essential for Fusel Alcohol Production by *Saccharomyces cerevisiae*," *Appl. Environ. Microbiol.* 64(4):1303-1307, American Society for Microbiology, United States (1998).

Vuralhan, Z. et al., "Physiological Characterization of the ARO10-Dependent Broad-Substrate-Specificity 2-Oxo Acid Decarboxylase Activity of *Saccharomyces cerevisiae*," *Appl. Environ. Microbiol.* 71(6):3276-3284, American Society for Microbiology, United States (2005).

Request for Ex Parte Reexamination of U.S. Patent No. 7,993,889 with Exhibits, U.S. Control No. 90/012,503, filed Sep. 12, 2012.

Declaration of Dr. Stephanopoulos, filed Sep. 12, 2012, U.S. Control No. 90/012,503, filed Sep. 12, 2012.

Office Action mailed Sep. 21, 2012, in Inter Partes Reexamination of U.S. Patent No. 8,178,328, filed Jun. 21, 2012, U.S. Control No. 95/001,998.

Order Granting Request Inter Partes Reexamination of U.S. Patent No. 8,178,328, filed Jun. 21, 2012, U.S. Control No. 95/001,998.

*Researchers Significantly Boost Yield of Isobutanol from Engineered Yeast Using New Synthesis Pathway Located in the Cytosol*, published Nov. 6, 2012, available at http://www.greencarcongress.com/2012/11/boles-20121106.html.

*Engineered Yeast Produces Ethanol and Butanol from C5 and C6 Sugars from Biomass Feedstocks*, published Mar. 29, 2010, available at http://www.greencarcongress.com/2010/03/weber-20100329.html.

*Butalco to Begin Cellulosic Ethanol Production in Summer 2010 in Germany*, published Feb. 24, 2010, available at http://www.greencarcongress.com/2010/02/butalco-20100224.html.

(56) References Cited

OTHER PUBLICATIONS

*First Yeast to Produce Biobutanol*, published Sep. 7, 2009, available at http://www.pressebox.de/pressemitteilung/butalco-gmbh/First-Yeasts-to-Produce-Biobutanol/boxid/286731.
Savrasova, E.A., et al., "Use of the valine biosynthetic pathway to convert glucose into isobutanol," *J. Ind. Microbiol. Biotechnol.* 38:1287-1294, Springer, Germany (2011).
*Researchers Boost Isobutanol Production in Yeast*, published Jul. 28, 2011, available at http://www.greencarcongress.com/2011/07/tud-20110728.html.
Matsuda, F., et al., "Construction of an Artificial Pathway for Isobutanol Biosynthesis in the Cytosol of *Saccharomyces cerevisiae*," *Biosci. Biotechnol. Biochem.* 76(11):2139-2141, Japan Society for Bioscience, Biotechnology, and Agrochemistry, Japan (2012).
*Butamax Early Adopters Group surpasses capacity targets with addition of Big River; Membership represents 11 production facilities and nearly 900 million gallons of ethanol capacity*, published Jun. 26, 2012, available at http://www.prnewswire.com/news-releases/butamax-early-adopters-group-surpasses-capacity-targets-with-addition-of-big-river-membership-represents-11-production-facilities-and-nearly-900-million-gallons-of-ethanol-capacity-160348995.html#.
Brat, D., et al., "Cytosolic re-localization and optimization of valine synthesis and catabolism enables increased isobutanol production with the yeast *Saccharomyces cerevisiae*," *Biotechnology for Biofuels* 5(65):1-16, BioMed Central Ltd., England (2012).
Marquet, A., et al., "Biosynthesis of biotin and lipoic acid," *Vitam. Horm.* 61:51-101, Academic Press, United States (2001).
Ottenhoff, H.H., et al., "Organisation of the pantothenate (vitamin B5) biosynthesis pathway in higher plants," *Plant J.* 37:61-72, Blackwell Scientific Publishers, England (2004).
Streit, W.R. and Entcheva, P., "Biotin in microbes, the genes involved in its biosynthesis, its biochemical role and perspectives for biotechnological production," *Appl. Microbiol. Biotechnol.* 61:21-31, Springer Verlag, Germany (2003).
Magliano, P., et al., "Contributions of the peroxisome and β-oxidation cycle to biotin synthesis in fungi," *J. Biol. Chem.* 286:42133-42140, American Society for Biochemistry and Molecular Biology, United States (2011).
United States Court of Appeals for the Federal Circuit Decision, Case No. 11-CV-0054-SLR; Appeal from United States District Court for the District of Delaware, Nov. 16, 2012.
Complaint, *Butamax™ Advanced Biofuels LLC v. Gevo, Inc.*, 1:12-cv-00602-SLR, U.S. District Court, District of Delaware, filed May 15, 2012.
Answer to Complaint, *Butamax™ Advanced Biofuels LLC v. Gevo, Inc.*, 1:12-cv-00602-SLR, U.S. District Court, District of Delaware, filed Jun. 8, 2012.
"Getting Published in *Nature*: The Editorial Process," accessed at http://www.nature.com/nature/authors/get_published, accessed on Dec. 19, 2012.
Dumas, R., et al., "Isolation and kinetic properties of acetohydroxy acid isomeroredutase from spinach (*Spinacia oleracea*) chloroplasts overexpressed in *Escherichia coli*," *Biochem J.* 288:865-874, Published by Portland Press, Enlgand (1992).
Pang, S.S., et al., "The Crystal Structures of *Klebsiella pneumoniae* Acetolactate Synthase with Enzyme-bound Cofactor and with an Unusual Intermediate," *J. Biol. Chem.* 279(3):2242-2253, American Society for Biochemistry and Molecular Biology, Inc., United States (2004).
Flint, D.H., et al., "The Role and Properties of the Iron—Sulfur Cluster in *Escherichia coli* Dihydroxy-acid Dehydratase," *J. Biol. Chem.* 268 (20):14732-14742, American Society for Biochemistry and Molecular Biology, Inc., United States (1993).
Boonstra, B., et al., "Cofactor Regeneration by a Soluble Pyridine Nucleotide Transhydrogenase for Biological Production of Hydromorphone," *Applied and Environmental Microbiology* 66(12):5161-5166, American Society for Microbiology, United States (2000).

"Gevo Ramps Up Post-IPO: Executive Team Leads Next Round of Renewables," *Chemical Week* Oct. 3/10, 2011, IHS, Inc., accessed at http://www.gevo.com/wp-content/uploads/2011/10/044_cwk_101011_comp.pdf, accessed on Dec. 20, 2012.
Response to Inter Partes Reexamination Office Action filed Dec. 21, 2012, in Inter Partes Reexamination of U.S. Patent No. 8,178,328, filed Jun. 21, 2012, U.S. Control No. 95/001,998.
Declaration of Dr. Larry C. Anthony Accompanying Response to Inter Partes Reexamination Office Action, in Inter Partes Reexamination of U.S. Patent No. 8,178,328, filed Jun. 21, 2012, U.S. Control No. 95/001,998.
Declaration of Dr. Alexander M. Klibanov Accompanying Response to Inter Partes Reexamination Office Action, in Inter Partes Reexamination of U.S. Patent No. 8,178,328, filed Jun. 21, 2012, U.S. Control No. 95/001,998.
Declaration of Dr. Janice Pero Accompanying Response to Inter Partes Reexamination Office Action, in Inter Partes Reexamination of U.S. Patent No. 8,178,328, filed Jun. 21, 2012, U.S. Control No. 95/001,998.
Memorandum Opinion of District Judge Robinson, in *Butamax™ Advanced Biofuels LLC vs. Gevo, Inc.*, Case 1:11-cv-00054-SLR, United States District Court for the District of Delaware, filed Mar. 19, 2013; 57 pages.
Order of District Judge Robinson, in *Butamax™ Advanced Biofuels LLC vs. Gevo, Inc.*, Case 1:11-cv-00054-SLR, United States District Court for the District of Delaware, filed Mar. 19, 2013; 2 pages.
Final Judgment of District Judge Robinson, in *Butamax™ Advanced Biofuels LLC vs. Gevo, Inc.*, Case 1:11-cv-00054-SLR, United States District Court for the District of Delaware, filed Apr. 5, 2013; 2 pages.
Pronk, J.T., et al., "Pyruvate Metabolism in *Saccharomyces cerevisia*," *Yeast 12*:1607-1633, John Wiley Sons, Ltd., United States (1996).
Stephanopolous Deposition Testimony Transcript, pp. 258-265, *Butamax™ Advanced Biofuels LLC v. Gevo, Inc.*, Case 11-054-SLR-MPT, U.S. District Court for the District of Delaware, Nov. 19, 2012.
Avalos, J.L., et al., "Compartmentalization of metabolic pathways in yeast mitochondria improves the production of branched-chain alcohols," *Nature Biotechnology*, Advance Online Publication:1-9, Nature America, Inc., United States (2013).
Amended Final Judgment of District Judge Robinson, in *Butamax™ Advanced Biofuels LLC vs. Gevo, Inc.*, Case 1:11-cv-00054-SLR, United States District Court for the District of Delaware, filed Apr. 10, 2013; 2 pages.
"Occurrence of higher alcohols," in *Aroma of Beer, Wine and Distilled Alcoholic Beverages*, Nykanen, L., Ed., pp. 22-25, Akademie-Verlag, Berlin, Germany, (1983).
Jayaraj, R. and Smooker, P.M., "So you Need a Protein—A Guide to the Production of Recombinant Proteins," *The Open Veterinary Science Journal* 328-34, Bentham Open, England (2009).
Third Party Requester Comments Afer Non-Final Office Action, filed Sep. 4, 2013 in Inter Partes Reexamination of U.S. Patent No. 8,178,328, filed Jun. 21, 2012, U.S. Control No. 95/001,998.
Declaration of Gregory N. Stephanopoulos, Ph.D., Accompanying Third Party Requester Comments to Patent Owner's Response to Inter Partes Reexamination Office Action, in Inter Partes Reexamination of U.S. Patent No. 8,178,328, filed Jun. 21, 2012, U.S. Control No. 95/001,998.
Memorandum Opinion of District Judge Robinson, in *Gevo, Inc.* vs. *Butamax™ Advanced Biofuels LLC and E.I. Dupont De Nemours and Company*, Case 1:13-cv-00576-SLR, United States District Court for the District of Delaware, filed Jul. 26, 2013; 46 pages.
Sánchez, A.M., et al., "Efficient Succinic Acid Production from Glucose through Overexpression of Pyruvate Carboxylase in an *Escherichia coli* Alcohol Dehydrogenase and Lactate Dehydrogenase Mutant," *Biotechnol. Prog.* 21:358-365, American Chemical Society and American Institute of Chemical Engineers, United States (2005).
Debourg, A., "Yeast in Action: From Wort to Beer," *Cerevisia* 27(3):144-154, St. Martens-Latem Associations D Anciens Etudiants Des Ecole De Brasserie Belges, Belgium (2002).

(56) References Cited

OTHER PUBLICATIONS

*Butamax expands Biobutanol Early Adopters Group with Four New Members; Brings Capacity to Half a Billion Gallons*, published Jun. 18, 2012, Butamax™ Advanced Biofuels LLC.

Villanueba, K.D., et al., "Subthreshold Vicinal Diketome Levels in Lager Brewing Yeast Fermentations by Means of *ILV5* Gene Amplifications," *ASBCA Journal* 48(3):111-114, American Society of Brewing Chemists, Inc., United States (1990).

Villa, K.D. and Lee, S., "Control of Vicinal Diketone Production by Brewer's Yeast. I. Effects of *ILV5* and *ILV3* Gene Amplification on Vicinal Diketone Production and *ILV* Enzyme Activity," *ASBCA Journal* 53(2):49-53, American Society of Brewing Chemists, Inc., United States (1995).

*Strive to Become a Company 'Growing for Good'*, accessed at http://www.suntory.com/president/index.html on Nov. 15, 2013, Suntory Holdings Limited.

*Butamax™ Techology & Intellectual Property FAQ*, accessed at http://butamaxpatents.com/FAQ.aspx on Nov. 18, 2013, Butamax™ Advanced Biofuels LLC.

*Butamax and Highwater Ethanol Break Ground on Biobutanol Retrofit Project Including Installation of Novel Corn Oil Separation Technology*, published Oct. 2, 2013, Butamax™ Advanced Biofuels LLC.

Albertsen, L., et al., "Diversion of Flux toward Sesquiterpene Production in *Saccharomyces cerevisiae* by Fusion of Host and Heterologous Enzymes," *Applied and Enviro. Microbiol.* 77(3):1033-1040, American Society for Microbiology, United States (2011).

Becker, J.V.W., et al., "Metabolic Engineering of *Saccharomyces cerevisiae* for the synthesis of the wine-related antioxidant resveratrol," *FEMS Yeast Res.* 4:79-85, Elsevier B.V., Netherlands (2003).

Bricker, D.K., et al., "A Mitochondrial Pyruvate Carrier Required for Pyruvate Uptake in Yeast, *Drosophila*, and Humans," *Science* 337:96-100, American Association for the Advancement of Science, United States (2012).

Cordier, H., et al., "A metabolic and genomic study of engineered *Saccharomyces cerevisiae* strains for high glycerol production," *Metabolic Engineering* 9:364-378, Academic Press, United States (2007).

Deloache, W.C. and Dueber, J.E., "Compartmentalizing metabolic pathways in organelles," *Nature Biotech.* 31:320-321, Nature America, Inc., United States (2013).

Divakaruni, A.S. and Murphy, A.N., "A Mitochondrial Mystery, Solved," *Science* 337:41-43, American Association for the Advancement of Science, United States (2012).

Enari, T.-M., "Genetic Modification of Food and Beverage Yeast," *Annals New York Acad. Sci*, 646:181-192, New York Academy of Sciences, United States (1991).

Geertmam, J-M.A., et al., "Physiological and genetic engineering of cytosolic redox metabolism in *Saccharomyces cerevisiae* for improved glycerol production," *Metabolic Engineering* 8:532-542, Elsevier Inc., United States (2006).

Giudici, P., et al., "A biometric study of higher alcohol production in *Saccharomyces cerevisiae*," *Can. J. Microbiol.* 36:61-64, The National Research Council of Canada, Canada (1990).

Hackel, B.J., et al., "Production of Soluble and Active Transferrin Receptor-Targeting Single-Chain Antibody Using *Saccharomyces cerevisiae*," *Pharm. Res.* 23:790-797, Springer Science + Business Media, Inc., United States (2006).

Herzig, S., et al., "Identification and Functional Expression of the Mitochondrial Pyruvate Carrier," *Science* 337:93-96, American Association for the Advancement of Science, United States (2012).

Hutson, S.M. and Rannels, S.L., "Characterization of a Mitochondrial Transport System for Branched Chain α-Keto Acids," *J. Biol. Chem.* 260(26):14189-14193, American Society of Biological Chemists, Inc., United States (1985).

Ingraham, J.L. and Guymon, J.F., "The Formation of Higher Aliphatic Alcohols by Mutant Strains of *Saccharomyces cerevisiae*," *Arch. Biochem. Biophys.* 88:157-166, Academic Press Inc., United States (1960).

Kim, E-J, et al., "Expression of hepatitis B surface antigen S domain in recombinant *Saccharomyces cerevisiae* using *GAL1* promoter," *J. Biotechnol.* 141:155-159, Elsevier B.V., Netherlands (2009).

Lee, W., et al., "Application of sequential integration for metabolic engineering of 1,2-propanediol production in yeast," *Metabolic Engineering* 8:58-65, Elsevier Inc., United States (2006).

McCourt, J.A., et al., "Facile crystallization of *Escherichia coli* ketol-acid reductoisomerase," *Acta Crystallographica* D60:1432-1434, International Union of Crystallography by Munksgaard, United States (2004).

Minahan, D.M., et al., "Synthesis of Fuel Alcohols and MTBE from Syngas Using Spinel Oxide Based Catalysts," *Preprints Div. Fuel. Chem. ACS* 42(2):715-719, American Chemical Society, United States (1997).

Pirkov, I., et al., "Ethylene production by metabolic engineering of the yeast *Saccharomyces cerevisiae*," *Metabolic Engineering* 10:276-280, Elsevier Inc., United States (2008).

Raab, A.M., et al., "Metabolic engineering of *Saccharomyces cerevisiae* for the biotechnological production of succinic acid," *Metabolic Engineering* 12:518-525, Elsevier Inc., United States (2010).

Ro, D-K., et al., "Production of the antimalarial drug precursor artemisinic acid in engineered yeast," *Nature* 440:940-943, Nature Publishing Group, England (2006).

Sauer, M., et al., "Production of L-Ascorbic Acid by Metabolically Engineered *Saccharomyces cerevisiae* and *Zygosaccharomyces bailii*," *Applied and Environ. Microbiol.* 70(10):6086-6091, American Society for Microbiology, United States (2004).

Swiegers, J.H., et al., "The development of yeast strains as tools for adjusting the flavor of fermented beverages to market specifications," Chapter 1, D. Havkin-Frenkel & F.C. Belanger (Eds.): *Biotechnology in Flavor Production*, 1-55, Blackwell Publishing Ltd, Oxford, United Kingdom (2008).

Toivari, M.H., et al., "Enhancing the flux of D-Glucose to the pentose phosphate pathway in *Saccharomyces cerevisiae* for the production of D-Ribose and ribitol," *Appl Microbiol Biotechnol* 85:731-739, Springer-Verlag, Germany (2010).

Underwood, R.P., et al., "Development of Alternative Fuels from Coal-Derived Syngas," pp. 65-85, Air Products & Chemicals, Inc., United States (1991).

Vai, M., et al., "Improved Secretion of Native Human Insulin-Like Growth Factor 1 from *gas1* Mutant *Saccharomyces cerevisiae* Cells," *Applied and Enviro Microbiol* 66(12):5477-5479, American Society for Microbiology, United States (2000).

Van Bergen, B., "Diacetyl: identification and characterisation of molecular mechanisms for reduction in yeast and their application in a novel enzyme based assay for quantification in fermentation systems," Ph.D. Thesis, McGill University, Montreal, Canada (2006).

Vellanki, R.N., et al., "Expression of hepatitis B surface antigen in *Saccharomyces cerevisiae* utilizing glyceraldeyhyde-3-phosphate dehydrogenase promoter of *Pichia pastoris*," *Biotechnol. Lett.* 29:313-318, Springer Science+Business Media B.V., United States (2007).

Xu, G., et al., "Reconstruction of cytosolic fumaric acid biosynthetic pathways in *Saccharomyces cerevisiae*," *Microbial Cell Factories* 11:24, pp. 1-10, BioMed Central Ltd, England (2012).

Yoshimoto, H., et al., "Pyruvate Decarboxylase Encoded by the *PDC1* Gene Contributes, at Least partially, to the Decarboxylation of α-Ketoisocaproate for Isoamyl Alcohol Formation in *Saccharomyces cerevisiae*," *J. Biosci. Bioengineering* 92(1):83-85, Elsevier, Japan (2001).

Zelle, R.M., et al., "Malic Acid Production by *Saccharomyces cerevisiae*: Engineering of Pyruvate Carboxylation, Oxaloacetate Reduction, and Malate Export," *Applied Environ. Microbiol.* 74(9):2766-2777, American Society for Microbiology, United States (2008).

(56) References Cited

OTHER PUBLICATIONS

Zhang, B., et al., "Engineering the Monomer Composition of Polyhyroxyalkanoates Synthesized in *Saccharomyces cerevisiae*," *Applied Environ. Microbiol.* 72(1):536-543, American Society for Microbiology, United States (2006).

Information on EC 1.1.1.86—ketol-acid reductoisomerase, accessed at http://www.brenda-enzymes.org/php/result_flat.php4?ecno=1.1.1.86, accessed on Dec. 16, 2013, 42 pages.

Information on EC 2.2.1.6—acetolactate synthase, accessed at http://www.brenda-enzymes.org/php/result_flat.php4?ecno=2.2.1.6, accessed on Dec. 16, 2013, 126 pages.

Information on EC 4.2.1.9—dihydroxy-acid dehydratase, accessed at http://www.brenda-enzymes.org/php/result_flat.php4?ecno=4.2.1.9, accessed on Dec. 16, 2013, 24 pages.

Chica, R.A., et al., "Semi-rational approaches to engineering enzyme activity: combining the benefits of directed evolution and rational design," *Current Opinion in Biotechnology* 16:378-384, Elsevier Ltd., England (2005).

Sen, S., et al., "Developments in Directed Evolution for Improving Enzyme Funtions," *Appl Biochem Biotechnol* 143:212-223, Humana Press Inc., United States (2007).

*Butamax™ Advanced Biofuels LLC* vs. *Gevo, Inc.* (Fed. Cir. 2014), dated Feb. 18, 2014 [Appeal from the United States District Court for the District of Delaware in No. 11-cv-00054, Judge Sue L. Robinson].

Action Closing Prosecution in Inter Partes Reexamination of U.S. Patent No. 8,178,328, mailed Mar. 19, 2014, U.S. Control No. 95/001,998, filed Jun. 21, 2012.

\* cited by examiner

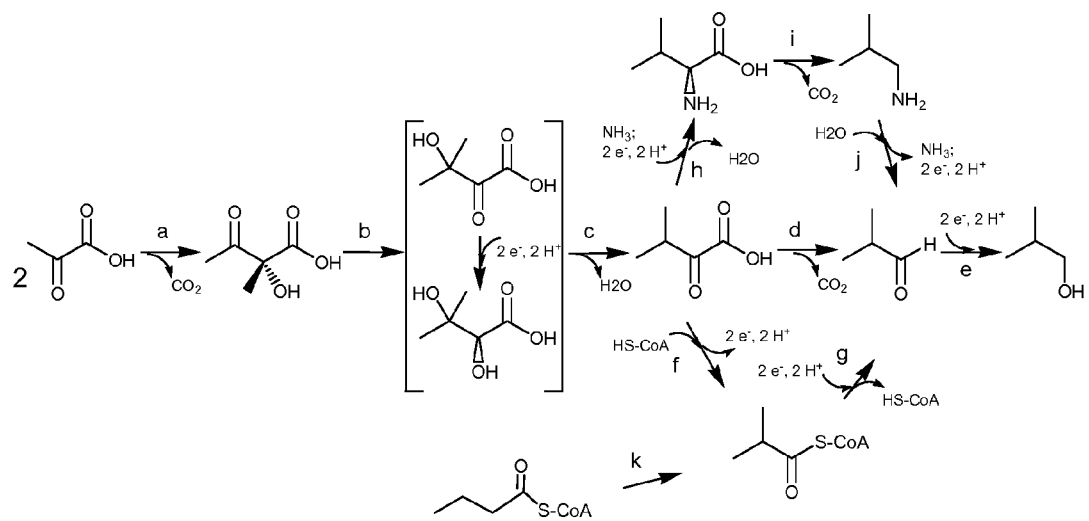

FERMENTIVE PRODUCTION OF FOUR CARBON ALCOHOLS

CROSS-REFERENCE TO RELATED APPLICATION

This application is a continuation of U.S. application Ser. No. 12/939,284, filed Nov. 4, 2010, which is a continuation of U.S. application Ser. No. 11/586,315, filed Oct. 25, 2006, now U.S. Pat. No. 7,851,188, issued Dec. 14, 2010, which claims priority under 35 U.S.C. §119 from U.S. Provisional Application Ser. No. 60/730,290, filed Oct. 26, 2005, each of which are incorporated by reference in their entirety.

REFERENCE TO A SEQUENCE LISTING SUBMITTED ELECTRONICALLY VIA EFS-WEB

The content of the electronically submitted sequence listing (Name: CL3243USCNT6_SequenceListing_CORRECTED_ascii.txt, Size: 380,433 bytes; and Date of Creation: Oct. 28, 2013) is herein incorporated by reference in its entirety.

FIELD OF THE INVENTION

The invention relates to the field of industrial microbiology and the production of alcohols. More specifically, isobutanol is produced via industrial fermentation of a recombinant microorganism.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Methods for the chemical synthesis of isobutanol are known, such as oxo synthesis, catalytic hydrogenation of carbon monoxide (*Ullmann's Encyclopedia of Industrial Chemistry*, 6$^{th}$ edition, 2003, Wiley-VCHVerlag GmbH and Co., Weinheim, Germany, Vol. 5, pp. 716-719) and Guerbet condensation of methanol with n-propanol (Carlini et al., *J. Mol. Catal. A: Chem.* 220:215-220 (2004)). These processes use starting materials derived from petrochemicals and are generally expensive and are not environmentally friendly. The production of isobutanol from plant-derived raw materials would minimize green house gas emissions and would represent an advance in the art.

Isobutanol is produced biologically as a by-product of yeast fermentation. It is a component of "fusel oil" that forms as a result of incomplete metabolism of amino acids by this group of fungi. Isobutanol is specifically produced from catabolism of L-valine. After the amine group of L-valine is harvested as a nitrogen source, the resulting α-keto acid is decarboxylated and reduced to isobutanol by enzymes of the so-called Ehrlich pathway (Dickinson et al., *J. Biol. Chem.* 273(40):25752-25756 (1998)). Yields of fusel oil and/or its components achieved during beverage fermentation are typically low. For example, the concentration of isobutanol produced in beer fermentation is reported to be less than 16 parts per million (Garcia et al., *Process Biochemistry* 29:303-309 (1994)). Addition of exogenous L-valine to the fermentation increases the yield of isobutanol, as described by Dickinson et al., supra, wherein it is reported that a yield of isobutanol of 3 g/L is obtained by providing L-valine at a concentration of 20 g/L in the fermentation. However, the use of valine as a feed-stock would be cost prohibitive for industrial scale isobutanol production. The biosynthesis of isobutanol directly from sugars would be economically viable and would represent an advance in the art. There have been no reports of a recombinant microorganism designed to produce isobutanol.

There is a need, therefore, for an environmentally responsible, cost-effective process for the production of isobutanol as a single product. The present invention addresses this need by providing a recombinant microbial production host that expresses an isobutanol biosynthetic pathway.

SUMMARY OF THE INVENTION

The invention provides a recombinant microorganism having an engineered isobutanol biosynthetic pathway. The engineered microorganism may be used for the commercial production of isobutanol. Accordingly, in one embodiment the invention provides a recombinant microbial host cell comprising at least one DNA molecule encoding a polypeptide that catalyzes a substrate to product conversion selected from the group consisting of:

i) pyruvate to acetolactate (pathway step a)
ii) acetolactate to 2,3-dihydroxyisovalerate (pathway step b)
iii) 2,3-dihydroxyisovalerate to α-ketoisovalerate (pathway step c)
iv) α-ketoisovalerate to isobutyraldehyde, (pathway step d), and
v) isobutyraldehyde to isobutanol; (pathway step e)

wherein the at least one DNA molecule is heterologous to said microbial host cell and wherein said microbial host cell produces isobutanol.

In another embodiment, the invention provides a recombinant microbial host cell comprising at least one DNA molecule encoding a polypeptide that catalyzes a substrate to product conversion selected from the group consisting of:

i) pyruvate to acetolactate, (pathway step a)
ii) acetolactate to 2,3-dihydroxyisovalerate, (pathway step b)
iii) 2,3-dihydroxyisovalerate to α-ketoisovalerate, (pathway step c)
iv) α-ketoisovalerate to isobutyryl-CoA, (pathway step f)
v) isobutyryl-CoA to isobutyraldehyde, (pathway step g), and
vi) isobutyraldehyde to isobutanol; (pathway step e)

wherein the at least one DNA molecule is heterologous to said microbial host cell and wherein said microbial host cell produces isobutanol.

In another embodiment, the invention provides a recombinant microbial host cell comprising at least one DNA molecule encoding a polypeptide that catalyzes a substrate to product conversion selected from the group consisting of:

i) pyruvate to acetolactate, (pathway step a)
ii) acetolactate to 2,3-dihydroxyisovalerate, (pathway step b)
iii) 2,3-dihydroxyisovalerate to α-ketoisovalerate, (pathway step c)
iv) α-ketoisovalerate to valine, (pathway step h)
v) valine to isobutylamine, (pathway step i)
vi) isobutylamine to isobutyraldehyde, (pathway step j), and
vii) isobutyraldehyde to isobutanol: (pathway step e)

wherein the at least one DNA molecule is heterologous to said microbial host cell and wherein said microbial host cell produces isobutanol.

In another embodiment, the invention provides a method for the production of isobutanol comprising:
1) providing a recombinant microbial host cell comprising at least one DNA molecule encoding a polypeptide that catalyzes a substrate to product conversion selected from the group consisting of:
   i) pyruvate to acetolactate (pathway step a)
   ii) acetolactate to 2,3-dihydroxyisovalerate (pathway step b)
   iii) 2,3-dihydroxyisovalerate to α-ketoisovalerate (pathway step c)
   iv) α-ketoisovalerate to isobutyraldehyde, (pathway step d), and
   v) isobutyraldehyde to isobutanol; (pathway step e)
wherein the at least one DNA molecule is heterologous to said microbial host cell; and
2) contacting the host cell of (i) with a fermentable carbon substrate in a fermentation medium under conditions whereby isobutanol is produced.

In another embodiment, the invention provides a method for the production of isobutanol comprising:
1) providing a recombinant microbial host cell comprising at least one DNA molecule encoding a polypeptide that catalyzes a substrate to product conversion selected from the group consisting of:
   i) pyruvate to acetolactate, (pathway step a)
   ii) acetolactate to 2,3-dihydroxyisovalerate, (pathway step b)
   iii) 2,3-dihydroxyisovalerate to α-ketoisovalerate, (pathway step c)
   iv) α-ketoisovalerate to isobutyryl-CoA, (pathway step f)
   v) isobutyryl-CoA to isobutyraldehyde, (pathway step g), and
   vi) isobutyraldehyde to isobutanol; (pathway step e)
wherein the at least one DNA molecule is heterologous to said microbial host cell; and
2) contacting the host cell of (i) with a fermentable carbon substrate in a fermentation medium under conditions whereby isobutanol is produced.

In another embodiment, the invention provides a method for the production of isobutanol comprising:
1) providing a recombinant microbial host cell comprising at least one DNA molecule encoding a polypeptide that catalyzes a substrate to product conversion selected from the group consisting of:
   i) pyruvate to acetolactate, (pathway step a)
   ii) acetolactate to 2,3-dihydroxyisovalerate, (pathway step b)
   iii) 2,3-dihydroxyisovalerate to α-ketoisovalerate, (pathway step c)
   iv) α-ketoisovalerate to valine, (pathway step h)
   v) valine to isobutylamine, (pathway step i)
   vi) isobutylamine to isobutyraldehyde, (pathway step j), and
   vii) isobutyraldehyde to isobutanol: (pathway step e)
wherein the at least one DNA molecule is heterologous to said microbial host cell; and
2) contacting the host cell of (i) with a fermentable carbon substrate in a fermentation medium under conditions whereby isobutanol is produced.

In an alternate embodiment the invention provides an isobutanol constaining fermentation medium produced by the methods of the invention.

BRIEF DESCRIPTION OF THE FIGURES AND SEQUENCE DESCRIPTIONS

The invention can be more fully understood from the following detailed description, FIGURE, and the accompanying sequence descriptions, which form a part of this application.

FIG. 1 shows four different isobutanol biosynthetic pathways. The steps labeled "a", "b", "c", "d", "e", "f", "g", "h", "i", "j" and "k" represent the substrate to product conversions described below.

The following sequences conform with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers

| Description | SEQ ID NO: Nucleic acid | SEQ ID NO: Peptide |
|---|---|---|
| *Klebsiella pneumoniae* budB (acetolactate synthase) | 1 | 2 |
| *Bacillus subtilis* alsS (acetolactate synthase) | 78 | 178 |
| *Lactococcus lactis* als (acetolactate synthase) | 179 | 180 |
| *E. coli* ilvC (acetohydroxy acid reductoisomerase) | 3 | 4 |
| *S. cerevisiae* ILV5 (acetohydroxy acid reductoisomerase) | 80 | 181 |
| *M. maripaludis* ilvC (Ketol-acid reductoisomerase) | 182 | 183 |
| *B. subtilis* ilvC (acetohydroxy acid reductoisomerase) | 184 | 185 |
| *E. coli* ilvD (acetohydroxy acid dehydratase) | 5 | 6 |
| *S. cerevisiae* ILV3 (Dihydroxyacid dehydratase) | 83 | 186 |
| *M. maripaludis* ilvD (Dihydroxy-acid dehydratase) | 187 | 188 |
| *B. subtilis* ilvD (dihydroxy-acid dehydratase) | 189 | 190 |
| *Lactococcus lactis* kivD (branched-chain α-keto acid decarboxylase), codon optimized | 7 | 8 |
| *Lactococcus lactis* kivD (branched-chain α-keto acid decarboxylase), | 191 | 8 |
| *Lactococcus lactis* kdcA (branched-chain alpha-ketoacid decarboxylase) | 192 | 193 |
| *Salmonella typhimurium* (indolepyruvate decarboxylase) | 194 | 195 |
| *Clostridium acetobutylicum* pdc (Pyruvate decarboxylase) | 196 | 197 |
| *E. coli* yqhD (branched-chain alcohol dehydrogenase) | 9 | 10 |
| *S. cerevisiae* YPR1 (2-methylbutyraldehyde reductase) | 198 | 199 |
| *S. cerevisiae* ADH6 (NADPH-dependent cinnamyl alcohol dehydrogenase) | 200 | 201 |
| *Clostridium acetobutylicum* bdhA (NADH-dependent butanol dehydrogenase A) | 202 | 203 |
| *Clostridium acetobutylicum* bdhB Butanol dehydrogenase | 158 | 204 |
| *B. subtilis* bkdAA (branched-chain keto acid dehydrogenase E1 subunit) | 205 | 206 |
| *B. subtilis* bkdAB (branched-chain alpha-keto acid dehydrogenase E1 subunit) | 207 | 208 |

TABLE 1-continued

Summary of Gene and Protein SEQ ID Numbers

| Description | SEQ ID NO: Nucleic acid | SEQ ID NO: Peptide |
|---|---|---|
| *B. subtilis* bkdB (branched-chain alpha-keto acid dehydrogenase E2 subunit) | 209 | 210 |
| *B. subtilis* lpdV (branched-chain alpha-keto acid dehydrogenase E3 subunit) | 211 | 212 |
| *P. putida* bkdA1 (keto acid dehydrogenase E1-alpha subunit) | 213 | 214 |
| *P. putida* bkdA2 (keto acid dehydrogenase E1-beta subunit) | 215 | 216 |
| *P. putida* bkdB (transacylase E2) | 217 | 218 |
| *P. putida* lpdV (lipoamide dehydrogenase) | 219 | 220 |
| *C. beijerinckii* ald (coenzyme A acylating aldehyde dehydrogenase) | 221 | 222 |
| *C. acetobutylicum* adhe1 (aldehyde dehydrogenase) | 223 | 224 |
| *C. acetobutylicum* adhe (alcohol-aldehyde dehydrogenase) | 225 | 226 |
| *P. putida* nahO (acetaldehyde dehydrogenase) | 227 | 228 |
| *T. thermophilus* (acetaldehyde dehydrogenase) | 229 | 230 |
| *E. coli* avtA (valine-pyruvate transaminase) | 231 | 232 |
| *B. licheniformis* avtA (valine-pyruvate transaminase) | 233 | 234 |
| *E. coli* ilvE (branched chain amino acid aminotransferase) | 235 | 236 |
| *S. cerevisiae* BAT2 (branched chain amino acid aminotransferase) | 237 | 238 |
| *M. thermoautotrophicum* (branched chain amino acid aminotransferase) | 239 | 240 |
| *S. coelicolor* (valine dehydrogenase) | 241 | 242 |
| *B.. subtilis* bcd (leucine dehydrogenase) | 243 | 244 |
| *S. viridifaciens* (valine decarboxyase) | 245 | 246 |
| *A. denitrificans* aptA (omega-amino acid:pyruvate transaminase) | 247 | 248 |
| *R. eutropha* (alanine-pyruvate transaminase) | 249 | 250 |
| *S. oneidensis* (beta alanine-pyruvate transaminase) | 251 | 252 |
| *P. putida* (beta alanine-pyruvate transaminase) | 253 | 254 |
| *S. cinnamonensis* icm (isobutyrl-CoA mutase) | 255 | 256 |
| *S. cinnamonensis* icmB (isobutyrl-CoA mutase) | 257 | 258 |
| *S. coelicolor* SCO5415 (isobutyrl-CoA mutase) | 259 | 260 |
| *S. coelicolor* SCO4800 (isobutyrl-CoA mutase) | 261 | 262 |
| *S. avermitilis* icmA (isobutyrl-CoA mutase) | 263 | 264 |
| *S. avermitilis* icmB (isobutyrl-CoA mutase) | 265 | 266 |

SEQ ID NOs:11-38, 40-69, 72-75, 85-138, 144, 145, 147-157, 159-176 are the nucleotide sequences of oligonucleotide cloning, screening or sequencing primers used in the Examples described herein.

SEQ ID NO:39 is the nucleotide sequence of the cscBKA gene cluster described in Example 16.

SEQ ID NO:70 is the nucleotide sequence of the glucose isomerase promoter 1.6GI described in Example 13.

SEQ ID NO:71 is the nucleotide sequence of the 1.5GI promoter described in Example 13.

SEQ ID NO:76 is the nucleotide sequence of the GPD promoter described in Example 17.

SEQ ID NO:77 is the nucleotide sequence of the CYC1 terminator described in Example 17.

SEQ ID NO:79 is the nucleotide sequence of the FBA promoter described in Example 17.

SEQ ID NO:81 is the nucleotide sequence of ADH1 promoter described in Example 17.

SEQ ID NO:82 is the nucleotide sequence of ADH1 terminator described in Example 17.

SEQ ID NO:84 is the nucleotide sequence of GPM promoter described in Example 17.

SEQ ID NO:139 is the amino acid sequence of sucrose hydrolase (CscA).

SEQ ID NO:140 is the amino acid sequence of D-fructokinase (CscK).

SEQ ID NO:141 is the amino acid sequence of sucrose permease (CscB).

SEQ ID NO:142 is the nucleotide sequence of plasmid pFP988DssPspac described in Example 20.

SEQ ID NO:143 is the nucleotide sequence of plasmid pFP988DssPgroE described in Example 20.

SEQ ID NO:146 is the nucleotide sequence of the pFP988Dss vector fragment described in Example 20.

SEQ ID NO:177 is the nucleotide sequence of the pFP988 integration vector described in Example 21.

SEQ ID NO:267 is the nucleotide sequence of plasmid pC194 described in Example 21.

DETAILED DESCRIPTION OF THE INVENTION

The present invention relates to methods for the production of isobutanol using recombinant microorganisms. The present invention meets a number of commercial and industrial needs. Butanol is an important industrial commodity chemical with a variety of applications, where its potential as a fuel or fuel additive is particularly significant. Although only a four-carbon alcohol, butanol has an energy content similar to that of gasoline and can be blended with any fossil fuel. Butanol is favored as a fuel or fuel additive as it yields only $CO_2$ and little or no $SO_X$ or $NO_X$ when burned in the standard internal combustion engine. Additionally butanol is less corrosive than ethanol, the most preferred fuel additive to date.

In addition to its utility as a biofuel or fuel additive, butanol has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or vehicles.

Finally the present invention produces isobutanol from plant derived carbon sources, avoiding the negative environmental impact associated with standard petrochemical processes for butanol production.

The following definitions and abbreviations are to be used for the interpretation of the claims and the specification.

The term "invention" or "present invention" as used herein is a non-limiting term and is not intended to refer to any single embodiment of the particular invention but encompasses all possible embodiments as described in the specification and the claims.

The term "isobutanol biosynthetic pathway" refers to an enzyme pathways to produce isobutanol.

The terms "acetolactate synthase" and "acetolactate synthetase" are used intechangeably herein to refer to an enzyme that catalyzes the conversion of pyruvate to acetolactate and $CO_2$. Preferred acetolactate synthases are known by the EC number 2.2.1.6 (*Enzyme Nomenclature* 1992, Academic Press, San Diego). These enzymes are available from a number of sources, including, but not limited to, *Bacillus subtilis* (GenBank Nos: CAB15618 (SEQ ID NO:178), Z99122 (SEQ ID NO:78), NCBI (National Center for Biotechnology Information) amino acid sequence, NCBI nucleotide sequence, respectively), *Klebsiella pneumoniae* (GenBank Nos: AAA25079 (SEQ ID NO:2), M73842 (SEQ ID NO:1)), and *Lactococcus lactis* (GenBank Nos: AAA25161 (SEQ ID NO:180), L16975 (SEQ ID NO:179)).

The terms "acetohydroxy acid isomeroreductase" and "acetohydroxy acid reductoisomerase" are used interchangeably herein to refer to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:4), NC_000913 (SEQ ID NO:3)), *Saccharomyces cerevisiae* (GenBank Nos: NP_013459 (SEQ ID NO:181), NC_001144 (SEQ ID NO:80)), *Methanococcus maripaludis* (GenBank Nos: CAF30210 (SEQ ID NO:183), BX957220 (SEQ ID NO:182)), and *Bacillus. subtilis* (GenBank Nos: CAB14789 (SEQ ID NO:185), Z99118 (SEQ ID NO:184)).

The term "acetohydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:6), NC_000913 (SEQ ID NO:5)), *S. cerevisiae* (GenBank Nos: NP_012550 (SEQ ID NO:186), NC_001142 (SEQ ID NO:83)), *M. maripaludis* (GenBank Nos: CAF29874 (SEQ ID NO:188), BX957219 (SEQ ID NO:187)), and *B. subtilis* (GenBank Nos: CAB14105 (SEQ ID NO:190), Z99115 (SEQ ID NO:189)).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166 (SEQ ID NO:193), AY548760 (SEQ ID NO:192); CAG34226 (SEQ ID NO:8), AJ746364 (SEQ ID NO:191), *Salmonella typhimurium* (GenBank Nos: NP_461346 (SEQ ID NO:195), NC_003197 (SEQ ID NO:194)), and *Clostridium acetobutylicum* (GenBank Nos: NP_149189 (SEQ ID NO:197), NC_001988 (SEQ ID NO:196)).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656 (SEQ ID NO:199), NC_001136 (SEQ ID NO:198); NP_014051 (SEQ ID NO:201) NC_001145 (SEQ ID NO:200)), *E. coli* (GenBank Nos: NP_417484 (SEQ ID NO:10), NC_000913 (SEQ ID NO:9)), and *C. acetobutylicum* (GenBank Nos: NP_349892 (SEQ ID NO:203), NC_003030 (SEQ ID NO:202); NP_349891 (SEQ ID NO:204), NC_003030 (SEQ ID NO:158)).

The term "branched-chain keto acid dehydrogenase" refers to an enzyme that catalyzes the conversion of α-ketoisovalerate to isobutyryl-CoA (isobutyryl-coenzyme A), using $NAD^+$ (nicotinamide adenine dinucleotide) as electron acceptor. Preferred branched-chain keto acid dehydrogenases are known by the EC number 1.2.4.4. These branched-chain keto acid dehydrogenases are comprised of four subunits and sequences from all subunits are available from a vast array of microorganisms, including, but not limited to, *B. subtilis* (GenBank Nos: CAB14336 (SEQ ID NO:206), Z99116 (SEQ ID NO:205); CAB14335 (SEQ ID NO:208), Z99116 (SEQ ID NO:207); CAB14334 (SEQ ID NO:210), Z99116 (SEQ ID NO:209); and CAB14337 (SEQ ID NO:212), Z99116 (SEQ ID NO:211)) and *Pseudomonas putida* (GenBank Nos: AAA65614 (SEQ ID NO:214), M57613 (SEQ ID NO:213); AAA65615 (SEQ ID NO:216), M57613 (SEQ ID NO:215); AAA65617 (SEQ ID NO:218), M57613 (SEQ ID NO:217); and AAA65618 (SEQ ID NO:220), M57613 (SEQ ID NO:219)).

The term "acylating aldehyde dehydrogenase" refers to an enzyme that catalyzes the conversion of isobutyryl-CoA to isobutyraldehyde, using either NADH or NADPH as electron donor. Preferred acylating aldehyde dehydrogenases are known by the EC numbers 1.2.1.10 and 1.2.1.57. These enzymes are available from multiple sources, including, but not limited to, *Clostridium beijerinckii* (GenBank Nos: AAD31841 (SEQ ID NO:222), AF157306 (SEQ ID NO:221)), *C. acetobutylicum* (GenBank Nos: NP_149325 (SEQ ID NO:224), NC_001988 (SEQ ID NO:223); NP_149199 (SEQ ID NO:226), NC_001988 (SEQ ID NO:225)), *P. putida* (GenBank Nos: AAA89106 (SEQ ID NO:228), U13232 (SEQ ID NO:227)), and *Thermus thermophilus* (GenBank Nos: YP_145486 (SEQ ID NO:230), NC_006461 (SEQ ID NO:229)).

The term "transaminase" refers to an enzyme that catalyzes the conversion of α-ketoisovalerate to L-valine, using either alanine or glutamate as amine donor. Preferred transaminases are known by the EC numbers 2.6.1.42 and 2.6.1.66. These enzymes are available from a number of sources. Examples of sources for alanine-dependent enzymes include, but are not limited to, *E. coli* (GenBank Nos: YP_026231 (SEQ ID NO:232), NC_000913 (SEQ ID NO:231)) and *Bacillus licheniformis* (GenBank Nos: YP_093743 (SEQ ID NO:234), NC_006322 (SEQ ID NO:233)). Examples of sources for glutamate-dependent enzymes include, but are not limited to, *E. coli* (GenBank Nos: YP_026247 (SEQ ID NO:236), NC_000913 (SEQ ID NO:235)), *S. cerevisiae* (GenBank Nos: NP_012682 (SEQ ID NO:238), NC_001142 (SEQ ID NO:237)) and *Methanobacterium thermoautotrophicum* (GenBank Nos: NP_276546 (SEQ ID NO:240), NC_000916 (SEQ ID NO:239)).

The term "valine dehydrogenase" refers to an enzyme that catalyzes the conversion of α-ketoisovalerate to L-valine, using NAD(P)H as electron donor and ammonia as amine donor. Preferred valine dehydrogenases are known by the EC numbers 1.4.1.8 and 1.4.1.9 and are available from a number of sources, including, but not limited to, *Streptomyces coelicolor* (GenBank Nos: NP_628270 (SEQ ID NO:242), NC_003888 (SEQ ID NO:241)) and *B. subtilis* (GenBank Nos: CAB14339 (SEQ ID NO:244), Z99116 (SEQ ID NO:243)).

The term "valine decarboxylase" refers to an enzyme that catalyzes the conversion of L-valine to isobutylamine and $CO_2$. Preferred valine decarboxylases are known by the EC number 4.1.1.14. These enzymes are found in Streptomycetes, such as for example, *Streptomyces viridifaciens* (GenBank Nos: AAN10242 (SEQ ID NO:246), AY116644 (SEQ ID NO:245)).

The term "omega transaminase" refers to an enzyme that catalyzes the conversion of isobutylamine to isobutyraldehyde using a suitable amino acid as amine donor. Preferred omega transaminases are known by the EC number 2.6.1.18 and are available from a number of sources, including, but not limited to, *Alcaligenes denitrificans* (AAP92672 (SEQ ID NO:248), AY330220 (SEQ ID NO:247)), *Ralstonia eutropha* (GenBank Nos: YP_294474 (SEQ ID NO:250), NC_007347 (SEQ ID NO:249)), *Shewanella oneidensis* (GenBank Nos: NP_719046 (SEQ ID NO:252), NC_004347 (SEQ ID NO:251)), and *P. putida* (GenBank Nos: AAN66223 (SEQ ID NO:254), AE016776 (SEQ ID NO:253)).

The term "isobutyryl-CoA mutase" refers to an enzyme that catalyzes the conversion of butyryl-CoA to isobutyryl-CoA. This enzyme uses coenzyme $B_{12}$ as cofactor. Preferred isobutyryl-CoA mutases are known by the EC number 5.4.99.13. These enzymes are found in a number of Streptomycetes, including, but not limited to, *Streptomyces cinnamonensis* (GenBank Nos: AAC08713 (SEQ ID NO:256), U67612 (SEQ ID NO:255); CAB59633 (SEQ ID NO:258), AJ246005 (SEQ ID NO:257)), *S. coelicolor* (GenBank Nos: CAB70645 (SEQ ID NO:260), AL939123 (SEQ ID NO:259); CAB92663 (SEQ ID NO:262), AL939121 (SEQ ID NO:261)), and *Streptomyces avermitilis* (GenBank Nos: NP_824008 (SEQ ID NO:264), NC_003155 (SEQ ID NO:263); NP_824637 (SEQ ID NO:266), NC_003155 (SEQ ID NO:265)).

The term "a facultative anaerobe" refers to a microorganism that can grow in both aerobic and anaerobic environments.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" or "heterologous gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein the term "codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

Standard recombinant DNA and molecular cloning techniques used herein are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987).

Isobutanol Biosynthetic Pathways

Carbohydrate utilizing microorganisms employ the Embden-Meyerhof-Parnas (EMP) pathway, the Entner-Doudoroff pathway and the pentose phosphate cycle as the central, metabolic routes to provide energy and cellular precursors for growth and maintenance. These pathways have in common the intermediate glyceraldehyde-3-phosphate and, ultimately, pyruvate is formed directly or in combination with the EMP pathway. Subsequently, pyruvate is transformed to acetyl-coenzyme A (acetyl-CoA) via a variety of means. Acetyl-CoA serves as a key intermediate, for example, in generating fatty acids, amino acids and secondary metabolites. The combined reactions of sugar conversion to pyruvate produce energy (e.g. adenosine-5'-triphosphate, ATP) and reducing equivalents (e.g. reduced nicotinamide adenine dinucleotide, NADH, and reduced nicotinamide adenine dinucleotide phosphate, NADPH). NADH and NADPH must be recycled to their oxidized forms ($NAD^+$ and $NADP^+$, respectively). In the presence of inorganic electron acceptors (e.g. $O_2$, $NO_3^-$ and $SO_4^{2-}$), the reducing equivalents may be used to augment the energy pool; alternatively, a reduced carbon by-product may be formed.

The invention enables the production of isobutanol from carbohydrate sources with recombinant microorganisms by providing four complete reaction pathways, as shown in FIG. 1. Three of the pathways comprise conversion of pyruvate to isobutanol via a series of enzymatic steps. The preferred isobutanol pathway (FIG. 1, steps a to e), comprises the following substrate to product conversions:
 a) pyruvate to acetolactate, as catalyzed for example by acetolactate synthase,
 b) acetolactate to 2,3-dihydroxyisovalerate, as catalyzed for example by acetohydroxy acid isomeroreductase,
 c) 2,3-dihydroxyisovalerate to α-ketoisovalerate, as catalyzed for example by acetohydroxy acid dehydratase,
 d) α-ketoisovalerate to isobutyraldehyde, as catalyzed for example by a branched-chain keto acid decarboxylase, and
 e) isobutyraldehyde to isobutanol, as catalyzed for example by, a branched-chain alcohol dehydrogenase.

This pathway combines enzymes known to be involved in well-characterized pathways for valine biosynthesis (pyruvate to α-ketoisovalerate) and valine catabolism (α-ketoisovalerate to isobutanol). Since many valine biosynthetic enzymes also catalyze analogous reactions in the isoleucine biosynthetic pathway, substrate specificity is a major consideration in selecting the gene sources. For this reason, the primary genes of interest for the acetolactate synthase enzyme are those from *Bacillus* (alsS) and *Klebsiella* (budB). These particular acetolactate synthases are known to participate in butanediol fermentation in these organisms and show increased affinity for pyruvate over ketobutyrate (Gollop et al., *J. Bacteriol.* 172(6):3444-3449 (1990); Holtzclaw et al., *J. Bacteriol.* 121(3):917-922 (1975)). The second and third pathway steps are catalyzed by acetohydroxy acid reductoisomerase and dehydratase, respectively. These enzymes have been characterized from a number of sources, such as for example, *E. coli* (Chunduru et al., *Biochemistry* 28(2):486-493 (1989); Flint et al., *J. Biol. Chem.* 268(29):14732-14742 (1993)). The final two steps of the preferred isobutanol pathway are known to occur in yeast, which can use valine as a nitrogen source and, in the process, secrete isobutanol. α-Ketoisovalerate can be converted to isobutyraldehyde by a number of keto acid decarboxylase enzymes, such as for example pyruvate decarboxylase. To prevent misdirection of pyruvate away from isobutanol production, a decarboxylase with decreased affinity for pyruvate is desired. So far, there are two such enzymes known in the art (Smit et al., *Appl. Environ. Microbiol.* 71(1):303-311 (2005); de la Plaza et al., *FEMS Microbiol. Lett.* 238(2):367-374 (2004)). Both enzymes are from strains of *Lactococcus lactis* and have a 50-200-fold preference for ketoisovalerate over pyruvate. Finally, a number of aldehyde reductases have been identified in yeast, many with overlapping substrate specificity. Those known to prefer branched-chain substrates over acetaldehyde include, but are not limited to, alcohol dehydrogenase VI (ADH6) and Ypr1 p (Larroy et al., *Biochem. J.* 361(Pt 1):163-172 (2002); Ford et al., *Yeast* 19(12):1087-1096 (2002)), both of which use NADPH as electron donor. An NADPH-dependent reductase, YqhD, active with branched-chain substrates has also been recently identified in *E. coli* (Sulzenbacher et al., *J. Mol. Biol.* 342(2):489-502 (2004)).

Another pathway for converting pyruvate to isobutanol comprises the following substrate to product conversions (FIG. 1, steps a, b, c, f, g, e):
 a) pyruvate to acetolactate, as catalyzed for example by acetolactate synthase,
 b) acetolactate to 2,3-dihydroxyisovalerate, as catalyzed for example by acetohydroxy acid isomeroreductase,
 c) 2,3-dihydroxyisovalerate to α-ketoisovalerate, as catalyzed for example by acetohydroxy acid dehydratase,
 f) α-ketoisovalerate to isobutyryl-CoA, as catalyzed for example by a branched-chain keto acid dehydrogenase,
 g) isobutyryl-CoA to isobutyraldehyde, as catalyzed for example by an acylating aldehyde dehydrogenase, and
 e) isobutyraldehyde to isobutanol, as catalyzed for example by, a branched-chain alcohol dehydrogenase.

The first three steps in this pathway (a, b, c) are the same as those described above. The α-ketoisovalerate is converted to isobutyryl-CoA by the action of a branched-chain keto acid dehydrogenase. While yeast can only use valine as a nitrogen source, many other organisms (both eukaryotes and prokaryotes) can use valine as the carbon source as well. These organisms have branched-chain keto acid dehydrogenase (Sokatch et al. *J. Bacteriol.* 148(2):647-652 (1981)), which generates isobutyryl-CoA. Isobutyryl-CoA may be converted to isobutyraldehyde by an acylating aldehyde dehydrogenase. Dehydrogenases active with the branched-chain substrate have been described, but not cloned, in *Leuconostoc* and *Propionibacterium* (Kazahaya et al., *J. Gen. Appl. Microbiol.* 18:43-55 (1972); Hosoi et al., *J. Ferment. Technol.* 57:418-427 (1979)). However, it is also possible that acylating aldehyde dehydrogenases known to function with straight-chain acyl-CoAs (i.e. butyryl-CoA), may also work with isobutyryl-CoA. The isobutyraldehyde is then converted to isobutanol by a branched-chain alcohol dehydrogenase, as described above for the first pathway.

Another pathway for converting pyruvate to isobutanol comprises the following substrate to product conversions (FIG. 1, steps a, b, c, h, i, j, e):

a) pyruvate to acetolactate, as catalyzed for example by acetolactate synthase,
b) acetolactate to 2,3-dihydroxyisovalerate, as catalyzed for example by acetohydroxy acid isomeroreductase,
c) 2,3-dihydroxyisovalerate to α-ketoisovalerate, as catalyzed for example by acetohydroxy acid dehydratase,
h) α-ketoisovalerate to valine, as catalyzed for example by valine dehydrogenase or transaminase,
i) valine to isobutylamine, as catalyzed for example by valine decarboxylase,
j) isobutylamine to isobutyraldehyde, as catalyzed for example by omega transaminase, and
e) isobutyraldehyde to isobutanol, as catalyzed for example by, a branched-chain alcohol dehydrogenase.

The first three steps in this pathway (a, b, c) are the same as those described above. This pathway requires the addition of a valine dehydrogenase or a suitable transaminase. Valine (and or leucine) dehydrogenase catalyzes reductive amination and uses ammonia; $K_m$ values for ammonia are in the millimolar range (Priestly et al., *Biochem J.* 261(3):853-861 (1989); Vancura et al., *J. Gen. Microbiol.* 134(12):3213-3219 (1988) Zink et al., *Arch. Biochem. Biophys.* 99:72-77 (1962); Sekimoto et al. *J. Biochem* (Japan) 116(1):176-182 (1994)). Transaminases typically use either glutamate or alanine as amino donors and have been characterized from a number of organisms (Lee-Peng et al., *J. Bacteriol.* 139(2):339-345 (1979); Berg et al., *J. Bacteriol.* 155(3):1009-1014 (1983)). An alanine-specific enzyme may be desirable, since the generation of pyruvate from this step could be coupled to the consumption of pyruvate later in the pathway when the amine group is removed (see below). The next step is decarboxylation of valine, a reaction that occurs in valanimycin biosynthesis in *Streptomyces* (Garg et al., *Mol. Microbiol.* 46(2): 505-517 (2002)). The resulting isobutylamine may be converted to isobutyraldehyde in a pyridoxal 5'-phosphate-dependent reaction by, for example, an enzyme of the omega-aminotransferase family. Such an enzyme from *Vibrio fluvialis* has demonstrated activity with isobutylamine (Shin et al., *Biotechnol. Bioeng.* 65(2):206-211 (1999)). Another omega-aminotransferase from *Alcaligenes denitrificans* has been cloned and has some activity with butylamine (Yun et al., *Appl. Environ. Microbiol.* 70(4):2529-2534 (2004)). In this direction, these enzymes use pyruvate as the amino acceptor, yielding alanine. As mentioned above, adverse affects on the pyruvate pool may be offset by using a pyruvate-producing transaminase earlier in the pathway. The isobutyraldehyde is then converted to isobutanol by a branched-chain alcohol dehydrogenase, as described above for the first pathway.

The fourth isobutanol biosynthetic pathway comprises the substrate to product conversions shown as steps k, g, e in FIG. 1. A number of organisms are known to produce butyrate and/or butanol via a butyryl-CoA intermediate (Durre et al., *FEMS Microbiol. Rev.* 17(3):251-262 (1995); Abbad-Andaloussi et al., *Microbiology* 142(5):1149-1158 (1996)). Isobutanol production may be engineered in these organisms by addition of a mutase able to convert butyryl-CoA to isobutyryl-CoA (FIG. 1, step k). Genes for both subunits of isobutyryl-CoA mutase, a coenzyme $B_{12}$-dependent enzyme, have been cloned from a Streptomycete (Ratnatilleke et al., *J. Biol. Chem.* 274(44):31679-31685 (1999)). The isobutyryl-CoA is converted to isobutyraldehyde (step g in FIG. 1), which is converted to isobutanol (step e in FIG. 1).

Thus, in providing multiple recombinant pathways from pyruvate to isobutanol, there exist a number of choices to fulfill the individual conversion steps, and the person of skill in the art will be able to utilize publicly available sequences to construct the relevant pathways. A listing of a representative number of genes known in the art and useful in the construction of isobutanol biosynthetic pathways are listed below in Table 2.

TABLE 2

Sources of Isobutanol Biosynthetic Pathway Genes

| Gene | GenBank Citation |
|---|---|
| acetolactate synthase | Z99122, *Bacillus subtilis* complete genome (section 19 of 21): from 3608981 to 3809670<br>gi\|32468830\|emb\|Z99122.2\|BSUB0019[32468830]<br>M73842, *Klebsiella pneumoniae* acetolactate synthase (iluk) gene, complete cds<br>gi\|149210\|gb\|M73842.1\|KPNILUK[149210]<br>L16975, *Lactococcus lactis* alpha-acetolactate synthase (als) gene, complete cds<br>gi\|473900\|gb\|L16975.1\|LACALS[473900] |
| acetohydroxy acid isomeroreductase | NC_000913, *Escherichia coli* K12, complete genome<br>gi\|49175990\|ref\|NC_000913.2\|[49175990]<br>NC_001144, *Saccharomyces cerevisiae* chromosome XII, complete chromosome sequence<br>gi\|42742286\|ref\|NC_001144.3\|[42742286]<br>BX957220, *Methanococcus maripaludis* S2 complete genome; segment 2/5<br>gi\|44920669\|emb\|BX957220.1\|[44920669]<br>Z99118, *Bacillus subtilis* complete genome (section 15 of 21): from 2812801 to 3013507<br>gi\|32468802\|emb\|Z99118.2\|BSUB0015[32468802] |

TABLE 2-continued

Sources of Isobutanol Biosynthetic Pathway Genes

| Gene | GenBank Citation |
|---|---|
| acetohydroxy acid dehydratase | NC_000913, *Escherichia coli* K12, complete genome<br>gi\|49175990\|ref\|NC_000913.2\|[49175990]<br>NC_001142, *Saccharomyces cerevisiae* chromosome X, complete chromosome sequence<br>gi\|42742252\|ref\|NC_001142.5\|[42742252]<br>BX957219, *Methanococcus maripaludis* S2 complete genome; segment 1/5<br>gi\|45047123\|emb\|BX957219.1\|[45047123]<br>Z99115, *Bacillus subtilis* complete genome (section 12 of 21): from 2207806 to 2409180<br>gi\|32468778\|emb\|Z99115.2\|BSUB0012[32468778] |
| branched-chain α-keto acid decarboxylase | AY548760, *Lactococcus lactis* branched-chain alpha-ketoacid decarboxylase (kdcA) gene, complete cds<br>gi\|44921616\|gb\|AY548760.1\|[44921616]<br>AJ746364, *Lactococcus lactis* subsp. *lactis* kivd gene for alpha-ketoisovalerate decarboxylase, strain IFPL730<br>gi\|51870501\|emb\|AJ746364.1\|[51870501]<br>NC_003197, *Salmonella typhimurium* LT2, complete genome<br>gi\|16763390\|ref\|NC_003197.1\|[16763390]<br>NC_001988, *Clostridium acetobutylicum* ATCC 824 plasmid pSOL1, complete sequence<br>gi\|15004705\|ref\|NC_001988.2\|[15004705] |
| branched-chain alcohol dehydrogenase | NC_001136, *Saccharomyces cerevisiae* chromosome IV, complete chromosome sequence<br>gi\|50593138\|ref\|NC_001136.6\|[50593138]<br>NC_001145, *Saccharomyces cerevisiae* chromosome XIII, complete chromosome sequence<br>gi\|44829554\|ref\|NC_001145.2\|[44829554]<br>NC_000913, *Escherichia coli* K12, complete genome<br>gi\|49175990\|ref\|NC_000913.2\|[49175990]<br>NC_003030, *Clostridium acetobutylicum* ATCC 824, complete genome<br>gi\|15893298\|ref\|NC_003030.1\|[15893298] |
| branched-chain keto acid dehydrogenase | Z99116, *Bacillus subtilis* complete genome (section 13 of 21): from 2409151 to 2613687<br>gi\|32468787\|emb\|Z99116.2\|BSUB0013[32468787]<br>M57613, *Pseudomonas putida* branched-chain keto acid dehydrogenase operon (bkdA1, bkdA1 and bkdA2), transacylase E2 (bkdB), bkdR and lipoamide dehydrogenase (lpdV) genes, complete cds<br>gi\|790512\|gb\|M57613.1\|PSEBKDPPG2[790512] |
| acylating aldehyde dehydrogenase | AF157306, *Clostridium beijerinckii* strain NRRL B593 hypothetical protein, coenzyme A acylating aldehyde dehydrogenase (ald), acetoacetate:butyrate/acetate coenzyme A transferase (ctfA), acetoacetate:butyrate/acetate coenzyme A transferase (ctfB), and acetoacetate decarboxylase (adc) genes, complete cds<br>gi\|47422980\|gb\|AF157306.2\|[47422980]<br>NC_001988, *Clostridium acetobutylicum* ATCC 824 plasmid pSOL1, complete sequence<br>gi\|15004705\|ref\|NC_001988.2\|[15004705]<br>U13232, *Pseudomonas putida* NCIB9816 acetaldehyde dehydrogenase (nahO) and 4-hydroxy-2-oxovalerate aldolase (nahM) genes, complete cds, and 4-oxalocrotonate decarboxylase (nahK) and 2-oxopent-4-enoate hydratase (nahL) genes, partial cds<br>gi\|595671\|gb\|U13232.1\|PPU13232[595671] |
| transaminase | NC_000913, *Escherichia coli* K12, complete genome<br>gi\|49175990\|ref\|NC_000913.2\|[49175990]<br>NC_006322, *Bacillus licheniformis* ATCC 14580, complete genome<br>gi\|52783855\|ref\|NC_006322.1\|[52783855]<br>NC_001142, *Saccharomyces cerevisiae* chromosome X, complete chromosome sequence<br>gi\|42742252\|ref\|NC_001142.5\|[42742252]<br>NC_000916, *Methanothermobacter thermautotrophicus* str. Delta H, complete genome<br>gi\|15678031\|ref\|NC_000916.1\|[15678031] |
| valine dehydrogenase | NC_003888, Streptomyces coelicolor A3(2), complete genome<br>gi\|32141095\|ref\|NC_003888.3\|[32141095]<br>Z99116, *Bacillus subtilis* complete genome (section 13 of 21): from 2409151 to 2613687<br>gi\|32468787\|emb\|Z99116.2\|BSUB0013[32468787] |

TABLE 2-continued

Sources of Isobutanol Biosynthetic Pathway Genes

| Gene | GenBank Citation |
|---|---|
| valine decarboxylase | AY116644, *Streptomyces viridifaciens* amino acid aminotransferase gene, partial cds; ketol-acid reductoisomerase, acetolactate synthetase small subunit, acetolactate synthetase large subunit, complete cds; azoxy antibiotic valanimycin gene cluster, complete sequence; and putative transferase, and putative secreted protein genes, complete cds gi\|27777548\|gb\|AY116644.1\|[27777548] |
| omega transaminase | AY330220, *Achromobacter denitrificans* omega-amino acid:pyruvate transaminase (aptA) gene, complete cds gi\|33086797\|gb\|AY330220.1\|[33086797] NC_007347, *Ralstonia eutropha* JMP134 chromosome 1, complete sequence gi\|73539706\|ref\|NC_007347.1\|[73539706] NC_004347, *Shewanella oneidensis* MR-1, complete genome gi\|24371600\|ref\|NC_004347.1\|[24371600] NZ_AAAG02000002, *Rhodospirillum rubrum* Rrub02_2, whole genome shotgun sequence gi\|48764549\|ref\|NZ_AAAG02000002.1\|[48764549] AE016776, *Pseudomonas putida* KT2440 section 3 of 21 of the complete genome gi\|26557019\|gb\|AE016776.1\|[26557019] |
| isobutyryl-CoA mutase | U67612, *Streptomyces cinnamonensis* coenzyme B12-dependent isobutyrylCoA mutase (icm) gene, complete cds gi\|3002491\|gb\|U67612.1\|SCU67612[3002491] AJ246005, *Streptomyces cinnamonensis* icmB gene for isobutyryl-CoA mutase, small subunit gi\|6137076\|emb\|AJ246005.1\|SCI246005[6137076] AL939123, *Streptomyces coelicolor* A3(2) complete genome; segment 20/29 gi\|24430032\|emb\|AL939123.1\|SCO939123[24430032] AL9939121, *Streptomyces coelicolor* A3(2) complete genome; segment 18/29 gi\|24429533\|emb\|AL939121.1\|SCO939121[24429533] NC_003155, *Streptomyces avermitilis* MA-4680, complete genome gi\|57833846\|ref\|NC_003155.3\|[57833846] |

Microbial Hosts for Isobutanol Production

Microbial hosts for isobutanol production may be selected from bacteria, cyanobacteria, filamentous fungi and yeasts. The microbial host used for isobutanol production is preferably tolerant to isobutanol so that the yield is not limited by butanol toxicity. Microbes that are metabolically active at high titer levels of isobutanol are not well known in the art. Although butanol-tolerant mutants have been isolated from solventogenic *Clostridia*, little information is available concerning the butanol tolerance of other potentially useful bacterial strains. Most of the studies on the comparison of alcohol tolerance in bacteria suggest that butanol is more toxic than ethanol (de Cavalho et al., *Microsc. Res. Tech.* 64:215-22 (2004) and Kabelitz et al., *FEMS Microbiol. Lett.* 220:223-227 (2003)). Tomas et al. (*J. Bacteriol.* 186:2006-2018 (2004)) report that the yield of 1-butanol during fermentation in *Clostridium acetobutylicum* may be limited by 1-butanol toxicity. The primary effect of 1-butanol on *Clostridium acetobutylicum* is disruption of membrane functions (Hermann et al., *Appl. Environ. Microbiol.* 50:1238-1243 (1985)).

The microbial hosts selected for the production of isobutanol are preferably tolerant to isobutanol and should be able to convert carbohydrates to isobutanol. The criteria for selection of suitable microbial hosts include the following: intrinsic tolerance to isobutanol, high rate of glucose utilization, availability of genetic tools for gene manipulation, and the ability to generate stable chromosomal alterations.

Suitable host strains with a tolerance for isobutanol may be identified by screening based on the intrinsic tolerance of the strain. The intrinsic tolerance of microbes to isobutanol may be measured by determining the concentration of isobutanol that is responsible for 50% inhibition of the growth rate (IC50) when grown in a minimal medium. The IC50 values may be determined using methods known in the art. For example, the microbes of interest may be grown in the presence of various amounts of isobutanol and the growth rate monitored by measuring the optical density at 600 nanometers. The doubling time may be calculated from the logarithmic part of the growth curve and used as a measure of the growth rate. The concentration of isobutanol that produces 50% inhibition of growth may be determined from a graph of the percent inhibition of growth versus the isobutanol concentration. Preferably, the host strain should have an IC50 for isobutanol of greater than about 0.5%.

The microbial host for isobutanol production should also utilize glucose at a high rate. Most microbes are capable of utilizing carbohydrates. However, certain environmental microbes cannot utilize carbohydrates to high efficiency, and therefore would not be suitable hosts.

The ability to genetically modify the host is essential for the production of any recombinant microorganism. The mode of gene transfer technology may be by electroporation, conjugation, transduction or natural transformation. A broad range of host conjugative plasmids and drug resistance markers are available. The cloning vectors are tailored to the host organisms based on the nature of antibiotic resistance markers that can function in that host.

The microbial host also has to be manipulated in order to inactivate competing pathways for carbon flow by deleting various genes. This requires the availability of either transposons to direct inactivation or chromosomal integration vectors. Additionally, the production host should be amenable to chemical mutagenesis so that mutations to improve intrinsic isobutanol tolerance may be obtained.

Based on the criteria described above, suitable microbial hosts for the production of isobutanol include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula* and *Saccharomyces*. Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis* and *Saccharomyces cerevisiae*.

Construction of Production Host

Recombinant organisms containing the necessary genes that will encode the enzymatic pathway for the conversion of a fermentable carbon substrate to isobutanol may be constructed using techniques well known in the art. In the present invention, genes encoding the enzymes of one of the isobutanol biosynthetic pathways of the invention, for example, acetolactate synthase, acetohydroxy acid isomeroreductase, acetohydroxy acid dehydratase, branched-chain α-keto acid decarboxylase, and branched-chain alcohol dehydrogenase, may be isolated from various sources, as described above.

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer-directed amplification methods such as polymerase chain reaction (U.S. Pat. No. 4,683,202) to obtain amounts of DNA suitable for transformation using appropriate vectors. Tools for codon optimization for expression in a heterologous host are readily available. Some tools for codon optimization are available based on the GC content of the host organism. The GC content of some exemplary microbial hosts is given Table 3.

TABLE 3

GC Content of Microbial Hosts

| Strain | % GC |
| --- | --- |
| B. licheniformis | 46 |
| B. subtilis | 42 |
| C. acetobutylicum | 37 |
| E. coli | 50 |
| P. putida | 61 |
| A. eutrophus | 61 |
| Paenibacillus macerans | 51 |
| Rhodococcus erythropolis | 62 |
| Brevibacillus | 50 |
| Paenibacillus polymyxa | 50 |

Once the relevant pathway genes are identified and isolated they may be transformed into suitable expression hosts by means well known in the art. Vectors or cassettes useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, CYC1, HIS3, GAL1, GAL10, ADH1, PGK, PHO5, GAPDH, ADC1, TRP1, URA3, LEU2, ENO, TPI, CUP1, FBA, GPD, and GPM (useful for expression in *Saccharomyces*); AOX1 (useful for expression in *Pichia*); and lac, ara, tet, trp, $IP_L$, $IP_R$, T7, tac, and trc (useful for expression in *Escherichia coli, Alcaligenes*, and *Pseudomonas*); the amy, apr, npr promoters and various phage promoters useful for expression in *Bacillus subtilis, Bacillus licheniformis*, and *Paenibacillus macerans*; nisA (useful for expression Gram-positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)).

Termination control regions may also be derived from various genes native to the preferred hosts. Optionally, a termination site may be unnecessary, however, it is most preferred if included.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., *Plasmid* 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to effect gene replacement in a range of Gram-positive bacteria (Maguin et al., *J. Bacteriol.* 174(17):5633-5638 (1992)). Additionally, in vitro transposomes are available to create random mutations in a variety of genomes from commercial sources such as EPICENTRE®.

The expression of an isobutanol biosynthetic pathway in various preferred microbial hosts is described in more detail below.

Expression of an Isobutanol Biosynthetic Pathway in *E. coli*

Vectors or cassettes useful for the transformation of *E. coli* are common and commercially available from the companies listed above. For example, the genes of an isobutanol biosynthetic pathway may be isolated from various sources, cloned into a modified pUC19 vector and transformed into *E. coli* NM522, as described in Examples 6 and 7.

Expression of an Isobutanol Biosynthetic Pathway in *Rhodococcus erythropolis*

A series of *E. coli*-*Rhodococcus* shuttle vectors are available for expression in *R. erythropolis*, including, but not limited to, pRhBR17 and pDA71 (Kostichka et al., *Appl. Microbiol. Biotechnol.* 62:61-68 (2003)). Additionally, a series of promoters are available for heterologous gene expression in *R. erythropolis* (see for example Nakashima et al., *Appl. Environ. Microbiol.* 70:5557-5568 (2004), and Tao et al., *Appl. Microbiol. Biotechnol.* 2005, DOI 10.1007/s00253-005-0064). Targeted gene disruption of chromosomal genes in *R. erythropolis* may be created using the method described by Tao et al., supra, and Brans et al. (*Appl. Environ. Microbiol.* 66: 2029-2036 (2000)).

The heterologous genes required for the production of isobutanol, as described above, may be cloned initially in pDA71 or pRhBR71 and transformed into *E. coli*. The vectors may then be transformed into *R. erythropolis* by electroporation, as described by Kostichka et al., supra. The recombinants may be grown in synthetic medium containing glucose and the production of isobutanol can be followed using methods known in the art.

Expression of an Isobutanol Biosynthetic Pathway in *B. Subtilis*

Methods for gene expression and creation of mutations in *B. subtilis* are also well known in the art. For example, the genes of an isobutanol biosynthetic pathway may be isolated from various sources, cloned into a modified pUC19 vector and transformed into *Bacillus subtilis* BE1010, as described in Example 8. Additionally, the five genes of an isobutanol biosynthetic pathway can be split into two operons for expression, as described in Example 20. The three genes of the pathway (bubB, ilvD, and kivD) were integrated into the chromosome of *Bacillus subtilis* BE1010 (Payne and Jackson, *J. Bacteriol.* 173:2278-2282 (1991)). The remaining two genes (ilvC and bdhB) were cloned into an expression vector and transformed into the *Bacillus* strain carrying the integrated isobutanol genes Expression of an Isobutanol Biosynthetic Pathway in *B. Licheniformis*

Most of the plasmids and shuttle vectors that replicate in *B. subtilis* may be used to transform *B. licheniformis* by either protoplast transformation or electroporation. The genes required for the production of isobutanol may be cloned in plasmids pBE20 or pBE60 derivatives (Nagarajan et al., *Gene* 114:121-126 (1992)). Methods to transform *B. licheniformis* are known in the art (for example see Fleming et al. *Appl. Environ. Microbiol.*, 61(11):3775-3780 (1995)). The plasmids constructed for expression in *B. subtilis* may be transformed into *B. licheniformis* to produce a recombinant microbial host that produces isobutanol.

Expression of an Isobutanol Biosynthetic Pathway in *Paenibacillus macerans*

Plasmids may be constructed as described above for expression in *B. subtilis* and used to transform *Paenibacillus macerans* by protoplast transformation to produce a recombinant microbial host that produces isobutanol.

Expression of the isobutanol biosynthetic pathway in *Alcaligenes* (*Ralstonia*) *eutrophus*

Methods for gene expression and creation of mutations in *Alcaligenes eutrophus* are known in the art (see for example Taghavi et al., *Appl. Environ. Microbiol.*, 60(10):3585-3591 (1994)). The genes for an isobutanol biosynthetic pathway may be cloned in any of the broad host range vectors described above, and electroporated to generate recombinants that produce isobutanol. The poly(hydroxybutyrate) pathway in *Alcaligenes* has been described in detail, a variety of genetic techniques to modify the *Alcaligenes eutrophus* genome is known, and those tools can be applied for engineering an isobutanol biosynthetic pathway.

Expression of an Isobutanol Biosynthetic Pathway in *Pseudomonas putida*

Methods for gene expression in *Pseudomonas putida* are known in the art (see for example Ben-Bassat et al., U.S. Pat. No. 6,586,229, which is incorporated herein by reference). The butanol pathway genes may be inserted into pPCU18 and this ligated DNA may be electroporated into electrocompetent *Pseudomonas putida* DOT-T1 C5aAR1 cells to generate recombinants that produce isobutanol.

Expression of an Isobutanol Biosynthetic Pathway in *Saccharomyces cerevisiae*

Methods for gene expression in *Saccharomyces cerevisiae* are known in the art (see for example *Methods in Enzymology, Volume* 194, *Guide to Yeast Genetics and Molecular and Cell Biology* (Part A, 2004, Christine Guthrie and Gerald R. Fink (Eds.), Elsevier Academic Press, San Diego, Calif.). Expression of genes in yeast typically requires a promoter, followed by the gene of interest, and a transcriptional terminator. A number of yeast promoters can be used in constructing expression cassettes for genes encoding an isobutanol biosynthetic pathway, including, but not limited to constitutive promoters FBA, GPD, ADH1, and GPM, and the inducible promoters GAL1, GAL10, and CUP1. Suitable transcriptional terminators include, but are not limited to FBAt, GPDt, GPMt, ERG10t, GAL1t, CYC1, and ADH1. For example, suitable promoters, transcriptional terminators, and the genes of an isobutanol biosynthetic pathway may be cloned into *E. coli*-yeast shuttle vectors as described in Example 17.

Expression of an Isobutanol Biosynthetic Pathway in *Lactobacillus plantarum*

The *Lactobacillus* genus belongs to the Lactobacillales family and many plasmids and vectors used in the transformation of *Bacillus subtilis* and *Streptococcus* may be used for *lactobacillus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (e.g., van Kranenburg R, Golic N, Bongers R, Leer R J, de Vos W M, Siezen R J, Kleerebezem M. *Appl. Environ. Microbiol.* 2005 March; 71(3): 1223-1230). For example, expression of an isobutanol biosynthetic pathway in *Lactobacillus plantarum* is described in Example 21.

Expression of an Isobutanol Biosynthetic Pathway in *Enterococcus faecium*, *Enterococcus gallinarium*, and *Enterococcus faecalis*

The *Enterococcus* genus belongs to the Lactobacillales family and many plasmids and vectors used in the transformation of *Lactobacillus, Bacillus subtilis*, and *Streptococcus* may be used for *Enterococcus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.*

63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Expression vectors for *E. faecalis* using the nisA gene from *Lactococcus* may also be used (Eichenbaum et al., *Appl. Environ. Microbiol.* 64:2763-2769 (1998). Additionally, vectors for gene replacement in the *E. faecium* chromosome may be used (Nallaapareddy et al., *Appl. Environ. Microbiol.* 72:334-345 (2006)). For example, expression of an isobutanol biosynthetic pathway in *Enterococcus faecalis* is described in Example 22.

Fermentation Media

Fermentation media in the present invention must contain suitable carbon substrates. Suitable substrates may include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for isobutanol production.

Culture Conditions

Typically cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

The amount of isobutanol produced in the fermentation medium can be determined using a number of methods known in the art, for example, high performance liquid chromatography (HPLC) or gas chromatography (GC).

Industrial Batch and Continuous Fermentations

The present process employs a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for isobutanol production.

Methods for Isobutanol Isolation from the Fermentation Medium

The bioproduced isobutanol may be isolated from the fermentation medium using methods known in the art. For example, solids may be removed from the fermentation medium by centrifugation, filtration, decantation, or the like. Then, the isobutanol may be isolated from the fermentation medium, which has been treated to remove solids as described above, using methods such as distillation, liquid-liquid extraction, or membrane-based separation. Because isobutanol forms a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify isobutanol include, but are not limited to, decantation, liquid-liquid extraction, adsorption, and membrane-based techniques. Additionally, isobutanol may be isolated using azeotropic distillation using an entrainer (see for example Doherty and Malone, *Conceptual Design of Distillation Systems*, McGraw Hill, New York, 2001).

The isobutanol-water mixture forms a heterogeneous azeotrope so that distillation may be used in combination with decantation to isolate and purify the isobutanol. In this method, the isobutanol containing fermentation broth is distilled to near the azeotropic composition. Then, the azeotropic mixture is condensed, and the isobutanol is separated from the fermentation medium by decantation. The decanted aqueous phase may be returned to the first distillation column as reflux. The isobutanol-rich decanted organic phase may be further purified by distillation in a second distillation column.

The isobutanol may also be isolated from the fermentation medium using liquid-liquid extraction in combination with distillation. In this method, the isobutanol is extracted from the fermentation broth using liquid-liquid extraction with a suitable solvent. The isobutanol-containing organic phase is then distilled to separate the isobutanol from the solvent.

Distillation in combination with adsorption may also be used to isolate isobutanol from the fermentation medium. In this method, the fermentation broth containing the isobutanol is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the isobutanol from the fermentation medium. In this method, the fermentation broth containing the isobutanol is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified.

Microbial strains were obtained from The American Type Culture Collection (ATCC), Manassas, Va., unless otherwise noted.

The oligonucleotide primers to use in the following Examples are given in Table 4. All the oligonucleotide primers are synthesized by Sigma-Genosys (Woodlands, Tex.).

TABLE 4

Oligonucleotide Cloning, Screening, and Sequencing Primers

| Name | Sequence | Description | SEQ ID NO: |
|---|---|---|---|
| N80 | CACCATGGACAAACAGTATCCGG TACGCC | budB forward | 11 |
| N81 | CGAAGGGCGATAGCTTTACCAAT CC | budB reverse | 12 |
| N100 | CACCATGGCTAACTACTTCAATA CACTGA | ilvC forward | 13 |
| N101 | CCAGGAGAAGGCCTTGAGTGTTT TCTCC | ilvC reverse | 14 |
| N102 | CACCATGCCTAAGTACCGTTCCG CCACCA | ilvD forward | 15 |
| N103 | CGCAGCACTGCTCTTAAATATTC GGC | ilvD reverse | 16 |
| N104 | CACCATGAACAACTTTAATCTGC ACACCC | yqhD forward | 17 |
| N105 | GCTTAGCGGGCGGCTTCGTATAT ACGGC | yqhD reverse | 18 |

TABLE 4-continued

Oligonucleotide Cloning, Screening, and Sequencing Primers

| Name | Sequence | Description | SEQ ID NO: |
|---|---|---|---|
| N110 | GCATGCCTTAAGAAAGGAGGGGGGTCACATGGACAAACAGTATCC | budB forward | 19 |
| N111 | ATGCATTTAATTAATTACAGAATCTGACTCAGATGCAGC | budB reverse | 20 |
| N112 | GTCGACGCTAGCAAAGGAGGGAATCACCATGGCTAACTACTTCAA | ilvC forward | 21 |
| N113 | TCTAGATTAACCCGCAACAGCAATACGTTTC | ilvC reverse | 22 |
| N114 | TCTAGAAAAGGAGGAATAAAGTATGCCTAAGTACCGTTC | ilvD forward | 23 |
| N115 | GGATCCTTATTAACCCCCCAGTTTCGATTTA | ilvD reverse | 24 |
| N116 | GGATCCAAAGGAGGCTAGACATATGTATACTGTGGGGA | kivD forward | 25 |
| N117 | GAGCTCTTAGCTTTTATTTTGCTCCGCAAAC | kivD reverse | 26 |
| N118 | GAGCTCAAAGGAGGAGCAAGTAATGAACAACTTTAATCT | yqhD forward | 27 |
| N119 | GAATTCACTAGTCCTAGGTTAGCGGGCGGCTTCGTATATACGG | yqhD reverse | 28 |
| BenNF | CAACATTAGCGATTTTCTTTTCTCT | Npr forward | 29 |
| BenASR | CATGAAGCTTACTAGTGGGCTTAAGTTTTGAAAATAATGAAAACT | Npr reverse | 30 |
| N110.2 | GAGCTCACTAGTCAATTGTAAGTAAGTAAAAGGAGGTGGGTCACATGGACAAACAGTATCC | budB forward | 31 |
| N111.2 | GGATCCGATCGACTTAAGCCTCAGCTTACAGAATCTGACTCAGATGCAGC | budB reverse | 32 |
| N112.2 | GAGCTCCTTAAGAAGGAGGTAATCACCATGGCTAACTACTTCAA | ilvC forward | 33 |
| N113.2 | GGATCCGATCGAGCTAGCGCGGCCGCTTAACCCGCAACAGCAATACGTTTC | ilvC reverse | 34 |
| N114.2 | GAGCTCGCTAGCAAGGAGGTATAAAGTATGCCTAAGTACCGTTC | ilvD forward | 35 |
| N115.2 | GGATCCGATCGATTAATTAACCTAAGGTTATTAACCCCCCAGTTTCGATTTA | ilvD reverse | 36 |
| N116.2 | GAGCTCTTAATTAAAAGGAGGTTAGACATATGTATACTGTGGGGA | kivD forward | 37 |
| N117.2 | GGATCCAGATCTCCTAGGACATGTTTAGCTTTTATTTTGCTCCGCAAAC | kivD reverse | 38 |
| N130SeqF1 | TGTTCCAACCTGATCACCG | sequencing primer | 40 |
| N130SeqF2 | GGAAAACAGCAAGGCGCT | sequencing primer | 41 |
| N130SeqF3 | CAGCTGAACCAGTTTGCC | sequencing primer | 42 |
| N130SeqF4 | AAAATACCAGCGCCTGTCC | sequencing primer | 43 |
| N130SeqR1 | TGAATGGCCACCATGTTG | sequencing primer | 44 |
| N130SeqR2 | GAGGATCTCCGCCGCCTG | sequencing primer | 45 |
| N130SeqR3 | AGGCCGAGCAGGAAGATC | sequencing primer | 46 |
| N130SeqR4 | TGATCAGGTTGGAACAGCC | sequencing primer | 47 |
| N131SeqF1 | AAGAACTGATCCCACAGGC | sequencing primer | 48 |
| N131SeqF2 | ATCCTGTGCGGTATGTTGC | sequencing primer | 49 |
| N131SeqF3 | ATTGCGATGGTGAAAGCG | sequencing primer | 50 |
| N131SeqR1 | ATGGTGTTGGCAATCAGCG | sequencing primer | 51 |
| N131SeqR2 | GTGCTTCGGTGATGGTTT | sequencing primer | 52 |
| N131SeqR3 | TTGAAACCGTGCGAGTAGC | sequencing primer | 53 |
| N132SeqF1 | TATTCACTGCCATCTCGCG | sequencing primer | 54 |
| N132SeqF2 | CCGTAAGCAGCTGTTCCT | sequencing primer | 55 |
| N132SeqF3 | GCTGGAACAATACGACGTTA | sequencing primer | 56 |
| N132SeqF4 | TGCTCTACCCAACCAGCTTC | sequencing primer | 57 |
| N132SeqR1 | ATGGAAAGACCAGAGGTGCC | sequencing primer | 58 |
| N132SeqR2 | TGCCTGTGTGGTACGAAT | sequencing primer | 59 |
| N132SeqR3 | TATTACGCGGCAGTGCACT | sequencing primer | 60 |
| N132SeqR4 | GGTGATTTGTCGCAGTTAGAG | sequencing primer | 61 |
| N133SeqF1 | TCGAAATTGTTGGGTCGC | sequencing primer | 62 |
| N133SeqF2 | GGTCACGCAGTTCATTTCTAAG | sequencing primer | 63 |
| N133SeqF3 | TGTGGCAAGCCGTAGAAA | sequencing primer | 64 |
| N133SeqF4 | AGGATCGCGTGGTGAGTAA | sequencing primer | 65 |
| N133SeqR1 | GTAGCCGTCGTTATTGATGA | sequencing primer | 66 |

TABLE 4-continued

Oligonucleotide Cloning, Screening, and Sequencing Primers

| Name | Sequence | Description | SEQ ID NO: |
|---|---|---|---|
| N133SeqR2 | GCAGCGAACTAATCAGAGATTC | sequencing primer | 67 |
| N133SeqR3 | TGGTCCGATGTATTGGAGG | sequencing primer | 68 |
| N133SeqR4 | TCTGCCATATAGCTCGCGT | sequencing primer | 69 |
| Scr1 | CCTTTCTTTGTGAATCGG | sequencing primer | 72 |
| Scr2 | AGAAACAGGGTGTGATCC | sequencing primer | 73 |
| Scr3 | AGTGATCATCACCTGTTGCC | sequencing primer | 74 |
| Scr4 | AGCACGGCGAGAGTCGACGG | sequencing primer | 75 |
| T-budB (BamHI) | AGATAGATGGATCCGGAGGTGGGTCACATGGACAAACAGT | budB forward | 144 |
| B-kivD (BamHI) | CTCTAGAGGATCCAGACTCCTAGGACATG | kivD reverse | 145 |
| T-groE (XhoI) | AGATAGATCTCGAGAGCTATTGTAACATAATCGGTACGGGGGTG | PgroE forward | 147 |
| B-groEL (SpeI, BamH1) | ATTATGTCAGGATCCACTAGTTTCCTCCTTTTAATTGGGAATTGTTATCCGC | PgroE reverse | 148 |
| T-groEL | AGCTATTGTAACATAATCGGTACGGGGGTG | PgroE forward | 149 |
| T-ilvCB.s. (BamHI) | ACATTGATGGATCCCATAACAAGGGAGAGATTGAAATGGTAAAAG | ilvC forward | 150 |
| B-ilvCB.s. (SpeI BamHI) | TAGACAACGGATCCACTAGTTTAATTTTGCGCAACGGAGACCACCGC | ilvC reverse | 151 |
| T-BD64 (DraIII) | TTACCGTGGACTCACCGAGTGGGTAACTAGCCTCGCCGGAAAGAGCG | pBD64 forward | 152 |
| B-BD64 (DraIII) | TCACAGTTAAGACACCTGGTGCCGTTAATGCGCCATGACAGCCATGAT | pBD64 reverse | 153 |
| T-Iaclq (DraIII) | ACAGATAGATCACCAGGTGCAAGCTAATTCCGGTGGAAACGAGGTCATC | Iaclq forward | 154 |
| B-Iaclq (DraIII) | ACAGTACGATACACGGGGTGTCACTGCCCGCTTTCCAGTCGGGAAACC | Iaclq reverse | 155 |
| T-groE (DraIII) | TCGGATTACGCACCCCGTGAGCTATTGTAACATAATCGGTACGGGGGTG | PgroE forward | 156 |
| B-B.s.ilvC (DraIII) | CTGCTGATCTCACACCGTGTGTTAATTTTGCGCAACGGAGACCACCGC | ilvC reverse | 157 |
| T-bdhB (DraIII) | TCGATAGCATACACACGGTGGTTAACAAAGGAGGGGTTAAAATGGTTGATTTCG | bdhB forward | 159 |
| B-bdhB (rrnBT1 DraIII) | ATCTACGCACTCGGTGATAAAACGAAAGGCCCAGTCTTTCGACTGAGCCTTTCGTTTTATCTTACACAGATTTTTTGAATATTTGTAGGAC | bdhB reverse | 160 |
| LDH EcoRV F | GACGTCATGACCACCCGCCGATCCCTTTT | IdhL forward | 161 |
| LDH AatIIR | GATATCCAACACCAGCGACCGACGTATTAC | IdhL reverse | 162 |
| Cm F | ATTTAAATCTCGAGTAGAGGATCCCAACAAACGAAAATTGGATAAAG | Cm forward | 163 |
| Cm R | ACGCGTTATTATAAAAGCCAGTCATTAGG | Cm reverse | 164 |
| P11 F-StuI | CCTAGCGCTATAGTTGTTGACAGAATGGACATACTATGATATATTGTTGCTATAGCGA | P11 promoter forward | 165 |
| P11 R-SpeI | CTAGTCGCTATAGCAACAATATATCATAGTATGTCCATTCTGTCAACAACTATAGCGCTAGG | P11 promoter reverse | 166 |
| PIdhL F-HindIII | AAGCTTGTCGACAAACCAACATTATGACGTGTCTGGGC | IdhL forward | 167 |
| PIdhL R-BamHI | GGATCCTCATCCTCTCGTAGTGAAAATT | IdhL reverse | 168 |
| F-bdhB-AvrII | TTCCTAGGAAGGAGGTGGTTAAAATGGTTGATTTCG | bdhB forward | 169 |
| R-bdhB-BamHI | TTGGATCCTTACACAGATTTTTTGAATAT | bdhB reverse | 170 |
| F-ilvC (B.s.)-AflIII | AACTTAAGAAGGAGGTGATTGAAATGGTAAAAGTATATT | ilvC forward | 171 |
| R-ilvC (B.s.)-NotI | AAGCGGCCGCTTAATTTTGCGCAACGGAGACC | ivlC reverse | 172 |
| F-PnisA (HindIII) | TTAAGCTTGACATACTTGAATGACCTAGTC | nisA promoter forward | 173 |
| R-PnisA (SpeI BamHI) | TTGGATCCAAACTAGTATAATTTATTTTGTAGTTCCTTC | nisA promoter reverse | 174 |

Methods for Determining Isobutanol Concentration in Culture Media

The concentration of isobutanol in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Isobutanol had a retention time of 46.6 min under the conditions used. Alternatively, gas chromatography (GC) methods are available. For example, a specific GC method utilized an HP-INNOWax column (30 m×0.53 mm id, 1 μm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of isobutanol was 4.5 min.

The meaning of abbreviations is as follows: "s" means second(s), "min" means minute(s), "h" means hour(s), "psi" means pounds per square inch, "nm" means nanometers, "d" means day(s), "µL" means microliter(s), "mL" means milliliter(s), "L" means liter(s), "mm" means millimeter(s), "nm" means nanometers, "mM" means millimolar, "µM" means micromolar, "M" means molar, "mmol" means millimole(s), "µmol" means micromole(s)", "g" means gram(s), "µg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "IPTG" means isopropyl-8-D-thiogalactopyranoiside, "RBS" means ribosome binding site, "HPLC" means high performance liquid chromatography, and "GC" means gas chromatography. The term "molar selectivity" is the number of moles of product produced per mole of sugar substrate consumed and is reported as a percent.

Example 1

Cloning and Expression of Acetolactate Synthase

The purpose of this Example was to clone the budB gene from *Klebsiella pneumoniae* and express it in *E. coli* BL21-AI. The budB gene was amplified from *Klebsiella pneumoniae* strain ATCC 25955 genomic DNA using PCR, resulting in a 1.8 kbp product.

Genomic DNA was prepared using the Gentra Puregene kit (Gentra Systems, Inc., Minneapolis, Minn.; catalog number D-5000A). The budB gene was amplified from *Klebsiella pneumoniae* genomic DNA by PCR using primers N80 and N81 (see Table 2), given as SEQ ID NOs:11 and 12, respectively. Other PCR amplification reagents were supplied in manufacturers' kits, for example, Finnzymes Phusion™ High-Fidelity PCR Master Mix (New England Biolabs Inc., Beverly, Mass.; catalog no. F-531) and used according to the manufacturer's protocol. Amplification was carried out in a DNA Thermocycler GeneAmp 9700 (PE Applied Biosystems, Foster city, CA).

For expression studies the Gateway cloning technology (Invitrogen Corp., Carlsbad, Calif.) was used. The entry vector pENTRSDD-TOPO allowed directional cloning and provided a Shine-Dalgarno sequence for the gene of interest. The destination vector pDEST14 used a T7 promoter for expression of the gene with no tag. The forward primer incorporated four bases (CACC) immediately adjacent to the translational start codon to allow directional cloning into pENTRSDD-TOPO (Invitrogen) to generate the plasmid pENTRSDD-TOPObudB. The pENTR construct was transformed into *E. coli* Top10 (Invitrogen) cells and plated according to manufacturer's recommendations. Transformants were grown overnight and plasmid DNA was prepared using the QIAprep Spin Miniprep kit (Qiagen, Valencia, Calif.; catalog no. 27106) according to manufacturer's recommendations. Clones were sequenced to confirm that the genes inserted in the correct orientation and to confirm the sequence. The nucleotide sequence of the open reading frame (ORF) for this gene and the predicted amino acid sequence of the enzyme are given as SEQ ID NO:1 and SEQ ID NO:2, respectively.

To create an expression clone, the budB gene was transferred to the pDEST 14 vector by recombination to generate pDEST14budB. The pDEST14budB vector was transformed into *E. coli* BL21-AI cells (Invitrogen). Transformants were inoculated into Luria Bertani (LB) medium supplemented with 50 µg/mL of ampicillin and grown overnight. An aliquot of the overnight culture was used to inoculate 50 mL of LB supplemented with 50 µg/mL of ampicillin. The culture was incubated at 37° C. with shaking until the $OD_{600}$ reached 0.6-0.8. The culture was split into two 25-mL cultures and arabinose was added to one of the flasks to a final concentration of 0.2% w/v. The negative control flask was not induced with arabinose. The flasks were incubated for 4 h at 37° C. with shaking. Cells were harvested by centrifugation and the cell pellets were resuspended in 50 mM MOPS, pH 7.0 buffer. The cells were disrupted either by sonication or by passage through a French Pressure Cell. The whole cell lysate was centrifuged yielding the supernatant or cell free extract and the pellet or the insoluble fraction. An aliquot of each fraction (whole cell lysate, cell free extract and insoluble fraction) was resuspended in SDS (MES) loading buffer (Invitrogen), heated to 85° C. for 10 min and subjected to SDS-PAGE analysis (NuPAGE 4-12% Bis-Tris Gel, catalog no. NP0322Box, Invitrogen). A protein of the expected molecular weight of about 60 kDa, as deduced from the nucleic acid sequence, was present in the induced culture but not in the uninduced control.

Acetolactate synthase activity in the cell free extracts is measured using the method described by Bauerle et al. (*Biochim. Biophys. Acta* 92(1):142-149 (1964)).

Example 2 (Prophetic)

Cloning and Expression of Acetohydroxy Acid Reductoisomerase

The purpose of this prophetic Example is to describe how to clone the ilvC gene from *E. coli* $K_{12}$ and express it in *E. coli* BL21-AI. The ilvC gene is amplified from *E. coli* genomic DNA using PCR.

The ilvC gene is cloned and expressed in the same manner as the budB gene described in Example 1. Genomic DNA from *E. coli* is prepared using the Gentra Puregene kit (Gentra Systems, Inc., Minneapolis, Minn.; catalog number D-5000A). The ilvC gene is amplified by PCR using primers N100 and N101 (see Table 2), given as SEQ ID NOs:13 and 14, respectively, creating a 1.5 kbp product. The forward primer incorporates four bases (CCAC) immediately adjacent to the translational start codon to allow directional cloning into pENTR/SD/D-TOPO (Invitrogen) to generate the plasmid pENTRSDD-TOPOilvC. Clones are sequenced to confirm that the genes are inserted in the correct orientation and to confirm the sequence. The nucleotide sequence of the open reading frame (ORF) for this gene and the predicted amino acid sequence of the enzyme are given as SEQ ID NO:3 and SEQ ID NO:4, respectively.

To create an expression clone, the ilvC gene is transferred to the pDEST 14 (Invitrogen) vector by recombination to generate pDEST14ilvC. The pDEST14ilvC vector is transformed into *E. coli* BL21-AI cells and expression from the T7 promoter is induced by addition of arabinose. A protein of the expected molecular weight of about 54 kDa, as deduced from the nucleic acid sequence, is present in the induced culture, but not in the uninduced control.

Acetohydroxy acid reductoisomerase activity in the cell free extracts is measured using the method described by Arfin and Umbarger (*J. Biol. Chem.* 244(5):1118-1127 (1969)).

Example 3 (Prophetic)

Cloning and Expression of Acetohydroxy Acid Dehydratase

The purpose of this prophetic Example is to describe how to clone the ilvD gene from *E. coli* K12 and express it in *E. coli* BL21-AI. The ilvD gene is amplified from *E. coli* genomic DNA using PCR.

The ilvD gene is cloned and expressed in the same manner as the budB gene described in Example 1. Genomic DNA from *E. coli* is prepared using the Gentra Puregene kit (Gentra Systems, Inc., Minneapolis, Minn.; catalog number D-5000A). The ilvD gene is amplified by PCR using primers N102 and N103 (see Table 2), given as SEQ ID NOs:15 and 16, respectively, creating a 1.9 kbp product. The forward primer incorporates four bases (CCAC) immediately adjacent to the translational start codon to allow directional cloning into pENTR/SD/D-TOPO (Invitrogen) to generate the plasmid pENTRSDD-TOPOiIvD. Clones are submitted for sequencing to confirm that the genes are inserted in the correct orientation and to confirm the sequence. The nucleotide sequence of the open reading frame (ORF) for this gene and the predicted amino acid sequence of the enzyme are given as SEQ ID NO:5 and SEQ ID NO:6, respectively.

To create an expression clone, the ilvD gene is transferred to the pDEST 14 (Invitrogen) vector by recombination to generate pDEST14ilvD. The pDEST14ilvD vector is transformed into *E. coli* BL21-AI cells and expression from the T7 promoter is induced by addition of arabinose. A protein of the expected molecular weight of about 66 kDa, as deduced from the nucleic acid sequence, is present in the induced culture, but not in the uninduced control.

Acetohydroxy acid dehydratase activity in the cell free extracts is measured using the method described by Flint et al. (*J. Biol. Chem.* 268(20):14732-14742 (1993)).

Example 4 (Prophetic)

Cloning and Expression of Branched-Chain Keto Acid Decarboxylase

The purpose of this prophetic example is to describe how to clone the kivD gene from *Lactococcus lactis* and express it in *E. coli* BL21-AI.

A DNA sequence encoding the branched-chain keto acid decarboxylase (kivD) from *L. lactis* is obtained from GenScript (Piscataway, N.J.). The sequence obtained is codon-optimized for expression in both *E. coli* and *B. subtilis* and is cloned into pUC57, to form pUC57-kivD. The codon-optimized nucleotide sequence of the open reading frame (ORF) for this gene and the predicted amino acid sequence of the enzyme are given as SEQ ID NO:7 and SEQ ID NO:8, respectively.

To create an expression clone NdeI and BamHI restriction sites are utilized to clone the 1.7 kbp kivD fragment from pUC57-kivD into vector pET-3a (Novagen, Madison, Wis.). This creates the expression clone pET-3a-kivD. The pET-3a-kivD vector is transformed into *E. coli* BL21-AI cells and expression from the T7 promoter is induced by addition of arabinose. A protein of the expected molecular weight of about 61 kDa, as deduced from the nucleic acid sequence, is present in the induced culture, but not in the uninduced control.

Branched-chain keto acid decarboxylase activity in the cell free extracts is measured using the method described by Smit et al. (*Appl. Microbiol. Biotechnol.* 64:396-402 (2003)).

Example 5 (Prophetic)

Cloning and Expression of Branched-Chain Alcohol Dehydrogenase

The purpose of this prophetic Example is to describe how to clone the yqhD gene from *E. coli* K12 and express it in *E. coli* BL21-AI. The yqhD gene is amplified from *E. coli* genomic DNA using PCR.

The yqhD gene is cloned and expressed in the same manner as the budB gene described in Example 1. Genomic DNA from *E. coli* is prepared using the Gentra Puregene kit (Gentra Systems, Inc., Minneapolis, Minn.; catalog number D-5000A). The yqhD gene is amplified by PCR using primers N104 and N105 (see Table 2), given as SEQ ID NOs:17 and 18, respectively, creating a 1.2 kbp product. The forward primer incorporates four bases (CCAC) immediately adjacent to the translational start codon to allow directional cloning into pENTR/SD/D-TOPO (Invitrogen) to generate the plasmid pENTRSDD-TOPOyqhD. Clones are submitted for sequencing to confirm that the genes are inserted in the correct orientation and to confirm the sequence. The nucleotide sequence of the open reading frame (ORF) for this gene and the predicted amino acid sequence of the enzyme are given as SEQ ID NO 9 and SEQ ID NO:10, respectively.

To create an expression clone, the yqhD gene is transferred to the pDEST 14 (Invitrogen) vector by recombination to generate pDEST14yqhD. The pDEST14ilvD vector is transformed into *E. coli* BL21-AI cells and expression from the T7 promoter is induced by addition of arabinose. A protein of the expected molecular weight of about 42 kDa, as deduced from the nucleic acid sequence, is present in the induced culture, but not in the uninduced control.

Branched-chain alcohol dehydrogenase activity in the cell free extracts is measured using the method described by Sulzenbacher et al. (*J. Mol. Biol.* 342(2):489-502 (2004)).

Example 6 (Prophetic)

Construction of a Transformation Vector for the Genes in an Isobutanol Biosynthetic Pathway The purpose of this prophetic Example is to describe how to construct a transformation vector comprising the genes encoding the five steps in an isobutanol biosynthetic pathway. All genes are placed in a single operon under the control of a single promoter. The individual genes are amplified by PCR with primers that incorporate restriction sites for later cloning and the forward primers contain an optimized *E. coli* ribosome binding site (AAAGGAGG). PCR products are TOPO cloned into the pCR 4Blunt-TOPO vector and transformed into *E. coli* Top10 cells (Invitrogen). Plasmid DNA is prepared from the TOPO clones and the sequence of the genes is verified. Restriction enzymes and T4 DNA ligase (New England Biolabs, Beverly, Mass.) are used according to manufacturer's recommendations. For cloning experiments, restriction fragments are gel-purified using QIAquick Gel Extraction kit (Qiagen). After confirmation of the sequence, the genes are subcloned into a modified pUC19 vector as a cloning platform. The pUC19 vector is modified by HindIII/

SapI digestion, creating pUC19dHS. The digest removes the lac promoter adjacent to the MCS (multiple cloning site), preventing transcription of the operons in the vector.

The budB gene is amplified from *K. pneumoniae* ATCC 25955 genomic DNA by PCR using primer pair N110 and N111 (see Table 2), given as SEQ ID NOs:19 and 20, respectively, creating a 1.8 kbp product. The forward primer incorporates SphI and AflII restriction sites and a ribosome binding site (RBS). The reverse primer incorporates PacI and NsiI restriction sites. The PCR product is cloned into pCR4 Blunt-TOPO creating pCR4 Blunt-TOPO-budB. Plasmid DNA is prepared from the TOPO clones and the sequence of the gene is verified. The ilvC gene is amplified from *E. coli* K12 genomic DNA by PCR using primer pair N112 and N113 (see Table 2) given as SEQ ID NOs:21 and 22, respectively, creating a 1.5 kbp product. The forward primer incorporates SalI and NheI restriction sites and a RBS. The reverse primer incorporates a XbaI restriction site. The PCR product is cloned into pCR4 Blunt-TOPO creating pCR4 Blunt-TOPO-ilvC. Plasmid DNA is prepared from the TOPO clones and the sequence of the gene is verified.

The ilvD gene is amplified from *E. coli* K12 genomic DNA by PCR using primer pair N114 and N115 (see Table 2) given as SEQ ID NOs:23 and 24, respectively, creating a 1.9 kbp product. The forward primer incorporates a XbaI restriction site and a RBS. The reverse primer incorporates a BamHI restriction site. The PCR product is cloned into pCR4 Blunt-TOPO creating pCR4 Blunt-TOPO-ilvD. Plasmid DNA is prepared from the TOPO clones and the sequence of the gene is verified.

The kivD gene is amplified from pUC57-kivD (described in Example 4) by PCR using primer pair N116 and N117 (see Table 2), given as SEQ ID NOs:25 and 26, respectively, creating a 1.7 bp product. The forward primer incorporates a BamHI restriction site and a RBS. The reverse primer incorporates a SacI restriction site. The PCR product is cloned into pCR4 Blunt-TOPO creating pCR4 Blunt-TOPO-kivD. Plasmid DNA is prepared from the TOPO clones and the sequence of the gene is verified.

The yqhD gene is amplified from *E. coli* K12 genomic DNA by PCR using primer pair N118 and N119 (see Table 2) given as SEQ ID NOs:27 and 28, respectively, creating a 1.2 kbp product. The forward primer incorporates a SacI restriction site. The reverse primer incorporates SpeI and EcoRI restriction sites. The PCR product is cloned into pCR4 Blunt-TOPO creating pCR4 Blunt-TOPO-yqhD. Plasmid DNA is prepared from the TOPO clones and the sequence of the gene is verified.

To construct the isobutanol pathway operon, the yqhD gene is excised from pCR4 Blunt-TOPO-yqhD with SacI and EcoRI, releasing a 1.2 kbp fragment. This is ligated with pUC19dHS, which has previously been digested with SacI and EcoRI. The resulting clone, pUC19dHS-yqhD, is confirmed by restriction digest. Next, the ilvC gene is excised from pCR4 Blunt-TOPO-ilvC with SalI and XbaI, releasing a 1.5 kbp fragment. This is ligated with pUC19dHS-yqhD, which has previously been digested with SalI and XbaI. The resulting clone, pUC19dHS-ilvC-yqhD, is confirmed by restriction digest. The budB gene is then excised from pCR4 Blunt-TOPO-budB with SphI and NsiI, releasing a 1.8 kbp fragment. pUC19dHS-ilvC-yqhD is digested with SphI and PstI and ligated with the SphI/NsiI budB fragment (NsiI and PstI generate compatible ends), forming pUC19dHS-budB-ilvC-yqhD. A 1.9 kbp fragment containing the ilvD gene is excised from pCR4 Blunt-TOPO-ilvD with XbaI and BamHI and ligated with pUC19dHS-budB-ilvC-yqhD, which is digested with these same enzymes, forming pUC19dHS-budB-ilvC-ilvD-yqhD. Finally, kivD is excised from pCR4 Blunt-TOPO-kivD with BamHI and SacI, releasing a 1.7 kbp fragment. This fragment is ligated with pUC19dHS-budB-ilvC-ilvD-yqhD, which has previously been digested with BamHI and SacI, forming pUC19dHS-budB-ilvC-ilvD-kivD-yqhD. The pUC19dHS-budB-ilvC-ilvD-kivD-yqhD vector is digested with AflII and SpeI to release a 8.2 kbp operon fragment that is cloned into pBenAS, an *E. coli-B. subtilis* shuttle vector. Plasmid pBenAS is created by modification of the pBE93 vector, which is described by Nagarajan, (WO 93/24631, Example 4). To make pBenAS the *Bacillus amyloliquefaciens* neutral protease promoter (NPR), signal sequence, and the phoA gene are removed with a NcoI/HindIII digest of pBE93. The NPR promoter is PCR amplified from pBE93 by primers BenNF and BenASR, given as SEQ ID NOS:29 and 30, respectively. Primer BenASR incorporates AflII, SpeI, and HindIII sites downstream of the promoter. The PCR product is digested with NcoI and HindIII and the fragment is cloned into the corresponding sites in the vector creating pBenAS. The operon fragment is subcloned into the AflII and SpeI sites in pBenAS creating pBen-budB-ilvC-ilvD-kivD-yqhD.

Example 7 (Prophetic)

Expression of the Isobutanol Biosynthetic Pathway in *E. coli*

The purpose of this prophetic Example is to describe how to express an isobutanol biosynthetic pathway in *E. coli*.

The plasmid pBen-budB-ilvC-ilvD-kivD-yqhD, constructed as described in Example 6, is transformed into *E. coli* NM522 (ATCC No. 47000) to give *E. coli* strain NM522/pBen-budB-ilvC-ilvD-kivD-yqhD and expression of the genes in the operon is monitored by SDS-PAGE analysis, enzyme assay and Western blot analysis. For Western blots, antibodies are raised to synthetic peptides by Sigma-Genosys (The Woodlands, Tex.).

*E. coli* strain NM522/pBen-budB-ilvC-ilvD-kivD-yqhD is inoculated into a 250 mL shake flask containing 50 mL of medium and shaken at 250 rpm and 35° C. The medium is composed of: glucose (5 g/L), MOPS (0.05 M), ammonium sulfate (0.01 M), potassium phosphate, monobasic (0.005 M), S10 metal mix (1% (v/v)) yeast extract (0.1% (w/v)), casamino acids (0.1% (w/v)), thiamine (0.1 mg/L), proline (0.05 mg/L), and biotin (0.002 mg/L), and is titrated to pH 7.0 with KOH. S10 metal mix contains: $MgCl_2$ (200 mM), $CaCl_2$ (70 mM), $MnCl_2$ (5 mM), $FeCl_3$ (0.1 mM), $ZnCl_2$ (0.1 mM), thiamine hydrochloride (0.2 mM), $CuSO_4$ (172 µM), $CoCl_2$ (253 µM), and $Na_2MoO_4$ (242 µM). After 18 h, isobutanol is detected by HPLC or GC analysis, using methods that are well known in the art, for example, as described in the General Methods section above.

Example 8 (Prophetic)

Expression of the Isobutanol Biosynthetic Pathway in *Bacillus subtilis*

The purpose of this prophetic Example is to describe how to express an isobutanol biosynthetic pathway in *Bacillus subtilis*. The same approach as described in Example 7 is used.

The plasmid pBen-budB-ilvC-ilvD-kivD-yqhD, constructed as described in Example 6, is used. This plasmid is transformed into *Bacillus subtilis* BE1010 (*J. Bacteriol*. 173: 2278-2282 (1991)) to give *B. subtilis* strain BE1010/pBenbudB-ilvC-ilvD-kivD-yqhD and expression of the genes in each operon is monitored as described in Example 7.

B. subtilis strain BE1010/pBen-budB-ilvC-ilvD-kivD-yqhD is inoculated into a 250 mL shake flask containing 50 mL of medium and shaken at 250 rpm and 35° C. for 18 h. The medium is composed of: dextrose (5 g/L), MOPS (0.05 M), glutamic acid (0.02 M), ammonium sulfate (0.01 M), potassium phosphate, monobasic buffer (0.005 M), S10 metal mix (as described in Example 11, 1% (v/v)), yeast extract (0.1% (w/v)), casamino acids (0.1% (w/v)), tryptophan (50 mg/L), methionine (50 mg/L), and lysine (50 mg/L), and is titrated to pH 7.0 with KOH. After 18 h, isobutanol is detected by HPLC or GC analysis using methods that are well known in the art, for example, as described in the General Methods section above.

Example 9

Cloning and Expression of Acetolactate Synthase

To create another acetolactate synthase expression clone, the budB gene was cloned into the vector pTrc99A. The budB gene was first amplified from pENTRSDD-TOPObudB (described in Example 1) using primers (N110.2 and N111.2, given as SEQ ID NOs:31 and 32, respectively) that introduced SacI, SpeI and MfeI sites at the 5' end and BbvCI, AflII, and BamHI sites at the 3' end. The resulting 1.75 kbp PCR product was cloned into pCR4-Blunt TOPO (Invitrogen) and the DNA sequence was confirmed (using N130Seq sequencing primers F1-F4 and R1-R4, given as SEQ ID NOs:40-47, respectively). The budB gene was then excised from this vector using SacI and BamHI and cloned into pTrc99A (Amann et al. *Gene* 69(2):301-315 (1988)), generating pTrc99A::budB. The pTrc99A::budB vector was transformed into *E. coli* TOP10 cells and the transformants were inoculated into LB medium supplemented with 50 μg/mL of ampicillin and grown overnight at 37° C.

An aliquot of the overnight culture was used to inoculate 50 mL of LB medium supplemented with 50 μg/mL of ampicillin. The culture was incubated at 37° C. with shaking until the $OD_{600}$ reached 0.6 to 0.8. Expression of budB from the Trc promoter was then induced by the addition of 0.4 mM IPTG. Negative control flasks were also prepared that were not induced with IPTG. The flasks were incubated for 4 h at 37° C. with shaking. Cell-free extracts were prepared as described in Example 1.

Acetolactate synthase activity in the cell free extracts was measured as described in Example 1. Three hours after induction with IPTG, an acetolactate synthase activity of 8 units/mg was detected. The control strain carrying only the pTrc99A plasmid exhibited 0.03 units/mg of acetolactate synthase activity.

Example 10

Cloning and Expression of Acetohydroxy Acid Reductoisomerase

The purpose of this Example was to clone the ilvC gene from *E. coli* K12 and express it in *E. coli* TOP10. The ilvC gene was amplified from *E. coli* K12 strain FM5 (ATCC 53911) genomic DNA using PCR.

The ilvC gene was cloned and expressed in a similar manner as described for the cloning and expression of ilvC in Example 2 above. PCR was used to amplify ilvC from the *E. coli* FM5 genome using primers N112.2 and N113.2 (SEQ ID NOs:33 and 34, respectively). The primers created SacI and AMU sites and an optimal RBS at the 5' end and NotI, NheI and BamHI sites at the 3' end of ilvC. The 1.5 kbp PCR product was cloned into pCR4Blunt TOPO according to the manufacturer's protocol (Invitrogen) generating pCR4Blunt TOPO::ilvC. The sequence of the PCR product was confirmed using sequencing primers (N131SeqF1-F3, and N131SeqR1-R3, given as SEQ ID NOs:48-53, respectively). To create an expression clone, the ilvC gene was excised from pCR4Blunt TOPO::ilvC using SacI and BamHI and cloned into pTrc99A. The pTrc99A::ilvC vector was transformed into *E. coli* TOP10 cells and expression from the Trc promoter was induced by addition of IPTG, as described in Example 9. Cell-free extracts were prepared as described in Example 1.

Acetohydroxy acid reductoisomerase activity in the cell free extracts was measured as described in Example 2. Three hours after induction with IPTG, an acetohydroxy acid reductoisomerase activity of 0.026 units/mg was detected. The control strain carrying only the pTrc99A plasmid exhibited less than 0.001 units/mg of acetohydroxy acid reductoisomerase activity.

Example 11

Cloning and Expression of Acetohydroxy Acid Dehydratase

The purpose of this Example was to clone the ilvD gene from *E. coli* K12 and express it in *E. coli* Top10. The ilvD gene was amplified from *E. coli* K12 strain FM5 (ATCC 53911) genomic DNA using PCR.

The ilvD gene was cloned and expressed in a similar manner as the ilvC gene described in Example 10. PCR was used to amplify ilvD from the *E. coli* FM5 genome using primers N114.2 and N115.2 (SEQ ID NOs:35 and 36, respectively). The primers created SacI and NheI sites and an optimal RBS at the 5' end and Bsu36I, PacI and BamHI sites at the 3' end of ilvD. The 1.9 kbp PCR product was cloned into pCR4Blunt TOPO according to the manufacturer's protocol (Invitrogen) generating pCR4Blunt TOPO::ilvD. The sequence of the PCR product was confirmed (sequencing primers N132SeqF1-F4 and N132SeqR1-R4, given as SEQ ID NOs: 54-61, respectively). To create an expression clone, the ilvD gene was excised from plasmid pCR4Blunt TOPO::ilvD using SacI and BamHI, and cloned into pTrc99A. The pTrc99A::ilvD vector was transformed into *E. coli* TOP10 cells and expression from the Trc promoter was induced by addition of IPTG, as described in Example 9. Cell-free extracts were prepared as described in Example 1.

Acetohydroxy acid dehydratase activity in the cell free extracts was measured as described in Example 3. Three hours after induction with IPTG, an acetohydroxy acid dehydratase activity of 46 units/mg was measured. The control strain carrying only the pTrc99A plasmid exhibited no detectable acetohydroxy acid dehydratase activity.

Example 12

Cloning and Expression of Branched-Chain Keto Acid Decarboxylase

The purpose of this Example was to clone the kivD gene from *Lactococcus lactis* and express it in *E. coli* TOP10.

The kivD gene was cloned and expressed in a similar manner as that described for ilvC in Example 10 above. PCR was used to amplify kivD from the plasmid pUC57-kivD (see Example 4, above) using primers N116.2 and N117.2 (SEQ ID NOs:37 and 38, respectively). The primers created SacI and PacI sites and an optimal RBS at the 5' end and PciI, AvrII, BglII and BamHI sites at the 3' end of kivD. The 1.7 kbp PCR product was cloned into pCR4Blunt TOPO according to the manufacturer's protocol (Invitrogen) generating pCR4Blunt TOPO::kivD. The sequence of the PCR product was confirmed using primers N133SeqF1-F4 and N133SeqR1-R4 (given as SEQ ID NOs:62-69, respectively). To create an expression clone, the kivD gene was excised from plasmid pCR4Blunt TOPO::kivD using SacI and BamHI, and cloned into pTrc99A. The pTrc99A::kivD vector was transformed into E. coli TOP10 cells and expression from the Trc promoter was induced by addition of IPTG, as described in Example 9. Cell-free extracts were prepared as described in Example 1.

Branched-chain keto acid decarboxylase activity in the cell free extracts was measured as described in Example 4, except that Purpald® reagent (Aldrich, Catalog No. 162892) was used to detect and quantify the aldehyde reaction products. Three hours after induction with IPTG, a branched-chain keto acid decarboxylase activity of greater than 3.7 units/mg was detected. The control strain carrying only the pTrc99A plasmid exhibited no detectable branched-chain keto acid decarboxylase activity.

Example 13

Expression of Branched-Chain Alcohol Dehydrogenase

E. coli contains a native gene (yqhD) that was identified as a 1,3-propanediol dehydrogenase (U.S. Pat. No. 6,514,733). The YqhD protein has 40% identity to AdhB (encoded by adhB) from Clostridium, a putative NADH-dependent butanol dehydrogenase. The yqhD gene was placed under the constitutive expression of a variant of the glucose isomerase promoter 1.6GI (SEQ ID NO. 70) in E. coli strain MG1655 1.6yqhD::Cm (WO 2004/033646) using λ Red technology (Datsenko and Wanner, Proc. Natl. Acad. Sci. U.S.A. 97:6640 (2000)). MG1655 1.6yqhD::Cm contains a FRT-CmR-FRT cassette so that the antibiotic marker can be removed. Similarly, the native promoter was replaced by the 1.5GI promoter (WO 2003/089621) (SEQ ID NO. 71), creating strain MG1655 1.5GI-yqhD::Cm, thus, replacing the 1.6GI promoter of MG1655 1.6yqhD::Cm with the 1.5GI promoter.

Strain MG1655 1.5GI-yqhD::Cm was grown in LB medium to mid-log phase and cell free extracts were prepared as described in Example 1. This strain was found to have NADPH-dependent isobutyraldehyde reductase activity when the cell extracts were assayed by following the decrease in absorbance at 340 nm at pH 7.5 and 35° C.

To generate a second expression strain containing 1.5GI yqhD::Cm, a P1 lysate was prepared from MG1655 1.5GI yqhD::Cm and the cassette was transferred to BL21 (DE3) (Invitrogen) by transduction, creating BL21 (DE3) 1.5GI-yqhD::Cm.

Example 14

Construction of a Transformation Vector for the First Four Genes in an Isobutanol Biosynthetic Pathway The purpose of this Example was to construct a transformation vector comprising the first four genes (i.e., budB, ilvC, ilvD and kivD) in an isobutanol biosynthetic pathway.

To construct the transformation vector, first, the ilvC gene was obtained from pTrc99A::ilvC (described in Example 10) by digestion with AflII and BamHI and cloned into pTrc99A:: budB (described in Example 9), which was digested with AflII and BamHI to produce plasmid pTrc99A::budB-ilvC. Next, the ilvD and kivD genes were obtained from pTrc99A:: ilvD (described in Example 11) and pTrc99A::kivD (described in Example 12), respectively, by digestion with NheI and PacI (ilvD) and PacI and BamHI (kivD). These genes were introduced into pTrc99A::budB-ilvC, which was first digested with NheI and BamHI, by three-way ligation. The presence of all four genes in the final plasmid, pTrc99A:: budB-ilvC-ilvD-kivD, was confirmed by PCR screening and restriction digestion.

Example 15

Expression of an Isobutanol Biosynthetic Pathway in E. coli Grown on Glucose

To create E. coli isobutanol production strains, pTrc99A:: budB-ilvC-ilvD-kivD (described in Example 14) was transformed into E. coli MG1655 1.5GI yqhD::Cm and E. coli BL21 (DE3) 1.5GI yqhD::Cm (described in Example 13). Transformants were initially grown in LB medium containing 50 μg/mL kanamycin and 100 μg/mL carbenicillin. The cells from these cultures were used to inoculate shake flasks (approximately 175 mL total volume) containing 50 or 170 mL of TM3a/glucose medium (with appropriate antibiotics) to represent high and low oxygen conditions, respectively. TM3a/glucose medium contained (per liter): glucose (10 g), $KH_2PO_4$ (13.6 g), citric acid monohydrate (2.0 g), $(NH_4)_2SO_4$ (3.0 g), $MgSO_4 \cdot 7H_2O$ (2.0 g), $CaCl_2 \cdot 2H_2O$ (0.2 g), ferric ammonium citrate (0.33 g), thiamine.HCl (1.0 mg), yeast extract (0.50 g), and 10 mL of trace elements solution. The pH was adjusted to 6.8 with $NH_4OH$. The trace elements solution contained: citric acid.$H_2O$ (4.0 g/L), $MnSO_4 \cdot H_2O$ (3.0 g/L), NaCl (1.0 g/L), $FeSO_4 \cdot 7H_2O$ (0.10 g/L), $CoCl_2 \cdot 6H_2O$ (0.10 g/L), $ZnSO_4 \cdot 7H_2O$ (0.10 g/L), $CuSO_4 \cdot 5H_2O$ (0.010 g/L), $H_3BO_3$ (0.010 g/L), and $Na_2MoO_4 \cdot 2H_2O$ (0.010 g/L).

The flasks were inoculated at a starting $OD_{600}$ of ≤0.01 units and incubated at 34° C. with shaking at 300 rpm. The flasks containing 50 mL of medium were closed with 0.2 μm filter caps; the flasks containing 150 mL of medium were closed with sealed caps. IPTG was added to a final concentration of 0.04 mM when the cells reached an $OD_{600}$ of ≥0.4 units. Approximately 18 h after induction, an aliquot of the broth was analyzed by HPLC (Shodex Sugar SH1011 column (Showa Denko America, Inc. NY) with refractive index (RI) detection) and GC (Varian CP-WAX 58(FFAP) CB, 0.25 mm×0.2 μm×25 m (Varian, Inc., Palo Alto, Calif.) with flame ionization detection (FID)) for isobutanol content, as described in the General Methods section. No isobutanol was detected in control strains carrying only the pTrc99A vector (results not shown). Molar selectivities and titers of isobutanol produced by strains carrying pTrc99A::budB-ilvC-ilvD-kivD are shown in Table 5. Significantly higher titers of isobutanol were obtained in the cultures grown under low oxygen conditions.

TABLE 5

Production of Isobutanol by E. coli Strains Grown on Glucose

| Strain | $O_2$ Conditions | Isobutanol mM* | Molar Selectivity (%) |
|---|---|---|---|
| MG1655 1.5GI yqhD/ pTrc99A::budB-ilvC-ilvD-kivD | High | 0.4 | 4.2 |

TABLE 5-continued

Production of Isobutanol by E. coli Strains Grown on Glucose

| Strain | O$_2$ Conditions | Isobutanol mM* | Molar Selectivity (%) |
|---|---|---|---|
| MG1655 1.5GI yqhD/ pTrc99A::budB-ilvC-ilvD-kivD | Low | 9.9 | 39 |
| BL21 (DE3) 1.5GI yqhD/ pTrc99A::budB-ilvC-ilvD-kivD | High | 0.3 | 3.9 |
| BL21 (DE3) 1.5GI yqhD/ pTrc99A::budB-ilvC-ilvD-kivD | Low | 1.2 | 12 |

*Determined by HPLC.

Example 16

Expression of an Isobutanol Biosynthetic Pathway in E. coli Grown on Sucrose Since the strains described in Example 15 were not capable of growth on sucrose, an additional plasmid was constructed to allow utilization of sucrose for isobutanol production. A sucrose utilization gene cluster cscBKA, given as SEQ ID NO:39, was isolated from genomic DNA of a sucrose-utilizing E. coli strain derived from ATCC strain 13281. The sucrose utilization genes (cscA, cscK, and cscB) encode a sucrose hydrolase (CscA), given as SEQ ID NO:139, D-fructokinase (CscK), given as SEQ ID NO:140, and sucrose permease (CscB), given as SEQ ID NO:141. The sucrose-specific repressor gene cscR was not included so that the three genes cscBKA were expressed constitutively from their native promoters in E. coli.

Genomic DNA from the sucrose-utilizing E. coli strain was digested to completion with BamHI and EcoRI. Fragments having an average size of about 4 kbp were isolated from an agarose gel and were ligated to plasmid pLitmus28 (New England Biolabs), digested with BamHI and EcoRI and transformed into ultracompetent E. coli TOP10F' cells (Invitrogen). The transformants were streaked onto MacConkey agar plates containing 1% sucrose and ampicillin (100 µg/mL) and screened for the appearance of purple colonies. Plasmid DNA was isolated from the purple transformants, and sequenced with M13 Forward and Reverse primers (Invitrogen), and Scr1-4 (given as SEQ ID NOs:72-75, respectively). The plasmid containing cscB, cscK, and cscA (cscBKA) genes was designated pScr1.

To create a sucrose utilization plasmid that was compatible with the isobutanol pathway plasmid (Example 14), the operon from pScr1 was subcloned into pBHR1 (MoBiTec, Goettingen, Germany). The cscBKA genes were isolated by digestion of pScr1 with XhoI (followed by incubation with Klenow enzyme to generate blunt ends) and then by digestion with AgeI. The resulting 4.2 kbp fragment was ligated into pBHR1 that had been digested with NaeI and AgeI, resulting in the 9.3 kbp plasmid pBHR1::cscBKA.

The sucrose plasmid pBHR1::cscBKA was transformed into E. coli BL21 (DE3) 1.5 yqhD/pTrc99A::budB-ilvC-ilvD-kivD and E. coli MG1655 1.5yqhD/pTrc99A::budB-ilvC-ilvD-kivD (described in Example 15) by electroporation. Transformants were first selected on LB medium containing 100 µg/mL ampicillin and 50 µg/mL kanamycin and then screened on MacConkey sucrose (1%) plates to confirm functional expression of the sucrose operon. For production of isobutanol, strains were grown in TM3a minimal defined medium (described in Example 15) containing 1% sucrose instead of glucose, and the culture medium was analyzed for the amount of isobutanol produced, as described in Example 15, except that samples were taken 14 h after induction. Again, no isobutanol was detected in control strains carrying only the pTrc99A vector (results not shown). Molar selectivities and titers of isobutanol produced by MG1655 1.5yqhD carrying pTrc99A::budB-ilvC-ilvD-kivD are shown in Table 6. Similar results were obtained with the analogous BL21 (DE3) strain.

TABLE 6

Production of Isobutanol by E. coli strain MG1655 1.5yqhD/pTrc99A:: budB-ilvC-ilvD-kivD/pBHR1::cscBKA Grown on Sucrose

| O$_2$ Conditions | IPTG, mM | Isobutanol, mM* | Molar Selectivity, % |
|---|---|---|---|
| High | 0.04 | 0.17 | 2 |
| High | 0.4 | 1.59 | 21 |
| Low | 0.04 | 4.03 | 26 |
| Low | 0.4 | 3.95 | 29 |

*Determined by HPLC.

Example 17

Expression of Isobutanol Pathway Genes in Saccharomyces Cerevisiae

To express isobutanol pathway genes in Saccharomyces cerevisiae, a number of E. coli-yeast shuttle vectors were constructed. A PCR approach (Yu, et al. Fungal Genet. Biol. 41:973-981 (2004)) was used to fuse genes with yeast promoters and terminators. Specifically, the GPD promoter (SEQ ID NO:76) and CYC1 terminator (SEQ ID NO:77) were fused to the alsS gene from Bacillus subtilis (SEQ ID NO:78), the FBA promoter (SEQ ID NO:79) and CYC1 terminator were fused to the ILV5 gene from S. cerevisiae (SEQ ID NO:80), the ADH1 promoter (SEQ ID NO:81) and ADH1 terminator (SEQ ID NO:82) were fused to the ILV3 gene from S. cerevisiae (SEQ ID NO:83), and the GPM promoter (SEQ ID NO:84) and ADH1 terminator were fused to the kivD gene from Lactococcus lactis (SEQ ID NO:7). The primers, given in Table 7, were designed to include restriction sites for cloning promoter/gene/terminator products into E. coli-yeast shuttle vectors from the pRS400 series (Christianson et al. Gene 110:119-122 (1992)) and for exchanging promoters between constructs. Primers for the 5' ends of ILV5 and ILV3 (N138 and N155, respectively, given as SEQ ID NOs: 95 and 107, respectively) generated new start codons to eliminate mitochondrial targeting of these enzymes.

All fused PCR products were first cloned into pCR4-Blunt by TOPO cloning reaction (Invitrogen) and the sequences were confirmed (using M13 forward and reverse primers (Invitrogen) and the sequencing primers provided in Table 7. Two additional promoters (CUP1 and GAL1) were cloned by TOPO reaction into pCR4-Blunt and confirmed by sequencing; primer sequences are indicated in Table 7. The plasmids that were constructed are described in Table 8. The plasmids were transformed into either Saccharomyces cerevisiae BY4743 (ATCC 201390) or YJR148w (ATCC 4036939) to assess enzyme specific activities using the enzyme assays described in Examples 1-4 and Examples 9-12. For the determination of enzyme activities, cultures were grown to an OD$_{600}$ of 1.0 in synthetic complete medium (Methods in Yeast Genetics, 2005, Cold Spring Harbor Laboratory Press, Cold Spring Harbor, N.Y., pp. 201-202) lacking any metabolite(s) necessary for selection of the expression plasmid(s), harvested by centrifugation (2600×g for 8 min at 4° C.), washed with buffer, centrifuged again, and frozen at −80° C. The cells were thawed, resuspended in 20 mM Tris-HCl, pH 8.0 to a final volume of 2 mL, and then disrupted using a bead beater with 1.2 g of glass beads (0.5 mm size). Each sample was processed on high speed for 3 minutes total (with incubation on ice after each minute of beating). Extracts were cleared of cell debris by centrifugation (20,000×g for 10 min at 4° C.).

TABLE 7

Primer Sequences for Cloning and Sequencing of *S. cerevisiae* Expression Vectors

| Name | Sequence | Description | SEQ ID NO: |
|---|---|---|---|
| N98SeqF1 | CGTGTTAGTCACATCAGGAC | *B. subtilis* alsS sequencing primer | 85 |
| N98SeqF2 | GGCCATAGCAAAAATCCAAACAGC | *B. subtilis* alsS sequencing primer | 86 |
| N98SeqF3 | CCACGATCAATCATATCGAACACG | *B. subtilis* alsS sequencing primer | 87 |
| N98SeqF4 | GGTTTCTGTCTCTGGTGACG | *B. subtilis* alsS sequencing primer | 88 |
| N99SeqR1 | GTCTGGTGATTCTACGCGCAAG | *B. subtilis* alsS sequencing primer | 89 |
| N99SeqR2 | CATCGACTGCATTACGCAACTC | *B. subtilis* alsS sequencing primer | 90 |
| N99SeqR3 | CGATCGTCAGAACAACATCTGC | *B. subtilis* alsS sequencing primer | 91 |
| N99SeqR4 | CCTTCAGTGTTCGCTGTCAG | *B. subtilis* alsS sequencing primer | 92 |
| N136 | CCGCGGATAGATCTGAAATGAATAACAATACTGACA | FBA promoter forward primer with SacII/BglII sites | 93 |
| N137 | TACCACCGAAGTTGATTTGCTTCAACATCCTCAGCTCTAGATTTGAATATGTATTACTGGTTAT | FBA promoter reverse primer with BbvCI site and ILV5-annealing region | 94 |
| N138 | ATGTTGAAGCAAATCAACTTCGGTGGTA | ILV5 forward primer (creates alternate start codon) | 95 |
| N139 | TTATTGGTTTTCTGGTCTCAAC | ILV5 reverse primer | 96 |
| N140 | AAGTTGAGACCAGAAAACCAATAATTAATTAATCATGTAATTAGTTATGTCACGCTT | CYC terminator forward primer with PacI site and ILV5-annealing region | 97 |
| N141 | GCGGCCGCCCGCAAATTAAAGCCTTCGAGC | CYC terminator reverse primer with NotI site | 98 |
| N142 | GGATCCGCATGCTTGCATTTAGTCGTGC | GPM promoter forward primer with BamHI site | 99 |
| N143 | CAGGTAATCCCCCACAGTATACATCCTCAGCTATTGTAATATGTGTGTTTGTTTGG | GPM promoter reverse primer with BbvCI site and kivD-annealing region | 100 |

TABLE 7-continued

Primer Sequences for Cloning and Sequencing of *S. cerevisiae* Expression Vectors

| Name | Sequence | Description | SEQ ID NO: |
|---|---|---|---|
| N144 | ATGTATACTGTGGGGGATTACC | kivD forward primer | 101 |
| N145 | TTAGCTTTTATTTTGCTCCGCA | kivD reverse primer | 102 |
| N146 | TTTGCGGAGCAAAATAAAGCTAATTAATTAAGAGTAAGCGAATTTCTTATGATTTA | ADH terminator forward primer with PacI site and kivD-annealing region | 103 |
| N147 | ACTAGTACCACAGGTGTTGTCCTCTGAG | ADH terminator reverse primer with SpeI site | 104 |
| N151 | CTAGAGAGCTTTCGTTTTCATG | alsS reverse primer | 105 |
| N152 | CTCATGAAAACGAAAGCTCTCTAGTTAATTAATCATGTAATTAGTTATGTCACGCTT | CYC terminator forward primer with PacI site and alsS-annealing region | 106 |
| N155 | ATGGCAAAGAAGCTCAACAAGTACT | ILV3 forward primer (alternate start codon) | 107 |
| N156 | TCAAGCATCTAAAACACAACCG | ILV3 reverse primer | 108 |
| N157 | AACGGTTGTGTTTTAGATGCTTGATTAATTAAGAGTAAGCGAATTTCTTATGATTTA | ADH terminator forward primer with PacI site and ILV3-annealing region | 109 |
| N158 | GGATCCTTTTCTGGCAACCAAACCCATA | ADH promoter forward primer with BamHI site | 110 |
| N159 | CGAGTACTTGTTGAGCTTCTTTGCCATCCTCAGCGAGATAGTTGATTGTATGCTTG | ADH promoter reverse primer with BbvCI site and ILV3-annealing region | 111 |
| N160SeqF1 | GAAAACGTGGCATCCTCTC | FBA::ILV5::CYC sequencing primer | 112 |
| N160SeqF2 | GCTGACTGGCCAAGAGAA | FBA::ILV5::CYC sequencing primer | 113 |
| N160SeqF3 | TGTACTTCTCCCACGGTTTC | FBA::ILV5::CYC sequencing primer | 114 |
| N160SeqF4 | AGCTACCCAATCTCTATACCCA | FBA::ILV5::CYC sequencing primer | 115 |
| N160SeqF5 | CCTGAAGTCTAGGTCCCTATTT | FBA::ILV5::CYC sequencing primer | 116 |
| N160SeqR1 | GCGTGAATGTAAGCGTGAC | FBA::ILV5::CYC sequencing primer | 117 |
| N160SeqR2 | CGTCGTATTGAGCCAAGAAC | FBA::ILV5::CYC sequencing primer | 118 |

TABLE 7-continued

Primer Sequences for Cloning and Sequencing of S. cerevisiae Expression Vectors

| Name | Sequence | Description | SEQ ID NO: |
|---|---|---|---|
| N160SeqR3 | GCATCGGACAACAAGTTCAT | FBA::ILV5::CYC sequencing primer | 119 |
| N160SeqR4 | TCGTTCTTGAAGTAGTCCAACA | FBA::ILV5::CYC sequencing primer | 120 |
| N160SeqR5 | TGAGCCCGAAAGAGAGGAT | FBA::ILV5::CYC sequencing primer | 121 |
| N161SeqF1 | ACGGTATACGGCCTTCCTT | ADH::ILV3::ADH sequencing primer | 122 |
| N161SeqF2 | GGGTTTGAAAGCTATGCAGT | ADH::ILV3::ADH sequencing primer | 123 |
| N161SeqF3 | GGTGGTATGTATACTGCCAACA | ADH::ILV3::ADH sequencing primer | 124 |
| N161SeqF4 | GGTGGTACCCAATCTGTGATTA | ADH::ILV3::ADH sequencing primer | 125 |
| N161SeqF5 | CGGTTTGGGTAAAGATGTTG | ADH::ILV3::ADH sequencing primer | 126 |
| N161SeqF6 | AAACGAAAATTCTTATTCTTAGA | ADH::ILV3::ADH sequencing primer | 127 |
| N161SeqR1 | TCGTTTTAAAACCTAAGAGTCA | ADH::ILV3::ADH sequencing primer | 128 |
| N161SeqR2 | CCAAACCGTAACCCATCAG | ADH::ILV3::ADH sequencing primer | 129 |
| N161SeqR3 | CACAGATTGGGTACCACCA | ADH::ILV3::ADH sequencing primer | 130 |
| N161SeqR4 | ACCACAAGAACCAGGACCTG | ADH::ILV3::ADH sequencing primer | 131 |
| N161SeqR5 | CATAGCTTTCAAACCCGCT | ADH::ILV3::ADH sequencing primer | 132 |
| N161SeqR6 | CGTATACCGTTGCTCATTAGAG | ADH::ILV3::ADH sequencing primer | 133 |
| N162 | ATGTTGACAAAAGCAACAAAAGA | a/sS forward primer | 134 |
| N189 | ATCCGCGGATAGATCTAGTTCGAGTTTATCATTATCAA | GPD forward primer with SacII/BglII sites | 135 |
| N190.1 | TTCTTTTGTTGCTTTTGTCAGACATCCTCAGCGTTTATGTGTGTTTATTCGAAA | GPD promoter reverse primer with BbvCI site and alsS-annealing region | 136 |
| N176 | ATCCGCGGATAGATCTATTAGAAGCCGCCGAGCGGGCG | GAL1 promoter forward primer with SacII/BglII sites | 137 |
| N177 | ATCCTCAGCTTTTCTCCTTGACGTTAAAGTA | GAL1 promoter reverse with BbvCI site | 138 |
| N191 | ATCCGCGGATAGATCTCCCATTACCGACATTTGGGCGC | CUP1 promoter forward primer with SacII/BglII sites | 175 |
| N192 | ATCCTCAGCGATGATTGATTGATTGATTGTA | CUP1 promoter reverse with BbvCI site | 176 |

TABLE 8

E. coli-Yeast Shuttle Vectors Carrying Isobutanol Pathway Genes

| Plasmid Name | Construction |
|---|---|
| pRS426 [ATCC No. 77107], URA3 selection | — |
| pRS426::GPD::alsS::CYC | GPD::alsS::CYC PCR product digested with SacII/NotI cloned into pRS426 digested with same |
| pRS426::FBA::ILV5::CYC | FBA::ILV5::CYC PCR product digested with SacII/NotI cloned into pRS426 digested with same |
| pRS425 [ATCC No. 77106], LEU2 selection | — |
| pRS425::ADH::ILV3::ADH | ADH::ILV3::ADH PCR product digested with BamHI/SpeI cloned into pRS425 digested with same |
| pRS425::GPM::kivD::ADH | GPM::kivD::ADH PCR product digested with BamHI/SpeI cloned into pRS425 digested with same |
| pRS426::CUP1::alsS | 7.7 kbp SacII/BbvCI fragment from pRS426::GPD::alsS::CYC ligated with SacII/BbvCI CUP1 fragment |
| pRS426::GAL1::ILV5 | 7 kbp SacII/BbvCI fragment from pRS426::FBA::ILV5::CYC ligated with SacII/BbvCI GAL1 fragment |
| pRS425::FBA::ILV3 | 8.9 kbp BamHI/BbvCI fragment from pRS425::ADH::ILV3::ADH ligated with 0.65 kbp BglII/BbvCI FBA fragment from pRS426::FBA::ILV5::CYC |

TABLE 8-continued

E. coli-Yeast Shuttle Vectors Carrying Isobutanol Pathway Genes

| Plasmid Name | Construction |
| --- | --- |
| pRS425::CUP1-alsS + FBA-ILV3 | 2.4 kbp SacII/NotI fragment from pRS426::CUP1::alsS cloned into pRS425::FBA::ILV3 cut with SacII/NotI |
| pRS426::FBA-ILV5 + GPM-kivD | 2.7 kbp BamHI/SpeI fragment from pRS425::GPM::kivD::ADH cloned into pRS426::FBA::ILV5::CYC cut with BamHI/SpeI |
| pRS426::GAL1-FBA + GPM-kivD | 8.5 kbp SacII/NotI fragment from pRS426:: FBA-ILV5 + GPM-kivD ligated with 1.8 kbp SacII/NotI fragment from pRS426::GAL1::ILV5 |
| pRS423 [ATCC No. 77104], HIS3 selection | — |
| pRS423::CUP1-alsS + FBA-ILV3 | 5.2 kbp SacI/SalI fragment from pRS425::CUP1-alsS + FBA-ILV3 ligated into pRS423 cut with SacI/SalI |
| pHR81 [ATCC No. 87541], URA3 and leu2-d selection | — |
| pHR81::FBA-ILV5 + GPM-kivD | 4.7 kbp SacI/BamHI fragment from pRS426::FBA-ILV5 + GPM-kivD ligated into pHR81 cut with SacI/BamHI |

Example 18

Production of Isobutanol by Recombinant *Saccharomyces Cerevisiae*

Plasmids pRS423::CUP1-alsS+FBA-ILV3 and pHR81::FBA-ILV5+GPM-kivD (described in Example 17) were transformed into *Saccharomyces cerevisiae* YJR148w to produce strain YJR148w/pRS423::CUP1-alsS+FBA-ILV3/pHR81::FBA-ILV5+GPM-kivD. A control strain was prepared by transforming vectors pRS423 and pHR81 (described in Example 17) into *Saccharomyces cerevisiae* YJR148w (strain YJR148w/pRS423/pHR81). Strains were maintained on standard *S. cerevisiae* synthetic complete medium (*Methods in Yeast Genetics*, 2005, Cold Spring Harbor Laboratory Press, Cold Spring Harbor, N.Y., pp. 201-202) containing either 2% glucose or sucrose but lacking uracil and histidine to ensure maintenance of plasmids.

For isobutanol production, cells were transferred to synthetic complete medium lacking uracil, histidine and leucine. Removal of leucine from the medium was intended to trigger an increase in copy number of the pHR81-based plasmid due to poor transcription of the leu2-d allele (Erhart and Hollenberg, *J. Bacteriol.* 156:625-635 (1983)). Aerobic cultures were grown in 175 mL capacity flasks containing 50 mL of medium in an Innova4000 incubator (New Brunswick Scientific, Edison, N.J.) at 30° C. and 200 rpm. Low oxygen cultures were prepared by adding 45 mL of medium to 60 mL serum vials that were sealed with crimped caps after inoculation and kept at 30° C. Sterile syringes were used for sampling and addition of inducer, as needed. Approximately 24 h after inoculation, the inducer $CuSO_4$ was added to a final concentration of 0.03 mM. Control cultures for each strain without $CuSO_4$ addition were also prepared. Culture supernatants were analyzed 18 or 19 h and 35 h after $CuSO_4$ addition by both GC and HPLC for isobutanol content, as described above in Example 15. The results for *S. cerevisiae* YJR148w/pRS423::CUP1-alsS+FBA-ILV3/pHR81::FBA-ILV5+GPM-kivD grown on glucose are presented in Table 9. For the results given in Table 9, the samples from the aerobic cultures were taken at 35 h and the samples from the low oxygen cultures were taken at 19 h and measured by HPLC.

The results for *S. cerevisiae* YJR148w/pRS423::CUP1-alsS+FBA-ILV3/pHR81::FBA-ILV5+GPM-kivD grown on sucrose are presented in Table 10. The results in this table were obtained with samples taken at 18 h and measured by HPLC.

TABLE 9

Production of Isobutanol by *S. cerevisiae* YJR148w/pRS423::CUP1-alsS + FBA-ILV3/pHR81::FBA-ILV5 + GPM-kivD Grown on Glucose

| Strain | $O_2$ level | Isobutanol, mM | Molar Selectivity % |
| --- | --- | --- | --- |
| YJR148w/pRS423/pHR81 (control) | Aerobic | 0.12 | 0.04 |
| YJR148w/pRS423/pHR81 (control) | Aerobic | 0.11 | 0.04 |
| YJR148w/pRS423::CUP1-alsS + IFBA-LV3/pHR81::FBA-ILV5 + GPM-kivD a | Aerobic | 0.97 | 0.34 |
| YJR148w/pRS423::CUP1-alsS + FBA-ILV3/pHR81::FBA-ILV5 + GPM-kivD b | Aerobic | 0.93 | 0.33 |
| YJR148w/pRS423::CUP1-alsS + FBA-ILV3/pHR81::FBA-ILV5 + GPM-kivD c | Aerobic | 0.85 | 0.30 |
| YJR148w/pRS423/pHR81 (control) | Low | 0.11 | 0.1 |
| YJR148w/pRS423/pHR81 (control) | Low | 0.08 | 0.1 |
| YJR148w/pRS423::CUP1-alsS + FBA-ILV3/pHR81::FBA-ILV5 + GPM-kivD | Low | 0.28 | 0.5 |
| YJR148w/pRS423::CUP1-alsS + FBA-ILV3/pHR81::FBA-ILV5 + GPM-kivD b | Low | 0.20 | 0.3 |
| YJR148w/pRS423::CUP1-alsS + FBA-ILV3/pHR81::FBA-ILV5 + GPM-kivD c | Low | 0.33 | 0.6 |

TABLE 10

Production of Isobutanol by *S. cerevisiae* YJR148w/pRS423::CUP1-alsS + FBA-ILV3/pHR81::FBA-ILV5 + GPM-kivD Grown on Sucrose

| Strain | $O_2$ Level | Isobutanol mM | Molar Selectivity, % |
| --- | --- | --- | --- |
| YJR148w/pRS423/pHR81 (control) | Aerobic | 0.32 | 0.6 |
| YJR148w/pRS423/pHR81 (control) | Aerobic | 0.17 | 0.3 |
| YJR148w/pRS423::CUP1-alsS + IFBA-LV3/pHR81::FBA-ILV5 + GPM-kivD a | Aerobic | 0.68 | 1.7 |

TABLE 10-continued

Production of Isobutanol by *S. cerevisiae* YJR148w/pRS423::CUP1-alsS + FBA-ILV3/pHR81::FBA-ILV5 + GPM-kivD Grown on Sucrose

| Strain | $O_2$ Level | Isobutanol mM | Molar Selectivity, % |
|---|---|---|---|
| YJR148w/pRS423::CUP1-alsS + FBA-ILV3/pHR81::FBA-ILV5 + GPM-kivD b | Aerobic | 0.54 | 1.2 |
| YJR148w/pRS423::CUP1-alsS + IFBA-LV3/pHR81::FBA-ILV5 + GPM-kivD c | Aerobic | 0.92 | 2.0 |
| YJR148w/pRS423/pHR81 (control) | Low | 0.18 | 0.3 |
| YJR148w/pRS423/pHR81 (control) | Low | 0.15 | 0.3 |
| YJR148w/pRS423::CUP1-alsS + FBA-ILV3/pHR81::FBA-ILV5 + GPM-kivD a | Low | 0.27 | 1.2 |
| YJR148w/pRS423::CUP1-alsS + FBA-ILV3/pHR81::FBA-ILV5 + GPM-kivD b | Low | 0.30 | 1.1 |
| YJR148w/pRS423::CUP1-alsS + FBA-ILV3/pHR81::FBA-ILV5 + GPM-kivD c | Low | 0.21 | 0.8 |

Strain suffixes "a", "b", and "c" indicate separate isolates.

The results indicate that, when grown on glucose or sucrose under both aerobic and low oxygen conditions, strain YJR148w/pRS423::CUP1-alsS+FBA-ILV3/pHR81::FBA-ILV5+GPM-kivD produced consistently higher levels of isobutanol than the control strain.

Example 19

Production of Isobutanol by Recombinant *Saccharomyces Cerevisiae*

Plasmids pRS425::CUP1-alsS+FBA-ILV3 and pRS426::GAL1-ILV5+GPM-kivD (described in Example 17) were transformed into *Saccharomyces cerevisiae* YJR148w to produce strain YJR148w/pRS425::CUP1-alsS+FBA-ILV3/pRS426::GAL1-ILV5+GPM-kivD. A control strain was prepared by transforming vectors pRS425 and pRS426 (described in Example 17) into *Saccharomyces cerevisiae* YJR148w (strain YJR148w/pRS425/pRS426). Strains were maintained on synthetic complete medium, as described in Example 18.

For isobutanol production, cells were transferred to synthetic complete medium containing 2% galactose and 1% raffinose, and lacking uracil and leucine. Aerobic and low oxygen cultures were prepared as described in Example 18. Approximately 12 h after inoculation, the inducer $CuSO_4$ was added up to a final concentration of 0.5 mM. Control cultures for each strain without $CuSO_4$ addition were also prepared. Culture supernatants were sampled 23 h after $CuSO_4$ addition for determination of isobutanol by HPLC, as described in Example 18. The results are presented in Table 11. Due to the widely different final optical densities observed and associated with quantifying the residual carbon source, the concentration of isobutanol per $OD_{600}$ unit (instead of molar selectivities) is provided in the table to allow comparison of strains containing the isobutanol biosynthetic pathway genes with the controls.

TABLE 11

Production of Isobutanol by *S. cerevisiae* YJR148w/pRS425::CUP1-alsS + FBA-ILV3/pRS426::GAL1-ILV5 + GPM-kivD Grown on Galactose and Raffinose

| Strain | $O_2$ level | $CuSO_4$, mM | Isobutanol mM | mM Isobutanol per OD unit |
|---|---|---|---|---|
| YJR148w/pRS425/pRS426 (control) | Aerobic | 0.1 | 0.12 | 0.01 |
| YJR148w/pRS425/pRS426 (control) | Aerobic | 0.5 | 0.13 | 0.01 |
| YJR148w/pRS425::CUP1-alsS + FBA-ILV3/pRS426::GAL1-ILV5 + GPM-kivD a | Aerobic | 0 | 0.20 | 0.03 |
| YJR148w/pRS425::CUP1-alsS + FBA-ILV3/pRS426::GAL1-ILV5 + GPM-kivD b | Aerobic | 0.03 | 0.82 | 0.09 |
| YJR148w/pRS425::CUP1-alsS + FBA-ILV3/pRS426::GAL1-ILV5 + GPM-kivD c | Aerobic | 0.1 | 0.81 | 0.09 |
| YJR148w/pRS425::CUP1-alsS + FBA-ILV3/pRS426::GAL1-ILV5 + GPM-kivD d | Aerobic | 0.5 | 0.16 | 0.04 |
| YJR148w/pRS425::CUP1-alsS + FBA-ILV3/pRS426::GAL1-ILV5 + GPM-kivD e | Aerobic | 0.5 | 0.18 | 0.01 |
| YJR148w/pRS425/pRS426 (control) | Low | 0.1 | 0.042 | 0.007 |
| YJR148w/pRS425/pRS426 (control) | Low | 0.5 | 0.023 | 0.006 |
| YJR148w/pRS425::CUP1-alsS + FBA-ILV3/pRS426::GAL1-ILV5 + GPM-kivD a | Low | 0 | 0.1 | 0.04 |
| YJR148w/pRS425::CUP1-alsS + FBA-ILV3/pRS426::GAL1-ILV5 + GPM-kivD b | Low | 0.03 | 0.024 | 0.02 |
| YJR148w/pRS425::CUP1-alsS + FBA-ILV3/pRS426::GAL1-ILV5 + GPM-kivD c | Low | 0.1 | 0.030 | 0.04 |
| YJR148w/pRS425::CUP1-alsS + FBA-ILV3/pRS426::GAL1-ILV5 + GPM-kivD d | Low | 0.5 | 0.008 | 0.02 |

TABLE 11-continued

Production of Isobutanol by S. cerevisiae YJR148w/pRS425::CUP1-alsS + FBA-ILV3/pRS426::GAL1-ILV5 + GPM-kivD Grown on Galactose and Raffinose

| Strain | O₂ level | CuSO₄, mM | Isobutanol mM | mM Isobutanol per OD unit |
|---|---|---|---|---|
| YJR148w/pRS425::CUP1-alsS + FBA-ILV3/pRS426::GAL1-ILV5 + GPM-kivD e | Low | 0.5 | 0.008 | 0.004 |

Strain suffixes "a", "b", "c", "d" and "e" indicate separate isolates.

The results indicate that in general, higher levels of isobutanol per optical density unit were produced by the YJR148w/pRS425::CUP1-alsS+FBA-ILV3/pRS426::GAL1-ILV5+GPM-kivD strain compared to the control strain under both aerobic and low oxygen conditions.

Example 20

Expression of an Isobutanol Biosynthetic Pathway in Bacillus subtilis

The purpose of this Example was to express an isobutanol biosynthetic pathway in Bacillus subtilis. The five genes of the isobutanol pathway (pathway steps (a) through (e) in FIG. 1) were split into two operons for expression. The three genes budB, ilvD, and kivD, encoding acetolactate synthase, acetohydroxy acid dehydratase, and branched-chain keto acid decarboxylase, respectively, were integrated into the chromosome of B. subtilis BE1010 (Payne and Jackson, J. Bacteriol. 173:2278-2282 (1991)). The two genes ilvC and bdhB, encoding acetohydroxy acid isomeroreductase and butanol dehydrogenase, respectively, were cloned into an expression vector and transformed into the Bacillus strain carrying the integrated isobutanol genes.

Integration of the Three Genes, budB, ilvD and kivD into the Chromosome of B. subtilis BE1010.

Bacillus integration vectors pFP988DssPspac and pFP988DssPgroE were used for the chromosomal integration of the three genes, budB (SEQ ID NO:1), ilvD (SEQ ID NO:5), and kivD (SEQ ID NO:7). Both plasmids contain an E. coli replicon from pBR322, an ampicillin antibiotic marker for selection in E. coli and two sections of homology to the sacB gene in the Bacillus chromosome that direct integration of the vector and intervening sequence by homologous recombination. Between the sacB homology regions is a spac promoter (PgroE) on pFP988DssPspac or a groEL promoter (PgroE) on pFP988DssPgroE, and a selectable marker for Bacillus, erythromycin. The promoter region also contains the lacO sequence for regulation of expression by a lacI repressor protein. The sequences of pFP988DssPspac (6,341 bp) and pFP988DssPgroE (6,221 bp) are given as SEQ ID NO:142 and SEQ ID NO:143 respectively.

The cassette with three genes budB-ilvD-kivD was constructed by deleting the ilvC gene from plasmid pTrc99a budB-ilvC-ilvD-kivD. The construction of the plasmid pTrc99A::budB-ilvC-ilvD-kivD is described in Example 14. Plasmid pTrc99A::budB-ilvC-ilvD-kivD was digested with AflII and NheI, treated with the Klenow fragment of DNA polymerase to make blunt ends, and the resulting 9.4 kbp fragment containing pTrc99a vector, budB, ilvD, and kivD was gel-purified. The 9.4 kbp vector fragment was self-ligated to create pTrc99A::budB-ilvD-kivD, and transformed into DH5α competent cells (Invitrogen). A clone of pTrc99a budB-ilvD-kivD was confirmed for the ilvC gene deletion by restriction mapping. The resulting plasmid pTrc99A::budB-ilvD-kivD was digested with SacI and treated with the Klenow fragment of DNA polymerase to make blunt ends. The plasmid was then digested with BamHI and the resulting 5,297 bp budB-ilvD-kivD fragment was gel-purified. The 5,297 bp budB-ilvD-kivD fragment was ligated into the SmaI and BamHI sites of the integration vector pFP988DssPspac. The ligation mixture was transformed into DH5α competent cells. Transformants were screened by PCR amplification of the 5.3 kbp budB-ilvD-kivD fragment with primers T-budB (BamHI) (SEQ ID NO:144) and B-kivD(BamHI) (SEQ ID NO:145). The correct clone was named pFP988DssPspac-budB-ilvD-kivD.

Plasmid pFP988DssPspac-budB-ilvD-kivD was prepared from the E. coli transformant, and transformed into B. subtilis BE1010 competent cells, which had been prepared as described by Doyle et al. (J. Bacteriol. 144:957 (1980)). Competent cells were harvested by centrifugation and the cell pellets were resuspended in a small volume of the supernatant. To one volume of competent cells, two volumes of SPII-EGTA medium (Methods for General and Molecular Bacteriology, P. Gerhardt et al., Ed., American Society for Microbiology, Washington, D.C. (1994)) was added. Aliquots (0.3 mL) of cells were dispensed into test tubes and then 2 to 3 µg of plasmid pFP988DssPspac-budB-ilvD-kivD was added to the tubes. The tubes were incubated for 30 min at 37° C. with shaking, after which 0.1 mL of 10% yeast extract was added to each tube and they were further incubated for 60 min. Transformants were grown for selection on LB plates containing erythromycin (1.0 µg/mL) using the double agar overlay method (Methods for General and Molecular Bacteriology, supra). Transformants were screened by PCR amplification with primers N130SeqF1 (SEQ ID NO:40) and N130SeqR1 (SEQ ID NO:44) for budB, and N133SeqF1 (SEQ ID NO:62) and N133SeqR1 (SEQ ID NO:66) for kivD. Positive integrants showed the expected 1.7 kbp budB and 1.7 kbp kivD PCR products. Two positive integrants were identified and named B. subtilis BE1010 ΔsacB::Pspac-budB-ilvD-kivD #2-3-2 and B. subtilis BE1010 ΔsacB::Pspac-budB-ilvD-kivD #6-12-7.

Assay of the enzyme activities in integrants B. subtilis BE1010 ΔsacB::Pspac-budB-ilvD-kivD #2-3-2 and B. subtilis BE1010 ΔsacB::Pspac-budB-ilvD-kivD #6-12-7 indicated that the activities of BudB, IlvD and KivD were low under the control of the spac promoter (Pspac). To improve expression of functional enzymes, the Pspac promoter was replaced by a PgroE promoter from plasmid pHT01 (MoBitec, Goettingen, Germany).

A 6,039 bp pFP988Dss vector fragment, given as SEQ ID NO:146, was excised from an unrelated plasmid by restriction digestion with XhoI and BamHI, and was gel-purified. The PgroE promoter was PCR-amplified from plasmid pHT01 with primers T-groE(XhoI) (SEQ ID NO:147) and B-groEL(SpeI,BamH1) (SEQ ID NO:148). The PCR product was digested with XhoI and BamHI, ligated with the 6,039 bp pFP988Dss vector fragment, and transformed into DH5α competent cells. Transformants were screened by PCR amplification with primers T-groE(XhoI) and B-groEL(SpeI, BamH1). Positive clones showed the expected 174 bp PgroE PCR product and were named pFP988DssPgroE. The plasmid pFP988DssPgroE was also confirmed by DNA sequence.

Plasmid pFP988DssPspac-budB-ilvD-kivD was digested with SpeI and PmeI and the resulting 5,313 bp budB-ilvD-kivD fragment was gel-purified. The budB-ilvD-kivD fragment was ligated into SpeI and PmeI sites of pFP988DssPgroE and transformed into DH5α competent cells. Positive clones were screened for a 1,690 bp PCR product by PCR amplification with primers T-groEL (SEQ ID NO:149) and N111 (SEQ ID NO:20). The positive clone was named pFP988DssPgroE-budB-ilvD-kivD.

Plasmid pFP988DssPgroE-budB-ilvD-kivD was prepared from the E. coli transformant, and transformed into Bacillus subtilis BE1010 competent cells as described above. Transformants were screened by PCR amplification with primers N130SeqF1 (SEQ ID NO:40) and N130SeqR1 (SEQ ID NO:44) for budB, and N133SegF1 (SEQ ID NO:62) and N133SeqR1 (SEQ ID NO:66) for kivD. Positive integrants showed the expected 1.7 kbp budB and 1.7 kbp kivD PCR products. Two positive integrants were isolated and named B. subtilis BE1010 ΔsacB::PgroE-budB-ilvD-kivD #1-7 and B. subtilis BE1010 ΔsacB::PgroE-budB-ilvD-kivD #8-16.

Plasmid Expression of ilvC and bdhB Genes.

Two remaining isobutanol genes, ilvC and bdhB, were expressed from a plasmid. Plasmid pHT01 (MoBitec), a Bacillus-E. coli shuttle vector, was used to fuse an ilvC gene from B. subtilis to a PgroE promoter so that the ilvC gene was expressed from the PgroE promoter containing a lacO sequence. The ilvC gene, given as SEQ ID NO:186, was PCR-amplified from B. subtilis BR151 (ATCC 33677) genomic DNA with primers T-ilvCB.s.(BamHI) (SEQ ID NO:150) and B-ilvCB.s.(SpeI BamHI) (SEQ ID NO:151). The 1,067 bp ilvC PCR product was digested with BamHI and ligated into the BamHI site of pHT01. The ligation mixture was transformed into DH5α competent cells. Positive clones were screened for a 1,188 bp PCR product by PCR amplification with primers T-groEL and B-ilvB.s.(SpeI BamHI). The positive clone was named pHT01-ilvC(B.s). Plasmid pHT01-ilvC(B.s) was used as a template for PCR amplification of the PgroE-ilvC fused fragment.

Plasmid pBD64 (Minton et al., Nucleic Acids Res. 18:1651 (1990)) is a fairly stable vector for expression of foreign genes in B. subtilis and contains a repB gene and chloramphenicol and kanamycin resistance genes for selection in B. subtilis. This plasmid was used for expression of ilvC and bdhB under the control of a PgroE promoter. To clone PgroE-ilvC, bdhB and a lacI repressor gene into plasmid pBD64, a one-step assembly method was used (Tsuge et al., Nucleic Acids Res. 31:e133 (2003)). A 3,588 bp pBD64 fragment containing a repB gene, which included the replication function, and the kanamycin antibiotic marker was PCR-amplified from pBD64 with primers T-BD64(DraIII) (SEQ ID NO:152), which introduced a DraIII sequence (CAC CGAGTG), and B-BD64(DraIII) (SEQ ID NO:153), which introduced a DraIII sequence (CACCTGGTG). A 1,327 bp lacI repressor gene was PCR-amplified from pMUTIN4 (Vagner et al., Microbiol. 144:3097-3104 (1998)) with T-lacIq(DraIII) (SEQ ID NO:154), which introduced a DraIII sequence (CACCAGGTG) and B-lacIq(DraIII) (SEQ ID NO:155), which introduced a DraIII sequence (CAC GGGGTG). A 1,224 bp PgroE-ilvC fused cassette was PCR-amplified from pHT01-ilvC(B.s) with T-groE(DraIII) (SEQ ID NO:156), which introduced a DraIII sequence (CAC CCCGTG), and B-B.s.ilvC(DraIII) (SEQ ID NO:157), which introduced a DraIII sequence (CACCGTGTG). A 1.2 kbp bdhB gene (SEQ ID NO:158) was PCR-amplified from Clostridium acetobutylicum (ATCC 824) genomic DNA with primers T-bdhB(DraIII) (SEQ ID NO:159), which introduced a DraIII sequence (CACACGGTG), and B-bdhB (rrnBT1DraIII) (SEQ ID NO:160), which introduced a DraIII sequence (CACTCGGTG). The three underlined letters in the variable region of the DraIII recognition sequences were designed for specific base-pairing to assemble the four fragments with an order of pBD64-lacI-PgroEilvC-bdhB. Each PCR product with DraIII sites at both ends was digested separately with DraIII, and the resulting DraIII fragments, 3,588 bp pBD64, lacI, PgroEilvC, and bdhB were gel-purified using a QIAGEN gel extraction kit (QIAGEN). A mixture containing an equimolar concentration of each fragment with a total DNA concentration of 30 to 50 μg/100 μL was prepared for ligation. The ligation solution was then incubated at 16° C. overnight. The ligation generated high molecular weight tandem repeat DNA. The ligated long, linear DNA mixture was directly transformed into competent B. subtilis BE1010, prepared as described above. B. subtilis preferentially takes up long repeated linear DNA forms, rather than circular DNA to establish a plasmid. After transformation the culture was spread onto an LB plate containing 10 μg/mL of kanamycin for selection. Positive recombinant plasmids were screened by DraIII digestion, giving four fragments with an expected size of 3,588 bp (pBD64), 1,327 bp (lacI), 1,224 bp (PgorE-ilvC), and 1,194 bp (bdhB). The positive plasmid was named pBDPgroE-ilvC(B.s.)-bdhB.

Demonstration of Isobutanol Production from Glucose or Sucrose by B. subtilis BE1010 ΔsacB::PqroE-budB-ilvD-kivD/pBDPqroE-ilvC(B.s.)-bdhB.

To construct the recombinant B. subtilis expressing the five genes of the isobutanol biosynthetic pathway, competent cells of the two integrants B. subtilis BE1010 ΔsacB-PgroE-budB-ilvD-kivD #1-7 and B. subtilis BE1010 ΔsacB::PgroE-budB-ilvD-kivD #8-16 were prepared as described above, and transformed with plasmid pBDPgroE-ilvC(B.s.)-bdhB, yielding B. subtilis BE1010 ΔsacB::PgroE-budB-ilvD-kivD #1-7/pBDPgroE-ilvC(B.s.)-bdhB and B. subtilis BE1010 ΔsacB::PgroE-budB-ilvD-kivD #8-16/pBDPgroE-ilvC (B.s.)-bdhB.

The two recombinant strains were inoculated in either 25 mL or 100 mL of glucose medium containing kanamycin (10 μg/mL) in 125 mL flasks to simulate high and low oxygen conditions, respectively, and aerobically grown at 37° C. with shaking at 200 rpm. The medium consisted of 10 mM $(NH_4)_2SO_4$, 5 mM potassium phosphate buffer (pH 7.0), 100 mM MOPS/KOH buffer (pH 7.0), 20 mM glutamic acid/KOH (pH 7.0), 2% S10 metal mix, 1% glucose, 0.01% yeast extract, 0.01% casamino acids, and 50 μg/mL each of L-tryptophan, L-methionine, and L-lysine. The S10 metal mix consisted of 200 mM $MgCl_2$, 70 mM $CaCl_2$, 5 mM $MnCl_2$, 0.1 mM $FeCl_3$, 0.1 mM $ZnCl_2$, 0.2 mM thiamine hydrochloride, 0.172 mM $CuSO_4$, 0.253 mM $CoCl_2$, and 0.242 mM $Na_2MoO_4$. The cells were induced with 1.0 mM isopropyl-β-D-thiogalactopyranoiside (IPTG) at early-log phase ($OD_{600}$ of approximately 0.2). At 24 h after inoculation, an aliquot of the broth was analyzed by HPLC (Shodex Sugar SH1011 column) with refractive index (RI) detection for isobutanol content, as described in the General Methods section. The HPLC results are shown in Table 12.

TABLE 12

Production of Isobutanol from Glucose by B. subtilis BE1010
ΔsacB::PgroE-budB-ilvD-kivD/pBDPgroE-ilvC(B.s.)-bdhB Strains

| Strain | O₂ Level | isobutanol, mM | molar selectivity, % |
|---|---|---|---|
| B. subtilis a (induced) | high | 1.00 | 1.8 |
| B. subtilis b (induced) | high | 0.87 | 1.6 |
| B. subtilis a (induced) | low | 0.06 | 0.1 |
| B. subtilis b (induced) | low | 0.14 | 0.3 |

B. subtilis a is B. subtilis BE1010 ΔsacB::PgroE-budB-ilvD-kivD #1-7/pBDPgroE-ilvC (B.s.)-bdhB
B. subtilis b is B. subtilis BE1010 ΔsacB::PgroE-budB-ilvD-kivD #8-16/pBDPgroE-ilvC (B.s.)-bdhB The isolate of B. subtilis BE1010 ΔsacB::PgroE-budB-ilvD-kivD #1-7/pBDPgroE-ilvC(B.s.)-bdhB was also examined for isobutanol production from sucrose, essentially as described above. The recombinant strain was inoculated in 25 mL or 75 mL of sucrose medium containing kanamycin (10 μg/mL) in 125 mL flasks to simulate high and medium oxygen levels, and grown at 37° C. with shaking at 200 rpm. The sucrose medium was identical to the glucose medium except that glucose (10 g/L) was replaced with 10 g/L of sucrose. The cells were uninduced, or induced with 1.0 mM isopropyl-β-D-thiogalactopyranoiside (IPTG) at early-log phase ($OD_{600}$ of approximately 0.2). At 24 h after inoculation, an aliquot of the broth was analyzed by HPLC (Shodex Sugar SH1011 column) with refractive index (RI) detection for isobutanol content, as described in the General Methods section. The HPLC results are given in Table 13.

TABLE 13

Production of Isobutanol from Sucrose by B. subtilis Strain BE1010
ΔsacB::PgroE-budB-ilvD-kivD/pBDPgroE-ilvC(B.s.)-bdhB

| Strain | O₂ Level | isobutanol, mM | molar selectivity, % |
|---|---|---|---|
| B. subtilis a (uninduced) | high | Not detected | Not detected |
| B. subtilis a (induced) | high | 0.44 | 4.9 |
| B. subtilis a (induced) | medium | 0.83 | 8.6 |

B. subtilis a is B. subtilis BE1010 ΔsacB::PgroE-budB-ilvD-kivD #1-7/pBDPgroE-ilvC (B.s.)-bdhB

Example 21 (Prophetic)

Expression of an Isobutanol Biosynthetic Pathway in Lactobacillus plantarum

The purpose of this prophetic Example is to describe how to express an isobutanol biosynthetic pathway in Lactobacillus plantarum. The five genes of the isobutanol pathway, encoding five enzyme activities, are divided into two operons for expression. The budB, ilvD and kivD genes, encoding the enzymes acetolactate synthase, acetohydroxy acid dehydratase, and branched-chain α-keto acid decarboxylase, respectively, are integrated into the chromosome of Lactobacillus plantarum by homologous recombination using the method described by Hols et al. (Appl. Environ. Microbiol. 60:1401-1413 (1994)). The remaining two genes (ilvC and bdhB, encoding the enzymes acetohydroxy acid reductoisomerase and butanol dehydrogenase, respectively) are cloned into an expression plasmid and transformed into the Lactobacillus strain carrying the integrated isobutanol genes. Lactobacillus plantarum is grown in MRS medium (Difco Laboratories, Detroit, Mich.) at 37° C., and chromosomal DNA is isolated as described by Moreira et al. (BMC Microbiol. 5:15 (2005)).

Integration.

The budB-ilvD-kivD cassette under the control of the synthetic P11 promoter (Rud et al., Microbiology 152:1011-1019 (2006)) is integrated into the chromosome of Lactobacillus plantarum ATCC BAA-793 (NCIMB 8826) at the ldhL1 locus by homologous recombination. To build the ldhL integration targeting vector, a DNA fragment from Lactobacillus plantarum (Genbank NC_004567) with homology to ldhL is PCR amplified with primers LDH EcoRV F (SEQ ID NO:161) and LDH AatIIR (SEQ ID NO:162). The 1986 bp PCR fragment is cloned into pCR4Blunt-TOPO and sequenced. The pCR4Blunt-TOPO-ldhL1 clone is digested with EcoRV and AatII releasing a 1982 bp ldhL1 fragment that is gel-purified. The integration vector pFP988, given as SEQ ID NO:177, is digested with HindIII and treated with Klenow DNA polymerase to blunt the ends. The linearized plasmid is then digested with AatII and the 2931 bp vector fragment is gel purified. The EcoRV/AatII ldhL1 fragment is ligated with the pFP988 vector fragment and transformed into E. coli Top10 cells. Transformants are selected on LB agar plates containing ampicillin (100 μg/mL) and are screened by colony PCR to confirm construction of pFP988-ldhL.

To add a selectable marker to the integrating DNA, the Cm gene with its promoter is PCR amplified from pC194 (GenBank NC_002013, SEQ ID NO:267) with primers Cm F (SEQ ID NO:163) and Cm R (SEQ ID NO:164), amplifying a 836 bp PCR product. This PCR product is cloned into pCR4Blunt-TOPO and transformed into E. coli Top10 cells, creating pCR4Blunt-TOPO-Cm. After sequencing to confirm that no errors are introduced by PCR, the Cm cassette is digested from pCR4Blunt-TOPO-Cm as an 828 bp MluI/SwaI fragment and is gel purified. The ldhL-homology containing integration vector pFP988-ldhL is digested with MluI and SwaI and the 4740 bp vector fragment is gel purified. The Cm cassette fragment is ligated with the pFP988-ldhL vector creating pFP988-DldhL::Cm.

Finally the budB-ilvD-kivD cassette from pFP988DssPspac-budB-ilvD-kivD, described in Example 20, is modified to replace the amylase promoter with the synthetic P11 promoter. Then, the whole operon is moved into pFP988-DldhL::Cm. The P11 promoter is built by oligonucleotide annealing with primer P11 F-StuI (SEQ ID NO:165) and P11 R-SpeI (SEQ ID NO:166). The annealed oligonucleotide is gel-purified on a 6% Ultra PAGE gel (Embi Tec, San Diego, Calif.). The plasmid pFP988DssPspac-budB-ilvD-kivD, containing the amylase promoter, is digested with StuI and SpeI and the resulting 10.9 kbp vector fragment is gel-purified. The isolated P11 fragment is ligated with the digested pFP988DssPspac-budB-ilvD-kivD to create pFP988-P11-budB-ilvD-kivD. Plasmid pFP988-P11-budB-ilvD-kivD is then digested with StuI and BamHI and the resulting 5.4 kbp P11-budB-ilvD-kivD fragment is gel-purified. pFP988-DldhL::Cm is digested with HpaI and BamHI and the 5.5 kbp vector fragment isolated. The budB-ilvD-kivD operon is ligated with the integration vector pFP988-DldhL::Cm to create pFP988-DldhL-P11-budB-ilvD-kivD::Cm.

Integration of pFP988-DldhL-P11-budB-ilvD-kivD::Cm into L. plantarum BAA-793 to Form L. plantarum ΔldhL1::budB-ilvD-kivD::Cm Comprising Exogenous budB, ilvD, and kivD Genes.

Electrocompetent cells of *L. plantarum* are prepared as described by Aukrust, T. W., et al. (In: *Electroporation Protocols for Microorganisms*; Nickoloff, J. A., Ed.; *Methods in Molecular Biology, Vol.* 47; Humana Press, Inc., Totowa, N.J., 1995, pp 201-208). After electroporation, cells are outgrown in MRSSM medium (MRS medium supplemented with 0.5 M sucrose and 0.1 M MgCl$_2$) as described by Aukrust et al. supra for 2 h at 37° C. without shaking. Electroporated cells are plated for selection on MRS plates containing chloramphenicol (10 µg/mL) and incubated at 37° C. Transformants are initially screened by colony PCR amplification to confirm integration, and initial positive clones are then more rigorously screened by PCR amplification with a battery of primers.

Plasmid Expression of ilvC and bdhB Genes.

The remaining two isobutanol genes are expressed from plasmid pTRKH3 (O'Sullivan D J and Klaenhammer TR, *Gene* 137:227-231 (1993)) under the control of the *L. plantarum* IdhL promoter (Ferain et al., *J. Bacteriol.* 176:596-601 (1994)). The IdhL promoter is PCR amplified from the genome of *L. plantarum* ATCC BAA-793 using primers PldhL F-HindIII (SEQ ID NO:167) and PldhL R-BamHI (SEQ ID NO:168). The 411 bp PCR product is cloned into pCR4Blunt-TOPO and sequenced. The resulting plasmid, pCR4Blunt-TOPO-PldhL is digested with HindIII and BamHI releasing the PldhL fragment.

Plasmid pTRKH3 is digested with HindIII and SphI and the gel-purified vector fragment is ligated with the PldhL fragment and the gel-purified 2.4 kbp BamHI/SphI fragment containing ilvC(B.s.)-bdhB from the *Bacillus* expression plasmid pBDPgroE-ilvC(B.s.)-bdhB (Example 20) in a three-way ligation. The ligation mixture is transformed into *E. coli* Top 10 cells and transformants are grown on Brain Heart Infusion (BHI, Difco Laboratories, Detroit, Mich.) plates containing erythromycin (150 mg/L). Transformants are screened by PCR to confirm construction. The resulting expression plasmid, pTRKH3-ilvC(B.s.)-bdhB is transformed into *L. plantarum* ΔldhL1::budB-ilvD-kivD::Cm by electroporation, as described above.

*L. plantarum* ΔldhL1::budB-ilvD-kivD::Cm containing pTRKH3-ilvC(B.s.)-bdhB is inoculated into a 250 mL shake flask containing 50 mL of MRS medium plus erythromycin (10 µg/mL) and grown at 37° C. for 18 to 24 h without shaking, after which isobutanol is detected by HPLC or GC analysis, as described in the General Methods section.

Example 22 (Prophetic)

Expression of an Isobutanol Biosynthetic Pathway in *Enterococcus faecalis*

The purpose of this prophetic Example is to describe how to express an isobutanol biosynthetic pathway in *Enterococcus faecalis*. The complete genome sequence of *Enterococcus faecalis* strain V583, which is used as the host strain for the expression of the isobutanol biosynthetic pathway in this Example, has been published (Paulsen et al., *Science* 299: 2071-2074 (2003)). An *E. coli*/Gram-positive shuttle vector, Plasmid pTRKH3 (O'Sullivan D J and Klaenhammer T R, *Gene* 137:227-231 (1993)), is used for expression of the five genes (budB, ilvC, ilvD, kivD, bdhB) of the isobutanol pathway in one operon. pTRKH3 contains an *E. coli* plasmid p15A replication origin, the pAMβ1 replicon, and two antibiotic resistance selection markers for tetracycline and erythromycin. Tetracycline resistance is only expressed in *E. coli*, and erythromycin resistance is expressed in both *E. coli* and Gram-positive bacteria. Plasmid pAMβ1 derivatives can replicate in *E. faecalis* (Poyart et al., *FEMS Microbiol. Lett.* 156:193-198 (1997)). The inducible nisA promoter (PnisA), which has been used for efficient control of gene expression by nisin in a variety of Gram-positive bacteria including *Enterococcus faecalis* (Eichenbaum et al., *Appl. Environ. Microbiol.* 64:2763-2769 (1998)), is used to control expression of the five desired genes encoding the enzymes of the isobutanol biosynthetic pathway.

The plasmid pTrc99A::budB-ilvC-ilvD-kivD (described in Example 14), which contains the isobutanol pathway operon, is modified to replace the *E. coli* ilvC gene (SEQ ID NO:3) with the *B. subtilis* ilvC gene (SEQ ID NO:184). Additionally, the bdhB gene (SEQ ID NO:158) from *Clostridium acetobutylicum* is added to the end of the operon. First, the bdhB gene from pBDPgroE-ilvC(B.s.)-bdhB (described in Example 20) is amplified using primers F-bdhB-AvrII (SEQ ID NO:169) and R-bdhB-BamHI (SEQ ID NO:170), and then TOPO cloned and sequenced. The 1194 bp bdhB fragment is isolated by digestion with AvrII and BamHI, followed by gel purification. This bdhB fragment is ligated with pTrc99A::budB-ilvC-ilvD-kivD that has previously been digested with AvrII and BamHI and the resulting fragment is gel purified. The ligation mixture is transformed into *E. coli* Top10 cells by electroporation and transformants are selected following overnight growth at 37° C. on LB agar plates containing ampicillin (100 µg/mL). The transformants are then screened by colony PCR to confirm the correct clone containing pTrc99A::budB-ilvC-ilvD-kivD-bdhB.

Next, ilvC(B.s.) is amplified from pBDPgroE-ilvC(B.s.)-bdhB (described in Example 20) using primers F-ilvC(B.s.)-AflII (SEQ ID NO:171) and R-ilvC(B.s.)-NotI (SEQ ID NO:172). The PCR product is TOPO cloned and sequenced. The 1051 bp ilvC(B.s.) fragment is isolated by digestion with AflII and NotI followed by gel purification. This fragment is ligated with pTrc99A::budB-ilvC-ilvD-kivD-bdhB that has been cut with AflII and NotI to release the *E. coli* ilvC (the 10.7 kbp vector band is gel purified prior to ligation with ilvC(B.s.)). The ligation mixture is transformed into *E. coli* Top10 cells by electroporation and transformants are selected following overnight growth at 37° C. on LB agar plates containing ampicillin (100 µg/mL). The transformants are then screened by colony PCR to confirm the correct clone containing pTrc99A::budB-ilvC(B.s.)-ilvD-kivD-bdhB.

To provide a promoter for the *E. coli*/Gram-positive shuttle vector pTRKH3, the nisA promoter (Chandrapati et al., *Mol. Microbiol.* 46(2):467-477 (2002)) is PCR-amplified from *Lactococcus lactis* genomic DNA with primers F-PnisA(HindIII) (SEQ ID NO:173) and R-PnisA(SpeI BamHI) (SEQ ID NO:174) and then TOPO cloned. After sequencing, the 213 bp nisA promoter fragment is isolated by digestion with HindIII and BamHI followed by gel purification. Plasmid pTRKH3 is digested with HindIII and BamHI and the vector fragment is gel-purified. The linearized pTRKH3 is ligated with the PnisA fragment and transformed into *E. coli* Top10 cells by electroporation. Transformants are selected following overnight growth at 37° C. on LB agar plates containing erythromycin (25 µg/mL). The transformants are then screened by colony PCR to confirm the correct clone of pTRKH3-PnisA.

Plasmid pTRKH3-PnisA is digested with SpeI and BamHI, and the vector is gel-purified. Plasmid pTrc99A:: budB-ilvC(B.s)-ilvD-kivD-bdhB, described above, is digested with SpeI and BamHI, and the 7.5 kbp fragment is gel-purified. The 7.5 kbp budB-ilvC(B.s)-ilvD-kivD-bdhB fragment is ligated into the pTRKH3-PnisA vector at the SpeI and BamHI sites. The ligation mixture is transformed into *E. coli* Top10 cells by electroporation and transformants are selected following overnight growth on LB agar plates containing erythromycin (25 µg/mL) at 37° C. The transformants are then screened by colony PCR. The resulting plasmid is named pTRKH3-PnisA-budB-ilvC(B.s)-ilvD-kivD-bdhB. This plasmid is prepared from the E. coli transformants and transformed into electrocompetent E. faecalis V583 cells by electroporation using methods known in the art (Aukrust, T. W., et al. In: *Electroporation Protocols for Microorganisms*; Nickoloff, J. A., Ed.; *Methods in Molecular Biology*, Vol. 47; Humana Press, Inc., Totowa, N.J., 1995, pp 217-226), resulting in E. faecalis V583/pTRKH3-PnisA-budB-ilvC(B.s)-ilvD-kivD-bdhB.

The second plasmid containing nisA regulatory genes, nisR and nisK, the add9 spectinomycin resistance gene, and the pSH71 origin of replication is transformed into E. faecalis V583/pTRKH3-PnisA-budB-ilvC(B.s)-ilvD-kivD-bdhB by electroporation. The plasmid containing pSH71 origin of replication is compatible with pAMJ31 derivatives in E. faecalis (Eichenbaum et al., supra). Double drug resistant transformants are selected on LB agar plates containing erythromycin (25 µg/mL) and spectinomycin (100 µg/mL), grown at 37° C.

The resulting E. faecalis strain V5838 harboring two plasmids, i.e., an expression plasmid (pTRKH3-PnisA-budB-ilvC(B.s)-ilvD-kivD-bdhB) and a regulatory plasmid (pSH71-nisRK), is inoculated into a 250 mL shake flask containing 50 mL of Todd-Hewitt broth supplemented with yeast extract (0.2%) (Fischetti et al., *J. Exp. Med.* 161:1384-1401 (1985)), nisin (20 µg/mL) (Eichenbaum et al., supra), erythromycin (25 µg/mL), and spectinomycin (100 µg/mL). The flask is incubated without shaking at 37° C. for 18-24 h, after which time, isobutanol production is measured by HPLC or GC analysis, as described in the General Methods section.

What is claimed is:

1. A method comprising:
   (a) determining the acetohydroxy acid isomeroreductase (KARI) activity of a cell free extract prepared from a host cell expressing a heterologous KARI enzyme; and
   (b) expressing a heterologous DNA molecule encoding the KARI enzyme in a recombinant microorganism expressing an engineered isobutanol biosynthetic pathway,
   wherein the cell free extract comprises higher KARI activity than a control cell free extract prepared from a host cell not expressing the heterologous KARI enzyme, and wherein the recombinant microorganism is capable of bioproducing isobutanol suitable for use in fuel cells or vehicles.

2. The method of claim 1, wherein the host cell of (a) is *E. coli*.

3. The method of claim 1, wherein the recombinant microorganism is selected from the group consisting of: a bacterium, a cyanobacterium, a filamentous fungus and a yeast.

4. The method of claim 3, wherein the recombinant microorganism is yeast.

5. The method of claim 1, wherein the recombinant microorganism is *Saccharomyces cerevisiae*.

6. The method of claim 1, wherein the recombinant microorganism using glucose as a carbon source produces more isobutanol than a control microorganism not expressing the engineered biosynthetic isobutanol pathway.

7. The method of claim 1, wherein the recombinant microorganism comprises an inactivated gene that reduces yield loss from competing pathways for carbon flow.

8. The method of claim 1, wherein the engineered biosynthetic isobutanol pathway comprises an acetolactate synthase (ALS) enzyme, a KARI enzyme, an acetohydroxy acid dehydratase (DHAD) enzyme, a branched chain keto acid decarboxylase enzyme, and a branched-chain alcohol dehydrogenase (ADH) enzyme, each of which is encoded by a heterologous DNA molecule.

9. The method of claim 1, wherein the engineered biosynthetic isobutanol pathway comprises an ALS enzyme, a KARI enzyme, a DHAD enzyme, a branched-chain keto acid dehydrogenase enzyme, an acylating aldehyde dehydrogenase enzyme, and an ADH enzyme, each of which is encoded by a heterologous DNA molecule.

10. The method of claim 1, wherein the engineered biosynthetic isobutanol pathway comprises an ALS enzyme, a KARI enzyme, a DHAD enzyme, at least one of a transaminase enzyme and a valine dehydrogenase enzyme, a valine decarboxylase enzyme, an omega transaminase enzyme, and an ADH enzyme, each of which is encoded by a heterologous DNA molecule.

11. The method of claim 8, wherein the branched chain keto acid decarboxylase enzyme has 50-200-fold preference for ketoisovalerate over pyruvate.

12. The method of claim 8, wherein the ALS, KARI, DHAD, branched chain keto acid decarboxylase, and ADH enzymes each lack a mitochondrial targeting sequence.

13. The method of claim 8, wherein the ALS enzyme has an EC number of 2.2.1.6, the KARI enzyme has an EC number of 1.1.1.86, the DHAD enzyme has an EC number of 4.2.1.9, the branched chain keto acid decarboxylase enzyme has an EC number of 4.1.1.72, and the ADH enzyme has an EC number of 1.1.1.1, 1.1.1.2, or 1.1.1.265.

14. The method of claim 13, wherein the ALS enzyme has an amino acid sequence selected from SEQ ID NOs: 2, 178, and 180.

15. The method of claim 13, wherein the KARI enzyme has an amino acid sequence selected from SEQ ID NOs: 4, 181, 183, and 185.

16. The method of claim 13, wherein the DHAD enzyme has an amino acid sequence selected from SEQ ID NOs: 6, 186, 188, and 190.

17. The method of claim 13, wherein the branched chain keto acid decarboxylase enzyme has an amino acid sequence selected from SEQ ID NOs: 8, 193, 195, and 197.

18. The method of claim 1, wherein the recombinant microorganism is capable of bioproducing isobutanol as a single product.

* * * * *

SEQUENCE LISTING

<160> NUMBER OF SEQ ID NOS: 267

<210> SEQ ID NO 1
<211> LENGTH: 1680
<212> TYPE: DNA
<213> ORGANISM: K. pneumoniae

<400> SEQUENCE: 1

```
atggacaaac agtatccggt acgccagtgg gcgcacggcg ccgatctcgt cgtcagtcag      60
ctggaagctc agggagtacg ccaggtgttc ggcatcccog gcgccaaaat cgacaaggtc     120
tttgattcac tgctggattc ctccattcgc attattccgg tacgccacga agccaacgcc     180
gcatttatgg ccgccgccgt cggacgcatt accggcaaag cgggcgtggc gctggtcacc     240
tccggtccgg gctgttccaa cctgatcacc ggcatggcca ccgcgaacag cgaaggcgac     300
ccggtggtgg ccctgggcgg cgcggtaaaa cgcgccgata aagcgaagca ggtccaccag     360
agtatggata cggtggcgat gttcagcccg gtcaccaaat acgccatcga ggtgacggcg     420
ccggatgcgc tggcggaagt ggtctccaac gccttccgcg ccgccgagca gggccggccg     480
ggcagcgcgt tcgttagcct gccgcaggat gtggtcgatg gccccggtcag cggcaaagtg     540 ctgccggcca gcggggcccc gcagatgggc gccgcgccgg atgatgccat cgaccaggtg     600
gcgaagctta tcgcccaggc gaagaacccg atcttcctgc tcggcctgat ggccagccag     660
ccggaaaaca gcaaggcgct gcgccgtttg ctggagacca gccatattcc agtcaccagc     720
acctatcagg ccgccggagc ggtgaatcag gataacttct ctcgcttcgc cggccgggtt     780
gggctgttta acaaccaggc cggggaccgt ctgctgcagc tcgccgacct ggtgatctgc     840
atcggctaca gcccggtgga atacgaaccg gcgatgtgga acagcggcaa cgcgacgctg     900
gtgcacatcg acgtgctgcc cgcctatgaa gagcgcaact acacccccgga tgtcgagctg     960 gtgggcgata tcgccggcac tctcaacaag ctggcgcaaa atatcgatca tcggctggtg    1020
ctctccccgc aggcggcgga gatcctccgc gaccgccagc accagcgcga gctgctggac    1080
cgccgcggcg cgcagctcaa ccagtttgcc ctgcatcccc tgcgcatcgt tcgcgccatg    1140
caggatatcg tcaacagcga cgtcacgttg accgtggaca tgggcagctt ccatatctgg    1200
attgcccgct acctgtacac gttccgcgcc cgtcaggtga tgatctccaa cggccagcag    1260
accatgggcg tcgccctgcc ctgggctatc ggcgcctggc tggtcaatcc tgagcgcaaa    1320
gtggtctccg tctccggcga cggcggcttc ctgcagtcga gcatggagct ggagaccgcc    1380
gtccgcctga aagccaacgt gctgcatctt atctgggtcg ataacggcta caatgtc       1440
```

```
gctatccagg aagagaaaaa atatcagcgc ctgtccggcg tcgagtttgg gccgatggat    1500
tttaaagcct atgccgaatc cttcggcgcg aaagggtttg ccgtggaaag cgccgaggcg    1560
ctggagccga ccctgcgcgc ggcgatggac gtcgacggcc cggcggtagt ggccatcccg    1620
gtggattatc gcgataaccc gctgctgatg ggccagctgc atctgagtca gattctgtaa    1680
```

<210> SEQ ID NO 2
<211> LENGTH: 559
<212> TYPE: PRT
<213> ORGANISM: K. pneumoniae

<400> SEQUENCE: 2

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Ile Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335
```

```
His Arg Leu Val Leu Ser Pro Gln Ala Ala Glu Ile Leu Arg Asp Arg
                340                 345                 350

Gln His Gln Arg Glu Leu Leu Asp Arg Arg Gly Ala Gln Leu Asn Gln
            355                 360                 365

Phe Ala Leu His Pro Leu Arg Ile Val Arg Ala Met Gln Asp Ile Val
        370                 375                 380

Asn Ser Asp Val Thr Leu Thr Val Asp Met Gly Ser Phe His Ile Trp
385                 390                 395                 400

Ile Ala Arg Tyr Leu Tyr Thr Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu Arg Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555

<210> SEQ ID NO 3
<211> LENGTH: 1476
<212> TYPE: DNA
<213> ORGANISM: E. coli

<400> SEQUENCE: 3
atggctaact acttcaatac actgaatctg cgccagcagc tggcacagct gggcaaatgt      60
cgctttatgg ccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
ctgatgaaag acggcgcggc gctgggctac tcgcacggtt tcaacatcgt cgaagtgggc     420
gagcagatcc gtaaagatat caccgtagtg atggttgcgc gaaatgccc aggcaccgaa     480 gtgcgtgaag agtacaaacg tgggttcggc gtaccgacgc tgattgccgt tcacccggaa     540
aacgatccga aggcgaagg catggcgatt gccaaagcct gggcggctgc aaccggtggt     600
caccgtgcgg gtgtgctgga atcgtccttc gttgcggaag tgaaatctga cctgatgggc     660
gagcaaacca tcctgtgcgg tatgttgcag ctggctctc tgctgtgctt cgacaagctg     720
gtggaagaag gtaccgatcc agcatacgca gaaaaactga ttcagttcgg ttgggaaacc     780
atcaccgaag cactgaaaca gggcggcatc accctgatga tggaccgtct ctctaacccg     840
```

-continued

```
gcgaaactgc gtgcttatgc gctttctgaa cagctgaaag agatcatggc acccctgttc      900
cagaaacata tggacgacat catctccggc gaattctctt ccggtatgat ggcggactgg      960
gccaacgatg ataagaaact gctgacctgg cgtgaagaga ccggcaaaac cgcgtttgaa     1020
accgcgccgc agtatgaagg caaaatcggc gagcaggagt acttcgataa aggcgtactg     1080
atgattgcga tggtgaaagc gggcgttgaa ctggcgttcg aaaccatggt cgattccggc     1140
atcattgaag agtctgcata ttatgaatca ctgcacgagc tgccgctgat tgccaacacc     1200
atcgcccgta agcgtctgta cgaaatgaac gtggttatct ctgataccgc tgagtacggt     1260
aactatctgt tctcttacgc ttgtgtgccg ttgctgaaac cgtttatggc agagctgcaa     1320
ccgggcgacc tgggtaaagc tattccggaa ggcgcggtag ataacgggca actgcgtgat     1380
gtgaacgaag cgattcgcag ccatgcgatt gagcaggtag gtaagaaact gcgcggctat     1440
atgacagata tgaaacgtat tgctgttgcg ggttaa                               1476
```

<210> SEQ ID NO 4
<211> LENGTH: 491
<212> TYPE: PRT
<213> ORGANISM: E. coli

<400> SEQUENCE: 4

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
```

```
                    260                 265                 270
Met Met Asp Arg Leu Ser Asn Pro Ala Lys Leu Arg Ala Tyr Ala Leu
            275                 280                 285

Ser Glu Gln Leu Lys Glu Ile Met Ala Pro Leu Phe Gln Lys His Met
        290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
        370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 5
<211> LENGTH: 1851
<212> TYPE: DNA
<213> ORGANISM: E. coli

<400> SEQUENCE: 5
atgcctaagt accgttccgc caccaccact catggtcgta atatggcggg tgctcgtgcg        60
ctgtggcgcg ccaccggaat gaccgacgcc gatttcggta agccgattat cgcggttgtg       120
aactcgttca cccaatttgt accgggtcac gtccatctgc gcgatctcgg taaactggtc       180
gccgaacaaa ttgaagcggc tggcggcgtt gccaaagagt tcaacaccat tgcggtggat       240
gatgggattg ccatgggcca cggggggatg ctttattcac tgccatctcg cgaactgatc       300
gctgattccg ttgagtatat ggtcaacgcc cactgcgccg acgccatggt ctgcatctct       360
aactgcgaca aaatcacccc gggggatgctg atggcttccc tgcgcctgaa tattccggtg       420
atctttgttt ccggcggccc cgatggaggcc gggaaaacca acttccga tcagatcatc       480 aagctcgatc tggttgatgc gatgatccag ggcgcagacc cgaaagtatc tgactcccag       540
agcgatcagg ttgaacgttc cgcgtgtccg acctgcggtt cctgctccgg gatgtttacc       600
gctaactcaa tgaactgcct gaccgaagcg ctgggcctgt cgcagccggg caacggctcg       660
ctgctggcaa cccacgccga ccgtaagcag ctgttcctta tgctggtaa acgcattgtt       720 gaattgacca acgttattac gagcaaaac gacgaaagtg cactgccgcg taatatcgcc       780
agtaaggcgg cgtttgaaaa cgccatgacg ctggatatcg cgatgggtgg atcgactaac       840
```

-continued

```
accgtacttc acctgctggc ggcggcgcag gaagcggaaa tcgacttcac catgagtgat      900
atcgataagc tttcccgcaa ggttccacag ctgtgtaaag ttgcgccgag cacccagaaa      960
taccatatgg aagatgttca ccgtgctggt ggtgttatcg gtattctcgg cgaactggat     1020
cgcgcggggt tactgaaccg tgatgtgaaa aacgtacttg gcctgacgtt gccgcaaacg     1080
ctggaacaat acgacgttat gctgacccag gatgacgcgg taaaaaatat gttccgcgca     1140
ggtcctgcag gcattcgtac cacacaggca ttctcgcaag attgccgttg ggatacgctg     1200
gacgacgatc gcgccaatgg ctgtatccgc tcgctggaac acgcctacag caaagacggc     1260
ggcctggcgg tgctctacgg taactttgcg gaaaacggct gcatcgtgaa aacggcaggc     1320
gtcgatgaca gcatcctcaa attcaccggc ccggcgaaag tgtacgaaag ccaggacgat     1380
gcggtagaag cgattctcgg cggtaaagtt gtcgccggag atgtggtagt aattcgctat     1440
gaaggcccga aaggcggtcc ggggatgcag gaaatgctct acccaaccag cttcctgaaa     1500
tcaatgggtc tcggcaaagc ctgtgcgctg atcaccgacg tcgtttctc tggtggcacc      1560 tctggtcttt ccatcggcca cgtctcaccg gaagcggcaa gcggcggcag cattggcctg     1620
attgaagatg gtgacctgat cgctatcgac atcccgaacc gtggcattca gttacaggta     1680
agcgatgccg aactggcggc gcgtcgtgaa gcgcaggacg ctcgaggtga caaagcctgg     1740
acgccgaaaa atcgtgaacg tcaggtctcc tttgccctgc gtgcttatgc cagcctggca     1800
accagcgccg acaaaggcgc ggtgcgcgat aaatcgaaac tggggggtta a              1851
```

<210> SEQ ID NO 6
<211> LENGTH: 616
<212> TYPE: PRT
<213> ORGANISM: E. coli

<400> SEQUENCE: 6

```
Met Pro Lys Tyr Arg Ser Ala Thr Thr Thr His Gly Arg Asn Met Ala
1               5                  10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190
```

```
Gly Ser Cys Ser Gly Met Phe Thr Ala Asn Ser Met Asn Cys Leu Thr
            195                 200                 205
Glu Ala Leu Gly Leu Ser Gln Pro Gly Asn Gly Ser Leu Leu Ala Thr
    210                 215                 220
His Ala Asp Arg Lys Gln Leu Phe Leu Asn Ala Gly Lys Arg Ile Val
225                 230                 235                 240
Glu Leu Thr Lys Arg Tyr Tyr Glu Gln Asn Asp Glu Ser Ala Leu Pro
                245                 250                 255
Arg Asn Ile Ala Ser Lys Ala Ala Phe Glu Asn Ala Met Thr Leu Asp
            260                 265                 270
Ile Ala Met Gly Gly Ser Thr Asn Thr Val Leu His Leu Leu Ala Ala
        275                 280                 285
Ala Gln Glu Ala Glu Ile Asp Phe Thr Met Ser Asp Ile Asp Lys Leu
    290                 295                 300
Ser Arg Lys Val Pro Gln Leu Cys Lys Val Ala Pro Ser Thr Gln Lys
305                 310                 315                 320
Tyr His Met Glu Asp Val His Arg Ala Gly Val Ile Gly Ile Leu
                325                 330                 335
Gly Glu Leu Asp Arg Ala Gly Leu Leu Asn Arg Asp Val Lys Asn Val
            340                 345                 350
Leu Gly Leu Thr Leu Pro Gln Thr Leu Glu Gln Tyr Asp Val Met Leu
        355                 360                 365
Thr Gln Asp Asp Ala Val Lys Asn Met Phe Arg Ala Gly Pro Ala Gly
    370                 375                 380
Ile Arg Thr Thr Gln Ala Phe Ser Gln Asp Cys Arg Trp Asp Thr Leu
385                 390                 395                 400
Asp Asp Asp Arg Ala Asn Gly Cys Ile Arg Ser Leu Glu His Ala Tyr
                405                 410                 415
Ser Lys Asp Gly Gly Leu Ala Val Leu Tyr Gly Asn Phe Ala Glu Asn
            420                 425                 430
Gly Cys Ile Val Lys Thr Ala Gly Val Asp Asp Ser Ile Leu Lys Phe
        435                 440                 445
Thr Gly Pro Ala Lys Val Tyr Glu Ser Gln Asp Asp Ala Val Glu Ala
    450                 455                 460
Ile Leu Gly Gly Lys Val Val Ala Gly Asp Val Val Ile Arg Tyr
465                 470                 475                 480
Glu Gly Pro Lys Gly Gly Pro Gly Met Gln Glu Met Leu Tyr Pro Thr
                485                 490                 495
Ser Phe Leu Lys Ser Met Gly Leu Gly Lys Ala Cys Ala Leu Ile Thr
            500                 505                 510
Asp Gly Arg Phe Ser Gly Gly Thr Ser Gly Leu Ser Ile Gly His Val
        515                 520                 525
Ser Pro Glu Ala Ala Ser Gly Gly Ser Ile Gly Leu Ile Glu Asp Gly
    530                 535                 540
Asp Leu Ile Ala Ile Asp Ile Pro Asn Arg Gly Ile Gln Leu Gln Val
545                 550                 555                 560
Ser Asp Ala Glu Leu Ala Ala Arg Arg Glu Ala Gln Asp Ala Arg Gly
                565                 570                 575
Asp Lys Ala Trp Thr Pro Lys Asn Arg Glu Arg Gln Val Ser Phe Ala
            580                 585                 590
Leu Arg Ala Tyr Ala Ser Leu Ala Thr Ser Ala Asp Lys Gly Ala Val
        595                 600                 605
Arg Asp Lys Ser Lys Leu Gly Gly
```

<210> SEQ ID NO 7
<211> LENGTH: 1662
<212> TYPE: DNA
<213> ORGANISM: Lactococcus lactis

<400> SEQUENCE: 7

```
tctagacata tgtatactgt gggggattac ctgctggatc gcctgcacga actggggatt      60
gaagaaattt tcggtgtgcc aggcgattat aacctgcagt tcctggacca gattatctcg     120
cacaaagata tgaagtgggt cggtaacgcc aacgaactga cgcgagcta tatggcagat      180
ggttatgccc gtaccaaaaa agctgctgcg tttctgacga cctttggcgt tggcgaactg     240
agcgccgtca acggactggc aggaagctac gccgagaacc tgccagttgt cgaaattgtt     300
gggtcgccta cttctaaggt tcagaatgaa ggcaaatttg tgcaccatac tctggctgat     360
ggggatttta acattttat gaaaatgcat gaaccggtta ctgcggcccg cacgctgctg     420
acagcagaga atgctacggt tgagatcgac cgcgtcctgt ctgcgctgct gaaagagcgc     480
aagccggtat atatcaatct gcctgtcgat gttgccgcag cgaaagccga aaagccgtcg     540
ctgccactga aaaagaaaa cagcacctcc aatacatcgg accaggaaat tctgaataaa      600
atccaggaat cactgaagaa tgcgaagaaa ccgatcgtca tcaccggaca tgagatcatc     660
tcttttggcc tggaaaaaac ggtcacgcag ttcatttcta agaccaaact gcctatcacc     720
accctgaact tcggcaaatc tagcgtcgat gaagcgctgc cgagttttct gggtatctat     780
aatggtaccc tgtccgaacc gaacctgaaa gaattcgtcg aaagcgcgga ctttatcctg     840
atgctgggcg tgaaactgac ggatagctcc acaggcgcat ttacccacca tctgaacgag     900
aataaaatga tttccctgaa tatcgacgaa ggcaaaatct ttaacgagcg catccagaac     960
ttcgatttg aatctctgat tagttcgctg ctggatctgt ccgaaattga gtataaaggt    1020
aaatatattg ataaaaaaca ggaggatttt gtgccgtcta atgcgctgct gagtcaggat    1080
cgtctgtggc aagccgtaga aaacctgaca cagtctaatg aaacgattgt tgcggaacag    1140
ggaacttcat ttttcggcgc ctcatccatt tttctgaaat ccaaaagcca tttcattggc    1200
caaccgctgt gggggagtat tggttatacc tttccggcgg cgctgggttc acagattgca    1260
gataaggaat cacgccatct gctgtttatt ggtgacggca gcctgcagct gactgtccag    1320
gaactggggc tggcgatccg tgaaaaaatc aatccgattt gctttatcat caataacgac    1380
ggctacaccg tcgaacgcga aattcatgga ccgaatcaaa gttacaatga catcccgatg    1440
tggaactata gcaaactgcc ggaatccttt ggcgcgacag aggatcgcgt ggtgagtaaa    1500
attgtgcgta cggaaaacga atttgtgtcg gttatgaaag aagcgcaggc tgacccgaat    1560
cgcatgtatt ggattgaact gatcctggca aaagaaggcg caccgaaagt tctgaaaaag    1620
atggggaaac tgtttgcgga gcaaaataaa agctaaggat cc                       1662
```

<210> SEQ ID NO 8
<211> LENGTH: 548
<212> TYPE: PRT
<213> ORGANISM: Lactococcus lactis

<400> SEQUENCE: 8

```
Met Tyr Thr Val Gly Asp Tyr Leu Leu Asp Arg Leu His Glu Leu Gly
1               5                   10                  15
Ile Glu Glu Ile Phe Gly Val Pro Gly Asp Tyr Asn Leu Gln Phe Leu
            20                  25                  30
```

```
Asp Gln Ile Ile Ser His Lys Asp Met Lys Trp Val Gly Asn Ala Asn
         35                  40                  45

Glu Leu Asn Ala Ser Tyr Met Ala Asp Gly Tyr Ala Arg Thr Lys Lys
 50                      55                  60

Ala Ala Ala Phe Leu Thr Thr Phe Gly Val Gly Glu Leu Ser Ala Val
 65              70                  75                      80

Asn Gly Leu Ala Gly Ser Tyr Ala Glu Asn Leu Pro Val Val Glu Ile
                 85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
        130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
                195                 200                 205

Ile Val Ile Thr Gly His Glu Ile Ile Ser Phe Gly Leu Glu Lys Thr
            210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445
```

```
Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545

<210> SEQ ID NO 9
<211> LENGTH: 1164
<212> TYPE: DNA
<213> ORGANISM: E. coli

<400> SEQUENCE: 9
atgaacaact ttaatctgca caccccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaacccggct tatgaaacgc tgatgaacgc cgtgaaactg     240
gttcgcgaac agaaagtgac tttcctgctg gcggttggcg gcggttctgt actggacggc     300
accaaattta tcgccgcagc ggctaactat ccggaaaata tcgatccgtg cacattctg      360 caaacgggcg gtaaagagat taaaagcgcc atcccgatgg gctgtgtgct gacgctgcca     420
gcaaccggtt cagaatccaa cgcaggcgcg gtgatctccc gtaaaaccac aggcgacaag     480
caggcgttcc attctgccca tgttcagccg gtatttgccg tgctcgatcc ggtttatacc     540
tacaccctgc cgccgcgtca ggtggctaac ggcgtagtgg acgcctttgt acacaccgtg     600
gaacagtatg ttaccaaacc ggttgatgcc aaaattcagg accgtttcgc agaaggcatt     660
ttgctgacgc taatcgaaga tggtccgaaa gccctgaaag agccagaaaa ctacgatgtg     720
cgcgccaacg tcatgtgggc ggcgactcag gcgctgaacg ttttgattgg cgctggcgta     780
ccgcaggact gggcaacgca tatgctgggc acgaactga ctgcgatgca cggtctggat      840
cacgcgcaaa cactggctat cgtcctgcct gcactgtgga tgaaaaacg cgataccaag     900 cgcgctaagc tgctgcaata tgctgaacgc gtctggaaca tcactgaagg ttccgatgat     960
gagcgtattg acgccgcgat tgccgcaacc cgcaatttct tgagcaatt aggcgtgccg    1020 acccacctct ccgactacgg tctggacggc agctccatcc cggctttgct gaaaaaactg    1080
gaagagcacg gcatgaccca actgggcgaa atcatgaca ttacgttgga tgtcagccgc     1140
cgtatatacg aagccgcccg ctaa                                           1164

<210> SEQ ID NO 10
<211> LENGTH: 387
<212> TYPE: PRT
<213> ORGANISM: E. coli

<400> SEQUENCE: 10

Met Asn Asn Phe Asn Leu His Thr Pro Thr Arg Ile Leu Phe Gly Lys
1               5                   10                  15
```

Gly Ala Ile Ala Gly Leu Arg Glu Gln Ile Pro His Asp Ala Arg Val
                20                  25                  30

Leu Ile Thr Tyr Gly Gly Ser Val Lys Thr Gly Val Leu Asp
        35                  40                  45

Gln Val Leu Asp Ala Leu Lys Gly Met Asp Val Leu Glu Phe Gly Gly
 50                  55                  60

Ile Glu Pro Asn Pro Ala Tyr Glu Thr Leu Met Asn Ala Val Lys Leu
 65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
370                 375                 380

Ala Ala Arg
385

<210> SEQ ID NO 11
<211> LENGTH: 29
<212> TYPE: DNA
<213> ORGANISM: Artificial Sequence
<220> FEATURE:

-continued

```
<223> OTHER INFORMATION: Primer

<400> SEQUENCE: 11
caccatggac aaacagtatc cggtacgcc                                29

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
cgaagggcga tagctttacc aatcc                                    25

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
caccatggct aactacttca atacactga                                29

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
ccaggagaag gccttgagtg ttttctcc                                 28

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
caccatgcct aagtaccgtt ccgccacca                                29

<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
cgcagcactg ctcttaaata ttcggc                                   26

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
caccatgaac aactttaatc tgcacaccc                                29
```

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18
caccatgaac aactttaatc tgcacaccc                                29

<210> SEQ ID NO 19
<211> LENGTH: 45
<212> TYPE: DNA
<213> ORGANISM: Artificial Sequence
<220> FEATURE:
<223> OTHER INFORMATION: Primer

<400> SEQUENCE: 19
gcatgcctta agaaaggagg ggggtcacat ggacaaacag tatcc              45

<210> SEQ ID NO 20
<211> LENGTH: 39
<212> TYPE: DNA
<213> ORGANISM: Artificial Sequence
<220> FEATURE:
<223> OTHER INFORMATION: Primer

<400> SEQUENCE: 20
atgcatttaa ttaattacag aatctgactc agatgcagc                     39

<210> SEQ ID NO 21
<211> LENGTH: 45
<212> TYPE: DNA
<213> ORGANISM: Artificial Sequence
<220> FEATURE:
<223> OTHER INFORMATION: Primer

<400> SEQUENCE: 21
gtcgacgcta gcaaaggagg gaatcaccat ggctaactac ttcaa              45

<210> SEQ ID NO 22
<211> LENGTH: 31
<212> TYPE: DNA
<213> ORGANISM: Artificial Sequence
<220> FEATURE:
<223> OTHER INFORMATION: Primer

<400> SEQUENCE: 22
tctagattaa cccgcaacag caatacgttt c                             31

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
tctagaaaag gaggaataaa gtatgcctaa gtaccgttc                     39

<210> SEQ ID NO 24
<211> LENGTH: 31
<212> TYPE: DNA
<213> ORGANISM: Artificial Sequence
<220> FEATURE:
<223> OTHER INFORMATION: Primer

```
<400> SEQUENCE: 24
ggatccttat taaccccca gtttcgattt a                              31

<210> SEQ ID NO 25
<211> LENGTH: 39
<212> TYPE: DNA
<213> ORGANISM: Artificial Sequence
<220> FEATURE:
<223> OTHER INFORMATION: Primer

<400> SEQUENCE: 25
ggatccaaag gaggctagac atatgtatac tgtggggga                     39

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
gagctcttag cttttatttt gctccgcaaa c                             31

<210> SEQ ID NO 27
<211> LENGTH: 39
<212> TYPE: DNA
<213> ORGANISM: Artificial Sequence
<220> FEATURE:
<223> OTHER INFORMATION: Primer

<400> SEQUENCE: 27
gagctcaaag gaggagcaag taatgaacaa ctttaatct                     39

<210> SEQ ID NO 28
<211> LENGTH: 43
<212> TYPE: DNA
<213> ORGANISM: Artificial Sequence
<220> FEATURE:
<223> OTHER INFORMATION: Primer

<400> SEQUENCE: 28
gaattcacta gtcctaggtt agcgggcggc ttcgtatata cgg                43

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
caacattagc gattttcttt tctct                                    25

<210> SEQ ID NO 30
<211> LENGTH: 45
<212> TYPE: DNA
<213> ORGANISM: Artificial Sequence
<220> FEATURE:
<223> OTHER INFORMATION: Primer

<400> SEQUENCE: 30
catgaagctt actagtgggc ttaagttttg aaaataatga aaact              45

<210> SEQ ID NO 31
<211> LENGTH: 61
```

```
<212> TYPE: DNA
<213> ORGANISM: Artificial Sequence
<220> FEATURE:
<223> OTHER INFORMATION: Primer N110.2

<400> SEQUENCE: 31
gagctcacta gtcaattgta agtaagtaaa aggaggtggg tcacatggac aaacagtatc    60
c                                                                   61

<210> SEQ ID NO 32
<211> LENGTH: 50
<212> TYPE: DNA
<213> ORGANISM: Artificial Sequence
<220> FEATURE:
<223> OTHER INFORMATION: Primer N111.2

<400> SEQUENCE: 32
ggatccgatc gacttaagcc tcagcttaca gaatctgact cagatgcagc               50

<210> SEQ ID NO 33
<211> LENGTH: 44
<212> TYPE: DNA
<213> ORGANISM: Artificial Sequence
<220> FEATURE:
<223> OTHER INFORMATION: Primer N112.2

<400> SEQUENCE: 33
gagctcctta agaaggaggt aatcaccatg gctaactact tcaa                     44

<210> SEQ ID NO 34
<211> LENGTH: 51
<212> TYPE: DNA
<213> ORGANISM: Artificial Sequence
<220> FEATURE:
<223> OTHER INFORMATION: Primer N113.2

<400> SEQUENCE: 34
ggatccgatc gagctagcgc ggccgcttaa cccgcaacag caatacgttt c              51

<210> SEQ ID NO 35
<211> LENGTH: 44
<212> TYPE: DNA
<213> ORGANISM: Artificial Sequence
<220> FEATURE:
<223> OTHER INFORMATION: Primer N114.2

<400> SEQUENCE: 35
gagctcgcta gcaaggaggt ataaagtatg cctaagtacc gttc                     44

<210> SEQ ID NO 36
<211> LENGTH: 52
<212> TYPE: DNA
<213> ORGANISM: Artificial Sequence
<220> FEATURE:
<223> OTHER INFORMATION: Primer N115.2

<400> SEQUENCE: 36
ggatccgatc gattaattaa cctaaggtta ttaaccccccc agtttcgatt ta            52

<210> SEQ ID NO 37
<211> LENGTH: 46
<212> TYPE: DNA
<213> ORGANISM: Artificial Sequence
<220> FEATURE:
<223> OTHER INFORMATION: Primer N116.2
```

```
<400> SEQUENCE: 37
gagctcttaa ttaaaaggag gttagacata tgtatactgt ggggga                    46

<210> SEQ ID NO 38
<211> LENGTH: 49
<212> TYPE: DNA
<213> ORGANISM: Artificial Sequence
<220> FEATURE:
<223> OTHER INFORMATION: Primer 117.2

<400> SEQUENCE: 38
ggatccagat ctcctaggac atgtttagct tttattttgc tccgcaaac                 49

<210> SEQ ID NO 39
<211> LENGTH: 3883
<212> TYPE: DNA
<213> ORGANISM: Escherichia coli

<400> SEQUENCE: 39
ctatattgct gaaggtacag gcgtttccat aactatttgc tcgcgttttt tactcaagaa     60
gaaaatgcca atagcaaca tcaggcagac aatacccgaa attgcgaaga aaactgtctg    120
gtagcctgcg tggtcaaaga gtatcccagt cggcgttgaa agcagcacaa tcccaagcga    180
actggcaatt tgaaaaccaa tcagaaagat cgtcgacgac aggcgcttat caaagtttgc    240
cacgctgtat ttgaagacgg atatgacaca agtggaacc tcaatggcat gtaacaactt    300
cactaatgaa ataatccagg ggttaacgaa cagcgcgcag gaaaggatac gcaacgccat    360
aatcacaact ccgataagta atgcattttt tggccctacc cgattcacaa agaaaggaat    420
aatcgccatg cacagcgctt cgagtaccac ctggaatgag ttgagataac catacaggcg    480
cgttcctaca tcgtgtgatt cgaataaacc tgaataaaag acaggaaaaa gttgttgatc    540
aaaaatgtta tagaaagacc acgtccccac aataaatatg acgaaaaccc agaagtttcg    600
atccttgaaa actgcgataa aatcctcttt ttttaccccct cccgcatctg ccgctacgca    660
ctggtgatcc ttatctttaa aacgcatgtt gatcatcata aatacagcgc caaatagcga    720
gaccaaccag aagttgatat ggggactgat actaaaaaat atgccggcaa agaacgcgcc    780
aatagcatag ccaaaagatc cccaggcgcg cgctgttcca tattcgaaat gaaaatttcg    840
cgccattttt tcggtgaagc tatcaagcaa accgcatccc gccagatacc ccaagccaaa    900
aaatagcgcc cccagaatta gacctacaga aaaattgctt tgcagtaacg gttcataaac    960
gtaaatcata aacggtccgg tcaagaccag gatgaaactc atacaccaga tgagcggttt   1020
cttcagaccg agtttatcct gaacgatgcc gtagaacatc ataaatagaa tgctggtaaa   1080
ctggttgacc gaataaagtg tacctaattc cgtccctgtc aaccctagat gtcctttcag   1140
ccaaatagcg tataacgacc accacagcga ccaggaaata aaaagagaa atgagtaact   1200 ggatgcaaaa cgatagtacg catttctgaa tggaatattc agtgccataa ttacctgcct   1260
gtcgttaaaa aattcacgtc ctatttagag ataagagcga cttcgccgtt tacttctcac   1320
tattccagtt cttgtcgaca tggcagcgct gtcattgccc cttttcgccgt tactgcaagc   1380 gctccgcaac gttgagcgag atcgataatt cgtcgcattt ctctctcatc tgtagataat   1440
cccgtagagg acagacctgt gagtaacccg gcaacgaacg catctcccgc cccgtgcta   1500 tcgacacaat tcacagacat tccagcaaaa tggtgaactt gtcctcgata acagaccacc   1560
accccttctg caccttttagt caccaacagc atggcgatct catactcttt tgccagggcg   1620
catatatcct gatcgttctg tgtttttcca ctgataagtc gccattcttc ttccgagagc   1680
```

```
ttgacgacat ccgccagttg tagcgcctgc cgcaaacaca agcggagcaa atgctcgtct    1740
tgccatagat cttcacgaat attaggatcg aagctgacaa aacctccggc atgccggatc    1800
gccgtcatcg cagtaaatgc gctggtacgc gaaggctcgg cagacaacgc aattgaacag    1860
agatgtaacc attcgccatg tcgccagcag ggcaagtctg tcgtctctaa aaaaagatcg    1920
gcactggggc ggaccataaa cgtaaatgaa cgttcccctt gatcgttcag atcgacaagc    1980
accgtggatg tccggtgcca ttcatcttgc ttcagatacg tgatatcgac tccctcagtt    2040
agcagcgttc tttgcattaa cgcaccaaaa ggatcatccc ccacccgacc tataaaccca    2100
cttgttccgc ctaatctggc gattcccacc gcaacgttag ctggcgcgcc gccaggacaa    2160
ggcagtaggc gcccgtctga ttctggcaag agatctacga ccgcatcccc taaaacccat    2220
actttggctg acattttttt cccttaaatt catctgagtt acgcatagtg ataaacctct    2280
ttttcgcaaa atcgtcatgg atttactaaa acatgcatat tcgatcacaa aacgtcatag    2340
ttaacgttaa catttgtgat attcatcgca tttatgaaag taagggactt tatttttata    2400
aaagttaacg ttaacaattc accaaatttg cttaaccagg atgattaaaa tgacgcaatc    2460
tcgattgcat gcggcgcaaa acgccctagc aaaacttcat gagcaccggg gtaacacttt    2520
ctatccccat tttcacctcg cgcctcctgc cgggtggatg aacgatccaa acggcctgat    2580
ctggtttaac gatcgttatc acgcgtttta tcaacatcat ccgatgagcg aacactgggg    2640
gccaatgcac tggggacatg ccaccagcga cgatatgatc cactggcagc atgagcctat    2700
tgcgctagcg ccaggagacg ataatgacaa agacgggtgt ttttcaggta gtgctgtcga    2760
tgacaatggt gtcctctcac ttatctacac cggacacgtc tggctcgatg gtgcaggtaa    2820
tgacgatgca attcgcgaag tacaatgtct ggctaccagt cgggatggta ttcatttcga    2880
gaaacagggt gtgatcctca ctccaccaga aggaatcatg cacttccgcg atcctaaagt    2940
gtggcgtgaa gccgacacat ggtggatggt agtcggggcg aaagatccag caacacggg    3000 gcagatcctg ctttatcgcg gcagttcgtt gcgtgaatgg accttcgatc gcgtactggc    3060
ccacgctgat gcgggtgaaa gctatatgtg ggaatgtccg gacttttca gccttggcga    3120 tcagcattat ctgatgtttt ccccgcaggg aatgaatgcc gagggataca gttaccgaaa    3180
tcgctttcaa agtggcgtaa tacccggaat gtggtcgcca ggacgacttt ttgcacaatc    3240
cgggcatttt actgaacttg ataacgggca tgacttttat gcaccacaaa gcttttagc    3300 gaaggatggt cggcgtattg ttatcggctg gatggatatg tgggaatcgc caatgccctc    3360
aaaacgtgaa ggatgggcag gctgcatgac gctggcgcgc gagctatcag agagcaatgg    3420
caaacttcta caacgcccgg tacacgaagc tgagtcgtta cgccagcagc atcaatctgt    3480
ctctccccgc acaatcagca ataaatatgt tttgcaggaa aacgcgcaag cagttgagat    3540
tcagttgcag tgggcgctga agaacagtga tgccgaacat tacggattac agctcggcac    3600
tggaatgcgg ctgtatattg ataaccaatc tgagcgactt gttttgtggc ggtattaccc    3660
acacgagaat ttagacggct accgtagtat tcccctcccg cagcgtgaca cgctcgccct    3720
aaggatattt atcgatacat catccgtgga agtatttatt aacgacgggg aagcggtgat    3780
gagtagtcga atctatccgc agccagaaga acgggaactg tcgctttatg cctcccacgg    3840
agtggctgtg ctgcaacatg gagcactctg gctactgggt taa    3883
```

<210> SEQ ID NO 40
<211> LENGTH: 19
<212> TYPE: DNA

```
<213> ORGANISM: Artificial Sequence
<220> FEATURE:
<223> OTHER INFORMATION: Primer N130SeqF1

<400> SEQUENCE: 40
tgttccaacc tgatcaccg                                               19

<210> SEQ ID NO 41
<211> LENGTH: 18
<212> TYPE: DNA
<213> ORGANISM: Artificial Sequence
<220> FEATURE:
<223> OTHER INFORMATION: Primer N130SeqF2

<400> SEQUENCE: 41
ggaaaacagc aaggcgct                                                18

<210> SEQ ID NO 42
<211> LENGTH: 18
<212> TYPE: DNA
<213> ORGANISM: Artificial Sequence
<220> FEATURE:
<223> OTHER INFORMATION: Primer N130SeqF3

<400> SEQUENCE: 42
cagctgaacc agtttgcc                                                18

<210> SEQ ID NO 43
<211> LENGTH: 19
<212> TYPE: DNA
<213> ORGANISM: Artificial Sequence
<220> FEATURE:
<223> OTHER INFORMATION: Primer N130SeqF4

<400> SEQUENCE: 43
aaaataccag cgcctgtcc                                               19

<210> SEQ ID NO 44
<211> LENGTH: 18
<212> TYPE: DNA
<213> ORGANISM: Artificial Sequence
<220> FEATURE:
<223> OTHER INFORMATION: Primer N130SeqR1

<400> SEQUENCE: 44
tgaatggcca ccatgttg                                                18

<210> SEQ ID NO 45
<211> LENGTH: 18
<212> TYPE: DNA
<213> ORGANISM: Artificial Sequence
<220> FEATURE:
<223> OTHER INFORMATION: Primer N130SeqR2

<400> SEQUENCE: 45
gaggatctcc gccgcctg                                                18

<210> SEQ ID NO 46
<211> LENGTH: 18
<212> TYPE: DNA
<213> ORGANISM: Artificial Sequence
<220> FEATURE:
<223> OTHER INFORMATION: Primer N130SeqR3

<400> SEQUENCE: 46
aggccgagca ggaagatc                                                18
```

<210> SEQ ID NO 47
<211> LENGTH: 19
<212> TYPE: DNA
<213> ORGANISM: Artificial Sequence
<220> FEATURE:
<223> OTHER INFORMATION: Primer N130SeqR4

<400> SEQUENCE: 47
tgatcaggtt ggaacagcc                                                19

<210> SEQ ID NO 48
<211> LENGTH: 19
<212> TYPE: DNA
<213> ORGANISM: Artificial Sequence
<220> FEATURE:
<223> OTHER INFORMATION: Primer N131SeqF1

<400> SEQUENCE: 48
aagaactgat cccacaggc                                                19

<210> SEQ ID NO 49
<211> LENGTH: 19
<212> TYPE: DNA
<213> ORGANISM: Artificial Sequence
<220> FEATURE:
<223> OTHER INFORMATION: Primer N131SeqF2

<400> SEQUENCE: 49
atcctgtgcg gtatgttgc                                                19

<210> SEQ ID NO 50
<211> LENGTH: 18
<212> TYPE: DNA
<213> ORGANISM: Artificial Sequence
<220> FEATURE:
<223> OTHER INFORMATION: Primer N131Seqf3

<400> SEQUENCE: 50
attgcgatgg tgaaagcg                                                 18

<210> SEQ ID NO 51
<211> LENGTH: 19
<212> TYPE: DNA
<213> ORGANISM: Artificial Sequence
<220> FEATURE:
<223> OTHER INFORMATION: Primer N131SeqR1

<400> SEQUENCE: 51
atggtgttgg caatcagcg                                                19

<210> SEQ ID NO 52
<211> LENGTH: 18
<212> TYPE: DNA
<213> ORGANISM: Artificial Sequence
<220> FEATURE:
<223> OTHER INFORMATION: Primer N131SeqR2

<400> SEQUENCE: 52
gtgcttcggt gatggttt                                                 18

<210> SEQ ID NO 53
<211> LENGTH: 19
<212> TYPE: DNA
<213> ORGANISM: Artificial Sequence
<220> FEATURE:

```
<223> OTHER INFORMATION: Primer N131SeqR3

<400> SEQUENCE: 53
ttgaaaccgt gcgagtagc                                                19

<210> SEQ ID NO 54
<211> LENGTH: 19
<212> TYPE: DNA
<213> ORGANISM: Artificial Sequence
<220> FEATURE:
<223> OTHER INFORMATION: Primer N132SeqF1

<400> SEQUENCE: 54
tattcactgc catctcgcg                                                19

<210> SEQ ID NO 55
<211> LENGTH: 18
<212> TYPE: DNA
<213> ORGANISM: Artificial Sequence
<220> FEATURE:
<223> OTHER INFORMATION: Primer N132SeqF2

<400> SEQUENCE: 55
ccgtaagcag ctgttcct                                                 18

<210> SEQ ID NO 56
<211> LENGTH: 20
<212> TYPE: DNA
<213> ORGANISM: Artificial Sequence
<220> FEATURE:
<223> OTHER INFORMATION: Primer N132SeqF3

<400> SEQUENCE: 56
gctggaacaa tacgacgtta                                               20

<210> SEQ ID NO 57
<211> LENGTH: 20
<212> TYPE: DNA
<213> ORGANISM: Artificial Sequence
<220> FEATURE:
<223> OTHER INFORMATION: Primer N132SeqF4

<400> SEQUENCE: 57
tgctctaccc aaccagcttc                                               20

<210> SEQ ID NO 58
<211> LENGTH: 20
<212> TYPE: DNA
<213> ORGANISM: Artificial Sequence
<220> FEATURE:
<223> OTHER INFORMATION: Primer N132SeqR1

<400> SEQUENCE: 58
atggaaagac cagaggtgcc                                               20

<210> SEQ ID NO 59
<211> LENGTH: 18
<212> TYPE: DNA
<213> ORGANISM: Artificial Sequence
<220> FEATURE:
<223> OTHER INFORMATION: Primer N132SeqR2

<400> SEQUENCE: 59
tgcctgtgtg gtacgaat                                                 18
```

```
<210> SEQ ID NO 60
<211> LENGTH: 19
<212> TYPE: DNA
<213> ORGANISM: Artificial Sequence
<220> FEATURE:
<223> OTHER INFORMATION: Primer N132SeqR3

<400> SEQUENCE: 60
tattacgcgg cagtgcact                                              19

<210> SEQ ID NO 61
<211> LENGTH: 22
<212> TYPE: DNA
<213> ORGANISM: Artificial Sequence
<220> FEATURE:
<223> OTHER INFORMATION: Primer N132SeqR4

<400> SEQUENCE: 61
ggtgattttg tcgcagttag ag                                          22

<210> SEQ ID NO 62
<211> LENGTH: 18
<212> TYPE: DNA
<213> ORGANISM: Artificial Sequence
<220> FEATURE:
<223> OTHER INFORMATION: Primer N133SeqF1

<400> SEQUENCE: 62
tcgaaattgt tgggtcgc                                               18

<210> SEQ ID NO 63
<211> LENGTH: 22
<212> TYPE: DNA
<213> ORGANISM: Artificial Sequence
<220> FEATURE:
<223> OTHER INFORMATION: Primer N133SeqF2

<400> SEQUENCE: 63
ggtcacgcag ttcatttcta ag                                          22

<210> SEQ ID NO 64
<211> LENGTH: 18
<212> TYPE: DNA
<213> ORGANISM: Artificial Sequence
<220> FEATURE:
<223> OTHER INFORMATION: Primer N133SeqF3

<400> SEQUENCE: 64
tgtggcaagc cgtagaaa                                               18

<210> SEQ ID NO 65
<211> LENGTH: 19
<212> TYPE: DNA
<213> ORGANISM: Artificial Sequence
<220> FEATURE:
<223> OTHER INFORMATION: Primer N133SeqF4

<400> SEQUENCE: 65
aggatcgcgt ggtgagtaa                                              19

<210> SEQ ID NO 66
<211> LENGTH: 20
<212> TYPE: DNA
<213> ORGANISM: Artificial Sequence
<220> FEATURE:
<223> OTHER INFORMATION: Primer N133SeqR1
```

<400> SEQUENCE: 66
gtagccgtcg ttattgatga                                                          20

<210> SEQ ID NO 67
<211> LENGTH: 22
<212> TYPE: DNA
<213> ORGANISM: Artificial Sequence
<220> FEATURE:
<223> OTHER INFORMATION: Primer N133SeqR2

<400> SEQUENCE: 67
gcagcgaact aatcagagat tc                                                       22

<210> SEQ ID NO 68
<211> LENGTH: 19
<212> TYPE: DNA
<213> ORGANISM: Artificial Sequence
<220> FEATURE:
<223> OTHER INFORMATION: Primer N133SeqR3

<400> SEQUENCE: 68
tggtccgatg tattggagg                                                           19

<210> SEQ ID NO 69
<211> LENGTH: 19
<212> TYPE: DNA
<213> ORGANISM: Artificial Sequence
<220> FEATURE:
<223> OTHER INFORMATION: Primer N133SeqR4

<400> SEQUENCE: 69
tctgccatat agctcgcgt                                                           19

<210> SEQ ID NO 70
<211> LENGTH: 42
<212> TYPE: DNA
<213> ORGANISM: Artificial Sequence
<220> FEATURE:
<223> OTHER INFORMATION: Promoter 1.6GI Variant

<400> SEQUENCE: 70
gcccttgaca atgccacatc ctgagcaaat aattcaacca ct                                 42

<210> SEQ ID NO 71
<211> LENGTH: 42
<212> TYPE: DNA
<213> ORGANISM: Artificial Sequence
<220> FEATURE:
<223> OTHER INFORMATION: Promoter 1.5GI

<400> SEQUENCE: 71
gcccttgact atgccacatc ctgagcaaat aattcaacca ct                                 42

<210> SEQ ID NO 72
<211> LENGTH: 18
<212> TYPE: DNA
<213> ORGANISM: Artificial Sequence
<220> FEATURE:
<223> OTHER INFORMATION: Primer Scr1

<400> SEQUENCE: 72
cctttctttg tgaatcgg                                                            18

<210> SEQ ID NO 73
<211> LENGTH: 18

```
<212> TYPE: DNA
<213> ORGANISM: Artificial Sequence
<220> FEATURE:
<223> OTHER INFORMATION: Primer Scr2

<400> SEQUENCE: 73
agaaacaggg tgtgatcc                                                      18

<210> SEQ ID NO 74
<211> LENGTH: 20
<212> TYPE: DNA
<213> ORGANISM: Artificial Sequence
<220> FEATURE:
<223> OTHER INFORMATION: Primer Scr3

<400> SEQUENCE: 74
agtgatcatc acctgttgcc                                                    20

<210> SEQ ID NO 75
<211> LENGTH: 20
<212> TYPE: DNA
<213> ORGANISM: Artificial Sequence
<220> FEATURE:
<223> OTHER INFORMATION: Primer Scr4

<400> SEQUENCE: 75
agcacggcga gagtcgacgg                                                    20

<210> SEQ ID NO 76
<211> LENGTH: 672
<212> TYPE: DNA
<213> ORGANISM: Saccharomyces cerevisiae

<400> SEQUENCE: 76
agttcgagtt tatcattatc aatactgcca tttcaaagaa tacgtaaata attaatagta         60
gtgattttcc taactttatt tagtcaaaaa attagccttt taattctgct gtaacccgta        120
catgcccaaa atagggggcg ggttacacag aatatataac atcgtaggtg tctgggtgaa        180
cagtttattc ctggcatcca ctaaatataa tggagcccgc ttttttaagct ggcatccaga       240 aaaaaaaaga atcccagcac caaaatattg ttttcttcac caaccatcag ttcataggtc        300
cattctctta gcgcaactac agagaacagg ggcacaaaca ggcaaaaaac gggcacaacc        360
tcaatggagt gatgcaacct gcctggagta atgatgaca caaggcaatt gacccacgca        420
tgtatctatc tcattttctt acaccttcta ttaccttctg ctctctctga tttggaaaaa       480
gctgaaaaaa aaggttgaaa ccagttccct gaaattattc ccctacttga ctaataagta       540
tataaagacg gtaggtattg attgtaattc tgtaaatcta tttcttaaac ttcttaaatt       600 ctactttat agttagtctt tttttagtt ttaaaacacc aagaacttag tttcgaataa         660
acacacataa ac                                                           672

<210> SEQ ID NO 77
<211> LENGTH: 270
<212> TYPE: DNA
<213> ORGANISM: Saccharomyces cerevisiae

<400> SEQUENCE: 77
gacctcgagt catgtaatta gttatgtcac gcttacattc acgccctccc cccacatccg         60
ctctaaccga aaaggaagga gttagacaac ctgaagtcta ggtccctatt tattttttta        120
tagttatgtt agtattaaga acgttattta tatttcaaat ttttcttttt tttctgtaca        180
```

```
gacgcgtgta cgcatgtaac attatactga aaaccttgct tgagaaggtt ttgggacgct    240
cgaaggcttt aatttgcggc cggtacccaa                                      270
```

<210> SEQ ID NO 78
<211> LENGTH: 1716
<212> TYPE: DNA
<213> ORGANISM: Bacillus subtilis

<400> SEQUENCE: 78

```
atgttgacaa aagcaacaaa agaacaaaaa tcccttgtga aaaacagagg ggcggagctt     60
gttgttgatt gcttagtgga gcaaggtgtc acacatgtat ttggcattcc aggtgcaaaa    120
attgatgcgg tatttgacgc tttacaagat aaaggacctg aaattatcgt tgcccggcac    180
gaacaaaacg cagcattcat ggcccaagca gtcggccgtt taactggaaa accgggagtc    240
gtgttagtca catcaggacc gggtgcctct aacttggcaa caggcctgct gacagcgaac    300
actgaaggag accctgtcgt tgcgcttgct ggaaacgtga tccgtgcaga tcgtttaaaa    360
cggacacatc aatctttgga taatgcggcg ctattccagc cgattacaaa atacagtgta    420
gaagttcaag atgtaaaaaa tataccggaa gctgttacaa atgcatttag gatagcgtca    480
gcagggcagg ctggggccgc ttttgtgagc tttccgcaag atgttgtgaa tgaagtcaca    540
aatacgaaaa acgtgcgtgc tgttgcagcg ccaaaactcg gtcctgcagc agatgatgca    600
atcagtgcgg ccatagcaaa atccaaaca gcaaaacttc ctgtcgtttt ggtcggcatg    660
aaaggcggaa gaccggaagc aattaaagcg gttcgcaagc ttttgaaaaa ggttcagctt    720
ccatttgttg aaacatatca agctgccggt acccttttcta gagatttaga ggatcaatat    780
tttggccgta tcggtttgtt ccgcaaccag cctggcgatt tactgctaga gcaggcagat    840
gttgttctga cgatcggcta tgacccgatt gaatatgatc cgaaattctg gaatatcaat    900
ggagaccgga caattatcca tttagacgag attatcgctg acattgatca tgcttaccag    960
cctgatcttg aattgatcgg tgacattccg tccacgatca atcatatcga acacgatgct   1020
gtgaaagtgg aatttgcaga gcgtgagcag aaaatccttt ctgatttaaa acaatatatg   1080
catgaaggtg agcaggtgcc tgcagattgg aaatcagaca gagcgcaccc tcttgaaatc   1140
gttaaagagt tgcgtaatgc agtcgatgat catgttacag taacttgcga tatcggttcg   1200
cacgccattt ggatgtcacg ttatttccgc agctacgagc cgttaacatt aatgatcagt   1260
aacggtatgc aaacactcgg cgttgcgctt ccttgggcaa tcggcgcttc attggtgaaa   1320
ccgggagaaa aagtggtttc tgtctctggt gacggcggtt tcttattctc agcaatggaa   1380
ttagagacag cagttcgact aaaagcacca attgtacaca ttgtatggaa cgacagcaca   1440
tatgacatgg ttgcattcca gcaattgaaa aaatataacc gtacatctgc ggtcgatttc   1500
ggaaatatcg atatcgtgaa atatgcggaa agcttcggag caactggctt gcgcgtagaa   1560
tcaccagacc agctggcaga tgttctgcgt caaggcatga acgctgaagg tcctgtcatc   1620
atcgatgtcc cggttgacta cagtgataac attaatttag caagtgacaa gcttccgaaa   1680
gaattcgggg aactcatgaa aacgaaagct ctctag                              1716
```

<210> SEQ ID NO 79
<211> LENGTH: 643
<212> TYPE: DNA
<213> ORGANISM: Saccharomyces cerevisiae

<400> SEQUENCE: 79

```
gaaatgaata acaatactga cagtactaaa taattgccta cttggcttca catacgttgc     60
```

```
atacgtcgat atagataata atgataatga cagcaggatt atcgtaatac gtaatagttg    120
aaaatctcaa aaatgtgtgg gtcattacgt aaataatgat aggaatggga ttcttctatt    180
tttccttttt ccattctagc agccgtcggg aaaacgtggc atcctctctt tcgggctcaa    240
ttggagtcac gctgccgtga gcatcctctc tttccatatc taacaactga gcacgtaacc    300
aatggaaaag catgagctta gcgttgctcc aaaaagtat tggatggtta ataccatttg     360
tctgttctct tctgactttg actcctcaaa aaaaaaaat ctacaatcaa cagatcgctt     420
caattacgcc ctcacaaaaa cttttttcct tcttcttcgc ccacgttaaa ttttatccct    480
catgttgtct aacggatttc tgcacttgat ttattataaa aagacaaaga cataatactt    540
ctctatcaat ttcagttatt gttcttcctt gcgttattct tctgttcttc tttttctttt    600
gtcatatata accataacca agtaatacat attcaaatct aga                      643

<210> SEQ ID NO 80
<211> LENGTH: 1188
<212> TYPE: DNA
<213> ORGANISM: Saccharomyces cerevisiae

<400> SEQUENCE: 80
atgttgagaa ctcaagccgc cagattgatc tgcaactccc gtgtcatcac tgctaagaga    60
accttgtctt tggccacccg tgctgctgct tacagcagac cagctgcccg tttcgttaag    120
ccaatgatca ctacccgtgg tttgaagcaa atcaacttcg gtggtactgt tgaaaccgtc    180
tacgaaagag ctgactggcc aagagaaaag ttgttggact acttcaagaa cgacactttt    240
gctttgatcg gttacggttc ccaaggttac ggtcaaggtt tgaacttgag agacaacggt    300
ttgaacgtta tcattggtgt ccgtaaagat ggtgcttctt ggaaggctgc catcgaagac    360
ggttgggttc caggcaagaa cttgttcact gttgaagatg ctatcaagag aggtagttac    420
gttatgaact tgttgtccga tgccgctcaa tcagaaacct ggcctgctat caagccattg    480
ttgaccaagg gtaagacttt gtacttctcc cacggtttct ccccagtctt caaggacttg    540
actcacgttg aaccaccaaa ggacttagat gttatcttgg ttgctccaaa gggttccggt    600
agaactgtca gatctttgtt caaggaaggt cgtggtatta ctcttcttta cgccgtctgg    660
aacgatgtca ccggtaaggc tcacgaaaag gcccaagctt tggccgttgc cattggttcc    720
ggttacgttt accaaaccac tttcgaaaga gaagtcaact ctgacttgta cggtgaaaga    780
ggttgtttaa tgggtggtat ccacggtatg ttcttggctc aatacgacgt cttgagagaa    840
aacggtcact cccatctgaa gcttttcaac gaaaccgtcg aagaagctac caatctcta    900 tacccattga tcggtaagta cggtatggat tacatgtacg atgcttgttc caccaccgcc    960
agaagaggtg ctttggactg gtacccaatc ttcaagaatg ctttgaagcc tgttttccaa    1020
gacttgtacg aatctaccaa gaacggtacc gaaaccaaga gatctttgga attcaactct    1080
caacctgact acagagaaaa gctagaaaag gaattagaca ccatcagaaa catggaaatc    1140
tggaaggttg gtaaggaagt cagaaagttg agaccagaaa accaataa                1188

<210> SEQ ID NO 81
<211> LENGTH: 760
<212> TYPE: DNA
<213> ORGANISM: Saccharomyces cerevisiae

<400> SEQUENCE: 81
tcttttccga ttttttttcta aaccgtggaa tatttcggat atccttttgt tgtttccggg    60
```

```
tgtacaatat ggacttcctc ttttctggca accaaaccca tacatcggga ttcctataat      120
accttcgttg gtctccctaa catgtaggtg gcggagggga gatatacaat agaacagata      180
ccagacaaga cataatgggc taaacaagac tacaccaatt acactgcctc attgatggtg      240
gtacataacg aactaatact gtagccctag acttgatagc catcatcata tcgaagtttc      300
actacccttt ttccatttgc catctattga agtaataata ggcgcatgca acttctttc       360 tttttttttc ttttctctct ccccgttgt tgtctcacca tatccgcaat gacaaaaaaa       420
tgatggaaga cactaaagga aaaattaac gacaaagaca gcaccaacag atgtcgttgt       480
tccagagctg atgaggggta tctcgaagca cacgaaactt tttccttcct tcattcacgc      540
acactactct ctaatgagca acggtatacg gccttccttc cagttacttg aatttgaaat      600
aaaaaaaagt ttgctgtctt gctatcaagt ataaatagac ctgcaattat taatcttttg      660
tttcctcgtc attgttctcg ttccctttct tccttgtttc ttttctgca caatatttca      720 agctatacca agcatacaat caactatctc atatacaatg                            760

<210> SEQ ID NO 82
<211> LENGTH: 316
<212> TYPE: DNA
<213> ORGANISM: Saccharomyces cerevisiae

<400> SEQUENCE: 82
gagtaagcga atttcttatg atttatgatt tttattatta aataagttat aaaaaaaata       60
agtgtataca aattttaaag tgactcttag gttttaaaac gaaaattctt attcttgagt      120
aactctttcc tgtaggtcag gttgctttct caggtatagc atgaggtcgc tcttattgac      180
cacacctcta ccggcatgcc gagcaaatgc ctgcaaatcg ctccccattt cacccaattg      240
tagatatgct aactccagca atgagttgat gaatctcggt gtgtatttta tgtcctcaga      300
ggacaacacc tgtggt                                                     316

<210> SEQ ID NO 83
<211> LENGTH: 1758
<212> TYPE: DNA
<213> ORGANISM: Saccharomyces cerevisiae

<400> SEQUENCE: 83
atgggcttgt taacgaaagt tgctacatct agacaattct ctacaacgag atgcgttgca       60 agaagctca acaagtactc gtatatcatc actgaaccta agggccaagg tgcgtcccag      120
gccatgcttt atgccaccgg tttcaagaag gaagatttca agaagcctca agtcggggtt      180
ggttcctgtt ggtggtccgg taacccatgt aacatgcatc tattggactt gaataacaga      240
tgttctcaat ccattgaaaa agcgggtttg aaagctatgc agttcaacac catcggtgtt      300
tcagacggta tctctatggg tactaaaggt atgagatact cgttacaaag tagagaaatc      360
attgcagact cctttgaaac catcatgatg gcacaacact acgatgctaa catcgccatc      420
ccatcatgtg acaaaaacat gcccggtgtc atgatggcca tgggtagaca taacagacct      480
tccatcatgg tatatggtgg tactatcttg cccggtcatc aacatgtgg ttcttcgaag      540 atctctaaaa acatcgatat cgtctctgcg ttccaatcct acggtgaata tatttccaag      600
caattcactg aagaagaaag agaagatgtt gtggaacatg catgcccagg tcctggttct      660
tgtggtggta tgtatactgc aacacaatg gcttctgccg ctgaagtgct aggtttgacc      720
attccaaact cctcttcctt cccagccgtt tccaaggaga gttagctga gtgtgacaac      780 attggtgaat acatcaagaa gacaatggaa ttgggtattt acctcgtga tatcctcaca      840
```

```
aaagaggctt tgaaaacgc cattacttat gtcgttgcaa ccggtgggtc cactaatgct      900
gttttgcatt tggtggctgt tgctcactct gcgggtgtca agttgtcacc agatgatttc      960
caaagaatca gtgatactac accattgatc ggtgacttca aaccttctgg taaatacgtc     1020
atggccgatt tgattaacgt tggtggtacc caatctgtga ttaagtatct atatgaaaac     1080
aacatgttgc acggtaacac aatgactgtt accggtgaca ctttggcaga acgtgcaaag     1140
aaagcaccaa gcctacctga aggacaagag attattaagc cactctccca cccaatcaag     1200
gccaacggtc acttgcaaat tctgtacggt tcattggcac caggtggagc tgtgggtaaa     1260
attaccggta aggaaggtac ttacttcaag ggtagagcac gtgtgttcga agaggaaggt     1320
gcctttattg aagccttgga aagaggtgaa atcaagaagg gtgaaaaaac cgttgttgtt     1380
atcagatatg aaggtccaag aggtgcacca ggtatgcctg aaatgctaaa gccttcctct     1440
gctctgatgg gttacggttt gggtaaagat gttgcattgt tgactgatgg tagattctct     1500
ggtggttctc acgggttctt aatcggccac attgttcccg aagccgctga aggtggtcct     1560
atcgggttgg tcagagacgg cgatgagatt atcattgatg ctgataataa caagattgac     1620
ctattagtct ctgataagga aatggctcaa cgtaaacaaa gttgggttgc acctccacct     1680
cgttacacaa gaggtactct atccaagtat gctaagttgg tttccaacgc ttccaacggt     1740
tgtgttttag atgcttga                                                 1758

<210> SEQ ID NO 84
<211> LENGTH: 753
<212> TYPE: DNA
<213> ORGANISM: Saccharomyces cerevisiae

<400> SEQUENCE: 84
gcatgcttgc atttagtcgt gcaatgtatg actttaagat tgtgagcag gaagaaaagg       60 gagaatcttc taacgataaa cccttgaaaa actgggtaga ctacgctatg ttgagttgct     120
acgcaggctg cacaattaca cgagaatgct cccgcctagg atttaaggct aagggacgtg     180
caatgcagac gacagatcta aatgaccgtg tcggtgaagt gttcgccaaa ctttccggtt     240
aacacatgca gtgatgcacg cgcgatggtg ctaagttaca tatatatata tatagccata     300
gtgatgtcta gtaacctttt atggtatatt tcttaatgtg gaaagatact agcgcgcgca     360
cccacacaca agcttcgtct tttcttgaag aaaagaggaa gctcgctaaa tgggattcca     420
ctttccgttc cctgccagct gatggaaaaa ggttagtgga acgatgaaga ataaaaagag     480
agatccactg aggtgaaatt tcagctgaca gcgagtttca tgatcgtgat gaacaatggt     540
aacgagttgt ggctgttgcc agggagggtg gttctcaact tttaatgtat ggccaaatcg     600
ctacttgggt ttgttatata acaaagaaga aataatgaac tgattctctt cctccttctt     660
gtcctttctt aattctgttg taattacctt cctttgtaat tttttttgta attattcttc     720
ttaataatcc aaacaaacac acatattaca ata                                  753

<210> SEQ ID NO 85
<211> LENGTH: 20
<212> TYPE: DNA
<213> ORGANISM: Artificial Sequence
<220> FEATURE:
<223> OTHER INFORMATION: Primer N98SeqF1

<400> SEQUENCE: 85
cgtgttagtc acatcaggac                                                  20
```

```
<210> SEQ ID NO 86
<211> LENGTH: 24
<212> TYPE: DNA
<213> ORGANISM: Artificial Sequence
<220> FEATURE:
<223> OTHER INFORMATION: Primer N98SeqF2

<400> SEQUENCE: 86
ggccatagca aaatccaaa cagc                                              24

<210> SEQ ID NO 87
<211> LENGTH: 24
<212> TYPE: DNA
<213> ORGANISM: Artificial Sequence
<220> FEATURE:
<223> OTHER INFORMATION: Primer N98SeqF3

<400> SEQUENCE: 87
ccacgatcaa tcatatcgaa cacg                                             24

<210> SEQ ID NO 88
<211> LENGTH: 20
<212> TYPE: DNA
<213> ORGANISM: Artificial Sequence
<220> FEATURE:
<223> OTHER INFORMATION: Primer N98SeqF4

<400> SEQUENCE: 88
ggtttctgtc tctggtgacg                                                  20

<210> SEQ ID NO 89
<211> LENGTH: 22
<212> TYPE: DNA
<213> ORGANISM: Artificial Sequence
<220> FEATURE:
<223> OTHER INFORMATION: Primer N99SeqR1

<400> SEQUENCE: 89
gtctggtgat tctacgcgca ag                                               22

<210> SEQ ID NO 90
<211> LENGTH: 22
<212> TYPE: DNA
<213> ORGANISM: Artificial Sequence
<220> FEATURE:
<223> OTHER INFORMATION: Primer N99SeqR2

<400> SEQUENCE: 90
catcgactgc attacgcaac tc                                               22

<210> SEQ ID NO 91
<211> LENGTH: 22
<212> TYPE: DNA
<213> ORGANISM: Artificial Sequence
<220> FEATURE:
<223> OTHER INFORMATION: Primer N99SeqR3

<400> SEQUENCE: 91
cgatcgtcag aacaacatct gc                                               22

<210> SEQ ID NO 92
<211> LENGTH: 20
<212> TYPE: DNA
<213> ORGANISM: Artificial Sequence
<220> FEATURE:
<223> OTHER INFORMATION: Primer N99SeqR4
```

```
<400> SEQUENCE: 92
ccttcagtgt tcgctgtcag                                              20

<210> SEQ ID NO 93
<211> LENGTH: 36
<212> TYPE: DNA
<213> ORGANISM: Artificial Sequence
<220> FEATURE:
<223> OTHER INFORMATION: Primer N136

<400> SEQUENCE: 93
ccgcggatag atctgaaatg aataacaata ctgaca                            36

<210> SEQ ID NO 94
<211> LENGTH: 65
<212> TYPE: DNA
<213> ORGANISM: Artificial Sequence
<220> FEATURE:
<223> OTHER INFORMATION: Primer N137

<400> SEQUENCE: 94
taccaccgaa gttgatttgc ttcaacatcc tcagctctag atttgaatat gtattacttg  60
gttat                                                              65

<210> SEQ ID NO 95
<211> LENGTH: 28
<212> TYPE: DNA
<213> ORGANISM: Artificial Sequence
<220> FEATURE:
<223> OTHER INFORMATION: Primer N138

<400> SEQUENCE: 95
atgttgaagc aaatcaactt cggtggta                                     28

<210> SEQ ID NO 96
<211> LENGTH: 22
<212> TYPE: DNA
<213> ORGANISM: Artificial Sequence
<220> FEATURE:
<223> OTHER INFORMATION: Primer N139

<400> SEQUENCE: 96
ttattggttt tctggtctca ac                                           22

<210> SEQ ID NO 97
<211> LENGTH: 57
<212> TYPE: DNA
<213> ORGANISM: Artificial Sequence
<220> FEATURE:
<223> OTHER INFORMATION: Primer N140

<400> SEQUENCE: 97
aagttgagac cagaaaacca ataattaatt aatcatgtaa ttagttatgt cacgctt     57

<210> SEQ ID NO 98
<211> LENGTH: 30
<212> TYPE: DNA
<213> ORGANISM: Artificial Sequence
<220> FEATURE:
<223> OTHER INFORMATION: Primer N141

<400> SEQUENCE: 98
gcggccgccc gcaaattaaa gccttcgagc                                   30
```

<210> SEQ ID NO 99
<211> LENGTH: 28
<212> TYPE: DNA
<213> ORGANISM: Artificial Sequence
<220> FEATURE:
<223> OTHER INFORMATION: Primer N142

<400> SEQUENCE: 99
ggatccgcat gcttgcattt agtcgtgc                              28

<210> SEQ ID NO 100
<211> LENGTH: 56
<212> TYPE: DNA
<213> ORGANISM: Artificial Sequence
<220> FEATURE:
<223> OTHER INFORMATION: N143

<400> SEQUENCE: 100
caggtaatcc cccacagtat acatcctcag ctattgtaat atgtgtgttt gtttgg    56

<210> SEQ ID NO 101
<211> LENGTH: 22
<212> TYPE: DNA
<213> ORGANISM: Artificial Sequence
<220> FEATURE:
<223> OTHER INFORMATION: Primer N144

<400> SEQUENCE: 101
atgtatactg tgggggatta cc                                    22

<210> SEQ ID NO 102
<211> LENGTH: 22
<212> TYPE: DNA
<213> ORGANISM: Artificial Sequence
<220> FEATURE:
<223> OTHER INFORMATION: Primer N145

<400> SEQUENCE: 102
ttagctttta ttttgctccg ca                                    22

<210> SEQ ID NO 103
<211> LENGTH: 57
<212> TYPE: DNA
<213> ORGANISM: Artificial Sequence
<220> FEATURE:
<223> OTHER INFORMATION: Primer N146

<400> SEQUENCE: 103
tttgcggagc aaaataaaag ctaattaatt aagagtaagc gaatttctta tgattta   57

<210> SEQ ID NO 104
<211> LENGTH: 28
<212> TYPE: DNA
<213> ORGANISM: Artificial Sequence
<220> FEATURE:
<223> OTHER INFORMATION: Primer N147

<400> SEQUENCE: 104
actagtacca caggtgttgt cctctgag                              28

<210> SEQ ID NO 105
<211> LENGTH: 22
<212> TYPE: DNA
<213> ORGANISM: Artificial Sequence
<220> FEATURE:
<223> OTHER INFORMATION: Primer N151

```
<400> SEQUENCE: 105
ctagagagct ttcgttttca tg                                                22

<210> SEQ ID NO 106
<211> LENGTH: 57
<212> TYPE: DNA
<213> ORGANISM: Artificial Sequence
<220> FEATURE:
<223> OTHER INFORMATION: Primer N152

<400> SEQUENCE: 106
ctcatgaaaa cgaaagctct ctagttaatt aatcatgtaa ttagttatgt cacgctt        57

<210> SEQ ID NO 107
<211> LENGTH: 25
<212> TYPE: DNA
<213> ORGANISM: Artificial Sequence
<220> FEATURE:
<223> OTHER INFORMATION: Primer N155

<400> SEQUENCE: 107
atggcaaaga agctcaacaa gtact                                           25

<210> SEQ ID NO 108
<211> LENGTH: 22
<212> TYPE: DNA
<213> ORGANISM: Artificial Sequence
<220> FEATURE:
<223> OTHER INFORMATION: Primer N156

<400> SEQUENCE: 108
tcaagcatct aaaacacaac cg                                              22

<210> SEQ ID NO 109
<211> LENGTH: 57
<212> TYPE: DNA
<213> ORGANISM: Artificial Sequence
<220> FEATURE:
<223> OTHER INFORMATION: Primer N157

<400> SEQUENCE: 109
aacggttgtg ttttagatgc ttgattaatt aagagtaagc gaatttctta tgattta       57

<210> SEQ ID NO 110
<211> LENGTH: 28
<212> TYPE: DNA
<213> ORGANISM: Artificial Sequence
<220> FEATURE:
<223> OTHER INFORMATION: Primer N158

<400> SEQUENCE: 110 ggatccttttt ctggcaacca aacccata                                       28

<210> SEQ ID NO 111
<211> LENGTH: 56
<212> TYPE: DNA
<213> ORGANISM: Artificial Sequence
<220> FEATURE:
<223> OTHER INFORMATION: Primer N159

<400> SEQUENCE: 111
cgagtacttg ttgagcttct ttgccatcct cagcgagata gttgattgta tgcttg        56

<210> SEQ ID NO 112
```

<210> SEQ ID NO 112
<211> LENGTH: 19
<212> TYPE: DNA
<213> ORGANISM: Artificial Sequence
<220> FEATURE:
<223> OTHER INFORMATION: Primer N160SeqF1

<400> SEQUENCE: 112
gaaaacgtgg catcctctc                                                19

<210> SEQ ID NO 113
<211> LENGTH: 19
<212> TYPE: DNA
<213> ORGANISM: Artificial Sequence
<220> FEATURE:
<223> OTHER INFORMATION: Primer N160SeqF2

<400> SEQUENCE: 113
gctgactggc caagagaaa                                                19

<210> SEQ ID NO 114
<211> LENGTH: 20
<212> TYPE: DNA
<213> ORGANISM: Artificial Sequence
<220> FEATURE:
<223> OTHER INFORMATION: Primer N160SeqF3

<400> SEQUENCE: 114
tgtacttctc ccacggtttc                                               20

<210> SEQ ID NO 115
<211> LENGTH: 22
<212> TYPE: DNA
<213> ORGANISM: Artificial Sequence
<220> FEATURE:
<223> OTHER INFORMATION: Primer N160SeqF4

<400> SEQUENCE: 115
agctacccaa tctctatacc ca                                            22

<210> SEQ ID NO 116
<211> LENGTH: 22
<212> TYPE: DNA
<213> ORGANISM: Artificial Sequence
<220> FEATURE:
<223> OTHER INFORMATION: Primer N160SeqF5

<400> SEQUENCE: 116
cctgaagtct aggtccctat tt                                            22

<210> SEQ ID NO 117
<211> LENGTH: 19
<212> TYPE: DNA
<213> ORGANISM: Artificial Sequence
<220> FEATURE:
<223> OTHER INFORMATION: N160SeqR1

<400> SEQUENCE: 117
gcgtgaatgt aagcgtgac                                                19

<210> SEQ ID NO 118
<211> LENGTH: 20
<212> TYPE: DNA
<213> ORGANISM: Artificial Sequence
<220> FEATURE:
<223> OTHER INFORMATION: Primer N160SeqR2

<400> SEQUENCE: 118
cgtcgtattg agccaagaac                                              20

<210> SEQ ID NO 119
<211> LENGTH: 20
<212> TYPE: DNA
<213> ORGANISM: Artificial Sequence
<220> FEATURE:
<223> OTHER INFORMATION: Primer N160SeqR3

<400> SEQUENCE: 119
gcatcggaca acaagttcat                                              20

<210> SEQ ID NO 120
<211> LENGTH: 22
<212> TYPE: DNA
<213> ORGANISM: Artificial Sequence
<220> FEATURE:
<223> OTHER INFORMATION: Primer N160SeqR4

<400> SEQUENCE: 120
tcgttcttga agtagtccaa ca                                           22

<210> SEQ ID NO 121
<211> LENGTH: 19
<212> TYPE: DNA
<213> ORGANISM: Artificial Sequence
<220> FEATURE:
<223> OTHER INFORMATION: Primer N160SeqR5

<400> SEQUENCE: 121
tgagcccgaa agagaggat                                               19

<210> SEQ ID NO 122
<211> LENGTH: 19
<212> TYPE: DNA
<213> ORGANISM: Artificial Sequence
<220> FEATURE:
<223> OTHER INFORMATION: Primer N161SeqF1

<400> SEQUENCE: 122
acggtatacg gccttcctt                                               19

<210> SEQ ID NO 123
<211> LENGTH: 20
<212> TYPE: DNA
<213> ORGANISM: Artificial Sequence
<220> FEATURE:
<223> OTHER INFORMATION: Primer N161SeqF2

<400> SEQUENCE: 123
gggtttgaaa gctatgcagt                                              20

<210> SEQ ID NO 124
<211> LENGTH: 22
<212> TYPE: DNA
<213> ORGANISM: Artificial Sequence
<220> FEATURE:
<223> OTHER INFORMATION: Primer N161SeqF3

<400> SEQUENCE: 124
ggtggtatgt atactgccaa ca                                           22

<210> SEQ ID NO 125
<211> LENGTH: 22
<212> TYPE: DNA

<213> ORGANISM: Artificial Sequence
<220> FEATURE:
<223> OTHER INFORMATION: Primer N161SeqF4

<400> SEQUENCE: 125
ggtggtaccc aatctgtgat ta                                              22

<210> SEQ ID NO 126
<211> LENGTH: 20
<212> TYPE: DNA
<213> ORGANISM: Artificial Sequence
<220> FEATURE:
<223> OTHER INFORMATION: Primer N161SeqF5

<400> SEQUENCE: 126
cggtttgggt aaagatgttg                                                 20

<210> SEQ ID NO 127
<211> LENGTH: 22
<212> TYPE: DNA
<213> ORGANISM: Artificial Sequence
<220> FEATURE:
<223> OTHER INFORMATION: Primer N161SeqF6

<400> SEQUENCE: 127
aaacgaaaat tcttattctt ga                                              22

<210> SEQ ID NO 128
<211> LENGTH: 22
<212> TYPE: DNA
<213> ORGANISM: Artificial Sequence
<220> FEATURE:
<223> OTHER INFORMATION: Primer N161SeqR1

<400> SEQUENCE: 128
tcgttttaaa acctaagagt ca                                              22

<210> SEQ ID NO 129
<211> LENGTH: 19
<212> TYPE: DNA
<213> ORGANISM: Artificial Sequence
<220> FEATURE:
<223> OTHER INFORMATION: Primer N161SeqR2

<400> SEQUENCE: 129
ccaaaccgta acccatcag                                                  19

<210> SEQ ID NO 130
<211> LENGTH: 19
<212> TYPE: DNA
<213> ORGANISM: Artificial Sequence
<220> FEATURE:
<223> OTHER INFORMATION: Primer N161SeqR3

<400> SEQUENCE: 130
cacagattgg gtaccacca                                                  19

<210> SEQ ID NO 131
<211> LENGTH: 20
<212> TYPE: DNA
<213> ORGANISM: Artificial Sequence
<220> FEATURE:
<223> OTHER INFORMATION: Primer N161Seqr4

<400> SEQUENCE: 131
accacaagaa ccaggacctg                                                 20

<210> SEQ ID NO 132
<211> LENGTH: 19
<212> TYPE: DNA
<213> ORGANISM: Artificial Sequence
<220> FEATURE:
<223> OTHER INFORMATION: Primer N161SeqR5

<400> SEQUENCE: 132
catagctttc aaacccgct                                                    19

<210> SEQ ID NO 133
<211> LENGTH: 22
<212> TYPE: DNA
<213> ORGANISM: Artificial Sequence
<220> FEATURE:
<223> OTHER INFORMATION: Primer N161SeqR6

<400> SEQUENCE: 133
cgtataccgt tgctcattag ag                                                22

<210> SEQ ID NO 134
<211> LENGTH: 23
<212> TYPE: DNA
<213> ORGANISM: Artificial Sequence
<220> FEATURE:
<223> OTHER INFORMATION: Primer N162

<400> SEQUENCE: 134
atgttgacaa aagcaacaaa aga                                               23

<210> SEQ ID NO 135
<211> LENGTH: 38
<212> TYPE: DNA
<213> ORGANISM: Artificial Sequence
<220> FEATURE:
<223> OTHER INFORMATION: Primer N189

<400> SEQUENCE: 135
atccgcggat agatctagtt cgagtttatc attatcaa                               38

<210> SEQ ID NO 136
<211> LENGTH: 53
<212> TYPE: DNA
<213> ORGANISM: Artificial Sequence
<220> FEATURE:
<223> OTHER INFORMATION: Primer N190.1

<400> SEQUENCE: 136
ttcttttgtt gcttttgtca acatcctcag cgtttatgtg tgtttattcg aaa              53

<210> SEQ ID NO 137
<211> LENGTH: 38
<212> TYPE: DNA
<213> ORGANISM: Artificial Sequence
<220> FEATURE:
<223> OTHER INFORMATION: Primer N176

<400> SEQUENCE: 137
atccgcggat agatctatta gaagccgccg agcgggcg                               38

<210> SEQ ID NO 138
<211> LENGTH: 31
<212> TYPE: DNA
<213> ORGANISM: Artificial Sequence
<220> FEATURE:

<223> OTHER INFORMATION: Primer N177

<400> SEQUENCE: 138
atcctcagct tttctccttg acgttaaagt a                                31

<210> SEQ ID NO 139
<211> LENGTH: 477
<212> TYPE: PRT
<213> ORGANISM: Escherichia coli

<400> SEQUENCE: 139

```
Met Thr Gln Ser Arg Leu His Ala Ala Gln Asn Ala Leu Ala Lys Leu
1               5                   10                  15

His Glu His Arg Gly Asn Thr Phe Tyr Pro His Phe His Leu Ala Pro
            20                  25                  30

Pro Ala Gly Trp Met Asn Asp Pro Asn Gly Leu Ile Trp Phe Asn Asp
        35                  40                  45

Arg Tyr His Ala Phe Tyr Gln His His Pro Met Ser Glu His Trp Gly
    50                  55                  60

Pro Met His Trp Gly His Ala Thr Ser Asp Asp Met Ile His Trp Gln
65                  70                  75                  80

His Glu Pro Ile Ala Leu Ala Pro Gly Asp Asn Asp Lys Asp Gly
                85                  90                  95

Cys Phe Ser Gly Ser Ala Val Asp Asp Asn Gly Val Leu Ser Leu Ile
            100                 105                 110

Tyr Thr Gly His Val Trp Leu Asp Gly Ala Gly Asn Asp Asp Ala Ile
        115                 120                 125

Arg Glu Val Gln Cys Leu Ala Thr Ser Arg Asp Gly Ile His Phe Glu
    130                 135                 140

Lys Gln Gly Val Ile Leu Thr Pro Pro Glu Gly Ile Met His Phe Arg
145                 150                 155                 160

Asp Pro Lys Val Trp Arg Glu Ala Asp Thr Trp Trp Met Val Val Gly
                165                 170                 175

Ala Lys Asp Pro Gly Asn Thr Gly Gln Ile Leu Leu Tyr Arg Gly Ser
            180                 185                 190

Ser Leu Arg Glu Trp Thr Phe Asp Arg Val Leu Ala His Ala Asp Ala
        195                 200                 205

Gly Glu Ser Tyr Met Trp Glu Cys Pro Asp Phe Phe Ser Leu Gly Asp
    210                 215                 220

Gln His Tyr Leu Met Phe Ser Pro Gln Gly Met Asn Ala Glu Gly Tyr
225                 230                 235                 240

Ser Tyr Arg Asn Arg Phe Gln Ser Gly Val Ile Pro Gly Met Trp Ser
                245                 250                 255

Pro Gly Arg Leu Phe Ala Gln Ser Gly His Phe Thr Glu Leu Asp Asn
            260                 265                 270

Gly His Asp Phe Tyr Ala Pro Gln Ser Phe Leu Ala Lys Asp Gly Arg
        275                 280                 285

Arg Ile Val Ile Gly Trp Met Asp Met Trp Glu Ser Pro Met Pro Ser
    290                 295                 300

Lys Arg Glu Gly Trp Ala Gly Cys Met Thr Leu Ala Arg Glu Leu Ser
305                 310                 315                 320

Glu Ser Asn Gly Lys Leu Leu Gln Arg Pro Val His Glu Ala Glu Ser
                325                 330                 335

Leu Arg Gln Gln His Gln Ser Val Ser Pro Arg Thr Ile Ser Asn Lys
            340                 345                 350
```

Tyr Val Leu Gln Glu Asn Ala Gln Ala Val Glu Ile Gln Leu Gln Trp
            355                 360                 365

Ala Leu Lys Asn Ser Asp Ala Glu His Tyr Gly Leu Gln Leu Gly Thr
        370                 375                 380

Gly Met Arg Leu Tyr Ile Asp Asn Gln Ser Glu Arg Leu Val Leu Trp
385                 390                 395                 400

Arg Tyr Tyr Pro His Glu Asn Leu Asp Gly Tyr Arg Ser Ile Pro Leu
                405                 410                 415

Pro Gln Arg Asp Thr Leu Ala Leu Arg Ile Phe Ile Asp Thr Ser Ser
            420                 425                 430

Val Glu Val Phe Ile Asn Asp Gly Glu Ala Val Met Ser Ser Arg Ile
            435                 440                 445

Tyr Pro Gln Pro Glu Glu Arg Glu Leu Ser Leu Tyr Ala Ser His Gly
        450                 455                 460

Val Ala Val Leu Gln His Gly Ala Leu Trp Leu Leu Gly
465                 470                 475

<210> SEQ ID NO 140
<211> LENGTH: 304
<212> TYPE: PRT
<213> ORGANISM: Escherichia coli

<400> SEQUENCE: 140

Met Ser Ala Lys Val Trp Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
            100                 105                 110

Asp Leu Pro Cys Trp Arg His Gly Glu Trp Leu His Leu Cys Ser Ile
        115                 120                 125

Ala Leu Ser Ala Glu Pro Ser Arg Thr Ser Ala Phe Thr Ala Met Thr
    130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Glu Trp Arg
            180                 185                 190

Leu Ile Ser Gly Lys Thr Gln Asn Asp Gln Asp Ile Cys Ala Leu Ala
        195                 200                 205

Lys Glu Tyr Glu Ile Ala Met Leu Leu Val Thr Lys Gly Ala Glu Gly
    210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly

```
                       245                 250                 255
Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
            275                 280                 285

Thr Ala Lys Gly Ala Met Thr Ala Leu Pro Cys Arg Gln Glu Leu Glu
            290                 295                 300

<210> SEQ ID NO 141
<211> LENGTH: 415
<212> TYPE: PRT
<213> ORGANISM: Escherichia coli

<400> SEQUENCE: 141

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320
```

```
Ala Ile Glu Val Pro Leu Cys Val Ile Ser Val Phe Lys Tyr Ser Val
            325                 330                 335

Ala Asn Phe Asp Lys Arg Leu Ser Ser Thr Ile Phe Leu Ile Gly Phe
        340                 345                 350

Gln Ile Ala Ser Ser Leu Gly Ile Val Leu Leu Ser Thr Pro Thr Gly
            355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 142
<211> LENGTH: 6341
<212> TYPE: DNA
<213> ORGANISM: Artificial Sequence
<220> FEATURE:
<223> OTHER INFORMATION: Plasmid pFP988DssPspac

<400> SEQUENCE: 142
gatccaagtt taaactgtac actagatatt tcttctccgc ttaaatcatc aaagaaatct      60
ttatcacttg taaccagtcc gtccacatgt cgaattgcat ctgaccgaat tttacgtttc     120
cctgaataat tctcatcaat cgtttcatca attttatctt tatactttat attttgtgcg    180
ttaatcaaat cataattttt atatgttttc tcatgattta tgtctttatt attatagttt    240
ttattctctc tttgattatg tctttgtatc ccgtttgtat tacttgatcc tttaactctg    300
gcaaccctca aaattgaatg agacatgcta cacctccgga taataaatat atataaacgt    360
atatagattt cataaagtct aacacactag acttatttac ttcgtaatta agtcgttaaa    420
ccgtgtgctc tacgaccaaa actataaaac ctttaagaac tttctttttt tacaagaaaa    480
aagaaattag ataaatctct catatctttt attcaataat cgcatccgat tgcagtataa    540
atttaacgat cactcatcat gttcatattt atcagagctc gtgctataat tatactaatt    600
ttataaggag gaaaaaatat gggcattttt agtattttg taatcagcac agttcattat     660
caaccaaaca aaaataagt ggttataatg aatcgttaat aagcaaaatt catataacca     720
aattaaagag ggttataatg aacgagaaaa atataaaaca cagtcaaaac tttattactt    780
caaaacataa tatagataaa ataatgacaa atataagatt aaatgaacat gataatatct    840
ttgaaatcgg ctcaggaaaa ggccatttta cccttgaatt agtaaagagg tgtaatttcg    900
taactgccat tgaaatagac cataaattat gcaaaactac agaaaataaa cttgttgatc    960
acgataattt ccaagtttta aacaaggata tattgcagtt taaatttcct aaaaaccaat   1020
cctataaaat atatggtaat ataccttata acataagtac ggatataata cgcaaaattg   1080
tttttgatag tatagctaat gagatttatt aatcgtgga atacgggttt gctaaaagat    1140
tattaaatac aaaacgctca ttggcattac ttttaatggc agaagttgat atttctatat   1200
taagtatggt tccaagagaa tattttcatc ctaaacctaa agtgaatagc tcacttatca   1260
gattaagtag aaaaaaatca agaatatcac acaaagataa acaaagtat aattatttcg    1320 ttatgaaatg ggttaacaaa gaatacaaga aaatatttac aaaaaatcaa tttaacaatt   1380
ccttaaaaca tgcaggaatt gacgatttaa acaatattag ctttgaacaa ttcttatctc   1440
ttttcaatag ctataaatta tttaataagt aagttaaggg atgcagttca tcgatgaagg   1500
caactacagc tcaggcgaca accatacgct gagagatcct cactacgtag aagataaagg   1560
```

```
ccacaaatac ttagtatttg aagcaaacac tggaactgaa gatggctacc aaggcgaaga    1620
atctttattt aacaaagcat actatggcaa aagcacatca ttcttccgtc aagaaagtca    1680
aaaacttctg caaagcgata aaaacgcac ggctgagtta gcaaacggcg ctctcggtat     1740
gattgagcta aacgatgatt acacactgaa aaaagtgatg aaaccgctga ttgcatctaa    1800
cacagtaaca gatgaaattg aacgcgcgaa cgtctttaaa atgaacggca atggtacct    1860 gttcactgac tcccgcggat caaaaatgac gattgacggc attacgtcta acgatattta    1920
catgcttggt tatgtttcta attctttaac tggcccatac aagccgctga acaaaactgg    1980
ccttgtgtta aaaatggatc ttgatcctaa cgatgtaacc tttacttact cacacttcgc    2040
tgtacctcaa gcgaaaggaa acaatgtcgt gattacaagc tatatgacaa acagaggatt    2100
ctacgcagac aaacaatcaa cgtttgcgcc aagcttgcat gcgagagtag ggaactgcca    2160
ggcatcaaat aaaacgaaag gctcagtcga aagactgggc ctttcgtttt atctgttgtt    2220
tgtcggtgaa cgctctcctg agtaggacaa atccgccggg agcggatttg aacgttgcga    2280
agcaacggcc cggagggtgg cgggcaggac gcccgccata aactgccagg catcaaatta    2340
agcagaaggc catcctgacg gatggccttt ttgcgtttct acaaactctt tttgtttatt    2400
tttctaaata cattcaaata tgtatccgct catgctccgg atctgcatcg caggatgctg    2460
ctggctaccc tgtggaacac ctacatctgt attaacgaag cgctggcatt gaccctgagt    2520 gattttctc tggtcccgcc gcatccatac cgccagttgt ttaccctcac aacgttccag    2580
taaccgggca tgttcatcat cagtaacccg tatcgtgagc atcctctctc gtttcatcgg    2640
tatcattacc cccatgaaca gaaattcccc cttacacgga ggcatcaagt gaccaaacag    2700
gaaaaaaccg cccttaacat ggcccgcttt atcagaagcc agacattaac gcttctggag    2760
aaactcaacg agctggacgc ggatgaacag gcagacatct gtgaatcgct tcacgaccac    2820
gctgatgagc tttaccgcag ctgcctcgcg cgtttcggtg atgacggtga aaacctctga    2880
cacatgcagc tcccggagac ggtcacagct tgtctgtaag cggatgccgg gagcagacaa    2940
gcccgtcagg gcgcgtcagc gggtgttggc gggtgtcggg gcgcagccat gacccagtca    3000
cgtagcgata gcggagtgta tactggctta actatgcggc atcagagcag attgtactga    3060
gagtgcacca tatgcggtgt gaaataccgc acagatgcgt aaggagaaaa taccgcatca    3120
ggcgctcttc cgcttcctcg ctcactgact cgctgcgctc ggtcgttcgg ctgcggcgag    3180
cggtatcagc tcactcaaag gcggtaatac ggttatccac agaatcaggg gataacgcag    3240
gaaagaacat gtgagcaaaa ggccagcaaa aggccaggaa ccgtaaaaag gccgcgttgc    3300
tggcgttttt ccataggctc cgcccccctg acgagcatca caaaaatcga cgctcaagtc    3360
agaggtggcg aaacccgaca ggactataaa gataccaggc gtttccccct ggaagctccc    3420
tcgtgcgctc tcctgttccg accctgccgc ttaccggata cctgtccgcc tttctccctt    3480
cgggaagcgt ggcgctttct caatgctcac gctgtaggta tctcagttcg gtgtaggtcg    3540
ttcgctccaa gctgggctgt gtgcacgaac cccccgttca gcccgaccgc tgcgccttat    3600
ccggtaacta tcgtcttgag tccaacccgg taagacacga cttatcgcca ctggcagcag    3660
ccactggtaa caggattagc agagcgaggt atgtaggcgg tgctacagag ttcttgaagt    3720
ggtggcctaa ctacggctac actagaagga cagtatttgg tatctgcgct ctgctgaagc    3780
cagttacctt cggaaaaaga gttggtagct cttgatccgg caaacaaacc accgctggta    3840
gcggtggttt ttttgtttgc aagcagcaga ttacgcgcag aaaaaaagga tctcaagaag    3900
```

```
atcctttgat cttttctacg gggtctgacg ctcagtggaa cgaaaactca cgttaaggga    3960
ttttggtcat gagattatca aaaggatct tcacctagat cctttaaat taaaaatgaa     4020 gttttaaatc aatctaaagt atatatgagt aaacttggtc tgacagttac caatgcttaa   4080
tcagtgaggc acctatctca gcgatctgtc tatttcgttc atccatagtt gcctgactcc   4140
ccgtcgtgta gataactacg atacgggagg gcttaccatc tggcccagt gctgcaatga    4200 taccgcgaga cccacgctca ccggctccag atttatcagc aataaaccag ccagccggaa   4260
gggccgagcg cagaagtggt cctgcaactt tatccgcctc catccagtct attaattgtt   4320
gccgggaagc tagagtaagt agttcgccag ttaatagttt gcgcaacgtt gttgccattg   4380
ctgcaggcat cgtggtgtca cgctcgtcgt ttggtatggc ttcattcagc tccggttccc   4440
aacgatcaag gcgagttaca tgatcccca tgttgtgcaa aaagcggtt agctccttcg     4500 gtcctccgat cgttgtcaga agtaagttgg ccgcagtgtt atcactcatg gttatggcag   4560
cactgcataa ttctcttact gtcatgccat ccgtaagatg cttttctgtg actggtgagt   4620
actcaaccaa gtcattctga aatagtgta tgcggcgacc gagttgctct tgcccggcgt    4680
caatacggga taataccgcg ccacatagca gaactttaaa agtgctcatc attggaaaac   4740
gttcttcggg gcgaaaactc tcaaggatct taccgctgtt gagatccagt tcgatgtaac   4800
ccactcgtgc acccaactga tcttcagcat cttttacttt caccagcgtt tctgggtgag   4860
caaaaacagg aaggcaaaat gccgcaaaaa agggaataag ggcgacacgg aaatgttgaa   4920
tactcatact cttcctttt caatattatt gaagcattta tcagggttat tgtctcatga    4980
gcggatacat atttgaatgt atttagaaaa ataaacaaat aggggttccg cgcacatttc   5040
cccgaaaagt gccacctgac gtctaagaaa ccattattat catgacatta acctataaaa   5100
ataggcgtat cacgaggccc tttcgtctcg cgcgtttcgg tgatgacggt gaaaacctct   5160
gacacatgca gctcccggag acggtcacag cttgtctgta agcggatgcc gggagcagac   5220
aagcccgtca gggcgcgtca gcgggtgttc atgtgcgtaa ctaacttgcc atcttcaaac   5280
aggagggctg gaagaagcag accgctaaca cagtacataa aaaggagac atgaacgatg    5340 aacatcaaaa agtttgcaaa acaagcaaca gtattaacct ttactaccgc actgctggca   5400
ggaggcgcaa ctcaagcgtt tgcgaaagaa acgaaccaaa agccatataa ggaaacatac   5460
ggcatttccc atattacacg ccatgatatg ctgcaaatcc ctgaacagca aaaaaatgaa   5520
aaatatcaag ttcctgaatt cgattcgtcc acaattaaaa atatctcttc tgcaaaaggc   5580
ctggacgttt gggacagctg gccattacaa aacgctgacg gcactgtcgc aaactatcac   5640
ggctaccaca tcgtctttgc attagccgga gatcctaaaa atgcggatga cacatcgatt   5700
tacatgttct atcaaaaagt cggcgaaact tctattgaca gctggaaaaa cgctggccgc   5760
gtctttaaag acagcgacaa attcgatgca aatgattcta tcctaaaaga ccaaacacaa   5820
gaatggtcag gttcagccac atttacatct gacggaaaaa tccgtttatt ctacactgat   5880
ttctccggta acattacggg caaacaaaca ctgacaactg cacaagttaa cgtatcagca   5940
tcagacagct cttttgaacat caacggtgta gaggattata atcaatctt tgacggtgac   6000 ggaaaaacgt atcaaaatgt acagaattcg agctctcgag taattctaca cagcccagtc   6060
cagactattc ggcactgaaa ttatgggtga agtggtcaag acctcactag gcaccttaaa   6120
aatagcgcac cctgaagaag atttatttga ggtagccctt gcctacctag cttccaagaa   6180
agatatccta acagcacaag agcggaaaga tgttttgttc tacatccaga acaacctctg   6240
ctaaaattcc tgaaaaattt tgcaaaaagt tgttgacttt atctacaagg tgtggcataa   6300
```
tgtgtggaat tgtgagcgct cacaattaag cttgaattcc c            6341

<210> SEQ ID NO 143
<211> LENGTH: 6221
<212> TYPE: DNA
<213> ORGANISM: Artificial Sequence
<220> FEATURE:
<223> OTHER INFORMATION: Plasmid pFP988DssPgroE

<400> SEQUENCE: 143
tcgagagcta ttgtaacata atcggtacgg gggtgaaaaa gctaacggaa aagggagcgg     60
aaaagaatga tgtaagcgtg aaaaattttt tatcttatca cttgaaattg gaagggagat    120
tctttattat aagaattgtg gaattgtgag cggataacaa ttcccaatta aggaggaaa     180
ctagtggatc caagtttaaa ctgtacacta gatatttctt ctccgcttaa atcatcaaag    240
aaatctttat cacttgtaac cagtccgtcc acatgtcgaa ttgcatctga ccgaatttta    300
cgtttccctg aataattctc atcaatcgtt tcatcaattt tatctttata ctttatattt    360
tgtgcgttaa tcaaatcata attttttatat gtttcctcat gatttatgtc tttattatta    420
tagttttttat tctctctttg attatgtctt tgtatcccgt tgtattact tgatcctta    480
actctggcaa ccctcaaaat tgaatgagac atgctacacc tccggataat aaatatatat    540
aaacgtatat agatttcata agtctaaca cactagactt atttacttcg taattaagtc    600
gttaaaccgt gtgctctacg accaaaacta taaaaccttt aagaactttc ttttttttaca    660
agaaaaaaga aattagataa atctctcata tcttttattc aataatcgca tccgattgca    720
gtataaattt aacgatcact catcatgttc atatttatca gagctcgtgc tataattata    780
ctaattttat aaggaggaaa aaatatgggc attttttagta ttttttgtaat cagcacagtt    840
cattatcaac caaacaaaaa ataagtggtt ataatgaatc gttaataagc aaaattcata    900
taaccaaatt aaagagggtt ataatgaacg agaaaaatat aaaacacagt caaaacttta    960
ttacttcaaa acataatata gataaaataa tgacaaatat aagattaaat gaacatgata   1020
atatctttga atcggctca ggaaaaggcc attttaccct tgaattagta aagaggtgta   1080
atttcgtaac tgccattgaa atagaccata aattatgcaa aactacagaa ataaacttg   1140
ttgatcacga taatttccaa gttttaaaca aggatatatt gcagtttaaa tttcctaaaa   1200
accaatccta taaatatat ggtaatatac cttataacta agtacggat ataatacgca   1260
aaattgtttt tgatagtata gctaatgaga tttatttaat cgtggaatac gggtttgcta   1320
aaagattatt aaatacaaaa cgctcattgg cattactttt aatggcagaa gttgatatttt   1380
ctatattaag tatggttcca agagaatatt ttcatcctaa acctaaagtg aatagctcac   1440
ttatcagatt aagtagaaaa aaatcaagaa tatcacacaa agataaacaa agtataattt   1500
atttcgttat gaaatgggtt aacaaagaat acaagaaaat atttacaaaa aatcaattta   1560
acaattcctt aaaacatgca ggaattgacg atttaaacaa tattagcttt gaacaattct   1620
tatctctttt caatagctat aaattattta ataagtaagt taagggatgc agttcatcga   1680
tgaaggcaac tacagctcag gcgacaacca tacgctgaga gatcctcact acgtagaaga   1740
taaaggccac aaatacttag tatttgaagc aaacactgga actgaagatg ctaccaagg   1800
cgaagaatct ttatttaaca agcatacta tggcaaaagc acatcattct tccgtcaaga   1860
aagtcaaaaa cttctgcaaa gcgataaaaa acgcacggct gagttagcaa acggcgctct   1920
cggtatgatt gagctaaacg atgattacac actgaaaaaa gtgatgaaac cgctgattgc   1980

```
atctaacaca gtaacagatg aaattgaacg cgcgaacgtc tttaaaatga acggcaaatg      2040
gtacctgttc actgactccc gcggatcaaa aatgacgatt gacggcatta cgtctaacga      2100
tatttacatg cttggttatg tttctaattc tttaactggc ccatacaagc cgctgaacaa      2160
aactggcctt gtgttaaaaa tggatcttga tcctaacgat gtaacctttga cttactcaca      2220 cttcgctgta cctcaagcga aggaaacaa tgtcgtgatt acaagctata tgacaaacag      2280
aggattctac gcagacaaac aatcaacgtt gcgccaagc ttgcatgcga gagtagggaa      2340
ctgccaggca tcaaataaaa cgaaaggctc agtcgaaaga ctgggccttt cgttttatct      2400
gttgtttgtc ggtgaacgct ctcctgagta ggacaaatcc gccgggagcg gatttgaacg      2460
ttgcgaagca acggcccgga gggtggcggg caggacgccc gccataaact gccaggcatc      2520
aaattaagca aaggccatc ctgacggatg gccttttttgc gtttctacaa actctttttg      2580
tttatttttc taaatacatt caaatatgta tccgctcatg ctccggatct gcatcgcagg      2640
atgctgctgg ctaccctgtg gaacacctac atctgtatta acgaagcgct ggcattgacc      2700
ctgagtgatt tttctctggt cccgccgcat ccataccgcc agttgtttac cctcacaacg      2760
ttccagtaac cgggcatgtt catcatcagt aacccgtatc gtgagcatcc tctctcgttt      2820
catcggtatc attacccca tgaacagaaa ttccccctta cacggaggca tcaagtgacc      2880
aaacaggaaa aaaccgccct taacatggcc cgctttatca aagccagac attaacgctt      2940 ctggagaaac tcaacgagct ggacgcggat gaacaggcag acatctgtga atcgcttcac      3000
gaccacgctg atgagctttta ccgcagctgc ctcgcgcgtt cggtgatga cggtgaaaac      3060 ctctgacaca tgcagctccc ggagacggtc acagcttgtc tgtaagcgga tgccgggagc      3120
agacaagccc gtcagggcgc gtcagcgggt gttgcgggt gtcggggcgc agccatgacc      3180
cagtcacgta gcgatagcgg agtgtatact ggcttaacta tgcggcatca gagcagattg      3240
tactgagagt gcaccatatg cggtgtgaaa taccgcacag atgcgtaagg agaaaatacc      3300
gcatcaggcg ctcttccgct tcctcgctca ctgactcgct gcgctcggtc gttcggctgc      3360
ggcgagcggt atcagctcac tcaaaggcgg taatacggtt atccacagaa tcaggggata      3420
acgcaggaaa gaacatgtga gcaaaaggcc agcaaaggc caggaaccgt aaaaaggccg      3480
cgttgctggc gtttttccat aggctccgcc ccctgacga gcatcacaaa aatcgacgct      3540
caagtcagag gtggcgaaac ccgacaggac tataaagata ccaggcgttt ccccctggaa      3600
gctccctcgt gcgctctcct gttccgaccc tgccgcttac cggatacctg tccgcctttc      3660
tcccttcggg aagcgtggcg ctttctcaat gctcacgctg taggtatctc agttcggtgt      3720
aggtcgttcg ctccaagctg ggctgtgtgc acgaaccccc cgttcagccc gaccgctgcg      3780
ccttatccgg taactatcgt cttgagtcca acccggtaag acacgactta tcgccactgg      3840
cagcagccac tggtaacagg attagcagag cgaggtatgt aggcggtgct acagagttct      3900
tgaagtggtg gcctaactac ggctacacta aaggacagt attggtatc tgcgctctgc      3960 tgaagccagt taccttcgga aaagagttg gtagctcttg atccggcaaa caaaccaccg      4020
ctggtagcgg tggttttttt gtttgcaagc agcagattac gcgcagaaaa aaaggatctc      4080
aagaagatcc tttgatcttt tctacggggt ctgacgctca gtggaacgaa aactcacgtt      4140
aagggatttt ggtcatgaga ttatcaaaaa ggatcttcac ctagatcctt ttaaattaaa      4200
aatgaagttt taaatcaatc taaagtatat atgagtaaac ttggtctgac agttaccaat      4260
gcttaatcag tgaggcacct atctcagcga tctgtctatt tcgttcatcc atagttgcct      4320
gactccccgt cgtgtagata actacgatac gggagggctt accatctggc cccagtgctg      4380
```

```
caatgatacc gcgagaccca cgctcaccgg ctccagattt atcagcaata aaccagccag    4440
ccggaagggc cgagcgcaga agtggtcctg caactttatc cgcctccatc cagtctatta    4500
attgttgccg ggaagctaga gtaagtagtt cgccagttaa tagtttgcgc aacgttgttg    4560
ccattgctgc aggcatcgtg gtgtcacgct cgtcgtttgg tatggcttca ttcagctccg    4620
gttcccaacg atcaaggcga gttacatgat cccccatgtt gtgcaaaaaa gcggttagct    4680
ccttcggtcc tccgatcgtt gtcagaagta agttggccgc agtgttatca ctcatggtta    4740
tggcagcact gcataattct cttactgtca tgccatccgt aagatgcttt tctgtgactg    4800
gtgagtactc aaccaagtca ttctgagaat agtgtatgcg gcgaccgagt tgctcttgcc    4860
cggcgtcaat acgggataat accgcgccac atagcagaac tttaaaagtg ctcatcattg    4920
gaaaacgttc ttcggggcga aaactctcaa ggatcttacc gctgttgaga tccagttcga    4980
tgtaacccac tcgtgcaccc aactgatctt cagcatcttt tactttcacc agcgtttctg    5040
ggtgagcaaa aacaggaagg caaaatgccg caaaaaaggg aataagggcg acacggaaat    5100
gttgaatact catactcttc cttttcaat attattgaag catttatcag ggttattgtc    5160
tcatgagcgg atacatattt gaatgtattt agaaaaataa acaaataggg gttccgcgca    5220
catttccccg aaaagtgcca cctgacgtct aagaaaccat tattatcatg acattaacct    5280
ataaaaatag gcgtatcacg aggccctttc gtctcgcgcg tttcggtgat gacggtgaaa    5340
acctctgaca catgcagctc ccggagacgg tcacagcttg tctgtaagcg gatgccggga    5400
gcagacaagc ccgtcagggc gcgtcagcgg gtgttcatgt gcgtaactaa cttgccatct    5460
tcaaacagga gggctggaag aagcagaccg ctaacacagt acataaaaaa ggagacatga    5520
acgatgaaca tcaaaaagtt tgcaaaacaa gcaacagtat taacctttac taccgcactg    5580
ctggcaggag gcgcaactca agcgtttgcg aaagaaacga accaaaagcc atataaggaa    5640
acatacggca tttcccatat tacacgccat gatatgctgc aaatccctga acagcaaaaa    5700
aatgaaaaat atcaagttcc tgaattcgat tcgtccacaa ttaaaaatat ctcttctgca    5760
aaaggcctgg acgtttggga cagctggcca ttacaaaacg ctgacggcac tgtcgcaaac    5820
tatcacggct accacatcgt cttttgcatta gccggagatc ctaaaaatgc ggatgacaca    5880
tcgatttaca tgttctatca aaaagtcggc gaaacttcta ttgacagctg gaaaaacgct    5940
ggccgcgtct ttaaagacag cgacaaattc gatgcaaatg attctatcct aaaagaccaa    6000
acacaagaat ggtcaggttc agccacattt acatctgacg gaaaaatccg tttattctac    6060
actgatttct ccggtaaaca ttacggcaaa caaacactga caactgcaca agttaacgta    6120
tcagcatcag acagctcttt gaacatcaac ggtgtagagg attataaatc aatctttgac    6180
ggtgacggaa aaacgtatca aaatgtacag aattcgagct c                       6221
```

<210> SEQ ID NO 144
<211> LENGTH: 40
<212> TYPE: DNA
<213> ORGANISM: Artificial Sequence
<220> FEATURE:
<223> OTHER INFORMATION: Primer T-budB (BamHI)

<400> SEQUENCE: 144
agatagatgg atccggaggt gggtcacatg gacaaacagt                           40

<210> SEQ ID NO 145
<211> LENGTH: 29
<212> TYPE: DNA

```
<213> ORGANISM: Artificial Sequence
<220> FEATURE:
<223> OTHER INFORMATION: Primer B-kivD (BamHI)

<400> SEQUENCE: 145
ctctagagga tccagactcc taggacatg                                        29

<210> SEQ ID NO 146
<211> LENGTH: 6039
<212> TYPE: DNA
<213> ORGANISM: Artificial Sequence
<220> FEATURE:
<223> OTHER INFORMATION: Vector fragment pFP988Dss

<400> SEQUENCE: 146
gatccaagtt taaactgtac actagatatt tcttctccgc ttaaatcatc aaagaaatct      60
ttatcacttg taaccagtcc gtccacatgt cgaattgcat ctgaccgaat tttacgtttc     120
cctgaataat tctcatcaat cgtttcatca attttatctt tatacttttat attttgtgcg   180 ttaatcaaat cataattttt atatgttttcc tcatgattta tgtctttatt attatagttt   240
ttattctctc tttgattatg tctttgtatc ccgtttgtat tacttgatcc tttaactctg    300
gcaaccctca aaattgaatg agacatgcta cacctccgga taataaatat atataaacgt    360
atatagattt cataaagtct aacacactag acttatttac ttcgtaatta agtcgttaaa    420
ccgtgtgctc tacgaccaaa actataaaac ctttaagaac tttcttttttt tacaagaaaa   480 aagaaattag ataaatctct catatctttt attcaataat cgcatccgat gcagtataa     540 atttaacgat cactcatcat gttcatattt atcagagctc gtgctataat tatactaatt    600
ttataaggag gaaaaaatat gggcatttttt agtattttttg taatcagcac agttcattat   660
caaccaaaca aaaaataagt ggttataatg aatcgttaat aagcaaaatt catataacca    720
aattaaagag ggttataatg aacgagaaaa atataaaaca cagtcaaaac tttattactt    780
caaaacataa tatagataaa ataatgacaa atataagatt aaatgaacat gataatatct    840
ttgaaatcgg ctcaggaaaa ggccattttta cccttgaatt agtaaagagg tgtaatttcg    900
taactgccat tgaaatagac cataaattat gcaaaactac agaaaataaa cttgttgatc     960
acgataattt ccaagtttta aacaaggata tattgcagtt taaatttcct aaaaaccaat   1020
cctataaaat atatggtaat ataccttata acataagtac ggatataata cgcaaaattg   1080 ttttttgatag tatagctaat gagatttatt taatcgtgga atacgggttt gctaaaagat   1140 tattaaaatac aaaacgctca ttggcattac ttttaatggc agaagttgat atttctatat   1200
taagtatggt tccaagagaa tatttttcatc ctaaacctaa agtgaatagc tcacttatca   1260
gattaagtag aaaaaaatca agaatatcac acaaagataa acaaagtat aattatttcg    1320 ttatgaaatg ggttaacaaa gaatacaaga aaatatttac aaaaaatcaa tttaacaatt   1380
ccttaaaaca tgcaggaatt gacgatttaa acaatattag ctttgaacaa ttcttatctc   1440
ttttcaatag ctataaatta tttaataagt aagttaaggg atgcagttca tcgatgaagg   1500
caactacagc tcaggcgaca accatacgct gagagatcct cactacgtag aagataaagg   1560
ccacaaatac ttagtatttg aagcaaacac tggaactgaa gatggctacc aaggcgaaga   1620 atctttatttt aacaaagcat actatggcaa agcacatca ttcttccgtc aagaaagtca   1680
aaaacttctg caaagcgata aaaacgcac ggctgagtta gcaaacggcg ctctcggtat    1740
gattgagcta aacgatgatt acacactgaa aaaagtgatg aaaccgctga ttgcatctaa   1800
cacagtaaca gatgaaattg aacgcgcgaa cgtctttaaa atgaacggca atggtacct     1860
```

```
gttcactgac tcccgcggat caaaaatgac gattgacggc attacgtcta acgatattta    1920
catgcttggt tatgtttcta attctttaac tggcccatac aagccgctga acaaaactgg    1980
ccttgtgtta aaaatggatc ttgatcctaa cgatgtaacc tttacttact cacacttcgc    2040
tgtacctcaa gcgaaggaa acaatgtcgt gattacaagc tatatgacaa acagaggatt    2100
ctacgcagac aaacaatcaa cgtttgcgcc aagcttgcat gcgagagtag ggaactgcca    2160
ggcatcaaat aaaacgaaag gctcagtcga agactgggc ctttcgtttt atctgttgtt    2220
tgtcggtgaa cgctctcctg agtaggacaa atccgccggg agcggatttg aacgttgcga    2280
agcaacggcc cggagggtgg cgggcaggac gcccgccata aactgccagg catcaaatta    2340
agcagaaggc catcctgacg gatggccttt ttgcgtttct acaaactctt tttgtttatt    2400
tttctaaata cattcaaata tgtatccgct catgctccgg atctgcatcg caggatgctg    2460
ctggctaccc tgtggaacac ctacatctgt attaacgaag cgctggcatt gaccctgagt    2520 gattttctc tggtcccgcc gcatccatac cgccagttgt ttaccctcac aacgttccag    2580
taaccgggca tgttcatcat cagtaacccg tatcgtgagc atcctctctc gtttcatcgg    2640
tatcattacc cccatgaaca gaaattcccc cttacacgga ggcatcaagt gaccaaacag    2700
gaaaaaaccg cccttaacat ggcccgcttt atcagaagcc agacattaac gcttctggag    2760
aaactcaacg agctggacgc ggatgaacag gcagacatct gtgaatcgct tcacgaccac    2820
gctgatgagc tttaccgcag ctgcctcgcg cgtttcggtg atgacggtga aacctctga    2880 cacatgcagc tcccggagac ggtcacagct tgtctgtaag cggatgccgg gagcagacaa    2940
gcccgtcagg gcgcgtcagc gggtgttggc gggtgtcggg gcgcagccat gacccagtca    3000
cgtagcgata gcggagtgta tactggctta actatgcggc atcagagcag attgtactga    3060
gagtgcacca tatgcggtgt gaaataccgc acagatgcgt aaggagaaaa taccgcatca    3120
ggcgctcttc cgcttcctcg ctcactgact cgctgcgctc ggtcgttcgg ctgcggcgag    3180
cggtatcagc tcactcaaag gcggtaatac ggttatccac agaatcaggg gataacgcag    3240
gaaagaacat gtgagcaaaa ggccagcaaa aggccaggaa ccgtaaaaag gccgcgttgc    3300
tggcgttttt ccataggctc cgcccccctg acgagcatca caaaaatcga cgctcaagtc    3360
agaggtggcg aaacccgaca ggactataaa gataccaggc gtttccccct ggaagctccc    3420
tcgtgcgctc tcctgttccg accctgccgc ttaccggata cctgtccgcc tttctccctt    3480
cgggaagcgt ggcgctttct caatgctcac gctgtaggta tctcagttcg gtgtaggtcg    3540
ttcgctccaa gctgggctgt gtgcacgaac cccccgttca gcccgaccgc tgcgccttat    3600
ccggtaacta tcgtcttgag tccaacccgg taagacacga cttatcgcca ctggcagcag    3660
ccactggtaa caggattagc agagcgaggt atgtaggcgg tgctacagag ttcttgaagt    3720
ggtggcctaa ctacggctac actagaagga cagtatttgg tatctgcgct ctgctgaagc    3780
cagttacctt cggaaaaaga gttggtagct cttgatccgg caaacaaacc accgctggta    3840
gcggtggttt ttttgtttgc aagcagcaga ttacgcgcag aaaaaaagga tctcaagaag    3900
atcctttgat cttttctacg ggtctgacgc tcagtggaa cgaaaactca cgttaaggga    3960
ttttggtcat gagattatca aaaaggatct tcacctagat ccttttaaat taaaaatgaa    4020
gttttaaatc aatctaaagt atatatgagt aaacttggtc tgacagttac caatgcttaa    4080
tcagtgaggc acctatctca gcgatctgtc tatttcgttc atccatagtt gcctgactcc    4140
ccgtcgtgta gataactacg atacgggagg gcttaccatc tggccccagt gctgcaatga    4200
```

```
taccgcgaga cccacgctca ccggctccag atttatcagc aataaaccag ccagccggaa    4260
gggccgagcg cagaagtggt cctgcaactt tatccgcctc catccagtct attaattgtt    4320
gccgggaagc tagagtaagt agttcgccag ttaatagttt gcgcaacgtt gttgccattg    4380
ctgcaggcat cgtggtgtca cgctcgtcgt ttggtatggc ttcattcagc tccggttccc    4440
aacgatcaag gcgagttaca tgatccccca tgttgtgcaa aaaagcggtt agctccttcg    4500
gtcctccgat cgttgtcaga agtaagttgg ccgcagtgtt atcactcatg gttatggcag    4560
cactgcataa ttctcttact gtcatgccat ccgtaagatg ctttctgtg actggtgagt      4620
actcaaccaa gtcattctga gaatagtgta tgcggcgacc gagttgctct tgcccggcgt    4680
caatacggga taataccgcg ccacatagca gaactttaaa agtgctcatc attggaaaac    4740
gttcttcggg gcgaaaactc tcaaggatct taccgctgtt gagatccagt tcgatgtaac    4800
ccactcgtgc acccaactga tcttcagcat cttttacttt caccagcgtt tctgggtgag    4860
caaaaacagg aaggcaaaat gccgcaaaaa agggaataag ggcgacacgg aaatgttgaa    4920
tactcatact cttcctttt caatattatt gaagcattta tcagggttat tgtctcatga     4980
gcggatacat atttgaatgt atttagaaaa ataaacaaat aggggttccg cgcacatttc    5040
cccgaaaagt gccacctgac gtctaagaaa ccattattat catgacatta acctataaaa    5100
ataggcgtat cacgaggccc tttcgtctcg cgcgtttcgg tgatgacggt gaaaacctct    5160
gacacatgca gctcccggag acggtcacag cttgtctgta gcggatgcc gggagcagac     5220
aagcccgtca gggcgcgtca gcgggtgttc atgtgcgtaa ctaacttgcc atcttcaaac    5280
aggagggctg gaagaagcag accgctaaca cagtacataa aaaaggagac atgaacgatg    5340
aacatcaaaa agtttgcaaa acaagcaaca gtattaacct ttactaccgc actgctggca    5400
ggaggcgcaa ctcaagcgtt tgcgaaagaa acgaaccaaa agccatataa ggaaacatac    5460
ggcatttccc atattacacg ccatgatatg ctgcaaatcc ctgaacagca aaaaaatgaa    5520
aaatatcaag ttcctgaatt cgattcgtcc acaattaaaa atatctcttc tgcaaaaggc    5580
ctggacgttt gggacagctg gccattacaa aacgctgacg gcactgtcgc aaactatcac    5640
ggctaccaca tcgtctttgc attagccgga gatcctaaaa atgcggatga cacatcgatt    5700
tacatgttct atcaaaaagt cggcgaaact tctattgaca gctggaaaaa cgctggccgc    5760
gtctttaaag acagcgacaa attcgatgca atgattcta tcctaaaaga ccaaacacaa     5820
gaatggtcag gttcagccac atttacatct gacggaaaaa tccgtttatt ctacactgat    5880
ttctccggta acattacgg caaacaaaca ctgacaactg cacaagttaa cgtatcagca     5940
tcagacagct ctttgaacat caacggtgta gaggattata atcaatctt tgacggtgac     6000
ggaaaaacgt atcaaaatgt acagaattcg agctctcga                           6039
```

<210> SEQ ID NO 147
<211> LENGTH: 44
<212> TYPE: DNA
<213> ORGANISM: Artificial Sequence
<220> FEATURE:
<223> OTHER INFORMATION: Primer T-groE(XhoI)

<400> SEQUENCE: 147
agatagatct cgagagctat tgtaacataa tcggtacggg ggtg                    44

<210> SEQ ID NO 148
<211> LENGTH: 51
<212> TYPE: DNA
<213> ORGANISM: Artificial Sequence

```
<220> FEATURE:
<223> OTHER INFORMATION: Primer B-groEL (SpeI BamH1)

<400> SEQUENCE: 148
attatgtcag gatccactag tttcctcctt taattgggaa ttgttatccg c          51

<210> SEQ ID NO 149
<211> LENGTH: 30
<212> TYPE: DNA
<213> ORGANISM: Artificial Sequence
<220> FEATURE:
<223> OTHER INFORMATION: Primer T-groEL

<400> SEQUENCE: 149
agctattgta acataatcgg tacggggtg                                  30

<210> SEQ ID NO 150
<211> LENGTH: 45
<212> TYPE: DNA
<213> ORGANISM: Artificial Sequence
<220> FEATURE:
<223> OTHER INFORMATION: Primer T-ilvCB.s.(BamHI)

<400> SEQUENCE: 150
acattgatgg atcccataac aagggagaga ttgaaatggt aaaag                45

<210> SEQ ID NO 151
<211> LENGTH: 47
<212> TYPE: DNA
<213> ORGANISM: Artificial Sequence
<220> FEATURE:
<223> OTHER INFORMATION: Primer B-ilvCB.s.(SpeIBamHI)

<400> SEQUENCE: 151
tagacaacgg atccactagt ttaattttgc gcaacggaga ccaccgc              47

<210> SEQ ID NO 152
<211> LENGTH: 47
<212> TYPE: DNA
<213> ORGANISM: Artificial Sequence
<220> FEATURE:
<223> OTHER INFORMATION: Primer T-BD64 (DraIII)

<400> SEQUENCE: 152
ttaccgtgga ctcaccgagt gggtaactag cctcgccgga aagagcg              47

<210> SEQ ID NO 153
<211> LENGTH: 48
<212> TYPE: DNA
<213> ORGANISM: Artificial Sequence
<220> FEATURE:
<223> OTHER INFORMATION: Primer B-BD64 (DraIII)

<400> SEQUENCE: 153
tcacagttaa gacacctggt gccgttaatg cgccatgaca gccatgat             48

<210> SEQ ID NO 154
<211> LENGTH: 49
<212> TYPE: DNA
<213> ORGANISM: Artificial Sequence
<220> FEATURE:
<223> OTHER INFORMATION: Primer T-lacIq (DraIII)

<400> SEQUENCE: 154
acagatagat caccaggtgc aagctaattc cggtggaaac gaggtcatc            49
```

```
<210> SEQ ID NO 155
<211> LENGTH: 48
<212> TYPE: DNA
<213> ORGANISM: Artificial Sequence
<220> FEATURE:
<223> OTHER INFORMATION: Primer B-lacIq (DraIII)

<400> SEQUENCE: 155
acagtacgat acacggggtg tcactgcccg ctttccagtc gggaaacc                 48

<210> SEQ ID NO 156
<211> LENGTH: 49
<212> TYPE: DNA
<213> ORGANISM: Artificial Sequence
<220> FEATURE:
<223> OTHER INFORMATION: Primer T-groE (DraIII)

<400> SEQUENCE: 156
tcggattacg caccccgtga gctattgtaa cataatcggt acggggtg                 49

<210> SEQ ID NO 157
<211> LENGTH: 48
<212> TYPE: DNA
<213> ORGANISM: Artificial Sequence
<220> FEATURE:
<223> OTHER INFORMATION: Primer B-B.s.ilvC (DraIII)

<400> SEQUENCE: 157
ctgctgatct cacaccgtgt gttaattttg cgcaacggag accaccgc                 48

<210> SEQ ID NO 158
<211> LENGTH: 1221
<212> TYPE: DNA
<213> ORGANISM: Clostridium acetobutylicum

<400> SEQUENCE: 158
cacacggtgt aaataataat ctaaacagga ggggttaaaa tggttgattt cgaatattca      60
ataccaacta gaattttttt cggtaaagat aagataaatg tacttggaag agagcttaaa     120
aaatatggtt ctaaagtgct tatagtttat ggtggaggaa gtataaagag aaatggaata     180
tatgataaag ctgtaagtat acttgaaaaa acagtatta aattttatga acttgcagga      240
gtagagccaa atccaagagt aactacagtt gaaaaggag ttaaaatatg tagagaaaat      300
ggagttgaag tagtactagc tataggtgga ggaagtgcaa tagattgcgc aaaggttata     360
gcagcagcat gtgaatatga tggaaatcca tgggatattg tgttagatgg ctcaaaaata     420
aaaagggtgc ttcctatagc tagtatatta accattgctg caacaggatc agaaatggat     480
acgtgggcag taataaataa tatggataca acgaaaaac taattgcggc acatccagat     540
atggctccta gtttttctat attagatcca acgtatacgt ataccgtacc taccaatcaa     600
acagcagcag gaacagctga tattatgagt catatatttg aggtgtattt tagtaataca     660
aaaacagcat atttgcagga tagaatggca gaagcgttat taagaacttg tattaaatat     720
ggaggaatag ctcttgagaa gccggatgat tatgagcaa gagccaatct aatgtgggct      780
tcaagtcttg cgataaatgg acttttaaca tatggtaaag acactaattg gagtgtacac     840
ttaatggaac atgaattaag tgcttattac gacataacac acggcgtagg gcttgcaatt     900
ttaacaccta ttggatgga gtatattta aataatgata cagtgtacaa gtttgttgaa     960
tatggtgtaa atgttttggg gaatagacaa gaaaaaaatc actatgacat agcacatcaa    1020
gcaatacaaa aacaagaga ttactttgta aatgtactag gtttaccatc tagactgaga    1080
```

-continued

```
gatgttggaa ttgaagaaga aaaattggac ataatggcaa aggaatcagt aaagcttaca      1140
ggaggaacca taggaaacct aagaccagta acgcctccg aagtcctaca aatattcaaa      1200
aaatctgtgt aacaccgagt g                                                1221
```

<210> SEQ ID NO 159
<211> LENGTH: 54
<212> TYPE: DNA
<213> ORGANISM: Artificial Sequence
<220> FEATURE:
<223> OTHER INFORMATION: Primer T-bdhB (DraIII)

<400> SEQUENCE: 159

```
tcgatagcat acacacggtg gttaacaaag gaggggttaa aatggttgat ttcg             54
```

<210> SEQ ID NO 160
<211> LENGTH: 91
<212> TYPE: DNA
<213> ORGANISM: Artificial Sequence
<220> FEATURE:
<223> OTHER INFORMATION: Primer B-bdhB (rrnBT1DraIII)

<400> SEQUENCE: 160

```
atctacgcac tcggtgataa aacgaaaggc ccagtctttc gactgagcct ttcgttttat      60
cttacacaga tttttttgaat atttgtagga c                                     91
```

<210> SEQ ID NO 161
<211> LENGTH: 29
<212> TYPE: DNA
<213> ORGANISM: Artificial Sequence
<220> FEATURE:
<223> OTHER INFORMATION: Primer LDH EcoRV F

<400> SEQUENCE: 161

```
gacgtcatga ccacccgccg atcccttttt                                        29
```

<210> SEQ ID NO 162
<211> LENGTH: 30
<212> TYPE: DNA
<213> ORGANISM: Artificial Sequence
<220> FEATURE:
<223> OTHER INFORMATION: Primer LDH AatIIR

<400> SEQUENCE: 162

```
gatatccaac accagcgacc gacgtattac                                        30
```

<210> SEQ ID NO 163
<211> LENGTH: 47
<212> TYPE: DNA
<213> ORGANISM: Artificial Sequence
<220> FEATURE:
<223> OTHER INFORMATION: Primer Cm F

<400> SEQUENCE: 163

```
atttaaatct cgagtagagg atcccaacaa acgaaaattg gataaag                     47
```

<210> SEQ ID NO 164
<211> LENGTH: 29
<212> TYPE: DNA
<213> ORGANISM: Artificial Sequence
<220> FEATURE:
<223> OTHER INFORMATION: Primer Cm R

<400> SEQUENCE: 164

```
acgcgttatt ataaaagcca gtcattagg                                          29

<210> SEQ ID NO 165
<211> LENGTH: 58
<212> TYPE: DNA
<213> ORGANISM: Artificial Sequence
<220> FEATURE:
<223> OTHER INFORMATION: Primer P11 F-StuI

<400> SEQUENCE: 165
cctagcgcta tagttgttga cagaatggac atactatgat atattgttgc tatagcga       58

<210> SEQ ID NO 166
<211> LENGTH: 62
<212> TYPE: DNA
<213> ORGANISM: Artificial Sequence
<220> FEATURE:
<223> OTHER INFORMATION: Primer P11 R-SpeI

<400> SEQUENCE: 166
ctagtcgcta tagcaacaat atatcatagt atgtccattc tgtcaacaac tatagcgcta     60
gg                                                                     62

<210> SEQ ID NO 167
<211> LENGTH: 38
<212> TYPE: DNA
<213> ORGANISM: Artificial Sequence
<220> FEATURE:
<223> OTHER INFORMATION: Primer PldhL F-HindIII

<400> SEQUENCE: 167
aagcttgtcg acaaaccaac attatgacgt gtctgggc                              38

<210> SEQ ID NO 168
<211> LENGTH: 28
<212> TYPE: DNA
<213> ORGANISM: Artificial Sequence
<220> FEATURE:
<223> OTHER INFORMATION: Primer PldhL R-BamHI

<400> SEQUENCE: 168
ggatcctcat cctctcgtag tgaaaatt                                         28

<210> SEQ ID NO 169
<211> LENGTH: 36
<212> TYPE: DNA
<213> ORGANISM: Artificial Sequence
<220> FEATURE:
<223> OTHER INFORMATION: Primer F-bdhB-AvrII

<400> SEQUENCE: 169
ttcctaggaa ggaggtggtt aaaatggttg atttcg                                36

<210> SEQ ID NO 170
<211> LENGTH: 29
<212> TYPE: DNA
<213> ORGANISM: Artificial Sequence
<220> FEATURE:
<223> OTHER INFORMATION: Primer R-bdhB-BamHI

<400> SEQUENCE: 170
ttggatcctt acacagattt tttgaatat                                        29

<210> SEQ ID NO 171
<211> LENGTH: 39
```

<212> TYPE: DNA
<213> ORGANISM: Artificial Sequence
<220> FEATURE:
<223> OTHER INFORMATION: Primer F-ilvC(B.s.)-AflII

<400> SEQUENCE: 171
aacttaagaa ggaggtgatt gaaatggtaa aagtatatt                                39

<210> SEQ ID NO 172
<211> LENGTH: 32
<212> TYPE: DNA
<213> ORGANISM: Artificial Sequence
<220> FEATURE:
<223> OTHER INFORMATION: Primer R-ilvC(B.s.)-NotI

<400> SEQUENCE: 172
aagcggccgc ttaattttgc gcaacggaga cc                                       32

<210> SEQ ID NO 173
<211> LENGTH: 30
<212> TYPE: DNA
<213> ORGANISM: Artificial Sequence
<220> FEATURE:
<223> OTHER INFORMATION: Primer F-PnisA(HindIII)

<400> SEQUENCE: 173
ttaagcttga catacttgaa tgacctagtc                                          30

<210> SEQ ID NO 174
<211> LENGTH: 39
<212> TYPE: DNA
<213> ORGANISM: Artificial Sequence
<220> FEATURE:
<223> OTHER INFORMATION: Primer R-PnisA(SpeI BamHI)

<400> SEQUENCE: 174
ttggatccaa actagtataa tttattttgt agttccttc                                39

<210> SEQ ID NO 175
<211> LENGTH: 38
<212> TYPE: DNA
<213> ORGANISM: Artificial Sequence
<220> FEATURE:
<223> OTHER INFORMATION: Primer N191

<400> SEQUENCE: 175
atccgcggat agatctccca ttaccgacat ttgggcgc                                 38

<210> SEQ ID NO 176
<211> LENGTH: 31
<212> TYPE: DNA
<213> ORGANISM: Artificial Sequence
<220> FEATURE:
<223> OTHER INFORMATION: Primer N192

<400> SEQUENCE: 176
atcctcagcg atgattgatt gattgattgt a                                        31

<210> SEQ ID NO 177
<211> LENGTH: 6509
<212> TYPE: DNA
<213> ORGANISM: Artificial Sequence
<220> FEATURE:
<223> OTHER INFORMATION: Vector pFP988

<400> SEQUENCE: 177

```
tcgaggcccc gcacatacga aaagactggc tgaaaacatt gagcctttga tgactgatga      60
tttggctgaa gaagtggatc gattgtttga gaaaagaaga agaccataaa aataccttgt     120
ctgtcatcag acagggtatt ttttatgctg tccagactgt ccgctgtgta aaaatagga      180
ataaagggg gttgttatta ttttactgat atgtaaaata taatttgtat aaggaattgt      240
gagcggataa caattcctac gaaaatgaga gggagaggaa acatgattca aaaacgaaag     300
cggacagttt cgttcagact tgtgcttatg tgcacgctgt tatttgtcag tttgccgatt     360
acaaaaacat cagccggatc ccaccatcac catcaccatt aagaattcct agaaactcca     420
agctatcttt aaaaaatcta gtaaatgcac gagcaacatc ttttgttgct cagtgcattt     480
tttattttgt acactagata tttcttctcc gcttaaatca tcaagaaaat ctttatcact     540
tgtaaccagt ccgtccacat gtcgaattgc atctgaccga attttacgtt tccctgaata     600
attctcatca atcgtttcat caattttatc tttatacttt atattttgtg cgttaatcaa     660
atcataattt ttatatgttt cctcatgatt tatgtcttta ttattatagt ttttattctc     720
tctttgatta tgtctttgta tcccgtttgt attacttgat cctttaactc tggcaaccct     780
caaaattgaa tgagacatgc tacacctccg gataataaat atatataaac gtatatagat     840
ttcataaagt ctaacacact agacttattt acttcgtaat taagtcgtta aaccgtgtgc     900
tctacgacca aaactataaa acctttaaga acttctttt tttacaagaa aaagaaatt      960
agataaatct ctcatatctt ttattcaata atcgcatccg attgcagtat aaatttaacg    1020
atcactcatc atgttcatat ttatcagagc tcgtgctata attatactaa ttttataagg    1080
aggaaaaaat atgggcattt ttagtatttt tgtaatcagc acagttcatt atcaaccaaa    1140
caaaaaataa gtggttataa tgaatcgtta ataagcaaaa ttcatataac caaattaaag    1200
agggttataa tgaacgagaa aaatataaaa cacagtcaaa actttattac ttcaaaacat    1260
aatatagata aaataatgac aaatataaga ttaaatgaac atgataatat ctttgaaatc    1320
ggctcaggaa aaggccattt tacccttgaa ttagtaaaga ggtgtaattt cgtaactgcc    1380
attgaaatag accataaatt atgcaaaact acagaaaata aacttgttga tcacgataat    1440
ttccaagttt taaacaagga tatattgcag tttaaatttc ctaaaaacca atcctataaa    1500
atatatggta atatacctta taacataagt acggatataa tacgcaaaat tgttttgat    1560
agtatagcta atgagattta tttaatcgtg aatacgggt ttgctaaaag attattaaat    1620
acaaaacgct cattggcatt actttaatg gcagaagttg atatttctat attaagtatg    1680
gttccaagag aatattttca tcctaaacct aaagtgaata gctcacttat cagattaagt    1740
agaaaaaaat caagaatatc acacaaagat aaacaaaagt ataattattt cgttatgaaa    1800
tgggttaaca aagaatacaa gaaaatattt acaaaaaatc aatttaacaa ttccttaaaa    1860
catgcaggaa ttgacgattt aaacaatatt agctttgaac aattcttatc tcttttcaat    1920
agctataaat tatttaataa gtaagttaag ggatgcagtt catcgatgaa ggcaactaca    1980
gctcaggcga caaccatacg ctgagagatc ctcactacgt agaagataaa ggccacaaat    2040
acttagtatt tgaagcaaac actggaactg aagatggcta ccaaggcgaa gaatctttat    2100
ttaacaaagc atactatggc aaaagcacat cattcttccg tcaagaaagt caaaaacttc    2160
tgcaaagcga taaaaaacgc acggctgagt tagcaaacgg cgctctcggt atgattgagc    2220
taaacgatga ttcacactg aaaaaagtga tgaaaccgct gattgcatct aacacagtaa    2280
cagatgaaat tgaacgcgcg aacgtcttta aaatgaacgg caaatggtac ctgttcactg    2340
actcccgcgg atcaaaaatg acgattgacg gcattacgtc taacgatatt tacatgcttg    2400
```

```
gttatgtttc taattcttta actggcccat acaagccgct gaacaaaact ggccttgtgt   2460
taaaaatgga tcttgatcct aacgatgtaa cctttactta ctcacacttc gctgtacctc   2520
aagcgaaagg aaacaatgtc gtgattacaa gctatatgac aaacagagga ttctacgcag   2580
acaaacaatc aacgtttgcg ccaagcttgc atgcgagagt agggaactgc caggcatcaa   2640
ataaaacgaa aggctcagtc gaaagactgg gcctttcgtt ttatctgttg tttgtcggtg   2700
aacgctctcc tgagtaggac aaatccgccg ggagcggatt tgaacgttgc gaagcaacgg   2760
cccggagggt ggcgggcagg acgcccgcca taaactgcca ggcatcaaat taagcagaag   2820
gccatcctga cggatggcct ttttgcgttt ctacaaactc ttttttgttta tttttctaaa   2880 tacattcaaa tatgtatccg ctcatgctcc ggatctgcat cgcaggatgc tgctggctac   2940
cctgtggaac acctacatct gtattaacga agcgctggca ttgaccctga gtgatttttc   3000
tctggtcccg ccgcatccat accgccagtt gtttaccctc acaacgttcc agtaaccggg   3060
catgttcatc atcagtaacc cgtatcgtga gcatcctctc tcgtttcatc ggtatcatta   3120
cccccatgaa cagaaattcc cccttacacg gaggcatcaa gtgaccaaac aggaaaaaac   3180
cgcccttaac atggcccgct ttatcagaag ccagacatta acgcttctgg agaaactcaa   3240
cgagctggac gcggatgaac aggcagacat ctgtgaatcg cttcacgacc acgctgatga   3300
gctttaccgc agctgcctcg cgcgtttcgg tgatgacggt gaaaacctct gacacatgca   3360
gctcccggag acggtcacag cttgtctgta agcggatgcc gggagcagac aagcccgtca   3420
gggcgcgtca gcgggtgttg gcgggtgtcg ggcgcagcc atgacccagt cacgtagcga   3480
tagcggagtg tatactggct taactatgcg gcatcagagc agattgtact gagagtgcac   3540
catatgcggt gtgaaatacc gcacagatgc gtaaggagaa ataccgcat caggcgctct   3600 tccgcttcct cgctcactga ctcgctgcgc tcggtcgttc ggctgcggcg agcggtatca   3660
gctcactcaa aggcggtaat acggttatcc acagaatcag gggataacgc aggaaagaac   3720
atgtgagcaa aaggccagca aaaggccagg aaccgtaaaa aggccgcgtt gctggcgttt   3780
ttccataggc tccgcccccc tgacgagcat cacaaaaatc gacgctcaag tcagaggtgg   3840
cgaaacccga caggactata aagataccag gcgtttcccc ctggaagctc cctcgtgcgc   3900
tctcctgttc cgaccctgcc gcttaccgga tacctgtccg cctttctccc ttcgggaagc   3960
gtggcgcttt ctcaatgctc acgctgtagg tatctcagtt cggtgtaggt cgttcgctcc   4020
aagctgggct gtgtgcacga accccccgtt cagcccgacc gctgcgcctt atccggtaac   4080
tatcgtcttg agtccaaccc ggtaagacac gacttatcgc cactggcagc agccactggt   4140
aacaggatta gcagagcgag gtatgtaggc ggtgctacag agttcttgaa gtggtggcct   4200
aactacggct acactagaag gacagtattt ggtatctgcg ctctgctgaa gccagttacc   4260
ttcggaaaaa gagttggtag ctcttgatcc ggcaaacaaa ccaccgctgg tagcggtggt   4320
ttttttgttt gcaagcagca gattacgcgc agaaaaaaag gatctcaaga agatcctttg   4380
atcttttcta cggggtctga cgctcagtgg aacgaaaact cacgttaagg gattttggtc   4440
atgagattat caaaaaggat cttcacctag atccttttaa attaaaaatg aagttttaaa   4500
tcaatctaaa gtatatatga gtaaacttgg tctgacagtt accaatgctt aatcagtgag   4560
gcacctatct cagcgatctg tctatttcgt tcatccatag ttgcctgact ccccgtcgtg   4620
tagataacta cgatacggga gggcttacca tctggcccca gtgctgcaat gataccgcga   4680
gacccacgct caccggctcc agatttatca gcaataaacc agccagccgg aagggccgag   4740
```

```
cgcagaagtg gtcctgcaac tttatccgcc tccatccagt ctattaattg ttgccgggaa   4800
gctagagtaa gtagttcgcc agttaatagt ttgcgcaacg ttgttgccat tgctgcaggc   4860
atcgtggtgt cacgctcgtc gtttggtatg gcttcattca gctccggttc ccaacgatca   4920
aggcgagtta catgatcccc catgttgtgc aaaaaagcgg ttagctcctt cggtcctccg   4980
atcgttgtca gaagtaagtt ggccgcagtg ttatcactca tggttatggc agcactgcat   5040
aattctctta ctgtcatgcc atccgtaaga tgcttttctg tgactggtga gtactcaacc   5100
aagtcattct gagaatagtg tatgcggcga ccgagttgct cttgcccggc gtcaatacgg   5160
gataataccg cgccacatag cagaacttta aaagtgctca tcattggaaa acgttcttcg   5220
gggcgaaaac tctcaaggat cttaccgctg ttgagatcca gttcgatgta acccactcgt   5280
gcacccaact gatcttcagc atctttttact ttcaccagcg tttctgggtg agcaaaaaca   5340
ggaaggcaaa atgccgcaaa aagggaata agggcgacac ggaaatgttg aatactcata   5400
ctcttccttt ttcaatatta ttgaagcatt tatcagggtt attgtctcat gagcggatac   5460
atatttgaat gtatttagaa aaataaacaa ataggggttc cgcgcacatt tccccgaaaa   5520
gtgccacctg acgtctaaga aaccattatt atcatgacat taacctataa aaataggcgt   5580
atcacgaggc ccttcgtct cgcgcgtttc ggtgatgacg tgaaaacct ctgacacatg   5640
cagctcccgg agacggtcac agcttgtctg taagcggatg ccgggagcag acaagcccgt   5700
cagggcgcgt cagcgggtgt tcatgtgcgt aactaacttg ccatcttcaa acaggagggc   5760
tggaagaagc agaccgctaa cacagtacat aaaaaggag acatgaacga tgaacatcaa   5820
aaagtttgca aaacaagcaa cagtattaac ctttactacc gcactgctgg caggaggcgc   5880
aactcaagcg tttgcgaaag aaacgaacca aaagccatat aaggaaacat acggcatttc   5940
ccatattaca cgccatgata tgctgcaaat ccctgaacag caaaaaaatg aaaaatatca   6000
agttcctgaa ttcgattcgt ccacaattaa aaatatctct tctgcaaaag gcctggacgt   6060
ttgggacagc tggccattac aaaacgctga cggcactgtc gcaaactatc acggctacca   6120
catcgtcttt gcattagccg gagatcctaa aaatgcggat gacacatcga tttacatgtt   6180
ctatcaaaaa gtcggcgaaa cttctattga cagctggaaa aacgctggcc gcgtctttaa   6240
agacagcgac aaattcgatg caaatgattc tatcctaaaa gaccaaacac aagaatggtc   6300
aggttcagcc acatttacat ctgacggaaa aatccgttta ttctactctg atttctccgg   6360
taaacattac ggcaaacaaa cactgacaac tgcacaagtt aacgtatcag catcagacag   6420
ctcttttgaac atcaacggtg tagaggatta taaatcaatc tttgacggtg acggaaaaac   6480
gtatcaaaat gtacagcatg ccacgcgtc                                    6509
```

<210> SEQ ID NO 178
<211> LENGTH: 571
<212> TYPE: PRT
<213> ORGANISM: Bacillus subtilis

<400> SEQUENCE: 178

```
Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
                20                  25                  30

Val Phe Gly Ile Pro Gly Ala Lys Ile Asp Ala Val Phe Asp Ala Leu
            35                  40                  45

Gln Asp Lys Gly Pro Glu Ile Ile Val Ala Arg His Glu Gln Asn Ala
        50                  55                  60
```

```
Ala Phe Met Ala Gln Ala Val Gly Arg Leu Thr Gly Lys Pro Gly Val
 65                  70                  75                  80

Val Leu Val Thr Ser Gly Pro Gly Ala Ser Asn Leu Ala Thr Gly Leu
                 85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
        450                 455                 460

Val Arg Leu Lys Ala Pro Ile Val His Ile Val Trp Asn Asp Ser Thr
465                 470                 475                 480
```

```
Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
        530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 179
<211> LENGTH: 1665
<212> TYPE: DNA
<213> ORGANISM: Lactococcus lactis

<400> SEQUENCE: 179
```

| | | | | | |
|---|---|---|---|---|---|
| atgtctgaga | aacaatttgg | ggcgaacttg | gttgtcgata | gtttgattaa | ccataaagtg | 60 |
| aagtatgtat | ttgggattcc | aggagcaaaa | attgaccggg | ttttttgattt | attagaaaat | 120 |
| gaagaaggcc | ctcaaatggt | cgtgactcgt | catgagcaag | gagctgcttt | catggctcaa | 180 |
| gctgtcggtc | gtttaactgg | cgaacctggt | gtagtagttg | ttacgagtgg | gcctggtgta | 240 |
| tcaaaccttg | cgactccgct | tttgaccgcg | acatcagaag | gtgatgctat | tttggctatc | 300 |
| ggtggacaag | ttaaacgaag | tgaccgtctt | aaacgtgcgc | accaatcaat | ggataatgct | 360 |
| ggaatgatgc | aatcagcaac | aaaatattca | gcagaagttc | ttgaccctaa | tacactttct | 420 |
| gaatcaattg | ccaacgctta | tcgtattgca | aaatcaggac | atccaggtgc | aactttctta | 480 |
| tcaatccccc | aagatgtaac | ggatgccgaa | gtatcaatca | aagccattca | accactttca | 540 |
| gaccctaaaa | tggggaatgc | ctctattgat | gacattaatt | attagcaca | agcaattaaa | 600 |
| aatgctgtat | tgccagtaat | tttggttgga | gctggtgctt | cagatgctaa | agtcgcttca | 660 |
| tccttgcgta | atctattgac | tcatgttaat | attcctgtcg | ttgaaacatt | ccaaggtgca | 720 |
| ggggttattt | cacatgattt | agaacatact | ttttatggac | gtatcggtct | tttccgcaat | 780 |
| caaccaggcg | atatgcttct | gaaacgttct | gaccttgtta | ttgctgttgg | ttatgaccca | 840 |
| attgaatatg | aagctcgtaa | ctggaatgca | gaaattgata | gtcgaattat | cgttattgat | 900 |
| aatgccattg | ctgaaattga | tacttactac | caaccagagc | gtgaattaat | tggtgatatc | 960 |
| gcagcaacat | tggataatct | tttaccagct | gttcgtggct | acaaaattcc | aaaaggaaca | 1020 |
| aaagattatc | tcgatggcct | tcatgaagtt | gctgagcaac | acgaatttga | tactgaaaat | 1080 |
| actgaagaag | gtagaatgca | ccctcttgat | ttggtcagca | ctttccaaga | aatcgtcaag | 1140 |
| gatgatgaaa | cagtaaccgt | tgacgtaggt | tcactctaca | tttggatggc | acgtcatttc | 1200 |
| aaatcatacg | aaccacgtca | tctcctcttc | tcaaacggaa | tgcaaacact | cggagttgca | 1260 |
| cttccttggg | caattacagc | cgcattgttg | cgcccaggta | aaaaagttta | ttcacactct | 1320 |
| ggtgatggag | gcttcctttt | cacagggcaa | gaattggaaa | cagctgtacg | tttgaatctt | 1380 |
| ccaatcgttc | aaattatctg | gaatgacggc | cattatgata | tggttaaatt | ccaagaagaa | 1440 |
| atgaaatatg | gtcgttcagc | agccgttgat | tttggctatg | ttgattacgt | aaaatatgct | 1500 |
| gaagcaatga | gagcaaaagg | ttaccgtgca | cacagcaaag | aagaacttgc | tgaaattctc | 1560 |
| aaatcaatcc | cagatactac | tggaccggtg | gtaattgacg | ttcctttgga | ctattctgat | 1620 | aacattaaat tagcagaaaa attattgcct gaagagtttt attga    1665

<210> SEQ ID NO 180
<211> LENGTH: 554
<212> TYPE: PRT
<213> ORGANISM: Lactococcus lactis

<400> SEQUENCE: 180

```
Met Ser Glu Lys Gln Phe Gly Ala Asn Leu Val Val Asp Ser Leu Ile
1               5                   10                  15

Asn His Lys Val Lys Tyr Val Phe Gly Ile Pro Gly Ala Lys Ile Asp
                20                  25                  30

Arg Val Phe Asp Leu Leu Glu Asn Glu Gly Pro Gln Met Val Val
            35                  40                  45

Thr Arg His Glu Gln Gly Ala Ala Phe Met Ala Gln Ala Val Gly Arg
        50                  55                  60

Leu Thr Gly Glu Pro Gly Val Val Val Thr Ser Gly Pro Gly Val
65                  70                  75                  80

Ser Asn Leu Ala Thr Pro Leu Leu Thr Ala Thr Ser Glu Gly Asp Ala
                85                  90                  95

Ile Leu Ala Ile Gly Gly Gln Val Lys Arg Ser Asp Arg Leu Lys Arg
            100                 105                 110

Ala His Gln Ser Met Asp Asn Ala Gly Met Met Gln Ser Ala Thr Lys
        115                 120                 125

Tyr Ser Ala Glu Val Leu Asp Pro Asn Thr Leu Ser Glu Ser Ile Ala
    130                 135                 140

Asn Ala Tyr Arg Ile Ala Lys Ser Gly His Pro Gly Ala Thr Phe Leu
145                 150                 155                 160

Ser Ile Pro Gln Asp Val Thr Asp Ala Glu Val Ser Ile Lys Ala Ile
                165                 170                 175

Gln Pro Leu Ser Asp Pro Lys Met Gly Asn Ala Ser Ile Asp Asp Ile
            180                 185                 190

Asn Tyr Leu Ala Gln Ala Ile Lys Asn Ala Val Leu Pro Val Ile Leu
        195                 200                 205

Val Gly Ala Gly Ala Ser Asp Ala Lys Val Ala Ser Ser Leu Arg Asn
    210                 215                 220

Leu Leu Thr His Val Asn Ile Pro Val Val Glu Thr Phe Gln Gly Ala
225                 230                 235                 240

Gly Val Ile Ser His Asp Leu Glu His Thr Phe Tyr Gly Arg Ile Gly
                245                 250                 255

Leu Phe Arg Asn Gln Pro Gly Asp Met Leu Leu Lys Arg Ser Asp Leu
            260                 265                 270

Val Ile Ala Val Gly Tyr Asp Pro Ile Glu Tyr Glu Ala Arg Asn Trp
        275                 280                 285

Asn Ala Glu Ile Asp Ser Arg Ile Ile Val Ile Asp Asn Ala Ile Ala
    290                 295                 300

Glu Ile Asp Thr Tyr Tyr Gln Pro Glu Arg Glu Leu Ile Gly Asp Ile
305                 310                 315                 320

Ala Ala Thr Leu Asp Asn Leu Leu Pro Ala Val Arg Gly Tyr Lys Ile
                325                 330                 335

Pro Lys Gly Thr Lys Asp Tyr Leu Asp Gly Leu His Glu Val Ala Glu
            340                 345                 350

Gln His Glu Phe Asp Thr Glu Asn Thr Glu Glu Gly Arg Met His Pro
        355                 360                 365
```

```
Leu Asp Leu Val Ser Thr Phe Gln Glu Ile Val Lys Asp Asp Glu Thr
    370                 375                 380

Val Thr Val Asp Val Gly Ser Leu Tyr Ile Trp Met Ala Arg His Phe
385                 390                 395                 400

Lys Ser Tyr Glu Pro Arg His Leu Leu Phe Ser Asn Gly Met Gln Thr
                405                 410                 415

Leu Gly Val Ala Leu Pro Trp Ala Ile Thr Ala Ala Leu Leu Arg Pro
            420                 425                 430

Gly Lys Lys Val Tyr Ser His Ser Gly Asp Gly Phe Leu Phe Thr
        435                 440                 445

Gly Gln Glu Leu Glu Thr Ala Val Arg Leu Asn Leu Pro Ile Val Gln
    450                 455                 460

Ile Ile Trp Asn Asp Gly His Tyr Asp Met Val Lys Phe Gln Glu Glu
465                 470                 475                 480

Met Lys Tyr Gly Arg Ser Ala Ala Val Asp Phe Gly Tyr Val Asp Tyr
                485                 490                 495

Val Lys Tyr Ala Glu Ala Met Arg Ala Lys Gly Tyr Arg Ala His Ser
            500                 505                 510

Lys Glu Glu Leu Ala Glu Ile Leu Lys Ser Ile Pro Asp Thr Thr Gly
        515                 520                 525

Pro Val Val Ile Asp Val Pro Leu Asp Tyr Ser Asp Asn Ile Lys Leu
    530                 535                 540

Ala Glu Lys Leu Leu Pro Glu Glu Phe Tyr
545                 550

<210> SEQ ID NO 181
<211> LENGTH: 395
<212> TYPE: PRT
<213> ORGANISM: Saccharomyces cerevisiae

<400> SEQUENCE: 181

Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
```

```
                180             185                 190
Leu Val Ala Pro Lys Gly Ser Gly Arg Thr Val Arg Ser Leu Phe Lys
        195                 200             205
Glu Gly Arg Gly Ile Asn Ser Ser Tyr Ala Val Trp Asn Asp Val Thr
        210                 215             220
Gly Lys Ala His Glu Lys Ala Gln Ala Leu Ala Val Ala Ile Gly Ser
225                 230             235                 240
Gly Tyr Val Tyr Gln Thr Thr Phe Glu Arg Glu Val Asn Ser Asp Leu
                245             250                 255
Tyr Gly Glu Arg Gly Cys Leu Met Gly Gly Ile His Gly Met Phe Leu
                260             265                 270
Ala Gln Tyr Asp Val Leu Arg Glu Asn Gly His Ser Pro Ser Glu Ala
        275                 280             285
Phe Asn Glu Thr Val Glu Glu Ala Thr Gln Ser Leu Tyr Pro Leu Ile
        290                 295             300
Gly Lys Tyr Gly Met Asp Tyr Met Tyr Asp Ala Cys Ser Thr Thr Ala
305                 310             315                 320
Arg Arg Gly Ala Leu Asp Trp Tyr Pro Ile Phe Lys Asn Ala Leu Lys
                325             330                 335
Pro Val Phe Gln Asp Leu Tyr Glu Ser Thr Lys Asn Gly Thr Glu Thr
                340             345                 350
Lys Arg Ser Leu Glu Phe Asn Ser Gln Pro Asp Tyr Arg Glu Lys Leu
        355                 360             365
Glu Lys Glu Leu Asp Thr Ile Arg Asn Met Glu Ile Trp Lys Val Gly
        370                 375             380
Lys Glu Val Arg Lys Leu Arg Pro Glu Asn Gln
385                 390             395

<210> SEQ ID NO 182
<211> LENGTH: 993
<212> TYPE: DNA
<213> ORGANISM: Methanococcus maripaludis

<400> SEQUENCE: 182
atgaaggtat tctatgactc agattttaaa ttagatgctt taaaagaaaa aacaattgca      60
gtaatcggtt atggaagtca aggtagggca cagtccttaa acatgaaaga cagcggatta     120
aacgttgttg ttggtttaag aaaaaacggt gcttcatgga caacgctaa agcagacggt     180 cacaatgtaa tgaccattga agaagctgct gaaaaagcgg acatcatcca catcttaata     240
cctgatgaat tacaggcaga agtttatgaa agccagataa aaccatacct aaaagaagga     300
aaaacactaa gcttttcaca tggttttaac atccactatg gattcattgt tccaccaaaa     360
ggagttaacg tggttttagt tgctccaaaa tcacctggaa aatggttag aagaacatac     420 gaagaaggtt tcggtgttcc aggtttaatc tgtattgaaa ttgatgcaac aaacaacgca     480
tttgatattg tttcagcaat ggcaaaagga atcggtttat caagagctgg agttatccag     540
acaactttca agaagaaac agaaactgac cttttcggtg aacaagctgt tttatgcggt     600
ggagttaccg aattaatcaa ggcaggattt gaaacactcg ttgaagcagg atacgcacca     660
gaaatggcat actttgaaac ctgccacgaa ttgaaattaa tcgttgactt aatctaccaa     720
aaaggattca aaacatgtg gaacgatgta agtaacactg cagaatacgg cggacttaca     780
agaagaagca gatcgttac agctgattca aaagctgcaa tgaaagaaat cttaagagaa     840
atccaagatg gaagattcac aaaagaattc cttctcgaaa aacaggtaag ctatgctcat     900
```

```
ttaaaatcaa tgagaagact cgaaggagac ttacaaatcg aagaagtcgg cgcaaaatta    960
agaaaaatgt gcggtcttga aaagaagaa taa                                  993
```

<210> SEQ ID NO 183
<211> LENGTH: 330
<212> TYPE: PRT
<213> ORGANISM: Methanococcus maripaludis

<400> SEQUENCE: 183

| | | | | | | | | | | | | | | |
|---|---|---|---|---|---|---|---|---|---|---|---|---|---|---|
| Met | Lys | Val | Phe | Tyr | Asp | Ser | Asp | Phe | Lys | Leu | Asp | Ala | Leu | Lys | Glu |
| 1 | | | | 5 | | | | | 10 | | | | | 15 | |
| Lys | Thr | Ile | Ala | Val | Ile | Gly | Tyr | Gly | Ser | Gln | Gly | Arg | Ala | Gln | Ser |
| | | | 20 | | | | | 25 | | | | | 30 | | |
| Leu | Asn | Met | Lys | Asp | Ser | Gly | Leu | Asn | Val | Val | Gly | Leu | Arg | Lys | |
| | | | 35 | | | | | 40 | | | | | 45 | | |
| Asn | Gly | Ala | Ser | Trp | Asn | Asn | Ala | Lys | Ala | Asp | Gly | His | Asn | Val | Met |
| | 50 | | | | | 55 | | | | | 60 | | | | |
| Thr | Ile | Glu | Glu | Ala | Ala | Glu | Lys | Ala | Asp | Ile | Ile | His | Ile | Leu | Ile |
| 65 | | | | | 70 | | | | | 75 | | | | | 80 |
| Pro | Asp | Glu | Leu | Gln | Ala | Glu | Val | Tyr | Glu | Ser | Gln | Ile | Lys | Pro | Tyr |
| | | | | 85 | | | | | 90 | | | | | 95 | |
| Leu | Lys | Glu | Gly | Lys | Thr | Leu | Ser | Phe | Ser | His | Gly | Phe | Asn | Ile | His |
| | | | | 100 | | | | | 105 | | | | | 110 | |
| Tyr | Gly | Phe | Ile | Val | Pro | Pro | Lys | Gly | Val | Asn | Val | Leu | Val | Ala | |
| | | | 115 | | | | | 120 | | | | | 125 | | |
| Pro | Lys | Ser | Pro | Gly | Lys | Met | Val | Arg | Arg | Thr | Tyr | Glu | Glu | Gly | Phe |
| | 130 | | | | | 135 | | | | | 140 | | | | |
| Gly | Val | Pro | Gly | Leu | Ile | Cys | Ile | Glu | Ile | Asp | Ala | Thr | Asn | Asn | Ala |
| 145 | | | | | 150 | | | | | 155 | | | | | 160 |
| Phe | Asp | Ile | Val | Ser | Ala | Met | Ala | Lys | Gly | Ile | Gly | Leu | Ser | Arg | Ala |
| | | | | 165 | | | | | 170 | | | | | 175 | |
| Gly | Val | Ile | Gln | Thr | Thr | Phe | Lys | Glu | Glu | Thr | Glu | Thr | Asp | Leu | Phe |
| | | | 180 | | | | | 185 | | | | | 190 | | |
| Gly | Glu | Gln | Ala | Val | Leu | Cys | Gly | Gly | Val | Thr | Glu | Leu | Ile | Lys | Ala |
| | | | 195 | | | | | 200 | | | | | 205 | | |
| Gly | Phe | Glu | Thr | Leu | Val | Glu | Ala | Gly | Tyr | Ala | Pro | Glu | Met | Ala | Tyr |
| | 210 | | | | | 215 | | | | | 220 | | | | |
| Phe | Glu | Thr | Cys | His | Glu | Leu | Lys | Leu | Ile | Val | Asp | Leu | Ile | Tyr | Gln |
| 225 | | | | | 230 | | | | | 235 | | | | | 240 |
| Lys | Gly | Phe | Lys | Asn | Met | Trp | Asn | Asp | Val | Ser | Asn | Thr | Ala | Glu | Tyr |
| | | | | 245 | | | | | 250 | | | | | 255 | |
| Gly | Gly | Leu | Thr | Arg | Arg | Ser | Arg | Ile | Val | Thr | Ala | Asp | Ser | Lys | Ala |
| | | | 260 | | | | | 265 | | | | | 270 | | |
| Ala | Met | Lys | Glu | Ile | Leu | Arg | Glu | Ile | Gln | Asp | Gly | Arg | Phe | Thr | Lys |
| | | | 275 | | | | | 280 | | | | | 285 | | |
| Glu | Phe | Leu | Leu | Glu | Lys | Gln | Val | Ser | Tyr | Ala | His | Leu | Lys | Ser | Met |
| | 290 | | | | | 295 | | | | | 300 | | | | |
| Arg | Arg | Leu | Glu | Gly | Asp | Leu | Gln | Ile | Glu | Glu | Val | Gly | Ala | Lys | Leu |
| 305 | | | | | 310 | | | | | 315 | | | | | 320 |
| Arg | Lys | Met | Cys | Gly | Leu | Glu | Lys | Glu | Glu | | | | | | |
| | | | | 325 | | | | | 330 | | | | | | |

<210> SEQ ID NO 184
<211> LENGTH: 1476
<212> TYPE: DNA

<213> ORGANISM: Bacillus subtilis

<400> SEQUENCE: 184

```
atggctaact acttcaatac actgaatctg cgccagcagc tggcacagct gggcaaatgt      60
cgctttatgg ccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
ctgatgaaag acggcgcggc gctgggctac tcgcacggtt tcaacatcgt cgaagtgggc     420
gagcagatcc gtaaagatat caccgtagtg atggttgcgc cgaaatgccc aggcaccgaa     480
gtgcgtgaag agtacaaacg tgggttcggc gtaccgacgc tgattgccgt tcacccggaa     540
aacgatccga aggcgaagg catggcgatt gccaaagcct gggcggctgc aaccggtggt     600
caccgtgcgg gtgtgctgga atcgtccttc gttgcggaag tgaaatctga cctgatgggc     660
gagcaaacca tcctgtgcgg tatgttgcag gctggctctc tgctgtgctt cgacaagctg     720
gtggaagaag gtaccgatcc agcatacgca gaaaaactga ttcagttcgg ttgggaaacc     780
atcaccgaag cactgaaaca gggcggcatc accctgatga tggaccgtct ctctaacccg     840
gcgaaactgc gtgcttatgc gctttctgaa cagctgaaag atcatggc acccctgttc     900
cagaaacata tggacgacat catctccggc gaattctctt ccggtatgat ggcggactgg     960
gccaacgatg ataagaaact gctgacctgg cgtgaagaga ccggcaaaac cgcgtttgaa    1020
accgcgccgc agtatgaagg caaaatcggc gagcaggagt acttcgataa aggcgtactg    1080
atgattgcga tggtgaaagc gggcgttgaa ctggcgttcg aaaccatggt cgattccggc    1140
atcattgaag agtctgcata ttatgaatca ctgcacgagc tgccgctgat gccaacacc    1200
atcgcccgta gcgtctgta cgaaatgaac gtggttatct ctgataccgc tgagtacggt    1260
aactatctgt tctcttacgc ttgtgtgccg ttgctgaaac cgtttatggc agagctgcaa    1320
ccgggcgacc tgggtaaagc tattccggaa ggcgcggtag ataacgggca actgcgtgat    1380
gtgaacgaag cgattcgcag ccatgcgatt gagcaggtag gtaagaaact gcgcggctat    1440
atgacagata tgaaacgtat tgctgttgcg ggttaa                              1476
```

<210> SEQ ID NO 185
<211> LENGTH: 342
<212> TYPE: PRT
<213> ORGANISM: Bacillus subtilis

<400> SEQUENCE: 185

```
Met Val Lys Val Tyr Tyr Asn Gly Asp Ile Lys Glu Asn Val Leu Ala
1               5                   10                  15

Gly Lys Thr Val Ala Val Ile Gly Tyr Gly Ser Gln Gly His Ala His
            20                  25                  30

Ala Leu Asn Leu Lys Glu Ser Gly Val Asp Val Ile Val Gly Val Arg
        35                  40                  45

Gln Gly Lys Ser Phe Thr Gln Ala Gln Glu Asp Gly His Lys Val Phe
    50                  55                  60

Ser Val Lys Glu Ala Ala Ala Gln Ala Glu Ile Ile Met Val Leu Leu
65                  70                  75                  80

Pro Asp Glu Gln Gln Lys Val Tyr Glu Ala Glu Ile Lys Asp Glu
                85                  90                  95
```

Leu Thr Ala Gly Lys Ser Leu Val Phe Ala His Gly Phe Asn Val His
            100                 105                 110

Phe His Gln Ile Val Pro Pro Ala Asp Val Asp Val Phe Leu Val Ala
            115                 120                 125

Pro Lys Gly Pro Gly His Leu Val Arg Arg Thr Tyr Glu Gln Gly Ala
130                 135                 140

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Ala Arg Ala
                165                 170                 175

Gly Val Leu Glu Thr Thr Phe Lys Glu Thr Glu Thr Asp Leu Phe
            180                 185                 190

Gly Glu Gln Ala Val Leu Cys Gly Gly Leu Ser Ala Leu Val Lys Ala
            195                 200                 205

Gly Phe Glu Thr Leu Thr Glu Ala Gly Tyr Gln Pro Glu Leu Ala Tyr
            210                 215                 220

Phe Glu Cys Leu His Glu Leu Lys Leu Ile Val Asp Leu Met Tyr Glu
225                 230                 235                 240

Glu Gly Leu Ala Gly Met Arg Tyr Ser Ile Ser Asp Thr Ala Gln Trp
                245                 250                 255

Gly Asp Phe Val Ser Gly Pro Arg Val Val Asp Ala Lys Val Lys Glu
            260                 265                 270

Ser Met Lys Glu Val Leu Lys Asp Ile Gln Asn Gly Thr Phe Ala Lys
            275                 280                 285

Glu Trp Ile Val Glu Asn Gln Val Asn Arg Pro Arg Phe Asn Ala Ile
            290                 295                 300

Asn Ala Ser Glu Asn Glu His Gln Ile Glu Val Val Gly Arg Lys Leu
305                 310                 315                 320

Arg Glu Met Met Pro Phe Val Lys Gln Gly Lys Lys Glu Ala Val
                325                 330                 335

Val Ser Val Ala Gln Asn
            340

<210> SEQ ID NO 186
<211> LENGTH: 585
<212> TYPE: PRT
<213> ORGANISM: Saccharomyces cerevisiae

<400> SEQUENCE: 186

Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
            20                  25                  30

Pro Lys Gly Gln Gly Ala Ser Gln Ala Met Leu Tyr Ala Thr Gly Phe
        35                  40                  45

Lys Lys Glu Asp Phe Lys Lys Pro Gln Val Gly Val Gly Ser Cys Trp
    50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile

-continued

```
            115                 120                 125
Met Met Ala Gln His Tyr Asp Ala Asn Ile Ala Ile Pro Ser Cys Asp
        130                 135                 140

Lys Asn Met Pro Gly Val Met Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Arg Glu
        195                 200                 205

Asp Val Val Glu His Ala Cys Pro Gly Pro Gly Ser Cys Gly Gly Met
        210                 215                 220

Tyr Thr Ala Asn Thr Met Ala Ser Ala Ala Val Leu Gly Leu Thr
225                 230                 235                 240

Ile Pro Asn Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
            260                 265                 270

Ile Leu Pro Arg Asp Ile Leu Thr Lys Glu Ala Phe Glu Asn Ala Ile
        275                 280                 285

Thr Tyr Val Val Ala Thr Gly Gly Ser Thr Asn Ala Val Leu His Leu
        290                 295                 300

Val Ala Val Ala His Ser Ala Gly Val Lys Leu Ser Pro Asp Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
            340                 345                 350

Val Ile Lys Tyr Leu Tyr Glu Asn Asn Met Leu His Gly Asn Thr Met
        355                 360                 365

Thr Val Thr Gly Asp Thr Leu Ala Glu Arg Ala Lys Lys Ala Pro Ser
        370                 375                 380

Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
            420                 425                 430

Ala Arg Val Phe Glu Glu Gly Ala Phe Ile Glu Ala Leu Glu Arg
        435                 440                 445

Gly Glu Ile Lys Lys Gly Glu Lys Thr Val Val Ile Arg Tyr Glu
        450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
            500                 505                 510

Pro Glu Ala Ala Glu Gly Gly Pro Ile Gly Leu Val Arg Asp Gly Asp
        515                 520                 525

Glu Ile Ile Ile Asp Ala Asp Asn Asn Lys Ile Asp Leu Leu Val Ser
        530                 535                 540
```

Asp Lys Glu Met Ala Gln Arg Lys Gln Ser Trp Val Ala Pro Pro Pro
545                 550                 555                 560

Arg Tyr Thr Arg Gly Thr Leu Ser Lys Tyr Ala Lys Leu Val Ser Asn
            565                 570                 575

Ala Ser Asn Gly Cys Val Leu Asp Ala
            580                 585

<210> SEQ ID NO 187
<211> LENGTH: 1653
<212> TYPE: DNA
<213> ORGANISM: Methanococcus maripaludis

<400> SEQUENCE: 187

```
atgataagtg ataacgtcaa aaagggagtt ataagaactc caaaccgagc tcttttaaag    60
gcttgcggat atacagacga agacatggaa aaaccattta ttggaattgt aaacagcttt   120
acagaagttg ttcccggcca cattcactta agaacattat cagaagcggc taaacatggt   180
gtttatgcaa acggtggaac accatttgaa tttaatacca ttggaatttg cgacggtatt   240
gcaatgggcc acgaaggtat gaaatactct ttaccttcaa gagaaattat tgcagacgct   300
gttgaatcaa tggcaagagc acatggattt gatggtcttg ttttaattcc tacgtgtgat   360
aaaatcgttc ctggaatgat aatgggtgct ttaagactaa acattccatt tattgtagtt   420
actggaggac caatgcttcc cggagaattc caaggtaaaa aatacgaact tatcagccct   480
tttgaaggtg tcggagaata ccaagttgga aaaattactg aagaagagtt aaagtgcatt   540
gaagactgtg catgttcagg tgctggaagt tgtgcagggc tttacactgc aaacagtatg   600
gcctgcctta cagaagcttt gggactctct cttccaatgt gtgcaacaac gcatgcagtt   660
gatgcccaaa aagttaggct tgctaaaaaa agtggctcaa aaattgttga tatggtaaaa   720
gaagacctaa aaccaacaga catattaaca aaagaagctt tgaaaatgc tatttttagtt   780
gaccttgcac ttggtggatc aacaaacaca acattacaca ttcctgcaat tgcaaatgaa   840
attgaaaata aattcataac tctcgatgac tttgacaggt taagcgatga agttccacac   900
attgcatcaa tcaaaccagg tggagaacac tacatgattg atttacacaa tgctggaggt   960
attcctgcgg tattgaacgt tttaaaagaa aaaattagag atacaaaaac agttgatgga  1020
agaagcattt tggaaatcgc agaatctgtt aaatacataa attcgacgt tataagaaaa  1080
gtggaagctc cggttcacga aactgctggt ttaagggttt taagggaaa tcttgctcca  1140
aacggttgcg ttgtaaaaat cggtgcagta catccgaaaa tgtacaaaca cgatggacct  1200
gcaaaagttt acaattccga agatgaagca atttctgcga tacttggcgg aaaaattgta  1260
gaagggacg ttatagtaat cagatacgaa ggaccatcag gaggccctgg aatgagagaa  1320
atgctctccc caacttcagc aatctgtgga atgggtcttg atgacagcgt tgcattgatt  1380
actgatggaa gattcagtgg tggaagtagg ggcccatgta tcggacacgt ttctccagaa  1440
gctgcagctg gcggagtaat tgctgcaatt gaaaacgggg atatcatcaa aatcgacatg  1500
attgaaaaag aaataaatgt tgatttagat gaatcagtca ttaaagaaag actctcaaaa  1560
ctgggagaat tgagcctaa aatcaaaaaa ggctatttat caagatactc aaaacttgtc  1620
tcatctgctg acgaagggc agttttaaaa taa                                1653
```

<210> SEQ ID NO 188
<211> LENGTH: 550
<212> TYPE: PRT
<213> ORGANISM: Methanococcus maripaludis

<400> SEQUENCE: 188

Met Ile Ser Asp Asn Val Lys Lys Gly Val Ile Arg Thr Pro Asn Arg
1               5                   10                  15

Ala Leu Leu Lys Ala Cys Gly Tyr Thr Asp Glu Asp Met Glu Lys Pro
                20                  25                  30

Phe Ile Gly Ile Val Asn Ser Phe Thr Glu Val Val Pro Gly His Ile
            35                  40                  45

His Leu Arg Thr Leu Ser Glu Ala Ala Lys His Gly Val Tyr Ala Asn
        50                  55                  60

Gly Gly Thr Pro Phe Glu Phe Asn Thr Ile Gly Ile Cys Asp Gly Ile
65                  70                  75                  80

Ala Met Gly His Glu Gly Met Lys Tyr Ser Leu Pro Ser Arg Glu Ile
                85                  90                  95

Ile Ala Asp Ala Val Glu Ser Met Ala Arg Ala His Gly Phe Asp Gly
            100                 105                 110

Leu Val Leu Ile Pro Thr Cys Asp Lys Ile Val Pro Gly Met Ile Met
            115                 120                 125

Gly Ala Leu Arg Leu Asn Ile Pro Phe Ile Val Thr Gly Gly Pro
130                 135                 140

Met Leu Pro Gly Glu Phe Gln Gly Lys Lys Tyr Glu Leu Ile Ser Leu
145                 150                 155                 160

Phe Glu Gly Val Gly Glu Tyr Gln Val Gly Lys Ile Thr Glu Glu Glu
                165                 170                 175

Leu Lys Cys Ile Glu Asp Cys Ala Cys Ser Gly Ala Gly Ser Cys Ala
            180                 185                 190

Gly Leu Tyr Thr Ala Asn Ser Met Ala Cys Leu Thr Glu Ala Leu Gly
            195                 200                 205

Leu Ser Leu Pro Met Cys Ala Thr Thr His Ala Val Asp Ala Gln Lys
210                 215                 220

Val Arg Leu Ala Lys Lys Ser Gly Ser Lys Ile Val Asp Met Val Lys
225                 230                 235                 240

Glu Asp Leu Lys Pro Thr Asp Ile Leu Thr Lys Glu Ala Phe Glu Asn
                245                 250                 255

Ala Ile Leu Val Asp Leu Ala Leu Gly Gly Ser Thr Asn Thr Thr Leu
            260                 265                 270

His Ile Pro Ala Ile Ala Asn Glu Ile Glu Asn Lys Phe Ile Thr Leu
            275                 280                 285

Asp Asp Phe Asp Arg Leu Ser Asp Glu Val Pro His Ile Ala Ser Ile
290                 295                 300

Lys Pro Gly Gly Glu His Tyr Met Ile Asp Leu His Asn Ala Gly Gly
305                 310                 315                 320

Ile Pro Ala Val Leu Asn Val Leu Lys Glu Lys Ile Arg Asp Thr Lys
                325                 330                 335

Thr Val Asp Gly Arg Ser Ile Leu Glu Ile Ala Glu Ser Val Lys Tyr
            340                 345                 350

Ile Asn Tyr Asp Val Ile Arg Lys Val Glu Ala Pro Val His Glu Thr
            355                 360                 365

Ala Gly Leu Arg Val Leu Lys Gly Asn Leu Ala Pro Asn Gly Cys Val
            370                 375                 380

Val Lys Ile Gly Ala Val His Pro Lys Met Tyr Lys His Asp Gly Pro
385                 390                 395                 400

Ala Lys Val Tyr Asn Ser Glu Asp Glu Ala Ile Ser Ala Ile Leu Gly

```
            405                 410                 415
Gly Lys Ile Val Glu Gly Asp Val Ile Val Arg Tyr Glu Gly Pro
            420                 425                 430

Ser Gly Gly Pro Gly Met Arg Glu Met Leu Ser Pro Thr Ser Ala Ile
        435                 440                 445

Cys Gly Met Gly Leu Asp Asp Ser Val Ala Leu Ile Thr Asp Gly Arg
    450                 455                 460

Phe Ser Gly Gly Ser Arg Gly Pro Cys Ile Gly His Val Ser Pro Glu
465                 470                 475                 480

Ala Ala Ala Gly Gly Val Ile Ala Ile Glu Asn Gly Asp Ile Ile
                485                 490                 495

Lys Ile Asp Met Ile Glu Lys Glu Ile Asn Val Asp Leu Asp Glu Ser
            500                 505                 510

Val Ile Lys Glu Arg Leu Ser Lys Leu Gly Glu Phe Glu Pro Lys Ile
            515                 520                 525

Lys Lys Gly Tyr Leu Ser Arg Tyr Ser Lys Leu Val Ser Ser Ala Asp
        530                 535                 540

Glu Gly Ala Val Leu Lys
545             550

<210> SEQ ID NO 189
<211> LENGTH: 1677
<212> TYPE: DNA
<213> ORGANISM: Bacillus subtilis

<400> SEQUENCE: 189
atggcagaat tacgcagtaa tatgatcaca caaggaatcg atagagctcc gcaccgcagt      60
ttgcttcgtg cagcaggggt aaaagaagag gatttcggca agccgtttat tgcggtgtgt     120
aattcataca ttgatatcgt tcccggtcat gttcacttgc aggagtttgg gaaaatcgta     180
aaagaagcaa tcagagaagc aggggggcgtt ccgtttgaat ttaataccat tggggtagat     240
gatggcatcg caatggggca tatcggtatg agatattcgc tgccaagccg tgaaattatc     300
gcagactctg tggaaacggt tgtatccgca cactggtttg acggaatggt ctgtattccg     360
aactgcgaca aaatcacacc gggaatgctt atggcggcaa tgcgcatcaa cattccgacg     420
atttttgtca gcggcggacc gatggcggca ggaagaacaa gttacgggcg aaaaatctcc     480
ctttcctcag tattcgaagg ggtaggcgcc taccaagcag ggaaaatcaa cgaaaacgag     540
cttcaagaac tagagcagtt cggatgccca acgtgcgggt cttgctcagg catgtttacg     600
gcgaactcaa tgaactgtct gtcagaagca cttggtcttg cttttgccggg taatggaacc     660 attctggcaa catctccgga acgcaaagag tttgtgagaa aatcggctgc gcaattaatg     720
gaaacgattc gcaagatat caaaccgcgt gatattgtta cagtaaaagc gattgataac     780
gcgtttgcac tcgatatggc gctcggaggt tctacaaata ccgttcttca tacccttgcc     840
cttgcaaacg aagccggcgt tgaatactct ttagaacgca ttaacgaagt cgctgagcgc     900
gtgccgcact ggctaagct ggcgcctgca tcggatgtgt ttattgaaga tcttcacgaa     960
gcgggcggcg tttcagcggc tctgaatgag ctttcgaaga aagaaggagc gcttcattta    1020
gatgcgctga ctgttacagg aaaaactctt ggagaaacca ttgccggaca tgaagtaaag    1080
gattatgacg tcattcaccc gctggatcaa ccattcactg aaaagggagg ccttgctgtt    1140
ttattcggta atctagctcc ggacggcgct atcattaaaa caggcggcgt acagaatggg    1200
attacaagac acgaagggcc ggctgtcgta ttcgattctc aggacgaggc gcttgacggc    1260
```

```
attatcaacc gaaaagtaaa agaaggcgac gttgtcatca tcagatacga agggccaaaa   1320
ggcggacctg gcatgccgga atgctggcg ccaacatccc aaatcgttgg aatgggactc    1380
gggccaaaag tggcattgat tacggacgga cgttttccg gagcctcccg tggcctctca    1440
atcggccacg tatcacctga ggccgctgag ggcgggccgc ttgcctttgt tgaaaacgga   1500
gaccatatta tcgttgatat tgaaaaacgc atcttggatg tacaagtgcc agaagaagag   1560
tgggaaaaac gaaaagcgaa ctggaaaggt tttgaaccga aagtgaaaac cggctacctg   1620
gcacgttatt ctaaacttgt gacaagtgcc aacaccggcg gtattatgaa atctag       1677
```

<210> SEQ ID NO 190
<211> LENGTH: 558
<212> TYPE: PRT
<213> ORGANISM: Bacillus subtilis

<400> SEQUENCE: 190

```
Met Ala Glu Leu Arg Ser Asn Met Ile Thr Gln Gly Ile Asp Arg Ala
1               5                   10                  15

Pro His Arg Ser Leu Leu Arg Ala Ala Gly Val Lys Glu Glu Asp Phe
            20                  25                  30

Gly Lys Pro Phe Ile Ala Val Cys Asn Ser Tyr Ile Asp Ile Val Pro
        35                  40                  45

Gly His Val His Leu Gln Glu Phe Gly Lys Ile Val Lys Glu Ala Ile
    50                  55                  60

Arg Glu Ala Gly Gly Val Pro Phe Glu Phe Asn Thr Ile Gly Val Asp
65                  70                  75                  80

Asp Gly Ile Ala Met Gly His Ile Gly Met Arg Tyr Ser Leu Pro Ser
                85                  90                  95

Arg Glu Ile Ile Ala Asp Ser Val Glu Thr Val Val Ser Ala His Trp
            100                 105                 110

Phe Asp Gly Met Val Cys Ile Pro Asn Cys Asp Lys Ile Thr Pro Gly
        115                 120                 125

Met Leu Met Ala Ala Met Arg Ile Asn Ile Pro Thr Ile Phe Val Ser
    130                 135                 140

Gly Gly Pro Met Ala Ala Gly Arg Thr Ser Tyr Gly Lys Lys Ile Ser
145                 150                 155                 160

Leu Ser Ser Val Phe Glu Gly Val Gly Ala Tyr Gln Ala Gly Lys Ile
                165                 170                 175

Asn Glu Asn Glu Leu Gln Glu Leu Gly Gln Phe Gly Cys Pro Thr Cys
            180                 185                 190

Gly Ser Cys Ser Gly Met Phe Thr Ala Asn Ser Met Asn Cys Leu Ser
        195                 200                 205

Glu Ala Leu Gly Leu Ala Leu Pro Gly Asn Gly Thr Ile Leu Ala Thr
    210                 215                 220

Ser Pro Glu Arg Lys Glu Phe Val Arg Lys Ser Ala Ala Gln Leu Met
225                 230                 235                 240

Glu Thr Ile Arg Lys Asp Ile Lys Pro Arg Asp Ile Val Thr Val Lys
                245                 250                 255

Ala Ile Asp Asn Ala Phe Ala Leu Asp Met Ala Leu Gly Gly Ser Thr
            260                 265                 270

Asn Thr Val Leu His Thr Leu Ala Leu Ala Asn Glu Ala Gly Val Glu
        275                 280                 285

Tyr Ser Leu Glu Arg Ile Asn Gly Val Ala Glu Arg Val Pro His Leu
    290                 295                 300
```

Ala Lys Leu Ala Pro Ala Ser Asp Val Phe Ile Glu Asp Leu His Glu
305                 310                 315                 320

Ala Gly Gly Val Ser Ala Ala Leu Asn Glu Leu Ser Lys Lys Glu Gly
            325                 330                 335

Ala Leu His Leu Asp Ala Leu Thr Val Thr Gly Lys Thr Leu Gly Glu
            340                 345                 350

Thr Ile Ala Gly His Glu Val Lys Asp Tyr Asp Val Ile His Pro Leu
        355                 360                 365

Asp Gln Pro Phe Thr Glu Lys Gly Gly Leu Ala Val Leu Phe Gly Asn
    370                 375                 380

Leu Ala Pro Asp Gly Ala Ile Ile Lys Thr Gly Gly Val Gln Asn Gly
385                 390                 395                 400

Ile Thr Arg His Glu Gly Pro Ala Val Val Phe Asp Ser Gln Asp Glu
            405                 410                 415

Ala Leu Asp Gly Ile Ile Asn Arg Lys Val Lys Glu Gly Asp Val Val
            420                 425                 430

Ile Ile Arg Tyr Glu Gly Pro Lys Gly Pro Gly Met Pro Glu Met
        435                 440                 445

Leu Ala Pro Thr Ser Gln Ile Val Gly Met Gly Leu Gly Pro Lys Val
    450                 455                 460

Ala Leu Ile Thr Asp Gly Arg Phe Ser Gly Ala Ser Arg Gly Leu Ser
465                 470                 475                 480

Ile Gly His Val Ser Pro Glu Ala Ala Glu Gly Gly Pro Leu Ala Phe
            485                 490                 495

Val Glu Asn Gly Asp His Ile Ile Val Asp Ile Glu Lys Arg Ile Leu
            500                 505                 510

Asp Val Gln Val Pro Glu Glu Glu Trp Glu Lys Arg Lys Ala Asn Trp
    515                 520                 525

Lys Gly Phe Glu Pro Lys Val Lys Thr Gly Tyr Leu Ala Arg Tyr Ser
    530                 535                 540

Lys Leu Val Thr Ser Ala Asn Thr Gly Gly Ile Met Lys Ile
545                 550                 555

<210> SEQ ID NO 191
<211> LENGTH: 1647
<212> TYPE: DNA
<213> ORGANISM: Lactococcus lactis

<400> SEQUENCE: 191

```
atgtatacag taggagatta cctattagac cgattacacg agttaggaat tgaagaaatt      60
tttggagtcc ctggagacta taacttacaa tttttagatc aaattatttc ccacaaggat     120
atgaaatggg tcggaaatgc taatgaatta aatgcttcat atatggctga tggctatgct     180
cgtactaaaa aagctgccgc atttcttaca acctttggag taggtgaatt gagtgcagtt     240
aatggattag caggaagtta cgccgaaaat ttaccagtag tagaaatagt gggatcacct     300
acatcaaaag ttcaaaatga aggaaaattt gttcatcata cgctggctga cggtgatttt     360
aaacacttta tgaaaatgca cgaacctgtt acagcagctc gaacttact gacagcagaa     420
aatgcaaccg ttgaaattga ccgagtactt tctgcactat aaaagaaag aaaacctgtc     480
tatatcaact taccagttga tgttgctgct gcaaaagcag agaaaccctc actcccttg      540
aaaaaggaaa actcaacttc aaatacaagt gaccaagaaa ttttgaacaa aattcaagaa     600
agcttgaaaa atgccaaaaa accaatcgtg attacaggac atgaaataat tagttttggc     660
ttagaaaaaa cagtcactca atttatttca aagacaaaac tacctattac gacattaaac     720
```

```
tttggtaaaa gttcagttga tgaagccctc ccttcatttt taggaatcta taatggtaca    780
ctctcagagc ctaatcttaa agaattcgtg gaatcagccg acttcatctt gatgcttgga    840
gttaaactca cagactcttc aacaggagcc ttcactcatc atttaaatga aaataaaatg    900
atttcactga atatagatga aggaaaaata tttaacgaaa gaatccaaaa ttttgatttt    960
gaatccctca tctcctctct cttagaccta agcgaaatag aatacaaagg aaaatatatc   1020
gataaaaagc aagaagactt tgttccatca aatgcgcttt tatcacaaga ccgcctatgg   1080
caagcagttg aaaacctaac tcaaagcaat gaaacaatcg ttgctgaaca agggacatca   1140
ttctttggcg cttcatcaat tttcttaaaa tcaaagagtc attttattgg tcaacccttca   1200 tggggatcaa ttggatatac attcccagca gcattaggaa gccaaattgc agataaagaa   1260
agcagacacc ttttatttat tggtgatggt tcacttcaac ttacagtgca agaattagga   1320
ttagcaatca gagaaaaaat taatccaatt tgctttatta tcaataatga tggttataca   1380
gtcgaaagag aaattcatgg accaaatcaa agctacaatg atattccaat gtggaattac   1440
tcaaaattac cagaatcgtt tggagcaaca aagatcgag tagtctcaaa aatcgttaga   1500
actgaaaatg aatttgtgtc tgtcatgaaa gaagctcaag cagatccaaa tagaatgtac   1560
tggattgagt taattttggc aaaagaaggt gcaccaaaag tactgaaaaa aatgggcaaa   1620
ctatttgctg aacaaaataa atcataa                                      1647
```

<210> SEQ ID NO 192
<211> LENGTH: 1644
<212> TYPE: DNA
<213> ORGANISM: Lactococcus lactis

<400> SEQUENCE: 192

```
atgtatacag taggagatta cctgttagac cgattacacg agttgggaat tgaagaaatt     60
tttggagttc ctggtgacta taacttacaa tttttagatc aaattattc acgcgaagat    120 atgaaatgga ttggaaatgc taatgaatta aatgcttctt atatggctga tggttatgct    180
cgtactaaaa aagctgccgc atttctcacc acatttggag tcggcgaatt gagtgcgatc    240
aatggactgg caggaagtta tgccgaaaat ttaccgtag tagaaattgt tggttcacca    300
acttcaaaag tacaaaatga cggaaaattt gtccatcata cactagcaga tggtgatttt    360
aaacacttta tgaagatgca tgaacctgtt acagcagcgc ggactttact gacagcagaa    420
aatgccacat atgaaattga ccgagtactt tctcaattac taaaagaaag aaaaccagtc    480
tatattaact taccagtcga tgttgctgca gcaaaagcag agaagcctgc attatcttta    540
gaaaaagaaa gctctacaac aaatacaact gaacaagtga ttttgagtaa gattgaagaa    600
agtttgaaaa atgcccaaaa accagtagtg attgcaggac acgaagtaat tagttttggt    660
ttagaaaaaa cggtaactca gtttgtttca gaaacaaaac taccgattac gacactaaat    720
tttggtaaaa gtgctgttga tgaatctttg ccctcatttt taggaatata taacgggaaa    780 cttttcagaaa tcagtcttaa aaattttgtg gagtccgcag actttatcct aatgcttgga    840
gtgaagctta cggactcctc aacaggtgca ttcacacatc atttagatga aaataaaatg    900
atttcactaa acatagatga aggaataatt ttcaataaag tggtagaaga ttttgatttt    960
agagcagtgg tttcttcttt atcagaatta aaaggaatag aatatgaagg acaatatatt   1020
gataagcaat atgaagaatt tattccatca agtgctccct tatcacaaga ccgtctatgg   1080
caggcagttg aaagtttgac tcaaagcaat gaaacaatcg ttgctgaaca aggaacctca   1140
```

```
tttttggag cttcaacaat tttcttaaaa tcaaatagtc gttttattgg acaaccttta   1200
tggggttcta ttggatatac ttttccagcg gctttaggaa gccaaattgc ggataaagag   1260
agcagacacc ttttatttat tggtgatggt tcacttcaac ttaccgtaca agaattagga   1320
ctatcaatca gagaaaaact caatccaatt tgttttatca taaataatga tggttataca   1380
gttgaaagag aaatccacgg acctactcaa agttataacg acattccaat gtggaattac   1440
tcgaaattac cagaaacatt tggagcaaca gaagatcgtg tagtatcaaa aattgttaga   1500
acagagaatg aatttgtgtc tgtcatgaaa gaagcccaag cagatgtcaa tagaatgtat   1560
tggatagaac tagttttgga aaagaagat gcgccaaaat tactgaaaaa atgggtaaa   1620 ttatttgctg agcaaaataa atag   1644
```

<210> SEQ ID NO 193
<211> LENGTH: 547
<212> TYPE: PRT
<213> ORGANISM: Lactococcus lactis

<400> SEQUENCE: 193

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285
```

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Glu Phe Ile Pro Ser Ser Ala
            340                 345                 350

Pro Leu Ser Gln Asp Arg Leu Trp Gln Ala Val Glu Ser Leu Thr Gln
        355                 360                 365

Ser Asn Glu Thr Ile Val Ala Glu Gln Gly Thr Ser Phe Phe Gly Ala
370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
    450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Asp Arg Val Val Ser
                485                 490                 495

Lys Ile Val Arg Thr Glu Asn Glu Phe Val Ser Val Met Lys Glu Ala
            500                 505                 510

Gln Ala Asp Val Asn Arg Met Tyr Trp Ile Glu Leu Val Leu Glu Lys
        515                 520                 525

Glu Asp Ala Pro Lys Leu Leu Lys Lys Met Gly Lys Leu Phe Ala Glu
    530                 535                 540

Gln Asn Lys
545

<210> SEQ ID NO 194
<211> LENGTH: 1653
<212> TYPE: DNA
<213> ORGANISM: Salmonella typhimurium

<400> SEQUENCE: 194
ttatcccccg ttgcgggctt ccagcgcccg ggtcacggta cgcagtaatt ccggcagatc     60
ggcttttggc aacatcactt caataaatga cagacgttgt gggcgcgcca accgttcgag    120
gacctctgcc agttggatag cctgcgtcac ccgccagcac tccgcctgtt gcgccgcgtt    180
tagcgccggt ggtatctgcg tccagttcca gctcgcgatg tcgttatacc gctgggccgc    240
gccgtgaatg gcgcgctcta cggtatagcc gtcattgttg agcagcagga tgaccggcgc    300
ctgcccgtcg cgtaacatcg agcccatctc ctgaatcgtg agctgcgccg cgccatcgcc    360
gataatcaga atcacccgcc gatcgggaca ggcggtttgc gcgccaaacg cggcgggcaa    420
ggaatagccg atagaccccc acagcggctg taacacaact tccgcgccgt caggaagcga    480
cagcgcggca gcgccaaaag ctgctgtccc ctggtcgaca aggataatat ctccgggttt    540
gagatactgc tgtaaggttt gccagaagct ttcctgggtc agttctcctt tatcaatccg    600

```
cactggctgt ccggcggaac gcgtcggcgg cggcgcaaaa gcgcattcca ggcacagttc    660
gcgcagcgta gacaccgcct gcgccatcgg gaggttgaac caggtttcgc cgatgcgcga    720
cgcgtaaggc tgaatctcca gcgtgcgttc cgccggtaat tgttgggtaa atccggccgt    780
aagggtatcg acaaaacggg tgccgacgca gataacccta tcggcgtcct ctatggcctg    840
acgcacttct ttgctgctgg cgccagcgct ataggtgcca acgaagttcg ggtgctgttc    900
atcaaaaagc cccttcccca tcagtagtgt cgcatgagcg atgggcgttt ccgccatcca    960
gcgctgcaac agtggtcgta aaccaaaacg cccggcaaga aagtcggcca atagcgcaat   1020
gcgccgactg ttcatcaggc actgacgggc gtgataacga aaggccgtct ccacgccgct   1080
ttgcgcttca tgcacgggca acgccagcgc ctgcgtaggt gggatggccg ttttttttcgc  1140 cacatcggcg gcaacatga tgtatcctgg cctgcgtgcg gcaagcattt cacccaacac   1200
gcggtcaatc tcgaaacagg cgttctgttc atctaatatt gcgctggcag cggatatcgc   1260
ctgactcatg cgataaaaat gacgaaaatc gccgtcaccg agggtatggt gcatcaattc   1320
gccacgctgc tgcgcagcgc tacagggcgc gccgacgata tgcaagaccg ggacatattc   1380
cgcgtaactg cccgcgatac cgttaatagc gctaagttct cccacgccaa aggtggtgag   1440
tagcgctcca gcgcccgaca tgcgcgcata gccgtccgcg gcataagcgg cgttcagctc   1500
attggcgcat cccacccaac gcagggtcgg gtggtcaatc acatggtcaa gaaactgcaa   1560
gttataatcg cccggtacgc caaaaagatg gccaatgccg catcctgcca gtctgtccag   1620
caaatagtcg gccacggtat aggggttttg cat                                 1653
```

<210> SEQ ID NO 195
<211> LENGTH: 550
<212> TYPE: PRT
<213> ORGANISM: Salmonella typhimurium
<400> SEQUENCE: 195

```
Met Gln Asn Pro Tyr Thr Val Ala Asp Tyr Leu Leu Asp Arg Leu Ala
1               5                   10                  15

Gly Cys Gly Ile Gly His Leu Phe Gly Val Pro Gly Asp Tyr Asn Leu
            20                  25                  30

Gln Phe Leu Asp His Val Ile Asp His Pro Thr Leu Arg Trp Val Gly
        35                  40                  45

Cys Ala Asn Glu Leu Asn Ala Ala Tyr Ala Ala Asp Gly Tyr Ala Arg
    50                  55                  60

Met Ser Gly Ala Gly Ala Leu Leu Thr Thr Phe Gly Val Gly Glu Leu
65                  70                  75                  80

Ser Ala Ile Asn Gly Ile Ala Gly Ser Tyr Ala Glu Tyr Val Pro Val
                85                  90                  95

Leu His Ile Val Gly Ala Pro Cys Ser Ala Ala Gln Gln Arg Gly Glu
            100                 105                 110

Leu Met His His Thr Leu Gly Asp Gly Asp Phe Arg His Phe Tyr Arg
        115                 120                 125

Met Ser Gln Ala Ile Ser Ala Ala Ser Ala Ile Leu Asp Glu Gln Asn
    130                 135                 140

Ala Cys Phe Glu Ile Asp Arg Val Leu Gly Glu Met Leu Ala Ala Arg
145                 150                 155                 160

Arg Pro Gly Tyr Ile Met Leu Pro Ala Asp Val Ala Lys Lys Thr Ala
                165                 170                 175

Ile Pro Pro Thr Gln Ala Leu Ala Leu Pro Val His Glu Ala Gln Ser
```

```
            180                 185                 190
Gly Val Glu Thr Ala Phe Arg Tyr His Ala Arg Gln Cys Leu Met Asn
            195                 200                 205

Ser Arg Arg Ile Ala Leu Leu Ala Asp Phe Leu Ala Gly Arg Phe Gly
            210                 215                 220

Leu Arg Pro Leu Leu Gln Arg Trp Met Ala Glu Thr Pro Ile Ala His
225                 230                 235                 240

Ala Thr Leu Leu Met Gly Lys Gly Leu Phe Asp Glu Gln His Pro Asn
                245                 250                 255

Phe Val Gly Thr Tyr Ser Ala Gly Ala Ser Ser Lys Glu Val Arg Gln
            260                 265                 270

Ala Ile Glu Asp Ala Asp Arg Val Ile Cys Val Gly Thr Arg Phe Val
            275                 280                 285

Asp Thr Leu Thr Ala Gly Phe Thr Gln Gln Leu Pro Ala Glu Arg Thr
            290                 295                 300

Leu Glu Ile Gln Pro Tyr Ala Ser Arg Ile Gly Glu Thr Trp Phe Asn
305                 310                 315                 320

Leu Pro Met Ala Gln Ala Val Ser Thr Leu Arg Glu Leu Cys Leu Glu
                325                 330                 335

Cys Ala Phe Ala Pro Pro Thr Arg Ser Ala Gly Gln Pro Val Arg
                340                 345                 350

Ile Asp Lys Gly Glu Leu Thr Gln Glu Ser Phe Trp Gln Thr Leu Gln
            355                 360                 365

Gln Tyr Leu Lys Pro Gly Asp Ile Ile Leu Val Asp Gln Gly Thr Ala
            370                 375                 380

Ala Phe Gly Ala Ala Leu Ser Leu Pro Asp Gly Ala Glu Val Val
385                 390                 395                 400

Leu Gln Pro Leu Trp Gly Ser Ile Gly Tyr Ser Leu Pro Ala Ala Phe
                405                 410                 415

Gly Ala Gln Thr Ala Cys Pro Asp Arg Arg Val Ile Leu Ile Gly
            420                 425                 430

Asp Gly Ala Ala Gln Leu Thr Ile Gln Glu Met Gly Ser Met Leu Arg
            435                 440                 445

Asp Gly Gln Ala Pro Val Ile Leu Leu Leu Asn Asn Asp Gly Tyr Thr
            450                 455                 460

Val Glu Arg Ala Ile His Gly Ala Ala Gln Arg Tyr Asn Asp Ile Ala
465                 470                 475                 480

Ser Trp Asn Trp Thr Gln Ile Pro Pro Ala Leu Asn Ala Ala Gln Gln
                485                 490                 495

Ala Glu Cys Trp Arg Val Thr Gln Ala Ile Gln Leu Ala Glu Val Leu
            500                 505                 510

Glu Arg Leu Ala Arg Pro Gln Arg Leu Ser Phe Ile Glu Val Met Leu
            515                 520                 525

Pro Lys Ala Asp Leu Pro Glu Leu Leu Arg Thr Val Thr Arg Ala Leu
            530                 535                 540

Glu Ala Arg Asn Gly Gly
545                 550

<210> SEQ ID NO 196
<211> LENGTH: 1665
<212> TYPE: DNA
<213> ORGANISM: Clostridium acetobutylicum

<400> SEQUENCE: 196
```

```
ttgaagagtg aatacacaat tggaagatat tgttagacc gtttatcaga gttgggtatt      60
cggcatatct tggtgtacc tggagattac aatctatcct ttttagacta tataatggag     120
tacaaaggga tagattgggt tggaaattgc aatgaattga atgctgggta tgctgctgat    180
ggatatgcaa gaataaatgg aattggagcc atacttacaa catttggtgt tggagaatta    240
agtgccatta acgcaattgc tggggcatac gctgagcaag ttccagttgt taaaattaca    300
ggtatcccca cagcaaaagt tagggacaat ggattatatg tacaccacac attaggtgac    360
ggaaggtttg atcactttt tgaaatgttt agagaagtaa cagttgctga ggcattacta    420
agcgaagaaa atgcagcaca agaaattgat cgtgttctta tttcatgctg gagacaaaaa    480
cgtcctgttc ttataaattt accgattgat gtatatgata aaccaattaa caaaccatta    540
aagccattac tcgattatac tatttcaagt aacaaagagg ctgcatgtga atttgttaca    600
gaaatagtac ctataataaa tagggcaaaa agcctgtta ttcttgcaga ttatggagta    660
tatcgttacc aagttcaaca tgtgcttaaa acttggccg aaaaaaccgg atttcctgtg    720
gctacactaa gtatgggaaa aggtgttttc aatgaagcac accctcaatt tattggtgtt    780
tataatggtg atgtaagttc tccttattta aggcagcgag ttgatgaagc agactgcatt    840
attagcgttg gtgtaaaatt gacgattca accacaggggg gattttctca tggattttct    900
aaaaggaatg taattcacat tgatccttt tcaataaagg caaaggtaa aaaatatgca    960
cctattacga tgaagatgc tttaacagaa ttaacaagta aaattgagca tagaaacttt   1020
gaggatttag atataaagcc ttacaaatca gataatcaaa agtattttgc aaaagagaag   1080
ccaattacac aaaaacgttt ttttgagcgt attgctcact ttataaaaga aaagatgta    1140
ttattagcag aacagggtac atgcttttt ggtgcgtcaa ccatacaact acccaaagat   1200
gcaacttta ttggtcaacc tttatggga tctattggat acacacttcc tgctttatta   1260
ggttcacaat tagctgatca aaaaaggcgt aatattcttt taattgggga tggtgcattt   1320
caaatgacag cacaagaaat ttcaacaatg cttcgtttac aaatcaaacc tattattttt   1380
ttaattaata cgatggtta tacaattgaa cgtgctattc atggtagaga acaagtatat   1440
aacaatattc aaatgtggcg atatcataat gttccaaagg ttttaggtcc taagaatgc   1500
agcttaacct ttaaagtaca aagtgaaact gaacttgaaa aggctctttt agtggcagat   1560
aaggattgtg aacatttgat ttttatgaa gttgttatgg atcgttatga taaacccgag   1620
ccttagaac gtctttcgaa acgttttgca aatcaaaata attag                    1665
```

<210> SEQ ID NO 197
<211> LENGTH: 554
<212> TYPE: PRT
<213> ORGANISM: Clostridium acetobutylicum

<400> SEQUENCE: 197

```
Met Lys Ser Glu Tyr Thr Ile Gly Arg Tyr Leu Leu Asp Arg Leu Ser
1               5                   10                  15

Glu Leu Gly Ile Arg His Ile Phe Gly Val Pro Gly Asp Tyr Asn Leu
            20                  25                  30

Ser Phe Leu Asp Tyr Ile Met Glu Tyr Lys Gly Ile Asp Trp Val Gly
        35                  40                  45

Asn Cys Asn Glu Leu Asn Ala Gly Tyr Ala Ala Asp Gly Tyr Ala Arg
    50                  55                  60

Ile Asn Gly Ile Gly Ala Ile Leu Thr Thr Phe Gly Val Gly Glu Leu
65                  70                  75                  80
```

-continued

```
Ser Ala Ile Asn Ala Ile Ala Gly Ala Tyr Ala Glu Gln Val Pro Val
                 85                  90                  95

Val Lys Ile Thr Gly Ile Pro Thr Ala Lys Val Arg Asp Asn Gly Leu
            100                 105                 110

Tyr Val His His Thr Leu Gly Asp Gly Arg Phe Asp His Phe Phe Glu
            115                 120                 125

Met Phe Arg Glu Val Thr Val Ala Glu Ala Leu Leu Ser Glu Glu Asn
            130                 135                 140

Ala Ala Gln Glu Ile Asp Arg Val Leu Ile Ser Cys Trp Arg Gln Lys
145                 150                 155                 160

Arg Pro Val Leu Ile Asn Leu Pro Ile Asp Val Tyr Asp Lys Pro Ile
                165                 170                 175

Asn Lys Pro Leu Lys Pro Leu Leu Asp Tyr Thr Ile Ser Ser Asn Lys
            180                 185                 190

Glu Ala Ala Cys Glu Phe Val Thr Glu Ile Val Pro Ile Ile Asn Arg
            195                 200                 205

Ala Lys Lys Pro Val Ile Leu Ala Asp Tyr Gly Val Tyr Arg Tyr Gln
        210                 215                 220

Val Gln His Val Leu Lys Asn Leu Ala Glu Lys Thr Gly Phe Pro Val
225                 230                 235                 240

Ala Thr Leu Ser Met Gly Lys Gly Val Phe Asn Glu Ala His Pro Gln
                245                 250                 255

Phe Ile Gly Val Tyr Asn Gly Asp Val Ser Ser Pro Tyr Leu Arg Gln
            260                 265                 270

Arg Val Asp Glu Ala Asp Cys Ile Ile Ser Val Gly Val Lys Leu Thr
            275                 280                 285

Asp Ser Thr Thr Gly Gly Phe Ser His Gly Phe Ser Lys Arg Asn Val
        290                 295                 300

Ile His Ile Asp Pro Phe Ser Ile Lys Ala Lys Gly Lys Lys Tyr Ala
305                 310                 315                 320

Pro Ile Thr Met Lys Asp Ala Leu Thr Glu Leu Thr Ser Lys Ile Glu
                325                 330                 335

His Arg Asn Phe Glu Asp Leu Asp Ile Lys Pro Tyr Lys Ser Asp Asn
            340                 345                 350

Gln Lys Tyr Phe Ala Lys Glu Lys Pro Ile Thr Gln Lys Arg Phe Phe
            355                 360                 365

Glu Arg Ile Ala His Phe Ile Lys Glu Lys Asp Val Leu Leu Ala Glu
        370                 375                 380

Gln Gly Thr Cys Phe Phe Gly Ala Ser Thr Ile Gln Leu Pro Lys Asp
385                 390                 395                 400

Ala Thr Phe Ile Gly Gln Pro Leu Trp Gly Ser Ile Gly Tyr Thr Leu
                405                 410                 415

Pro Ala Leu Leu Gly Ser Gln Leu Ala Asp Gln Lys Arg Arg Asn Ile
            420                 425                 430

Leu Leu Ile Gly Asp Gly Ala Phe Gln Met Thr Ala Gln Glu Ile Ser
            435                 440                 445

Thr Met Leu Arg Leu Gln Ile Lys Pro Ile Ile Phe Leu Ile Asn Asn
        450                 455                 460

Asp Gly Tyr Thr Ile Glu Arg Ala Ile His Gly Arg Glu Gln Val Tyr
465                 470                 475                 480

Asn Asn Ile Gln Met Trp Arg Tyr His Asn Val Pro Lys Val Leu Gly
                485                 490                 495

Pro Lys Glu Cys Ser Leu Thr Phe Lys Val Gln Ser Glu Thr Glu Leu
```

```
                500             505             510
Glu Lys Ala Leu Leu Val Ala Asp Lys Asp Cys Glu His Leu Ile Phe
            515                 520                 525

Ile Glu Val Val Met Asp Arg Tyr Asp Lys Pro Glu Pro Leu Glu Arg
        530                 535                 540

Leu Ser Lys Arg Phe Ala Asn Gln Asn Asn
545                 550

<210> SEQ ID NO 198
<211> LENGTH: 939
<212> TYPE: DNA
<213> ORGANISM: Saccharomyces cerevisiae

<400> SEQUENCE: 198
atgcctgcta cgttaaagaa ttcttctgct acattaaaac taaatactgg tgcctccatt      60
ccagtgttgg gtttcggcac ttggcgttcc gttgacaata acggttacca ttctgtaatt     120
gcagctttga aagctggata cagacacatt gatgctgcgg ctatctattt gaatgaagaa     180
gaagttggca gggctattaa agattccgga gtccctcgtg aggaaatttt tattactact     240
aagcttgggg tacggaaca acgtgatccg gaagctgctc taaacaagtc tttgaaaaga     300
ctaggcttgg attatgttga cctatatctg atgcattggc cagtgccttt gaaaaccgac     360
agagttactg atggtaacgt tctgtgcatt ccaacattag aagatggcac tgttgacatc     420
gatactaagg aatggaattt tatcaagacg tgggagttga tgcaagagtt gccaaagacg     480
ggcaaaacta agccgttgg tgtctctaat ttttctatta acaacattaa agaattatta     540
gaatctccaa ataacaaggt ggtaccagct actaatcaaa ttgaaattca tccattgcta     600
ccacaagacg aattgattgc cttttgtaag gaaaagggta ttgttgttga agcctactca     660
ccatttggga gtgctaatgc tcctttacta aaagagcaag caattattga tatggctaaa     720
aagcacggcg ttgagccagc acagcttatt atcagttgga gtattcaaag aggctacgtt     780
gttctggcca atcggttaa tcctgaaaga attgtatcca attttaagat tttcactctg     840
cctgaggatg atttcaagac tattagtaac ctatccaaag tgcatggtac aaagagagtc     900
gttgatatga agtggggatc cttcccaatt ttccaatga                             939

<210> SEQ ID NO 199
<211> LENGTH: 312
<212> TYPE: PRT
<213> ORGANISM: Saccharomyces cerevisiae

<400> SEQUENCE: 199

Met Pro Ala Thr Leu Lys Asn Ser Ser Ala Thr Leu Lys Leu Asn Thr
1               5                   10                  15

Gly Ala Ser Ile Pro Val Leu Gly Phe Gly Thr Trp Arg Ser Val Asp
            20                  25                  30

Asn Asn Gly Tyr His Ser Val Ile Ala Ala Leu Lys Ala Gly Tyr Arg
        35                  40                  45

His Ile Asp Ala Ala Ala Ile Tyr Leu Asn Glu Glu Glu Val Gly Arg
    50                  55                  60

Ala Ile Lys Asp Ser Gly Val Pro Arg Glu Glu Ile Phe Ile Thr Thr
65                  70                  75                  80

Lys Leu Trp Gly Thr Glu Gln Arg Asp Pro Glu Ala Ala Leu Asn Lys
                85                  90                  95

Ser Leu Lys Arg Leu Gly Leu Asp Tyr Val Asp Leu Tyr Leu Met His
            100                 105                 110
```

```
Trp Pro Val Pro Leu Lys Thr Asp Arg Val Thr Asp Gly Asn Val Leu
        115                 120                 125
Cys Ile Pro Thr Leu Glu Asp Gly Thr Val Asp Ile Asp Thr Lys Glu
        130                 135                 140
Trp Asn Phe Ile Lys Thr Trp Glu Leu Met Gln Glu Leu Pro Lys Thr
145                 150                 155                 160
Gly Lys Thr Lys Ala Val Gly Val Ser Asn Phe Ser Ile Asn Asn Ile
                165                 170                 175
Lys Glu Leu Leu Glu Ser Pro Asn Asn Lys Val Val Pro Ala Thr Asn
                180                 185                 190
Gln Ile Glu Ile His Pro Leu Leu Pro Gln Asp Glu Leu Ile Ala Phe
                195                 200                 205
Cys Lys Glu Lys Gly Ile Val Val Glu Ala Tyr Ser Pro Phe Gly Ser
        210                 215                 220
Ala Asn Ala Pro Leu Leu Lys Glu Gln Ala Ile Ile Asp Met Ala Lys
225                 230                 235                 240
Lys His Gly Val Glu Pro Ala Gln Leu Ile Ile Ser Trp Ser Ile Gln
                245                 250                 255
Arg Gly Tyr Val Val Leu Ala Lys Ser Val Asn Pro Glu Arg Ile Val
                260                 265                 270
Ser Asn Phe Lys Ile Phe Thr Leu Pro Glu Asp Asp Phe Lys Thr Ile
        275                 280                 285
Ser Asn Leu Ser Lys Val His Gly Thr Lys Arg Val Val Asp Met Lys
        290                 295                 300
Trp Gly Ser Phe Pro Ile Phe Gln
305                 310
```

<210> SEQ ID NO 200
<211> LENGTH: 1083
<212> TYPE: DNA
<213> ORGANISM: Saccharomyces cerevisiae

<400> SEQUENCE: 200

```
ctagtctgaa aattctttgt cgtagccgac taaggtaaat ctatatctaa cgtcacccctt    60
ttccatcctt tcgaaggctt catggacgcc ggcttcacca acaggtaatg tttccaccca   120
aattttgata tcttttttcag agactaattt caagagttgg ttcaattctt tgatggaacc   180
taaagcactg taagaaatgg agacagcctt taagccatat ggctttagcg ataacatttc   240
gtgttgttct ggtatagaga ttgagacaat tctaccacca accttcatag cctttggcat   300
aatgttgaag tcaatgtcgg taagggagga agcacagact acaatcaggt cgaaggtgtc   360
aaagtacttt tcacccccaat caccttcttc taatgtagca atgtagtgat cggcgcccat   420
cttcattgca tcttctcttt ttctcgaaga acgagaaata acatacgtct ctgcccccat   480
ggctttggaa atcaatgtac ccatactgcc gataccacca agaccaacta taccaacttt   540
tttacctgga ccgcaaccgt tacgaaccaa tggagagtac acagtcaaac caccacataa   600
tagtggagca gccaaatgtg atggaatatt ctctgggata ggcaccacaa aatgttcatg   660
aactctgacg tagtttgcat agccaccctg cgacacatag ccgtcttcat aaggctgact   720
gtatgtggta acaaacttgg tgcagtatgg ttcattatca ttcttacaac ggtcacattc   780
caagcatgaa aagacttgag cacctacacc aacacgttga ccgactttca acccactgtt   840
tgacttgggc cctagcttga caactttacc aacgatttca tgaccaacga ctagcggcat   900
cttcatattg ccccaatgac cagctgcaca atgaatatca ctaccgcaga caccacatgc   960
```

```
ttcgatctta atgtcaatgt catgatcgta aaatggtttt gggtcatact ttgtcttctt   1020
tgggtttttc caatcttcgt gtgattgaat agcgatacct tcaaatttct caggataaga   1080
cat                                                                  1083
```

<210> SEQ ID NO 201
<211> LENGTH: 360
<212> TYPE: PRT
<213> ORGANISM: Saccharomyces cerevisiae

<400> SEQUENCE: 201

```
Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
```

```
            340             345             350
Gly Tyr Asp Lys Glu Phe Ser Asp
        355             360

<210> SEQ ID NO 202
<211> LENGTH: 1170
<212> TYPE: DNA
<213> ORGANISM: Clostridium acetobutylicum

<400> SEQUENCE: 202
ttaataagat tttttaaata tctcaagaac atcctctgca tttattggtc ttaaacttcc      60
tattgttcct ccagaatttc taacagcttg ctttgccatt agttctagtt tatcttttcc     120
tattccaact tctctaagct ttgaaggaat acccaatgaa ttaaagtatt ctctcgtatt     180
tttaatagcc tctcgtgcta tttcatagtt atctttgttc ttgtctattc cccaaacatt     240
tattccataa gaaacaaatt tatgaagtgt atcgtcattt agaatatatt ccatccaatt     300
aggtgttaaa attgcaagtc ctacaccatg tgttatatca taatatgcac ttaactcgtg     360
ttccatagga tgacaactcc attttctatc cttaccaagt gataatagac catttatagc     420
taaacttgaa gcccacatca aattagctct agcctcgtaa tcatcagtct tctccattgc     480 tattttttcca tactttatac atgttcttaa gattgcttct gctataccgt cctgcacata     540
agcaccttca acaccactaa agtaagattc aaaggtgtga ctcataatgt cagctgttcc     600
cgctgctgtt tgattttttag gtactgtaaa agtatatgta ggatctaaca ctgaaaattt     660
aggtctcata tcatcatgtc ctactccaag cttttcatta gtctccatat ttgaaattac     720
tgcaatttga tccatttcag accctgttgc tgaaagagta agtatacttg caattggaag     780
aactttagtt attttagatg gatctttaac catgtcccat gtatcgccat cataataaac     840
tccagctgca attaccttag aacagtctat tgcacttcct cccctattg ctaatactaa      900 atccacatta ttttctctac atatttctat gccttttttt actgttgtta tcctaggatt     960
tggctctact cctgaaagtt catagaaagc tatattgttt tcttttaata tagctgttgc    1020
tctatcatat ataccgttcc tttttatact tcctccgcca taaactataa gcactcttga    1080
gccatatttc ttaatttctt ctccaattac gtctattttt cctttccaa aaaaaacttt      1140 agttggtatt gaataatcaa aacttagcat                                     1170

<210> SEQ ID NO 203
<211> LENGTH: 389
<212> TYPE: PRT
<213> ORGANISM: Clostridium acetobutylicum

<400> SEQUENCE: 203

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95
```

Gly Gly Ser Ala Ile Asp Cys Ser Lys Val Ile Ala Ala Gly Val Tyr
                100                 105                 110

Tyr Asp Gly Asp Thr Trp Asp Met Val Lys Asp Pro Ser Lys Ile Thr
            115                 120                 125

Lys Val Leu Pro Ile Ala Ser Ile Leu Thr Leu Ser Ala Thr Gly Ser
        130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asp Asp Thr Leu His Lys
    290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
    370                 375                 380

Phe Lys Lys Ser Tyr
385

<210> SEQ ID NO 204
<211> LENGTH: 390
<212> TYPE: PRT
<213> ORGANISM: Clostridium acetobutylicum

<400> SEQUENCE: 204

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
                20                  25                  30

Val Leu Ile Val Tyr Gly Gly Gly Ser Ile Lys Arg Asn Gly Ile Tyr
            35                  40                  45

Asp Lys Ala Val Ser Ile Leu Glu Lys Asn Ser Ile Lys Phe Tyr Glu
        50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Leu Ala Ile Gly
                85                  90                  95
Gly Gly Ser Ala Ile Asp Cys Ala Lys Val Ile Ala Ala Cys Glu
            100                 105                 110
Tyr Asp Gly Asn Pro Trp Asp Ile Val Leu Asp Gly Ser Lys Ile Lys
            115                 120                 125
Arg Val Leu Pro Ile Ala Ser Ile Leu Thr Ile Ala Ala Thr Gly Ser
        130                 135                 140
Glu Met Asp Thr Trp Ala Val Ile Asn Asn Met Asp Thr Asn Glu Lys
145                 150                 155                 160
Leu Ile Ala Ala His Pro Asp Met Ala Pro Lys Phe Ser Ile Leu Asp
                165                 170                 175
Pro Thr Tyr Thr Tyr Thr Val Pro Thr Asn Gln Thr Ala Ala Gly Thr
            180                 185                 190
Ala Asp Ile Met Ser His Ile Phe Glu Val Tyr Phe Ser Asn Thr Lys
        195                 200                 205
Thr Ala Tyr Leu Gln Asp Arg Met Ala Glu Ala Leu Leu Arg Thr Cys
    210                 215                 220
Ile Lys Tyr Gly Gly Ile Ala Leu Glu Lys Pro Asp Asp Tyr Glu Ala
225                 230                 235                 240
Arg Ala Asn Leu Met Trp Ala Ser Ser Leu Ala Ile Asn Gly Leu Leu
                245                 250                 255
Thr Tyr Gly Lys Asp Thr Asn Trp Ser Val His Leu Met Glu His Glu
            260                 265                 270
Leu Ser Ala Tyr Tyr Asp Ile Thr His Gly Val Gly Leu Ala Ile Leu
        275                 280                 285
Thr Pro Asn Trp Met Glu Tyr Ile Leu Asn Asn Asp Thr Val Tyr Lys
    290                 295                 300
Phe Val Glu Tyr Gly Val Asn Val Trp Gly Ile Asp Lys Glu Lys Asn
305                 310                 315                 320
His Tyr Asp Ile Ala His Gln Ala Ile Gln Lys Thr Arg Asp Tyr Phe
                325                 330                 335
Val Asn Val Leu Gly Leu Pro Ser Arg Leu Arg Asp Val Gly Ile Glu
            340                 345                 350
Glu Glu Lys Leu Asp Ile Met Ala Lys Glu Ser Val Lys Leu Thr Gly
        355                 360                 365
Gly Thr Ile Gly Asn Leu Arg Pro Val Asn Ala Ser Glu Val Leu Gln
    370                 375                 380
Ile Phe Lys Lys Ser Val
385                 390

<210> SEQ ID NO 205
<211> LENGTH: 993
<212> TYPE: DNA
<213> ORGANISM: Bacillus subtilis

<400> SEQUENCE: 205
atgagtacaa accgacatca agcactaggg ctgactgatc aggaagccgt tgatatgtat     60
agaaccatgc tgttagcaag aaaaatcgat gaaagaatgt ggctgttaaa ccgttctggc    120
aaaattccat ttgtaatctc ttgtcaagga caggaagcag cacaggtagg agcggctttc    180
gcacttgacc gtgaaatgga ttatgtattg ccgtactaca gagacatggg tgtcgtgctc    240
gcgtttggca tgacagcaaa ggacttaatg atgtccgggt ttgcaaaagc agcagatccg    300

```
aactcaggag gccgccagat gccgggacat tcggacaaa agaaaaaccg cattgtgacg      360
ggatcatctc cggttacaac gcaagtgccg cacgcagtcg gtattgcgct tgcgggacgt      420
atggagaaaa aggatatcgc agcctttgtt acattcgggg aagggtcttc aaaccaaggc      480
gatttccatg aaggggcaaa ctttgccgct gtccataagc tgccggttat tttcatgtgt      540
gaaaacaaca atacgcaat ctcagtgcct tacgataagc aagtcgcatg tgagaacatt      600
tccgaccgtg ccataggcta tgggatgcct ggcgtaactg tgaatggaaa tgatccgctg      660
gaagtttatc aagcggttaa agaagcacgc gaaagggcac gcagaggaga aggcccgaca      720
ttaattgaaa cgattttctta ccgccttaca ccacattcca gtgatgacga tgacagcagc      780
tacagaggcc gtgaagaagt agaggaagcg aaaaaaagtg atcccctgct tacttatcaa      840
gcttacttaa aggaaacagg cctgctgtcc gatgagatag aacaaaccat gctggatgaa      900
attatggcaa tcgtaaatga agcgacggat gaagcggaga acgccccata tgcagctcct      960
gagtcagcgc ttgattatgt ttatgcgaag tag                                   993
```

<210> SEQ ID NO 206
<211> LENGTH: 330
<212> TYPE: PRT
<213> ORGANISM: Bacillus subtilis

<400> SEQUENCE: 206

```
Met Ser Thr Asn Arg His Gln Ala Leu Gly Leu Thr Asp Gln Glu Ala
1               5                   10                  15

Val Asp Met Tyr Arg Thr Met Leu Leu Ala Arg Lys Ile Asp Glu Arg
            20                  25                  30

Met Trp Leu Leu Asn Arg Ser Gly Lys Ile Pro Phe Val Ile Ser Cys
        35                  40                  45

Gln Gly Gln Glu Ala Ala Gln Val Gly Ala Ala Phe Ala Leu Asp Arg
    50                  55                  60

Glu Met Asp Tyr Val Leu Pro Tyr Tyr Arg Asp Met Gly Val Val Leu
65                  70                  75                  80

Ala Phe Gly Met Thr Ala Lys Asp Leu Met Met Ser Gly Phe Ala Lys
                85                  90                  95

Ala Ala Asp Pro Asn Ser Gly Gly Arg Gln Met Pro Gly His Phe Gly
            100                 105                 110

Gln Lys Lys Asn Arg Ile Val Thr Gly Ser Ser Pro Val Thr Thr Gln
        115                 120                 125

Val Pro His Ala Val Gly Ile Ala Leu Ala Gly Arg Met Glu Lys Lys
    130                 135                 140

Asp Ile Ala Ala Phe Val Thr Phe Gly Glu Gly Ser Ser Asn Gln Gly
145                 150                 155                 160

Asp Phe His Glu Gly Ala Asn Phe Ala Ala Val His Lys Leu Pro Val
                165                 170                 175

Ile Phe Met Cys Glu Asn Asn Lys Tyr Ala Ile Ser Val Pro Tyr Asp
            180                 185                 190

Lys Gln Val Ala Cys Glu Asn Ile Ser Asp Arg Ala Ile Gly Tyr Gly
        195                 200                 205

Met Pro Gly Val Thr Val Asn Gly Asn Asp Pro Leu Glu Val Tyr Gln
    210                 215                 220

Ala Val Lys Glu Ala Arg Glu Arg Ala Arg Gly Glu Gly Pro Thr
225                 230                 235                 240

Leu Ile Glu Thr Ile Ser Tyr Arg Leu Thr Pro His Ser Ser Asp Asp
                245                 250                 255
```

Asp Asp Ser Ser Tyr Arg Gly Arg Glu Glu Val Glu Ala Lys Lys
            260                 265                 270

Ser Asp Pro Leu Leu Thr Tyr Gln Ala Tyr Leu Lys Glu Thr Gly Leu
        275                 280                 285

Leu Ser Asp Glu Ile Glu Gln Thr Met Leu Asp Glu Ile Met Ala Ile
        290                 295                 300

Val Asn Glu Ala Thr Asp Glu Ala Glu Asn Ala Pro Tyr Ala Ala Pro
305                 310                 315                 320

Glu Ser Ala Leu Asp Tyr Val Tyr Ala Lys
                325                 330

<210> SEQ ID NO 207
<211> LENGTH: 984
<212> TYPE: DNA
<213> ORGANISM: Bacillus subtilis

<400> SEQUENCE: 207

```
atgtcagtaa tgtcatatat tgatgcaatc aatttggcga tgaaagaaga aatggaacga      60
gattctcgcg ttttcgtcct tggggaagat gtaggaagaa aaggcggtgt gtttaaagcg     120
acagcgggac tctatgaaca atttggggaa gagcgcgtta tggatacgcc gcttgctgaa     180
tctgcaatcg caggagtcgg tatcggagcg gcaatgtacg gaatgagacc gattgctgaa     240
atgcagtttg ctgatttcat tatgccggca gtcaaccaaa ttatttctga gcggctaaa     300
atccgctacc gcagcaacaa tgactggagc tgtccgattg tcgtcagagc gccatacggc     360
ggaggcgtgc acgagccct gtatcattct caatcagtcg aagcaatttt cgccaaccag     420
cccggactga aaattgtcat gccatcaaca ccatatgacg cgaaagggct cttaaaagcc     480
gcagttcgtg acgaagaccc cgtgctgttt tttgagcaca gcgggcata ccgtctgata     540
aagggcgagg ttccggctga tgattatgtc ctgccaatcg gcaaggcgga cgtaaaaagg     600
gaaggcgacg acatcacagt gatcacatac ggcctgtgtg tccacttcgc cttacaagct     660
gcagaacgtc tcgaaaaaga tggcatttca gcgcatgtgg tggatttaag aacagtttac     720
ccgcttgata agaagccat catcgaagct gcgtccaaaa ctggaaaggt tcttttggtc     780
acagaagata caaagaagg cagcatcatg agcgaagtag ccgcaattat atccgagcat     840
tgtctgttcg acttagacgc gccgatcaaa cggcttgcag tcctgatat tccggctatg     900
ccttatgcgc cgacaatgga aaatactttt atggtcaacc ctgataaagt ggaagcggcg     960
atgagagaat tagcggagtt ttaa                                            984
```

<210> SEQ ID NO 208
<211> LENGTH: 327
<212> TYPE: PRT
<213> ORGANISM: Bacillus subtilis

<400> SEQUENCE: 208

Met Ser Val Met Ser Tyr Ile Asp Ala Ile Asn Leu Ala Met Lys Glu
1               5                   10                  15

Glu Met Glu Arg Asp Ser Arg Val Phe Val Leu Gly Glu Asp Val Gly
            20                  25                  30

Arg Lys Gly Gly Val Phe Lys Ala Thr Ala Gly Leu Tyr Glu Gln Phe
        35                  40                  45

Gly Glu Glu Arg Val Met Asp Thr Pro Leu Ala Glu Ser Ala Ile Ala
    50                  55                  60

Gly Val Gly Ile Gly Ala Ala Met Tyr Gly Met Arg Pro Ile Ala Glu

```
            65                  70                  75                  80
Met Gln Phe Ala Asp Phe Ile Met Pro Ala Val Asn Gln Ile Ile Ser
                85                  90                  95

Glu Ala Ala Lys Ile Arg Tyr Arg Ser Asn Asn Asp Trp Ser Cys Pro
            100                 105                 110

Ile Val Val Arg Ala Pro Tyr Gly Gly Val His Gly Ala Leu Tyr
            115                 120                 125

His Ser Gln Ser Val Glu Ala Ile Phe Ala Asn Gln Pro Gly Leu Lys
            130                 135                 140

Ile Val Met Pro Ser Thr Pro Tyr Asp Ala Lys Gly Leu Leu Lys Ala
145                 150                 155                 160

Ala Val Arg Asp Glu Asp Pro Val Leu Phe Phe Glu His Lys Arg Ala
                165                 170                 175

Tyr Arg Leu Ile Lys Gly Glu Val Pro Ala Asp Asp Tyr Val Leu Pro
            180                 185                 190

Ile Gly Lys Ala Asp Val Lys Arg Glu Gly Asp Ile Thr Val Ile
            195                 200                 205

Thr Tyr Gly Leu Cys Val His Phe Ala Leu Gln Ala Ala Glu Arg Leu
            210                 215                 220

Glu Lys Asp Gly Ile Ser Ala His Val Val Asp Leu Arg Thr Val Tyr
225                 230                 235                 240

Pro Leu Asp Lys Glu Ala Ile Ile Glu Ala Ala Ser Lys Thr Gly Lys
                245                 250                 255

Val Leu Leu Val Thr Glu Asp Thr Lys Glu Gly Ser Ile Met Ser Glu
            260                 265                 270

Val Ala Ala Ile Ile Ser Glu His Cys Leu Phe Asp Leu Asp Ala Pro
            275                 280                 285

Ile Lys Arg Leu Ala Gly Pro Asp Ile Pro Ala Met Pro Tyr Ala Pro
            290                 295                 300

Thr Met Glu Lys Tyr Phe Met Val Asn Pro Asp Lys Val Glu Ala Ala
305                 310                 315                 320

Met Arg Glu Leu Ala Glu Phe
                325

<210> SEQ ID NO 209
<211> LENGTH: 1275
<212> TYPE: DNA
<213> ORGANISM: Bacillus subtilis

<400> SEQUENCE: 209
atggcaattg aacaaatgac gatgccgcag cttggagaaa gcgtaacaga ggggacgatc        60
agcaaatggc ttgtcgcccc cggtgataaa gtgaacaaat acgatccgat cgcggaagtc       120
atgacagata aggtaaatgc agaggttccg tcttcttttta ctggtacgat aacagagctt      180
gtgggagaag aaggccaaac cctgcaagtc ggagaaatga tttgcaaaat tgaaacagaa       240
ggcgcgaatc cggctgaaca aaaacaagaa cagccagcag catcagaagc cgctgagaac       300
cctgttgcaa aaagtgctgg agcagccgat cagcccaata aaaagcgcta ctcgccagct       360
gttctccgtt tggccggaga gcacggcatt gacctcgatc aagtgacagg aactggtgcc       420
ggcgggcgca tcacacgaaa agatattcag cgcttaattg aaacaggcgg cgtgcaagaa       480
cagaatcctg aggagctgaa acagcagcct cctgcaccga gtctgcatc aaaacctgag       540 ccaaaagaag agacgtcata tcctgcgtct gcagccggtg ataaagaaat ccctgtcaca       600
ggtgtaagaa aagcaattgc ttccaatatg aagcgaagca aaacagaaat tccgcatgct       660
```

```
tggacgatga tggaagtcga cgtcacaaat atggttgcat atcgcaacag tataaaagat      720
tcttttaaga agacagaagg ctttaattta acgttcttcg cctttttgt aaaagcggtc       780 gctcaggcgt taaagaatt cccgcaaatg aatagcatgt gggcggggga caaaattatt      840
cagaaaaagg atatcaatat ttcaattgca gttgccacag aggattcttt atttgttccg     900
gtgattaaaa acgctgatga aaaaacaatt aaaggcattg cgaaagacat taccggccta     960
gctaaaaaag taagagacgg aaaactcact gcagatgaca tgcagggagg cacgtttacc    1020
gtcaacaaca caggttcgtt cgggtctgtt cagtcgatgg cattatcaa ctaccctcag     1080 gctgcgattc ttcaagtaga atccatcgtc aaacgcccgg ttgtcatgga caatggcatg    1140
attgctgtca gagacatggt taatctgtgc ctgtcattag atcacagagt gcttgacggt    1200
ctcgtgtgcg gacgattcct cggacgagtg aaacaaattt tagaatcgat tgacgagaag    1260
acatctgttt actaa                                                      1275
```

<210> SEQ ID NO 210
<211> LENGTH: 424
<212> TYPE: PRT
<213> ORGANISM: Bacillus subtilis

<400> SEQUENCE: 210

```
Met Ala Ile Glu Gln Met Thr Met Pro Gln Leu Gly Glu Ser Val Thr
1               5                   10                  15

Glu Gly Thr Ile Ser Lys Trp Leu Val Ala Pro Gly Asp Lys Val Asn
            20                  25                  30

Lys Tyr Asp Pro Ile Ala Glu Val Met Thr Asp Lys Val Asn Ala Glu
        35                  40                  45

Val Pro Ser Ser Phe Thr Gly Thr Ile Thr Glu Leu Val Gly Glu Glu
    50                  55                  60

Gly Gln Thr Leu Gln Val Gly Glu Met Ile Cys Lys Ile Glu Thr Glu
65                  70                  75                  80

Gly Ala Asn Pro Ala Glu Gln Lys Gln Glu Gln Pro Ala Ala Ser Glu
                85                  90                  95

Ala Ala Glu Asn Pro Val Ala Lys Ser Ala Gly Ala Ala Asp Gln Pro
            100                 105                 110

Asn Lys Lys Arg Tyr Ser Pro Ala Val Leu Arg Leu Ala Gly Glu His
        115                 120                 125

Gly Ile Asp Leu Asp Gln Val Thr Gly Thr Gly Ala Gly Gly Arg Ile
    130                 135                 140

Thr Arg Lys Asp Ile Gln Arg Leu Ile Glu Thr Gly Gly Val Gln Glu
145                 150                 155                 160

Gln Asn Pro Glu Glu Leu Lys Thr Ala Ala Pro Ala Pro Lys Ser Ala
                165                 170                 175

Ser Lys Pro Glu Pro Lys Glu Glu Thr Ser Tyr Pro Ala Ser Ala Ala
            180                 185                 190

Gly Asp Lys Glu Ile Pro Val Thr Gly Val Arg Lys Ala Ile Ala Ser
        195                 200                 205

Asn Met Lys Arg Ser Lys Thr Glu Ile Pro His Ala Trp Thr Met Met
    210                 215                 220

Glu Val Asp Val Thr Asn Met Val Ala Tyr Arg Asn Ser Ile Lys Asp
225                 230                 235                 240

Ser Phe Lys Lys Thr Glu Gly Phe Asn Leu Thr Phe Phe Ala Phe Phe
                245                 250                 255
```

```
Val Lys Ala Val Ala Gln Ala Leu Lys Glu Phe Pro Gln Met Asn Ser
            260                 265                 270

Met Trp Ala Gly Asp Lys Ile Ile Gln Lys Lys Asp Ile Asn Ile Ser
        275                 280                 285

Ile Ala Val Ala Thr Glu Asp Ser Leu Phe Val Pro Val Ile Lys Asn
        290                 295                 300

Ala Asp Glu Lys Thr Ile Lys Gly Ile Ala Lys Asp Ile Thr Gly Leu
305                 310                 315                 320

Ala Lys Lys Val Arg Asp Gly Lys Leu Thr Ala Asp Asp Met Gln Gly
                325                 330                 335

Gly Thr Phe Thr Val Asn Asn Thr Gly Ser Phe Gly Ser Val Gln Ser
            340                 345                 350

Met Gly Ile Ile Asn Tyr Pro Gln Ala Ala Ile Leu Gln Val Glu Ser
            355                 360                 365

Ile Val Lys Arg Pro Val Met Asp Asn Gly Met Ile Ala Val Arg
        370                 375                 380

Asp Met Val Asn Leu Cys Leu Ser Leu Asp His Arg Val Leu Asp Gly
385                 390                 395                 400

Leu Val Cys Gly Arg Phe Leu Gly Arg Val Lys Gln Ile Leu Glu Ser
                405                 410                 415

Ile Asp Glu Lys Thr Ser Val Tyr
            420

<210> SEQ ID NO 211
<211> LENGTH: 1374
<212> TYPE: DNA
<213> ORGANISM: Bacillus subtilis

<400> SEQUENCE: 211
atggcaactg agtatgacgt agtcattctg gcggcggta ccggcggtta tgttgcggcc      60
atcagagccg ctcagctcgg cttaaaaaca gccgttgtgg aaaaggaaaa actcggggga     120
acatgtctgc ataaaggctg tatcccgagt aaagcgctgc ttagaagcgc agaggtatac     180
cggacagctc gtgaagccga tcaattcgga gtggaaacgg ctggcgtgtc cctcaacttt     240
gaaaaagtgc agcagcgtaa gcaagccgtt gttgataagc ttgcagcggg tgtaaatcat     300
ttaatgaaaa aggaaaaat tgacgtgtac accggatatg gacgtatcct tggaccgtca     360
atcttctctc cgctgccggg aacaatttct gttgagcggg gaaatggcga agaaaatgac     420
atgctgatcc cgaaacaagt gatcattgca acaggatcaa gaccgagaat gcttccgggt     480
cttgaagtgg acggtaagtc tgtactgact tcagatgagg cgctccaaat ggaggagctg     540
ccacagtcaa tcatcattgt cggcggaggg gttatcggta tcgaatgggc gtctatgctt     600
catgattttg gcgttaaggt aacggttatt gaatacgcgg atcgcatatt gccgactgaa     660
gatctagaga tttcaaaaga aatggaaagt cttcttaaga aaaaggcat ccagttcata     720 acagggcaa aagtgctgcc tgacacaatg acaaaaacat cagacgatat cagcatacaa     780
gcggaaaaag acggagaaac cgttacctat tctgctgaga aatgcttgt ttccatcggc     840 agacaggcaa atatcgaagg catcggccta gagaacaccg atattgttac tgaaaatggc     900
atgatttcag tcaatgaaag ctgccaaacg aaggaatctc atatttatgc aatcggagac     960
gtaatcggtg gcctgcagtt agctcacgtt gcttcacatg agggaattat tgctgttgag    1020
cattttgcag gtctcaatcc gcatccgctt gatccgacgc ttgtgccgaa gtgcatttac    1080
tcaagccctg aagctgccag tgtcggctta accgaagacg aagcaaaggc gaacgggcat    1140
```

```
aatgtcaaaa tcggcaagtt cccatttatg gcgattggaa aagcgcttgt atacggtgaa    1200
agcgacggtt ttgtcaaaat cgtggctgac cgagatacag atgatattct cggcgttcat    1260
atgattggcc cgcatgtcac cgacatgatt tctgaagcgg tcttgccaa agtgctggac     1320 gcaacaccgt gggaggtcgg gcaaacgatt tcacccgcat ccaacgcttt ctga          1374
```

```
<210> SEQ ID NO 212
<211> LENGTH: 457
<212> TYPE: PRT
<213> ORGANISM: Bacillus subtilis

<400> SEQUENCE: 212

Met Ala Thr Glu Tyr Asp Val Val Ile Leu Gly Gly Gly Thr Gly Gly
1               5                   10                  15

Tyr Val Ala Ala Ile Arg Ala Ala Gln Leu Gly Leu Lys Thr Ala Val
                20                  25                  30

Val Glu Lys Glu Lys Leu Gly Gly Thr Cys Leu His Lys Gly Cys Ile
            35                  40                  45

Pro Ser Lys Ala Leu Leu Arg Ser Ala Glu Val Tyr Arg Thr Ala Arg
        50                  55                  60

Glu Ala Asp Gln Phe Gly Val Glu Thr Ala Gly Val Ser Leu Asn Phe
65                  70                  75                  80

Glu Lys Val Gln Gln Arg Lys Gln Ala Val Val Asp Lys Leu Ala Ala
                85                  90                  95

Gly Val Asn His Leu Met Lys Lys Gly Lys Ile Asp Val Tyr Thr Gly
            100                 105                 110

Tyr Gly Arg Ile Leu Gly Pro Ser Ile Phe Ser Pro Leu Pro Gly Thr
        115                 120                 125

Ile Ser Val Glu Arg Gly Asn Gly Glu Glu Asn Asp Met Leu Ile Pro
130                 135                 140

Lys Gln Val Ile Ala Thr Gly Ser Arg Pro Arg Met Leu Pro Gly
145                 150                 155                 160

Leu Glu Val Asp Gly Lys Ser Val Leu Thr Ser Asp Glu Ala Leu Gln
                165                 170                 175

Met Glu Glu Leu Pro Gln Ser Ile Ile Val Gly Gly Gly Val Ile
            180                 185                 190

Gly Ile Glu Trp Ala Ser Met Leu His Asp Phe Gly Val Lys Val Thr
        195                 200                 205

Val Ile Glu Tyr Ala Asp Arg Ile Leu Pro Thr Glu Asp Leu Glu Ile
    210                 215                 220

Ser Lys Glu Met Glu Ser Leu Leu Lys Lys Gly Ile Gln Phe Ile
225                 230                 235                 240

Thr Gly Ala Lys Val Leu Pro Asp Thr Met Thr Lys Thr Ser Asp Asp
                245                 250                 255

Ile Ser Ile Gln Ala Glu Lys Asp Gly Glu Thr Val Thr Tyr Ser Ala
            260                 265                 270

Glu Lys Met Leu Val Ser Ile Gly Arg Gln Ala Asn Ile Glu Gly Ile
        275                 280                 285

Gly Leu Glu Asn Thr Asp Ile Val Thr Glu Asn Gly Met Ile Ser Val
    290                 295                 300

Asn Glu Ser Cys Gln Thr Lys Glu Ser His Ile Tyr Ala Ile Gly Asp
305                 310                 315                 320

Val Ile Gly Gly Leu Gln Leu Ala His Val Ala Ser His Glu Gly Ile
                325                 330                 335
```

```
Ile Ala Val Glu His Phe Ala Gly Leu Asn Pro His Pro Leu Asp Pro
                340                 345                 350

Thr Leu Val Pro Lys Cys Ile Tyr Ser Ser Pro Glu Ala Ala Ser Val
            355                 360                 365

Gly Leu Thr Glu Asp Glu Ala Lys Ala Asn Gly His Asn Val Lys Ile
        370                 375                 380

Gly Lys Phe Pro Phe Met Ala Ile Gly Lys Ala Leu Val Tyr Gly Glu
385                 390                 395                 400

Ser Asp Gly Phe Val Lys Ile Val Ala Asp Arg Asp Thr Asp Asp Ile
                405                 410                 415

Leu Gly Val His Met Ile Gly Pro His Val Thr Asp Met Ile Ser Glu
            420                 425                 430

Ala Gly Leu Ala Lys Val Leu Asp Ala Thr Pro Trp Glu Val Gly Gln
        435                 440                 445

Thr Ile Ser Pro Ala Ser Asn Ala Phe
    450                 455
```

<210> SEQ ID NO 213
<211> LENGTH: 1233
<212> TYPE: DNA
<213> ORGANISM: Pseudomonas putida

<400> SEQUENCE: 213

```
atgaacgagt acgcccccct gcgtttgcat gtgcccgagc ccaccggccg gccaggctgc    60
cagaccgatt tttcctacct gcgcctgaac gatgcaggtc aagcccgtaa acccctgtc    120
gatgtcgacg ctgccgacac cgccgacctg tcctacagcc tggtccgcgt gctcgacgag    180
caaggcgacg cccaaggccc gtgggctgaa gacatcgacc gcagatcct gcgccaaggc    240
atgcgcgcca tgctcaagac gcggatcttc gacagccgca tggtggttgc ccagcgccag    300
aagaagatgt ccttctacat gcagagcctg ggcgaagaag ccatcggcag cggccaggcg    360
ctggcgctta accgcaccga catgtgcttc ccaccctacc gtcagcaaag catcctgatg    420
gcccgcgacg tgtcgctggt ggagatgatc tgccagttgc tgtccaacga acgcgacccc    480
ctcaagggcc gccagctgcc gatcatgtac tcggtacgcg aggccggctt cttcaccatc    540
agcggcaacc tggcgaccca gttcgtgcag gcggtcggct gggccatggc ctcggcgatc    600
aagggcgata ccaagattgc ctcggcctgg atcggcgacg cgccactgc cgaatcggac    660
ttccacaccg ccctcacctt tgcccacgtt taccgcgccc cggtgatcct caacgtggtc    720
aacaaccagt gggccatctc aaccttccag gccatcgccg tggcgagtc gaccaccttc    780
gccggccgtg gcgtgggctg cggcatcgct tcgctgcggg tggacggcaa cgacttcgtc    840
gccgtttacg ccgcttcgcg ctgggctgcc gaacgtgccc gcgtggtttt gggcccgagc    900
ctgatcgagt gggtcaccta ccgtgccggc cgcactcga cctcggacga cccgtccaag    960
taccgccctg ccgatgactg gagccacttc ccgctgggtg acccgatcgc cgcctgaag    1020
cagcacctga tcaagatcgg ccactggtcc gaagaagaac accaggccac acggccgag    1080
ttcgaagcgg ccgtgattgc tgcgcaaaaa gaagccgagc agtacggcac cctggccaac    1140
ggtcacatcc cgagcgccgc ctcgatgttc gaggacgtgt acaaggagat gcccgaccac    1200
ctgcgccgcc aacgccagga actggggggtt tga                               1233
```

<210> SEQ ID NO 214
<211> LENGTH: 410
<212> TYPE: PRT
<213> ORGANISM: Pseudomonas putida

<400> SEQUENCE: 214

```
Met Asn Glu Tyr Ala Pro Leu Arg Leu His Val Pro Glu Pro Thr Gly
1               5                   10                  15

Arg Pro Gly Cys Gln Thr Asp Phe Ser Tyr Leu Arg Leu Asn Asp Ala
            20                  25                  30

Gly Gln Ala Arg Lys Pro Val Asp Val Asp Ala Asp Thr Ala
        35                  40                  45

Asp Leu Ser Tyr Ser Leu Val Arg Val Leu Asp Glu Gln Gly Asp Ala
    50                  55                  60

Gln Gly Pro Trp Ala Glu Asp Ile Asp Pro Gln Ile Leu Arg Gln Gly
65                  70                  75                  80

Met Arg Ala Met Leu Lys Thr Arg Ile Phe Asp Ser Arg Met Val Val
                85                  90                  95

Ala Gln Arg Gln Lys Lys Met Ser Phe Tyr Met Gln Ser Leu Gly Glu
            100                 105                 110

Glu Ala Ile Gly Ser Gly Gln Ala Leu Ala Leu Asn Arg Thr Asp Met
            115                 120                 125

Cys Phe Pro Thr Tyr Arg Gln Gln Ser Ile Leu Met Ala Arg Asp Val
130                 135                 140

Ser Leu Val Glu Met Ile Cys Gln Leu Leu Ser Asn Glu Arg Asp Pro
145                 150                 155                 160

Leu Lys Gly Arg Gln Leu Pro Ile Met Tyr Ser Val Arg Glu Ala Gly
                165                 170                 175

Phe Phe Thr Ile Ser Gly Asn Leu Ala Thr Gln Phe Val Gln Ala Val
                180                 185                 190

Gly Trp Ala Met Ala Ser Ala Ile Lys Gly Asp Thr Lys Ile Ala Ser
        195                 200                 205

Ala Trp Ile Gly Asp Gly Ala Thr Ala Glu Ser Asp Phe His Thr Ala
210                 215                 220

Leu Thr Phe Ala His Val Tyr Arg Ala Pro Val Ile Leu Asn Val Val
225                 230                 235                 240

Asn Asn Gln Trp Ala Ile Ser Thr Phe Gln Ala Ile Ala Gly Gly Glu
                245                 250                 255

Ser Thr Thr Phe Ala Gly Arg Gly Val Gly Cys Gly Ile Ala Ser Leu
                260                 265                 270

Arg Val Asp Gly Asn Asp Phe Val Ala Val Tyr Ala Ala Ser Arg Trp
            275                 280                 285

Ala Ala Glu Arg Ala Arg Arg Gly Leu Gly Pro Ser Leu Ile Glu Trp
290                 295                 300

Val Thr Tyr Arg Ala Gly Pro His Ser Thr Ser Asp Asp Pro Ser Lys
305                 310                 315                 320

Tyr Arg Pro Ala Asp Asp Trp Ser His Phe Pro Leu Gly Asp Pro Ile
                325                 330                 335

Ala Arg Leu Lys Gln His Leu Ile Lys Ile Gly His Trp Ser Glu Glu
            340                 345                 350

Glu His Gln Ala Thr Thr Ala Glu Phe Glu Ala Ala Val Ile Ala Ala
            355                 360                 365

Gln Lys Glu Ala Glu Gln Tyr Gly Thr Leu Ala Asn Gly His Ile Pro
        370                 375                 380

Ser Ala Ala Ser Met Phe Glu Asp Val Tyr Lys Glu Met Pro Asp His
385                 390                 395                 400

Leu Arg Arg Gln Arg Gln Glu Leu Gly Val
```

<210> SEQ ID NO 215
<211> LENGTH: 1059
<212> TYPE: DNA
<213> ORGANISM: Pseudomonas putida

<400> SEQUENCE: 215

| | | | |
|---|---|---|---|
| atgaacgacc acaacaacag catcaacccg gaaaccgcca tggccaccac taccatgacc | 60 |
| atgatccagg ccctgcgctc ggccatggat gtcatgcttg agcgcgacga caatgtggtg | 120 |
| gtgtacggcc aggacgtcgg ctacttcggc ggcgtgttcc gctgcaccga aggcctgcag | 180 |
| accaagtacg gcaagtcccg cgtgttcgac gcgcccatct ctgaaagcgg catcgtcggc | 240 |
| accgccgtgg gcatgggtgc ctacggcctg cgcccggtgg tggaaatcca gttcgctgac | 300 |
| tacttctacc cggcctccga ccagatcgtt tctgaaatgg cccgcctgcg ctaccgttcg | 360 |
| gccggcgagt tcatcgcccc gctgaccctg cgtatgccct gcggtggcgg tatctatggc | 420 |
| ggccagacac acagccagag cccggaagcg atgttcactc aggtgtgcgg cctgcgcacc | 480 |
| gtaatgccat ccaacccgta cgacgccaaa ggcctgctga ttgcctcgat cgaatgcgac | 540 |
| gacccggtga tcttcctgga gcccaagcgc ctgtacaacg gccgttcga cggccaccat | 600 |
| gaccgcccgg ttacgccgtg gtcgaaacac ccgcacagcg ccgtgcccga tggctactac | 660 |
| accgtgccac tggacaaggc cgccatcacc cgccccggca tgacgtgag cgtgctcacc | 720 |
| tatggcacca ccgtgtacgt ggcccaggtg gccgccgaag aaagtggcgt ggatgccgaa | 780 |
| gtgatcgacc tgcgcagcct gtggccgcta gacctggaca ccatcgtcga gtcggtgaaa | 840 |
| aagaccggcc gttgcgtggt agtacacgag gccacccgta cttgtggctt ggcgcagaa | 900 |
| ctggtgtcgc tggtgcagga gcactgcttc caccacctgg aggcgccgat cgagcgcgtc | 960 |
| accggttggg acacccccta ccctcacgcg caggaatggg cttacttccc agggccttcg | 1020 |
| cgggtaggtg cggcattgaa aaaggtcatg gaggtctga | 1059 |

<210> SEQ ID NO 216
<211> LENGTH: 352
<212> TYPE: PRT
<213> ORGANISM: Pseudomonas putida

<400> SEQUENCE: 216

Met Asn Asp His Asn Asn Ser Ile Asn Pro Glu Thr Ala Met Ala Thr
1               5                   10                  15

Thr Thr Met Thr Met Ile Gln Ala Leu Arg Ser Ala Met Asp Val Met
            20                  25                  30

Leu Glu Arg Asp Asp Asn Val Val Tyr Gly Gln Asp Val Gly Tyr
        35                  40                  45

Phe Gly Gly Val Phe Arg Cys Thr Glu Gly Leu Gln Thr Lys Tyr Gly
    50                  55                  60

Lys Ser Arg Val Phe Asp Ala Pro Ile Ser Glu Ser Gly Ile Val Gly
65                  70                  75                  80

Thr Ala Val Gly Met Gly Ala Tyr Gly Leu Arg Pro Val Val Glu Ile
                85                  90                  95

Gln Phe Ala Asp Tyr Phe Tyr Pro Ala Ser Asp Gln Ile Val Ser Glu
            100                 105                 110

Met Ala Arg Leu Arg Tyr Arg Ser Ala Gly Glu Phe Ile Ala Pro Leu
        115                 120                 125

Thr Leu Arg Met Pro Cys Gly Gly Gly Ile Tyr Gly Gly Gln Thr His

```
                    130                 135                 140
Ser Gln Ser Pro Glu Ala Met Phe Thr Gln Val Cys Gly Leu Arg Thr
145                 150                 155                 160

Val Met Pro Ser Asn Pro Tyr Asp Ala Lys Gly Leu Leu Ile Ala Ser
                165                 170                 175

Ile Glu Cys Asp Asp Pro Val Ile Phe Leu Glu Pro Lys Arg Leu Tyr
            180                 185                 190

Asn Gly Pro Phe Asp Gly His His Asp Arg Pro Val Thr Pro Trp Ser
                195                 200                 205

Lys His Pro His Ser Ala Val Pro Asp Gly Tyr Tyr Thr Val Pro Leu
            210                 215                 220

Asp Lys Ala Ala Ile Thr Arg Pro Gly Asn Asp Val Ser Val Leu Thr
225                 230                 235                 240

Tyr Gly Thr Thr Val Tyr Val Ala Gln Val Ala Ala Glu Glu Ser Gly
                245                 250                 255

Val Asp Ala Glu Val Ile Asp Leu Arg Ser Leu Trp Pro Leu Asp Leu
            260                 265                 270

Asp Thr Ile Val Glu Ser Val Lys Lys Thr Gly Arg Cys Val Val Val
            275                 280                 285

His Glu Ala Thr Arg Thr Cys Gly Phe Gly Ala Glu Leu Val Ser Leu
            290                 295                 300

Val Gln Glu His Cys Phe His His Leu Glu Ala Pro Ile Glu Arg Val
305                 310                 315                 320

Thr Gly Trp Asp Thr Pro Tyr Pro His Ala Gln Glu Trp Ala Tyr Phe
                325                 330                 335

Pro Gly Pro Ser Arg Val Gly Ala Ala Leu Lys Lys Val Met Glu Val
                340                 345                 350
```

<210> SEQ ID NO 217
<211> LENGTH: 1272
<212> TYPE: DNA
<213> ORGANISM: Pseudomonas putida

<400> SEQUENCE: 217

```
atgggcacgc acgtcatcaa gatgccggac attggcgaag gcatcgcgca ggtcgaattg      60
gtggaatggt tcgtcaaggt gggcgacatc atcgccgagg accaagtggt agccgacgtc     120
atgaccgaca aggccaccgt ggaaatcccg tcgccggtca gcggcaaggt gctggccctg     180
ggtggccagc aggtgaagt gatggcggtc ggcagtgagc tgatccgcat cgaagtggaa     240
ggcagcggca accatgtgga tgtgccgcaa gccaagccgg ccgaagtgcc tgcggcaccg     300
gtagccgcta aacctgaacc acagaaagac gttaaaccgg cggcgtacca ggcgtcagcc     360
agccacgagg cagcgcccat cgtgccgcgc agccgggcg acaagccgct ggcctcgccg     420
gcggtgcgca aacgcgccct cgatgccggc atcgaattgc gttatgtgca cggcagcggc     480
ccggccgggc gcatcctgca cgaagacctc gacgcgttca tgagcaaacc gcaaagcgct     540
gccgggcaaa ccccaatgg ctatgccagg cgcaccgaca gcgagcaggt gccggtgatc     600
ggcctgcgcc gcaagatcgc ccagcgcatg caggacgcca gcgccgggt cgcgcacttc     660
agctatgtgg aagaaatcga cgtcaccgcc ctggaagccc tgcgccagca gctcaacagc     720
aagcacggcg acagccgcgg caagctgaca ctgctgccgt tcctggtgcg cgccctggtc     780
gtggcactgc gtgacttccc gcagataaac gccacctacg atgacgaagc gcagatcatc     840
acccgccatg gcgcggtgca tgtgggcatc gccacccaag gtgacaacgg cctgatggta     900
```

-continued

```
cccgtgctgc gccacgccga agcgggcagc ctgtgggcca tgccggtga gatttcacgc   960 ctggccaacg ctgcgcgcaa caacaaggcc agccgcgaag agctgtccgg ttcgaccatt  1020
accctgacca gcctcggcgc cctgggcggc atcgtcagca cgccggtggt caacaccccg  1080
gaagtggcga tcgtcggtgt caaccgcatg gttgagcggc ccgtggtgat cgacggccag  1140
atcgtcgtgc gcaagatgat gaacctgtcc agctcgttcg accaccgcgt ggtcgatggc  1200
atggacgccg ccctgttcat ccaggccgtg cgtggcctgc tcgaacaacc cgcctgcctg  1260
ttcgtggagt ga                                                      1272
```

<210> SEQ ID NO 218
<211> LENGTH: 423
<212> TYPE: PRT
<213> ORGANISM: Pseudomonas putida

<400> SEQUENCE: 218

```
Met Gly Thr His Val Ile Lys Met Pro Asp Ile Gly Glu Gly Ile Ala
1               5                   10                  15

Gln Val Glu Leu Val Glu Trp Phe Lys Val Gly Asp Ile Ile Ala
            20                  25                  30

Glu Asp Gln Val Val Ala Asp Val Met Thr Asp Lys Ala Thr Val Glu
        35                  40                  45

Ile Pro Ser Pro Val Ser Gly Lys Val Leu Ala Leu Gly Gly Gln Pro
    50                  55                  60

Gly Glu Val Met Ala Val Gly Ser Glu Leu Ile Arg Ile Glu Val Glu
65                  70                  75                  80

Gly Ser Gly Asn His Val Asp Val Pro Gln Ala Lys Pro Ala Glu Val
                85                  90                  95

Pro Ala Ala Pro Val Ala Ala Lys Pro Glu Pro Gln Lys Asp Val Lys
            100                 105                 110

Pro Ala Ala Tyr Gln Ala Ser Ala Ser His Glu Ala Ala Pro Ile Val
        115                 120                 125

Pro Arg Gln Pro Gly Asp Lys Pro Leu Ala Ser Pro Ala Val Arg Lys
    130                 135                 140

Arg Ala Leu Asp Ala Gly Ile Glu Leu Arg Tyr Val His Gly Ser Gly
145                 150                 155                 160

Pro Ala Gly Arg Ile Leu His Glu Asp Leu Asp Ala Phe Met Ser Lys
                165                 170                 175

Pro Gln Ser Ala Ala Gly Gln Thr Pro Asn Gly Tyr Ala Arg Arg Thr
            180                 185                 190

Asp Ser Glu Gln Val Pro Val Ile Gly Leu Arg Arg Lys Ile Ala Gln
        195                 200                 205

Arg Met Gln Asp Ala Lys Arg Arg Val Ala His Phe Ser Tyr Val Glu
    210                 215                 220

Glu Ile Asp Val Thr Ala Leu Glu Ala Leu Arg Gln Gln Leu Asn Ser
225                 230                 235                 240

Lys His Gly Asp Ser Arg Gly Lys Leu Thr Leu Leu Pro Phe Leu Val
                245                 250                 255

Arg Ala Leu Val Val Ala Leu Arg Asp Phe Pro Gln Ile Asn Ala Thr
            260                 265                 270

Tyr Asp Asp Glu Ala Gln Ile Ile Thr Arg His Gly Ala Val His Val
        275                 280                 285

Gly Ile Ala Thr Gln Gly Asp Asn Gly Leu Met Val Pro Val Leu Arg
    290                 295                 300
```

```
His Ala Glu Ala Gly Ser Leu Trp Ala Asn Ala Gly Glu Ile Ser Arg
305                 310                 315                 320

Leu Ala Asn Ala Ala Arg Asn Asn Lys Ala Ser Arg Glu Glu Leu Ser
                325                 330                 335

Gly Ser Thr Ile Thr Leu Thr Ser Leu Gly Ala Leu Gly Gly Ile Val
            340                 345                 350

Ser Thr Pro Val Val Asn Thr Pro Glu Val Ala Ile Val Gly Val Asn
        355                 360                 365

Arg Met Val Glu Arg Pro Val Val Ile Asp Gly Gln Ile Val Val Arg
    370                 375                 380

Lys Met Met Asn Leu Ser Ser Ser Phe Asp His Arg Val Val Asp Gly
385                 390                 395                 400

Met Asp Ala Ala Leu Phe Ile Gln Ala Val Arg Gly Leu Leu Glu Gln
                405                 410                 415

Pro Ala Cys Leu Phe Val Glu
            420
```

<210> SEQ ID NO 219
<211> LENGTH: 1380
<212> TYPE: DNA
<213> ORGANISM: Pseudomonas putida

<400> SEQUENCE: 219

```
atgcaacaga ctatccagac aaccctgttg atcatcggcg gcggccctgg cggctatgtg      60
gcggccatcc gcgccgggca actgggcatc ctaccgtgc tggtggaagg ccaggcgctg     120
ggcggtacct gcctgaacat cggctgcatt ccgtccaagg cgctgatcca tgtggccgag     180
cagttccacc aggcctcgcg ctttaccgaa ccctcgccgc tgggcatcag cgtggcttcg     240
ccacgcctgg acatcggcca gagcgtggcc tggaaagacg gcatcgtcga tcgcctgacc     300
actggtgtcg ccgccctgct gaaaaagcac ggggtgaagg tggtgcacgg ctgggccaag     360
gtgcttgatg caagcaggt cgaggtggat ggccagcgca tccagtgcga gcacctgttg     420
ctggccacgg gctccagcag tgtcgaactg ccgatgctgc cgttgggtgg ccggtgatt     480
tcctcgaccg aggccctggc accgaaagcc ctgccgcaac acctggtggt ggtgggcggt     540
ggctacatcg gcctggagct gggtatcgcc taccgcaagc tcggcgcgca ggtcagcgtg     600
gtggaagcgc gcgagcgcat cctgccgact tacgacagcg aactgaccgc cccggtggcc     660
gagtcgctga aaaagctggg tatcgccctg caccttggcc acagcgtcga aggttacgaa     720
aatggctgcc tgctggccaa cgatggcaag ggcggacaac tgcgcctgga agccgaccgg     780
gtgctggtgg ccgtgggccg ccgcccacgc accaagggct tcaacctgga atgcctggac     840
ctgaagatga tggtgccgc gattgccatc gacgagcgct gccagaccag catgcacaac     900
gtctgggcca tcggcgacgt ggccggcgaa ccgatgctgg cgcaccgggc catggcccag     960
ggcgagatgg tggccgagat catcgccggc aaggcacgcc gcttcgaacc cgctgcgata    1020
gccgccgtgt gcttcaccga cccggaagtg gtcgtggtcg caagacgcc ggaacaggcc    1080
agtcagcaag gcctggactg catcgtcgcg cagttcccgt cgccgccaa cggccgggcc    1140
atgagcctgg agtcgaaaag cggtttcgtg cgcgtggtcg cgcggcgtga caaccacctg    1200
atcctgggct ggcaagcggt tggcgtggcg gtttccgagc tgtccacggc gtttgcccag    1260
tcgctggaga tgggtgcctg cctggaggat gtggccggta ccatccatgc ccacccgacc    1320
ctgggtgaag cggtacagga agcggcactg cgtgccctgg ccacgccct gcatatctga    1380
```

<210> SEQ ID NO 220
<211> LENGTH: 459
<212> TYPE: PRT
<213> ORGANISM: Pseudomonas putida

<400> SEQUENCE: 220

```
Met Gln Gln Thr Ile Gln Thr Thr Leu Leu Ile Ile Gly Gly Gly Pro
 1               5                  10                  15

Gly Gly Tyr Val Ala Ala Ile Arg Ala Gly Gln Leu Gly Ile Pro Thr
            20                  25                  30

Val Leu Val Glu Gly Gln Ala Leu Gly Gly Thr Cys Leu Asn Ile Gly
        35                  40                  45

Cys Ile Pro Ser Lys Ala Leu Ile His Val Ala Glu Gln Phe His Gln
    50                  55                  60

Ala Ser Arg Phe Thr Glu Pro Ser Pro Leu Gly Ile Ser Val Ala Ser
65                  70                  75                  80

Pro Arg Leu Asp Ile Gly Gln Ser Val Ala Trp Lys Asp Gly Ile Val
                85                  90                  95

Asp Arg Leu Thr Thr Gly Val Ala Ala Leu Leu Lys Lys His Gly Val
            100                 105                 110

Lys Val Val His Gly Trp Ala Lys Val Leu Asp Gly Lys Gln Val Glu
        115                 120                 125

Val Asp Gly Gln Arg Ile Gln Cys Glu His Leu Leu Leu Ala Thr Gly
    130                 135                 140

Ser Ser Ser Val Glu Leu Pro Met Leu Pro Leu Gly Gly Pro Val Ile
145                 150                 155                 160

Ser Ser Thr Glu Ala Leu Ala Pro Lys Ala Leu Pro Gln His Leu Val
                165                 170                 175

Val Val Gly Gly Gly Tyr Ile Gly Leu Glu Leu Gly Ile Ala Tyr Arg
            180                 185                 190

Lys Leu Gly Ala Gln Val Ser Val Val Glu Ala Arg Glu Arg Ile Leu
        195                 200                 205

Pro Thr Tyr Asp Ser Glu Leu Thr Ala Pro Val Ala Glu Ser Leu Lys
    210                 215                 220

Lys Leu Gly Ile Ala Leu His Leu Gly His Ser Val Glu Gly Tyr Glu
225                 230                 235                 240

Asn Gly Cys Leu Leu Ala Asn Asp Gly Lys Gly Gly Gln Leu Arg Leu
                245                 250                 255

Glu Ala Asp Arg Val Leu Val Ala Val Gly Arg Arg Pro Arg Thr Lys
            260                 265                 270

Gly Phe Asn Leu Glu Cys Leu Asp Leu Lys Met Asn Gly Ala Ala Ile
        275                 280                 285

Ala Ile Asp Glu Arg Cys Gln Thr Ser Met His Asn Val Trp Ala Ile
    290                 295                 300

Gly Asp Val Ala Gly Glu Pro Met Leu Ala His Arg Ala Met Ala Gln
305                 310                 315                 320

Gly Glu Met Val Ala Glu Ile Ile Ala Gly Lys Ala Arg Arg Phe Glu
                325                 330                 335

Pro Ala Ala Ile Ala Ala Val Cys Phe Thr Asp Pro Glu Val Val Val
            340                 345                 350

Val Gly Lys Thr Pro Glu Gln Ala Ser Gln Gln Gly Leu Asp Cys Ile
        355                 360                 365

Val Ala Gln Phe Pro Phe Ala Ala Asn Gly Arg Ala Met Ser Leu Glu
    370                 375                 380
```

```
Ser Lys Ser Gly Phe Val Arg Val Val Ala Arg Arg Asp Asn His Leu
385                 390                 395                 400

Ile Leu Gly Trp Gln Ala Val Gly Val Ala Val Ser Glu Leu Ser Thr
                405                 410                 415

Ala Phe Ala Gln Ser Leu Glu Met Gly Ala Cys Leu Glu Asp Val Ala
            420                 425                 430

Gly Thr Ile His Ala His Pro Thr Leu Gly Glu Ala Val Gln Glu Ala
        435                 440                 445

Ala Leu Arg Ala Leu Gly His Ala Leu His Ile
    450                 455

<210> SEQ ID NO 221
<211> LENGTH: 1407
<212> TYPE: DNA
<213> ORGANISM: Clostridium beijerinckii

<400> SEQUENCE: 221
atgaataaag acacactaat acctacaact aaagatttaa aattaaaaac aaatgttgaa      60
aacattaatt taaagaacta caaggataat tcttcatgtt tcggagtatt cgaaaatgtt     120
gaaaatgcta taaacagcgc tgtacacgcg caaaagatat tatcccttca ttatacaaaa     180
gaacaaagag aaaaaatcat aactgagata agaaaggccg cattagaaaa taaagaggtt     240
ttagctacca tgattctgga agaaacacat atgggaaggt atgaagataa aatattaaag     300
catgaattag tagctaaata tactcctggt acagaagatt taactactac tgcttggtca     360
ggtgataatg gtcttacagt tgtagaaatg tctccatatg gcgttatagg tgcaataact     420
ccttctacga atccaactga aactgtaata tgtaatagca tcggcatgat agctgctgga     480
aatgctgtag tatttaacgg acacccaggc gctaaaaaat gtgttgcttt tgctattgaa     540
atgataaata aagcaattat ttcatgtggc ggtcctgaga atttagtaac aactataaaa     600
aatccaacta tggaatccct agatgcaatt attaagcatc ctttaataaa acttctttgc     660
ggaactggag gtccaggaat ggtaaaaacc ctcttaaatt ctggcaagaa agctataggt     720
gctggtgctg gaaatccacc agttattgta gatgataccg ctgatataga aaaggctggt     780
aagagtatca ttgaaggctg ttcttttgat aataatttac cttgtattgc agaaaaagaa     840
gtatttgttt ttgagaatgt tgcagatgat ttaatatcta acatgctaaa aaataatgct     900
gtaattataa atgaagatca agtatcaaaa ttaatagatt tagtattaca aaaaaataat     960
gaaactcaag aatactttat aaacaaaaaa tgggtaggaa aagatgcaaa attattctca    1020
gatgaaatag atgttgagtc tccttcaaat attaaatgca tagtctgcga agtaaatgca    1080
aatcatccat ttgtcatgac agaactcatg atgccaatat taccaattgt aagagttaaa    1140
gatatagatg aagctgttaa atatacaaag atagcagaac aaaatagaaa acatagtgcc    1200
tatatttatt ctaaaaatat agacaaccta aatagatttg aaagagaaat tgatactact    1260
atttttgtaa agaatgctaa atcttttgct ggtgttggtt atgaagctga aggatttaca    1320
actttcacta ttgctggatc tactggtgaa ggcataacct ctgcaagaaa ttttacaaga    1380
caaagaagat gtgtacttgc cggctaa                                        1407

<210> SEQ ID NO 222
<211> LENGTH: 468
<212> TYPE: PRT
<213> ORGANISM: Clostridium beijerinckii

<400> SEQUENCE: 222
```

```
Met Asn Lys Asp Thr Leu Ile Pro Thr Thr Lys Asp Leu Lys Leu Lys
1               5                   10                  15
Thr Asn Val Glu Asn Ile Asn Leu Lys Asn Tyr Lys Asp Asn Ser Ser
            20                  25                  30
Cys Phe Gly Val Phe Glu Asn Val Glu Asn Ala Ile Asn Ser Ala Val
            35                  40                  45
His Ala Gln Lys Ile Leu Ser Leu His Tyr Thr Lys Glu Gln Arg Glu
    50                  55                  60
Lys Ile Ile Thr Glu Ile Arg Lys Ala Ala Leu Glu Asn Lys Glu Val
65                  70                  75                  80
Leu Ala Thr Met Ile Leu Glu Glu Thr His Met Gly Arg Tyr Glu Asp
                85                  90                  95
Lys Ile Leu Lys His Glu Leu Val Ala Lys Tyr Thr Pro Gly Thr Glu
                100                 105                 110
Asp Leu Thr Thr Thr Ala Trp Ser Gly Asp Asn Gly Leu Thr Val Val
            115                 120                 125
Glu Met Ser Pro Tyr Gly Val Ile Gly Ala Ile Thr Pro Ser Thr Asn
    130                 135                 140
Pro Thr Glu Thr Val Ile Cys Asn Ser Ile Gly Met Ile Ala Ala Gly
145                 150                 155                 160
Asn Ala Val Val Phe Asn Gly His Pro Gly Ala Lys Lys Cys Val Ala
                165                 170                 175
Phe Ala Ile Glu Met Ile Asn Lys Ala Ile Ile Ser Cys Gly Gly Pro
            180                 185                 190
Glu Asn Leu Val Thr Thr Ile Lys Asn Pro Thr Met Glu Ser Leu Asp
    195                 200                 205
Ala Ile Ile Lys His Pro Leu Ile Lys Leu Leu Cys Gly Thr Gly Gly
210                 215                 220
Pro Gly Met Val Lys Thr Leu Leu Asn Ser Gly Lys Lys Ala Ile Gly
225                 230                 235                 240
Ala Gly Ala Gly Asn Pro Pro Val Ile Val Asp Asp Thr Ala Asp Ile
                245                 250                 255
Glu Lys Ala Gly Lys Ser Ile Ile Glu Gly Cys Ser Phe Asp Asn Asn
            260                 265                 270
Leu Pro Cys Ile Ala Glu Lys Glu Val Phe Val Phe Glu Asn Val Ala
    275                 280                 285
Asp Asp Leu Ile Ser Asn Met Leu Lys Asn Asn Ala Val Ile Ile Asn
290                 295                 300
Glu Asp Gln Val Ser Lys Leu Ile Asp Leu Val Leu Gln Lys Asn Asn
305                 310                 315                 320
Glu Thr Gln Glu Tyr Phe Ile Asn Lys Lys Trp Val Gly Lys Asp Ala
            325                 330                 335
Lys Leu Phe Ser Asp Glu Ile Asp Val Glu Ser Pro Ser Asn Ile Lys
            340                 345                 350
Cys Ile Val Cys Glu Val Asn Ala Asn His Pro Phe Val Met Thr Glu
            355                 360                 365
Leu Met Met Pro Ile Leu Pro Ile Val Arg Val Lys Asp Ile Asp Glu
    370                 375                 380
Ala Val Lys Tyr Thr Lys Ile Ala Glu Gln Asn Arg Lys His Ser Ala
385                 390                 395                 400
Tyr Ile Tyr Ser Lys Asn Ile Asp Asn Leu Asn Arg Phe Glu Arg Glu
            405                 410                 415
Ile Asp Thr Thr Ile Phe Val Lys Asn Ala Lys Ser Phe Ala Gly Val
```

```
              420                 425                 430
Gly Tyr Glu Ala Glu Gly Phe Thr Thr Phe Thr Ile Ala Gly Ser Thr
            435                 440                 445

Gly Glu Gly Ile Thr Ser Ala Arg Asn Phe Thr Arg Gln Arg Arg Cys
450                 455                 460

Val Leu Ala Gly
465

<210> SEQ ID NO 223
<211> LENGTH: 2589
<212> TYPE: DNA
<213> ORGANISM: Clostridium acetobutylicum

<400> SEQUENCE: 223
```

| | | | | | |
|---|---|---|---|---|---|
| atgaaagtca | caacagtaaa | ggaattagat | gaaaaactca | aggtaattaa | agaagctcaa         60 |
| aaaaaattct | cttgttactc | gcaagaaatg | gttgatgaaa | tctttagaaa | tgcagcaatg        120 |
| gcagcaatcg | acgcaaggat | agagctagca | aaagcagctg | ttttggaaac | cggtatgggc        180 |
| ttagttgaag | acaaggttat | aaaaaatcat | tttgcaggcg | aatacatcta | taacaaatat        240 |
| aaggatgaaa | aaacctgcgg | tataattgaa | cgaaatgaac | cctacggaat | tacaaaaata        300 |
| gcagaaccta | taggagttgt | agctgctata | atccctgtaa | caaaccccac | atcaacaaca        360 |
| atatttaaat | ccttaatatc | ccttaaaact | agaaatggaa | ttttctttc | gcctcaccca        420 |
| agggcaaaaa | aatccacaat | actagcagct | aaaacaatac | ttgatgcagc | cgttaagagt        480 |
| ggtgccccgg | aaaatataat | aggttggata | gatgaacctt | caattgaact | aactcaatat        540 |
| ttaatgcaaa | aagcagatat | aacccttgca | actggtggtc | cctcactagt | taaatctgct        600 |
| tattcttccg | aaaaccagc | aataggtgtt | ggtccgggta | caccccagt | aataattgat        660 |
| gaatctgctc | atataaaaat | ggcagtaagt | tcaattatat | tatccaaaac | ctatgataat        720 |
| ggtgttatat | gtgcttctga | acaatctgta | atagtcttaa | aatccatata | taacaaggta        780 |
| aaagatgagt | tccaagaaag | aggagcttat | ataataaaga | aaacgaatt | ggataaagtc        840 |
| cgtgaagtga | tttttaaaga | tggatccgta | aaccctaaaa | tagtcggaca | gtcagcttat        900 |
| actatagcag | ctatggctgg | cataaaagta | cctaaaacca | aagaatatt | aataggagaa        960 |
| gttacctcct | taggtgaaga | gaacctttt | gcccacgaaa | aactatctcc | tgttttggct       1020 |
| atgtatgagg | ctgacaattt | tgatgatgct | ttaaaaaag | cagtaactct | aataaactta       1080 |
| ggaggcctcg | ccatacctc | aggaatatat | gcagatgaaa | taaaagcacg | agataaaata       1140 |
| gatagattta | gtagtgccat | gaaaaccgta | agaacctttg | taaatatccc | aacctcacaa       1200 |
| ggtgcaagtg | gagatctata | taatttaga | ataccacctt | ctttcacgct | tggctgcgga       1260 |
| tttggggag | gaaattctgt | ttccgagaat | gttggtccaa | acatctttt | gaatattaaa       1320 |
| accgtagctg | aaaggagaga | aaacatgctt | tggtttagag | ttccacataa | agtatatttt       1380 |
| aagttcggtt | gtcttcaatt | tgctttaaaa | gatttaaaag | atctaaagaa | aaaagagcc       1440 |
| tttatagtta | ctgatagtga | cccctataat | ttaaactatg | ttgattcaat | aataaaaata       1500 |
| cttgagcacc | tagatattga | ttttaaagta | tttaataagg | ttggaagaga | agctgatctt       1560 |
| aaaaccataa | aaaagcaac | tgaagaaatg | tcctccttta | tgccagacac | tataatagct       1620 |
| ttaggtggta | cccctgaaat | gagctctgca | aagctaatgt | gggtactata | tgaacatcca       1680 |
| gaagtaaat | ttgaagatct | tgcaataaaa | tttatggaca | taagaaagag | aatatatact       1740 |
| ttcccaaaac | tcggtaaaaa | ggctatgtta | gttgcaatta | caacttctgc | tggttccggt       1800 |

-continued

```
tctgaggtta ctccttttgc tttagtaact gacaataaca ctggaaataa gtacatgtta   1860
gcagattatg aaatgacacc aaatatggca attgtagatg cagaacttat gatgaaaatg   1920
ccaaagggat taaccgctta ttcaggtata gatgcactag taaatagtat agaagcatac   1980
acatccgtat atgcttcaga atacacaaac ggactagcac tagaggcaat acgattaata   2040
tttaaatatt tgcctgaggc ttacaaaaac ggaagaacca atgaaaaagc aagagagaaa   2100
atggctcacg cttcaactat ggcaggtatg gcatccgcta atgcatttct aggtctatgt   2160
cattccatgg caataaaatt aagttcagaa cacaatattc ctagtggcat tgccaatgca   2220
ttactaatag aagaagtaat aaaatttaac gcagttgata atcctgtaaa acaagcccct   2280
tgcccacaat ataagtatcc aaacaccata tttagatatg ctcgaattgc agattatata   2340
aagcttggag gaaatactga tgaggaaaag gtagatctct taattaacaa aatacatgaa   2400
ctaaaaaaag ctttaaatat accaacttca ataaggatg caggtgtttt ggaggaaaac   2460
ttctattcct cccttgatag aatatctgaa cttgcactag atgatcaatg cacaggcgct   2520
aatcctagat ttcctcttac aagtgagata aagaaatgt atataaattg ttttaaaaaa   2580
caaccttaa                                                          2589
```

<210> SEQ ID NO 224
<211> LENGTH: 862
<212> TYPE: PRT
<213> ORGANISM: Clostridium acetobutylicum

<400> SEQUENCE: 224

```
Met Lys Val Thr Thr Val Lys Glu Leu Asp Glu Lys Leu Lys Val Ile
1               5                   10                  15

Lys Glu Ala Gln Lys Lys Phe Ser Cys Tyr Ser Gln Glu Met Val Asp
            20                  25                  30

Glu Ile Phe Arg Asn Ala Ala Met Ala Ala Ile Asp Ala Arg Ile Glu
        35                  40                  45

Leu Ala Lys Ala Ala Val Leu Glu Thr Gly Met Gly Leu Val Glu Asp
    50                  55                  60

Lys Val Ile Lys Asn His Phe Ala Gly Glu Tyr Ile Tyr Asn Lys Tyr
65                  70                  75                  80

Lys Asp Glu Lys Thr Cys Gly Ile Ile Glu Arg Asn Glu Pro Tyr Gly
                85                  90                  95

Ile Thr Lys Ile Ala Glu Pro Ile Gly Val Val Ala Ala Ile Ile Pro
            100                 105                 110

Val Thr Asn Pro Thr Ser Thr Thr Ile Phe Lys Ser Leu Ile Ser Leu
        115                 120                 125

Lys Thr Arg Asn Gly Ile Phe Phe Ser Pro His Pro Arg Ala Lys Lys
    130                 135                 140

Ser Thr Ile Leu Ala Ala Lys Thr Ile Leu Asp Ala Ala Val Lys Ser
145                 150                 155                 160

Gly Ala Pro Glu Asn Ile Ile Gly Trp Ile Asp Glu Pro Ser Ile Glu
                165                 170                 175

Leu Thr Gln Tyr Leu Met Gln Lys Ala Asp Ile Thr Leu Ala Thr Gly
            180                 185                 190

Gly Pro Ser Leu Val Lys Ser Ala Tyr Ser Ser Gly Lys Pro Ala Ile
        195                 200                 205

Gly Val Gly Pro Gly Asn Thr Pro Val Ile Ile Asp Glu Ser Ala His
    210                 215                 220

Ile Lys Met Ala Val Ser Ser Ile Ile Leu Ser Lys Thr Tyr Asp Asn
```

```
              225                 230                 235                 240
Gly Val Ile Cys Ala Ser Glu Gln Ser Val Ile Val Leu Lys Ser Ile
                245                 250                 255

Tyr Asn Lys Val Lys Asp Glu Phe Gln Glu Arg Gly Ala Tyr Ile Ile
                260                 265                 270

Lys Lys Asn Glu Leu Asp Lys Val Arg Glu Val Ile Phe Lys Asp Gly
                275                 280                 285

Ser Val Asn Pro Lys Ile Val Gly Gln Ser Ala Tyr Thr Ile Ala Ala
                290                 295                 300

Met Ala Gly Ile Lys Val Pro Lys Thr Thr Arg Ile Leu Ile Gly Glu
305                 310                 315                 320

Val Thr Ser Leu Gly Glu Glu Pro Phe Ala His Glu Lys Leu Ser
                325                 330                 335

Pro Val Leu Ala Met Tyr Glu Ala Asp Asn Phe Asp Asp Ala Leu Lys
                340                 345                 350

Lys Ala Val Thr Leu Ile Asn Leu Gly Gly Leu Gly His Thr Ser Gly
                355                 360                 365

Ile Tyr Ala Asp Glu Ile Lys Ala Arg Asp Lys Ile Asp Arg Phe Ser
                370                 375                 380

Ser Ala Met Lys Thr Val Arg Thr Phe Val Asn Ile Pro Thr Ser Gln
385                 390                 395                 400

Gly Ala Ser Gly Asp Leu Tyr Asn Phe Arg Ile Pro Pro Ser Phe Thr
                405                 410                 415

Leu Gly Cys Gly Phe Trp Gly Gly Asn Ser Val Ser Glu Asn Val Gly
                420                 425                 430

Pro Lys His Leu Leu Asn Ile Lys Thr Val Ala Glu Arg Arg Glu Asn
                435                 440                 445

Met Leu Trp Phe Arg Val Pro His Lys Val Tyr Phe Lys Phe Gly Cys
                450                 455                 460

Leu Gln Phe Ala Leu Lys Asp Leu Lys Asp Leu Lys Lys Lys Arg Ala
465                 470                 475                 480

Phe Ile Val Thr Asp Ser Asp Pro Tyr Asn Leu Asn Tyr Val Asp Ser
                485                 490                 495

Ile Ile Lys Ile Leu Glu His Leu Asp Ile Asp Phe Lys Val Phe Asn
                500                 505                 510

Lys Val Gly Arg Glu Ala Asp Leu Lys Thr Ile Lys Lys Ala Thr Glu
                515                 520                 525

Glu Met Ser Ser Phe Met Pro Asp Thr Ile Ile Ala Leu Gly Gly Thr
                530                 535                 540

Pro Glu Met Ser Ser Ala Lys Leu Met Trp Val Leu Tyr Glu His Pro
545                 550                 555                 560

Glu Val Lys Phe Glu Asp Leu Ala Ile Lys Phe Met Asp Ile Arg Lys
                565                 570                 575

Arg Ile Tyr Thr Phe Pro Lys Leu Gly Lys Lys Ala Met Leu Val Ala
                580                 585                 590

Ile Thr Thr Ser Ala Gly Ser Gly Ser Glu Val Thr Pro Phe Ala Leu
                595                 600                 605

Val Thr Asp Asn Asn Thr Gly Asn Lys Tyr Met Leu Ala Asp Tyr Glu
                610                 615                 620

Met Thr Pro Asn Met Ala Ile Val Asp Ala Glu Leu Met Met Lys Met
625                 630                 635                 640

Pro Lys Gly Leu Thr Ala Tyr Ser Gly Ile Asp Ala Leu Val Asn Ser
                645                 650                 655
```

```
Ile Glu Ala Tyr Thr Ser Val Tyr Ala Ser Glu Tyr Thr Asn Gly Leu
            660                 665                 670
Ala Leu Glu Ala Ile Arg Leu Ile Phe Lys Tyr Leu Pro Glu Ala Tyr
        675                 680                 685
Lys Asn Gly Arg Thr Asn Glu Lys Ala Arg Glu Lys Met Ala His Ala
    690                 695                 700
Ser Thr Met Ala Gly Met Ala Ser Ala Asn Ala Phe Leu Gly Leu Cys
705                 710                 715                 720
His Ser Met Ala Ile Lys Leu Ser Ser Glu His Asn Ile Pro Ser Gly
                725                 730                 735
Ile Ala Asn Ala Leu Leu Ile Glu Glu Val Ile Lys Phe Asn Ala Val
            740                 745                 750
Asp Asn Pro Val Lys Gln Ala Pro Cys Pro Gln Tyr Lys Tyr Pro Asn
        755                 760                 765
Thr Ile Phe Arg Tyr Ala Arg Ile Ala Asp Tyr Ile Lys Leu Gly Gly
    770                 775                 780
Asn Thr Asp Glu Glu Lys Val Asp Leu Leu Ile Asn Lys Ile His Glu
785                 790                 795                 800
Leu Lys Lys Ala Leu Asn Ile Pro Thr Ser Ile Lys Asp Ala Gly Val
                805                 810                 815
Leu Glu Glu Asn Phe Tyr Ser Ser Leu Asp Arg Ile Ser Glu Leu Ala
            820                 825                 830
Leu Asp Asp Gln Cys Thr Gly Ala Asn Pro Arg Phe Pro Leu Thr Ser
        835                 840                 845
Glu Ile Lys Glu Met Tyr Ile Asn Cys Phe Lys Lys Gln Pro
    850                 855                 860

<210> SEQ ID NO 225
<211> LENGTH: 2577
<212> TYPE: DNA
<213> ORGANISM: Clostridium acetobutylicum

<400> SEQUENCE: 225
atgaaagtta caaatcaaaa agaactaaaa caaaagctaa atgaattgag agaagcgcaa      60
aagaagtttg caacctatac tcaagagcaa gttgataaaa tttttaaaca atgtgccata     120
gccgcagcta aagaaagaat aaacttagct aaattagcag tagaagaaac aggaataggt     180
cttgtagaag ataaaattat aaaaaatcat tttgcagcag aatatatata caataaatat     240
aaaaatgaaa aaacttgtgg cataatagac catgacgatt ctttaggcat aacaaaggtt     300
gctgaaccaa ttggaattgt tgcagccata gttcctacta ctaatccaac ttccacagca     360
attttcaaat cattaatttc tttaaaaaca agaaacgcaa tattcttttc accacatcca     420
cgtgcaaaaa aatctacaat tgctgcagca aaattaattt tagatgcagc tgttaaagca     480
ggagcaccta aaaatataat aggctggata gatgagccat caatagaact ttctcaagat     540
ttgatgagtg aagctgatat aatattagca acaggaggtc cttcaatggt taaagcggcc     600
tattcatctg gaaaacctgc aattggtgtt ggagcaggaa atacaccagc aataatagat     660
gagagtgcag atatagatat ggcagtaagc tccataattt tatcaaagac ttatgacaat     720
ggagtaatat gcgcttctga acaatcaata ttagttatga attcaatata cgaaaaagtt     780
aaagaggaat tgtaaaacg aggatcatat atactcaatc aaaatgaaat agctaaaata     840
aaagaaacta tgtttaaaaa tggagctatt aatgctgaca tagttggaaa atctgcttat     900
ataattgcta aaatggcagg aattgaagtt cctcaaacta caaagatact tataggcgaa     960
```

```
gtacaatctg ttgaaaaaag cgagctgttc tcacatgaaa aactatcacc agtacttgca   1020
atgtataaag ttaaggattt tgatgaagct ctaaaaaagg cacaaaggct aatagaatta   1080
ggtggaagtg acacacgtc atctttatat atagattcac aaaacaataa ggataaagtt    1140
aaagaatttg gattagcaat gaaaacttca aggacattta ttaacatgcc ttcttcacag   1200
ggagcaagcg gagatttata caattttgcg atagcaccat catttactct tggatgcggc   1260
acttggggag gaaactctgt atcgcaaaat gtagagccta acatttatt aaatattaaa    1320 agtgttgctg aaagaaggga aaatatgctt tggtttaaag tgccacaaaa aatatatttt   1380
aaatatggat gtcttagatt tgcattaaaa gaattaaaag atatgaataa gaaaagagcc   1440
tttatagtaa cagataaaga tcttttttaaa cttggatatg ttaataaaat aacaaaggta  1500
ctagatgaga tagatattaa atacagtata tttacagata ttaaatctga tccaactatt   1560
gattcagtaa aaaaaggtgc taaagaaatg cttaactttg aacctgatac tataatctct   1620
attggtggtg gatcgccaat ggatgcagca aaggttatgc acttgttata tgaatatcca   1680
gaagcagaaa ttgaaaatct agctataaac tttatggata taagaaagag aatatgcaat   1740
ttccctaaat taggtacaaa ggcgatttca gtagctattc ctacaactgc tggtaccggt   1800
tcagaggcaa cacctttttgc agttataact aatgatgaaa caggaatgaa ataccctta   1860 acttcttatg aattgacccc aaacatggca ataatagata ctgaattaat gttaaatatg   1920
cctagaaaat taacagcagc aactggaata gatgcattag ttcatgctat agaagcatat   1980
gtttcggtta tggctacgga ttatactgat gaattagcct taagagcaat aaaaaatgata  2040 tttaaatatt tgcctagagc ctataaaaat gggactaacg acattgaagc aagagaaaaa   2100
atggcacatg cctctaatat tgcggggatg gcatttgcaa atgctttctt aggtgtatgc   2160
cattcaatgg ctcataaact tgggcaatg catcacgttc cacatggaat tgcttgtgct   2220
gtattaatag aagaagttat taaatataac gctacagact gtccaacaaa gcaaacagca   2280
ttccctcaat ataaatctcc taatgctaag agaaaatatg ctgaaattgc agagtatttg   2340
aatttaaagg gtactagcga taccgaaaag gtaacagcct taatagaagc tatttcaaag   2400
ttaaagatag atttgagtat tccacaaaat ataagtgccg ctggaataaa taaaaaagat   2460
ttttataata cgctagataa aatgtcagag cttgcttttg atgaccaatg tacaacagct   2520
aatcctaggt atccacttat aagtgaactt aaggatatct atataaaatc atttaa       2577
```

<210> SEQ ID NO 226
<211> LENGTH: 800
<212> TYPE: PRT
<213> ORGANISM: Clostridium acetobutylicum

<400> SEQUENCE: 226

Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
65                  70                  75                  80

Lys Asn Glu Lys Thr Cys Gly Ile Ile Asp His Asp Asp Ser Leu Gly

```
             85                  90                  95
Ile Thr Lys Val Ala Glu Pro Ile Gly Ile Ala Ala Ile Val Pro
            100                 105                 110

Thr Thr Asn Pro Thr Ser Thr Ala Ile Phe Lys Ser Leu Ile Ser Leu
            115                 120                 125

Lys Thr Arg Asn Ala Ile Phe Phe Ser Pro His Pro Arg Ala Lys Lys
130                 135                 140

Ser Thr Ile Ala Ala Ala Lys Leu Ile Leu Asp Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
                180                 185                 190

Gly Pro Ser Met Val Lys Ala Ala Tyr Ser Ser Gly Lys Pro Ala Ile
                195                 200                 205

Gly Val Gly Ala Gly Asn Thr Pro Ala Ile Ile Asp Glu Ser Ala Asp
            210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                    245                 250                 255

Tyr Glu Lys Val Lys Glu Phe Val Lys Arg Gly Ser Tyr Ile Leu
                260                 265                 270

Asn Gln Asn Glu Ile Ala Lys Ile Lys Glu Thr Met Phe Lys Asn Gly
                275                 280                 285

Ala Ile Asn Ala Asp Ile Val Gly Lys Ser Ala Tyr Ile Ile Ala Lys
            290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
                340                 345                 350

Lys Ala Gln Arg Leu Ile Glu Leu Gly Gly Ser Gly His Thr Ser Ser
            355                 360                 365

Leu Tyr Ile Asp Ser Gln Asn Asn Lys Asp Lys Val Lys Glu Phe Gly
                370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
                420                 425                 430

Pro Lys His Leu Leu Asn Ile Lys Ser Val Ala Glu Arg Arg Glu Asn
                435                 440                 445

Met Leu Trp Phe Lys Val Pro Gln Lys Ile Tyr Phe Lys Tyr Gly Cys
450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                485                 490                 495

Ile Thr Lys Val Leu Asp Glu Ile Asp Ile Lys Tyr Ser Ile Phe Thr
                500                 505                 510
```

```
Asp Ile Lys Ser Asp Pro Thr Ile Asp Ser Val Lys Lys Gly Ala Lys
            515                 520                 525

Glu Met Leu Asn Phe Glu Pro Asp Thr Ile Ile Ser Ile Gly Gly Gly
        530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
            580                 585                 590

Ile Pro Thr Thr Ala Gly Thr Gly Ser Glu Ala Thr Pro Phe Ala Val
        595                 600                 605

Ile Thr Asn Asp Glu Thr Gly Met Lys Tyr Pro Leu Thr Ser Tyr Glu
610                 615                 620

Leu Thr Pro Asn Met Ala Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
            660                 665                 670

Ala Leu Arg Ala Ile Lys Met Ile Phe Lys Tyr Leu Pro Arg Ala Tyr
        675                 680                 685

Lys Asn Gly Thr Asn Asp Ile Glu Ala Arg Glu Lys Met Ala His Ala
690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
            740                 745                 750

Asp Cys Pro Thr Lys Gln Thr Ala Phe Pro Gln Tyr Lys Ser Pro Asn
        755                 760                 765

Ala Lys Arg Lys Tyr Ala Glu Ile Ala Glu Tyr Leu Asn Leu Lys Gly
770                 775                 780

Thr Ser Asp Thr Glu Lys Val Thr Ala Leu Ile Glu Ala Ile Ser Lys
785                 790                 795                 800

<210> SEQ ID NO 227
<211> LENGTH: 924
<212> TYPE: DNA
<213> ORGANISM: Pseudomonas putida

<400> SEQUENCE: 227
atgagcaaga aactcaaggc ggccatcata ggccccggca atatcggtac cgatctggtg      60
atgaagatgc tccgttccga gtggattgag ccggtgtgga tggtcggcat cgaccccaac     120
tccgacggcc tcaaacgcgc cgcgatttc ggcatgaaga ccacagccga aggcgtcgac      180
ggcctgctcc gcacgtgct ggacgacgac atccgcatcg ccttcgacgc cacctcggcc      240
tatgtgcatg ccgagaatag ccgcaagctc aacgcgcttg gcgtgctgat ggtcgacctg     300
accccggcgg ccatcggccc ctactgcgtg ccgccggtca acctcaagca gcatgtcggc     360
cgcctggaaa tgaacgtcaa catggtcacc tgcggcggcc aggccaccat ccccatggtc     420
gccgcggtgt cccgcgtgca gccggtggcc tacgccgaga tcgtcgccac cgtctcctcg     480
```

-continued

```
cgctcggtcg gcccgggcac gcgcaagaac atcgacgagt tcacccgcac caccgccggc    540
gccatcgagc aggtcggcgg cgccagggaa ggcaaggcga tcatcgtcat caacccggcc    600
gagccgccgc tgatgatgcg cgacaccatc cactgcctga ccgacagcga gccggaccag    660
gctgcgatca ccgcttcggt tcacgcgatg atcgccgagg tgcagaaata cgtgcccggc    720
taccgcctga agaacggccc ggtgttcgac ggcaaccgcg tgtcgatctt catggaagtc    780
gaaggcctgg gcgactacct gcccaagtac gccggcaacc tcgacatcat gaccgccgcc    840
gcgctgcgta ccggcgagat gttcgccgag gaaatcgccg ccggcaccat tcaactgccg    900
cgtcgcgaca tcgcgctggc ttga                                           924
```

<210> SEQ ID NO 228
<211> LENGTH: 307
<212> TYPE: PRT
<213> ORGANISM: Pseudomonas putida

<400> SEQUENCE: 228

```
Met Ser Lys Lys Leu Lys Ala Ala Ile Ile Gly Pro Gly Asn Ile Gly
1               5                   10                  15

Thr Asp Leu Val Met Lys Met Leu Arg Ser Glu Trp Ile Glu Pro Val
                20                  25                  30

Trp Met Val Gly Ile Asp Pro Asn Ser Asp Gly Leu Lys Arg Ala Arg
            35                  40                  45

Asp Phe Gly Met Lys Thr Thr Ala Glu Gly Val Asp Gly Leu Leu Pro
        50                  55                  60

His Val Leu Asp Asp Ile Arg Ile Ala Phe Asp Ala Thr Ser Ala
65                  70                  75                  80

Tyr Val His Ala Glu Asn Ser Arg Lys Leu Asn Ala Leu Gly Val Leu
                85                  90                  95

Met Val Asp Leu Thr Pro Ala Ala Ile Gly Pro Tyr Cys Val Pro Pro
                100                 105                 110

Val Asn Leu Lys Gln His Val Gly Arg Leu Glu Met Asn Val Asn Met
            115                 120                 125

Val Thr Cys Gly Gly Gln Ala Thr Ile Pro Met Val Ala Ala Val Ser
        130                 135                 140

Arg Val Gln Pro Val Ala Tyr Ala Glu Ile Val Ala Thr Val Ser Ser
145                 150                 155                 160

Arg Ser Val Gly Pro Gly Thr Arg Lys Asn Ile Asp Glu Phe Thr Arg
                165                 170                 175

Thr Thr Ala Gly Ala Ile Glu Gln Val Gly Gly Ala Arg Glu Gly Lys
            180                 185                 190

Ala Ile Ile Val Ile Asn Pro Ala Glu Pro Pro Leu Met Met Arg Asp
        195                 200                 205

Thr Ile His Cys Leu Thr Asp Ser Glu Pro Asp Gln Ala Ala Ile Thr
    210                 215                 220

Ala Ser Val His Ala Met Ile Ala Glu Val Gln Lys Tyr Val Pro Gly
225                 230                 235                 240

Tyr Arg Leu Lys Asn Gly Pro Val Phe Asp Gly Asn Arg Val Ser Ile
                245                 250                 255

Phe Met Glu Val Glu Gly Leu Gly Asp Tyr Leu Pro Lys Tyr Ala Gly
            260                 265                 270

Asn Leu Asp Ile Met Thr Ala Ala Ala Leu Arg Thr Gly Glu Met Phe
        275                 280                 285

Ala Glu Glu Ile Ala Ala Gly Thr Ile Gln Leu Pro Arg Arg Asp Ile
```

290         295         300

Ala Leu Ala
305

<210> SEQ ID NO 229
<211> LENGTH: 924
<212> TYPE: DNA
<213> ORGANISM: Thermus thermophilus

<400> SEQUENCE: 229

```
atgtccgaaa gggttaaggt agccatcctg ggctccggca acatcgggac ggacctgatg     60
tacaagctcc tgaagaaccc gggccacatg gagcttgtgg cggtggtggg gatagacccc    120
aagtccgagg gcctggcccg ggcgcgggcc ttagggttag aggcgagcca cgaagggatc    180
gcctacatcc tggagaggcc ggagatcaag atcgtctttg acgccaccag cgccaaggcc    240
cacgtgcgcc acgccaagct cctgagggag gcggggaaga tcgccataga cctcacgccg    300
gcggccgggc cccttacgt ggtgcccccg gtgaacctga aggaacacct ggacaaggac    360
aacgtgaacc tcatcacctg cggggggcag gccaccatcc ccctggtcta cgcggtgcac    420
cgggtggccc ccgtgctcta cgcggagatg gtctccacgg tggcctcccg ctccgcgggc    480
cccggcaccc ggcagaacat cgacgagttc accttcacca ccgcccgggg cctggaggcc    540
atcgggggg ccaagaaggg gaaggccatc atcatcctga cccggcgga accccccatc    600
ctcatgacca acaccgtgcg ctgcatcccc gaggacgagg gctttgaccg ggaggccgtg    660
gtggcgagcg tccgggccat ggagcgggag gtccaggcct acgtgcccgg ctaccgcctg    720
aaggcggacc cggtgtttga gaggcttccc accccctggg gggagcgcac cgtggtctcc    780
atgctcctgg aggtggaggg ggcgggggac tatttgccca aatacgccgg caacctggac    840
atcatgacgg cttctgcccg gagggtgggg gaggtcttcg cccagcacct cctggggaag    900
cccgtggagg aggtggtggc gtga                                            924
```

<210> SEQ ID NO 230
<211> LENGTH: 307
<212> TYPE: PRT
<213> ORGANISM: Thermus thermophilus

<400> SEQUENCE: 230

Met Ser Glu Arg Val Lys Val Ala Ile Leu Gly Ser Gly Asn Ile Gly
1               5                   10                  15

Thr Asp Leu Met Tyr Lys Leu Leu Lys Asn Pro Gly His Met Glu Leu
            20                  25                  30

Val Ala Val Val Gly Ile Asp Pro Lys Ser Glu Gly Leu Ala Arg Ala
        35                  40                  45

Arg Ala Leu Gly Leu Glu Ala Ser His Glu Gly Ile Ala Tyr Ile Leu
    50                  55                  60

Glu Arg Pro Glu Ile Lys Ile Val Phe Asp Ala Thr Ser Ala Lys Ala
65                  70                  75                  80

His Val Arg His Ala Lys Leu Leu Arg Glu Ala Gly Lys Ile Ala Ile
                85                  90                  95

Asp Leu Thr Pro Ala Ala Arg Gly Pro Tyr Val Val Pro Val Asn
            100                 105                 110

Leu Lys Glu His Leu Asp Lys Asp Asn Val Asn Leu Ile Thr Cys Gly
        115                 120                 125

Gly Gln Ala Thr Ile Pro Leu Val Tyr Ala Val His Arg Val Ala Pro
    130                 135                 140

Val Leu Tyr Ala Glu Met Val Ser Thr Val Ala Ser Arg Ser Ala Gly
145                 150                 155                 160

Pro Gly Thr Arg Gln Asn Ile Asp Glu Phe Thr Phe Thr Thr Ala Arg
                165                 170                 175

Gly Leu Glu Ala Ile Gly Gly Ala Lys Lys Gly Lys Ala Ile Ile Ile
            180                 185                 190

Leu Asn Pro Ala Glu Pro Pro Ile Leu Met Thr Asn Thr Val Arg Cys
        195                 200                 205

Ile Pro Glu Asp Glu Gly Phe Asp Arg Glu Ala Val Val Ala Ser Val
    210                 215                 220

Arg Ala Met Glu Arg Glu Val Gln Ala Tyr Val Pro Gly Tyr Arg Leu
225                 230                 235                 240

Lys Ala Asp Pro Val Phe Glu Arg Leu Pro Thr Pro Trp Gly Glu Arg
                245                 250                 255

Thr Val Val Ser Met Leu Leu Glu Val Glu Gly Ala Gly Asp Tyr Leu
            260                 265                 270

Pro Lys Tyr Ala Gly Asn Leu Asp Ile Met Thr Ala Ser Ala Arg Arg
        275                 280                 285

Val Gly Glu Val Phe Ala Gln His Leu Leu Gly Lys Pro Val Glu Glu
    290                 295                 300

Val Val Ala
305

<210> SEQ ID NO 231
<211> LENGTH: 1254
<212> TYPE: DNA
<213> ORGANISM: Escherichia coli

<400> SEQUENCE: 231

```
atgacattct cccttttkgg tgacaaattt acccgccact ccggcattac gctgttgatg      60
gaagatctga acgacggttt acgcacgcct ggcgcgatta tgctcggcgg cgtaatccg      120 gcgcagatcc cggaaatgca ggactacttc agacgctac tgaccgacat gctggaaagt      180
ggcaaagcga ctgatgcact gtgtaactac gacggtccac aggggaaaac ggagctactc      240
acactgcttg ccggaatgct gcgcgagaag ttgggttggg atatcgaacc acagaatatt      300
gcactaacaa acggcagcca gagcgcgttt ttctacttat ttaacctgtt tgccggacgc      360
cgtgccgatg gtcgggtcaa aaaagtgctg ttcccgcttg caccggaata cattggctat      420
gctgacgccg gactggaaga agatctgttt gtctctgcgc gtccgaatat tgaactgctg      480
ccggaaggcc agtttaaata ccacgtcgat tttgagcatc tgcatattgg cgaagaaacc      540
gggatgattt cgtctcccg gccgacgaat ccaacaggca atgtgattac tgacgaagag      600
ttgctgaagc ttgacgcgct ggcgaatcaa cacggcattc cgctggtgat tgataacgct      660
tatggcgtcc cgttcccggg tatcatcttc agtgaagcgc gccgctatg gaatccgaat      720 atcgtgctgt gcatgagtct ttccaagctg ggtctacctg ctcccgctg cggcattatc      780 atcgccaatg aaaaaatcat caccgccatc accaatatga acggcattat cagcctggca      840
cctggcggta ttggtccggc gatgatgtgt gaaatgatta gcgtaacga tctgctgcgc      900 ctgtctgaaa cagtcatcaa accgttttac taccagcgtg ttcaggaaac tatcgccatc      960
attcgccgct atttaccgga aaatcgctgc ctgattcata aaccggaagg agccattttc     1020
ctctggctat ggtttaagga tttgcccatt acgaccaagc agctctatca gcgcctgaaa     1080
gcacgcggcg tgctgatggt gccggggcac aacttcttcc cagggctgga taaaccgtgg     1140
```

-continued

```
ccgcatacgc atcaatgtat gcgcatgaac tacgtaccag agccggagaa aattgaggcg    1200
ggggtgaaga ttctggcgga agagatagaa agagcctggg ctgaaagtca ctaa          1254
```

<210> SEQ ID NO 232
<211> LENGTH: 417
<212> TYPE: PRT
<213> ORGANISM: Escherichia coli

<400> SEQUENCE: 232

```
Met Thr Phe Ser Leu Phe Gly Asp Lys Phe Thr Arg His Ser Gly Ile
1               5                   10                  15

Thr Leu Leu Met Glu Asp Leu Asn Asp Gly Leu Arg Thr Pro Gly Ala
            20                  25                  30

Ile Met Leu Gly Gly Gly Asn Pro Ala Gln Ile Pro Glu Met Gln Asp
        35                  40                  45

Tyr Phe Gln Thr Leu Leu Thr Asp Met Leu Glu Ser Gly Lys Ala Thr
    50                  55                  60

Asp Ala Leu Cys Asn Tyr Asp Gly Pro Gln Gly Lys Thr Glu Leu Leu
65                  70                  75                  80

Thr Leu Leu Ala Gly Met Leu Arg Glu Lys Leu Gly Trp Asp Ile Glu
                85                  90                  95

Pro Gln Asn Ile Ala Leu Thr Asn Gly Ser Gln Ser Ala Phe Phe Tyr
            100                 105                 110

Leu Phe Asn Leu Phe Ala Gly Arg Arg Ala Asp Gly Arg Val Lys Lys
        115                 120                 125

Val Leu Phe Pro Leu Ala Pro Glu Tyr Ile Gly Tyr Ala Asp Ala Gly
    130                 135                 140

Leu Glu Glu Asp Leu Phe Val Ser Ala Arg Pro Asn Ile Glu Leu Leu
145                 150                 155                 160

Pro Glu Gly Gln Phe Lys Tyr His Val Asp Phe Glu His Leu His Ile
                165                 170                 175

Gly Glu Glu Thr Gly Met Ile Cys Val Ser Arg Pro Thr Asn Pro Thr
            180                 185                 190

Gly Asn Val Ile Thr Asp Glu Glu Leu Leu Lys Leu Asp Ala Leu Ala
        195                 200                 205

Asn Gln His Gly Ile Pro Leu Val Ile Asp Asn Ala Tyr Gly Val Pro
    210                 215                 220

Phe Pro Gly Ile Ile Phe Ser Glu Ala Arg Pro Leu Trp Asn Pro Asn
225                 230                 235                 240

Ile Val Leu Cys Met Ser Leu Ser Lys Leu Gly Leu Pro Gly Ser Arg
                245                 250                 255

Cys Gly Ile Ile Ile Ala Asn Glu Lys Ile Ile Thr Ala Ile Thr Asn
            260                 265                 270

Met Asn Gly Ile Ile Ser Leu Ala Pro Gly Gly Ile Gly Pro Ala Met
        275                 280                 285

Met Cys Glu Met Ile Lys Arg Asn Asp Leu Leu Arg Leu Ser Glu Thr
    290                 295                 300

Val Ile Lys Pro Phe Tyr Tyr Gln Arg Val Gln Glu Thr Ile Ala Ile
305                 310                 315                 320

Ile Arg Arg Tyr Leu Pro Glu Asn Arg Cys Leu Ile His Lys Pro Glu
                325                 330                 335

Gly Ala Ile Phe Leu Trp Leu Trp Phe Lys Asp Leu Pro Ile Thr Thr
            340                 345                 350
```

Lys Gln Leu Tyr Gln Arg Leu Lys Ala Arg Gly Val Leu Met Val Pro
                355                 360                 365

Gly His Asn Phe Phe Pro Gly Leu Asp Lys Pro Trp Pro His Thr His
        370                 375                 380

Gln Cys Met Arg Met Asn Tyr Val Pro Glu Pro Glu Lys Ile Glu Ala
385                 390                 395                 400

Gly Val Lys Ile Leu Ala Glu Glu Ile Glu Arg Ala Trp Ala Glu Ser
                405                 410                 415

His

<210> SEQ ID NO 233
<211> LENGTH: 1278
<212> TYPE: DNA
<213> ORGANISM: Bacillus licheniformis

<400> SEQUENCE: 233
ttataagtat tcaacctgtt tctcatatac acccttcgca attttagcta aaacatcgat      60
tccccttata atatcttcat ccgccgcggt taggctgatt cgtatacact ggtgtgaatg     120
cgccaggcgc cgggattgac ggtgaaagaa agatgatccg gaacgataa tgactccatc     180
cgctttcata tactcataca cgctgcatc ggtcaccggc aggtcttcaa ccacagcca      240
tccgaaaagc gatccttccc cttgatgcag ataccatttg atgtcttcag gcatcttgca     300
taaaagcgtt tccttgagca gcatgaattt attgcggtaa tatggcctga cttcattcag     360
cgacacgtcg gcgaggcgcc cgtcattcaa tactgatgca gccatatact gccccagcct     420
tgaagaatgg atcgccgcat tcgactgaaa agcttccatt gcctgaatat accgggacgg     480
cccgatggcg attccgatcc tttcgccagg caggccggct tttgaaaggc tcatacagtg     540
aatgatctgc tcgttgaaaa tcggttccat gtcgataaag tgaatcgccg gaaaaggcgg     600
agcatatgcg gaatcaatga acagcggaac attcgcttct cggcatgcgt ctgaaatgaa     660
tgctacatct tctttaggca agatgtttcc gcaaggattg ttcgggcgcg atagcaagac     720
agcaccgatg cgcatcctct ctaaaaaccc cttacggtcg agctcatatc gaaacgtatg     780
atcatccaat ttcgatatga gcggagggat ccctcaatc atctcccgct ccagtgccgc     840
cccgctgtat cccgaatagt caggcagcat cgggatcaag gctttttca tcacagatcc      900
gcttcccatt ccgcaaaacg aattgatcgc cagaaaaaac agctgctggc ttccggctgt     960
aatcaacacg ttctctttc gaatgccggc gctataccgc tctgaaaaga agcggacaac    1020
acttgcaatc agttcatcgg ttccatagct cgatccgtat tggccgatca ccgaagaaaa    1080
cctgtcatcg tcaaggagat cggcaagagc cgacttccac atggctgaca cgccgggcaa    1140
aatcatcgga ttgcccgcac ttaaattaat gtatgaccgt tcaccgccgg ccaggacttc    1200
ctgaatatcg ctcatcacag ccctgacccc tgttttctca atcattttct ctccgatttt    1260
gcttaatggc ggcttcac                                                  1278

<210> SEQ ID NO 234
<211> LENGTH: 425
<212> TYPE: PRT
<213> ORGANISM: Bacillus licheniformis

<400> SEQUENCE: 234

Met Lys Pro Pro Leu Ser Lys Ile Gly Glu Lys Met Ile Glu Lys Thr
1               5                   10                  15

Gly Val Arg Ala Val Met Ser Asp Ile Gln Glu Val Leu Ala Gly Gly
                20                  25                  30

Glu Arg Ser Tyr Ile Asn Leu Ser Ala Gly Asn Pro Met Ile Leu Pro
        35                  40                  45

Gly Val Ser Ala Met Trp Lys Ser Ala Leu Ala Asp Leu Leu Asp Asp
    50                  55                  60

Asp Arg Phe Ser Val Ile Gly Gln Tyr Gly Ser Ser Tyr Gly Thr
65                  70                  75                  80

Asp Glu Leu Ile Ala Ser Val Val Arg Phe Phe Ser Glu Arg Tyr Ser
                85                  90                  95

Ala Gly Ile Arg Lys Glu Asn Val Leu Ile Thr Ala Gly Ser Gln Gln
                100                 105                 110

Leu Phe Phe Leu Ala Ile Asn Ser Phe Cys Gly Met Gly Ser Gly Ser
                115                 120                 125

Val Met Lys Lys Ala Leu Ile Pro Met Leu Pro Asp Tyr Ser Gly Tyr
        130                 135                 140

Ser Gly Ala Ala Leu Glu Arg Glu Met Ile Glu Gly Ile Pro Pro Leu
145                 150                 155                 160

Ile Ser Lys Leu Asp Asp His Thr Phe Arg Tyr Glu Leu Asp Arg Lys
                165                 170                 175

Gly Phe Leu Glu Arg Met Arg Ile Gly Ala Val Leu Leu Ser Arg Pro
            180                 185                 190

Asn Asn Pro Cys Gly Asn Ile Leu Pro Lys Glu Asp Val Ala Phe Ile
            195                 200                 205

Ser Asp Ala Cys Arg Glu Ala Asn Val Pro Leu Phe Ile Asp Ser Ala
        210                 215                 220

Tyr Ala Pro Pro Phe Pro Ala Ile His Phe Ile Asp Met Glu Pro Ile
225                 230                 235                 240

Phe Asn Glu Gln Ile Ile His Cys Met Ser Leu Ser Lys Ala Gly Leu
                245                 250                 255

Pro Gly Glu Arg Ile Gly Ile Ala Ile Gly Pro Ser Arg Tyr Ile Gln
            260                 265                 270

Ala Met Glu Ala Phe Gln Ser Asn Ala Ala Ile His Ser Ser Arg Leu
        275                 280                 285

Gly Gln Tyr Met Ala Ala Ser Val Leu Asn Asp Gly Arg Leu Ala Asp
        290                 295                 300

Val Ser Leu Asn Glu Val Arg Pro Tyr Tyr Arg Asn Lys Phe Met Leu
305                 310                 315                 320

Leu Lys Glu Thr Leu Leu Cys Lys Met Pro Glu Asp Ile Lys Trp Tyr
                325                 330                 335

Leu His Gln Gly Glu Gly Ser Leu Phe Gly Trp Leu Trp Phe Glu Asp
            340                 345                 350

Leu Pro Val Thr Asp Ala Ala Leu Tyr Glu Tyr Met Lys Ala Asp Gly
        355                 360                 365

Val Ile Ile Val Pro Gly Ser Ser Phe Phe His Arg Gln Ser Arg Arg
370                 375                 380

Leu Ala His Ser His Gln Cys Ile Arg Ile Ser Leu Thr Ala Ala Asp
385                 390                 395                 400

Glu Asp Ile Ile Arg Gly Ile Asp Val Leu Ala Lys Ile Ala Lys Gly
                405                 410                 415

Val Tyr Glu Lys Gln Val Glu Tyr Leu
            420                 425

<210> SEQ ID NO 235
<211> LENGTH: 930

<212> TYPE: DNA
<213> ORGANISM: Escherichia coli

<400> SEQUENCE: 235

```
atgaccacga agaaagctga ttacatttgg ttcaatgggg agatggttcg ctgggaagac    60
gcgaaggtgc atgtgatgtc gcacgcgctg cactatggca cttcggtttt tgaaggcatc   120
cgttgctacg actcgcacaa aggaccggtt gtattccgcc atcgtgagca tatgcagcgt   180
ctgcatgact ccgccaaaat ctatcgcttc ccggtttcgc agagcattga tgagctgatg   240
gaagcttgtc gtgacgtgat ccgcaaaaac aatctcacca gcgcctatat ccgtccgctg   300
atcttcgtcg gtgatgttgg catgggagta aacccgccag cgggatactc aaccgacgtg   360
attatcgctg cttttccgtg gggagcgtat ctgggcgcag aagcgctgga gcaggggatc   420
gatgcgatgg tttcctcctg gaaccgcgca gcaccaaaca ccatcccgac ggcggcaaaa   480
gccggtggta actacctctc ttccctgctg gtgggtagcg aagcgcgccg ccacggttat   540
caggaaggta tcgcgctgga tgtgaacggt tatatctctg aaggcgcagg cgaaaacctg   600
tttgaagtga agatggtgt gctgttcacc ccaccgttca cctcctccgc gctgccgggt   660
attcccgtg atgccatcat caaactggcg aaagagctgg aattgaagt acgtgagcag   720
gtgctgtcgc gcgaatccct gtacctggcg atgaagtgt ttatgtccgg tacggcggca   780
gaaatcacgc cagtgcgcag cgtagacggt attcaggttg gcgaaggccg ttgtggcccg   840
gttaccaaac gcattcagca gccttcttc ggcctcttca ctggcgaaac cgaagataaa   900
tggggctggt tagatcaagt taatcaataa                                    930
```

<210> SEQ ID NO 236
<211> LENGTH: 309
<212> TYPE: PRT
<213> ORGANISM: Escherichia coli

<400> SEQUENCE: 236

```
Met Thr Thr Lys Lys Ala Asp Tyr Ile Trp Phe Asn Gly Glu Met Val
1               5                   10                  15

Arg Trp Glu Asp Ala Lys Val His Val Met Ser His Ala Leu His Tyr
            20                  25                  30

Gly Thr Ser Val Phe Glu Gly Ile Arg Cys Tyr Asp Ser His Lys Gly
        35                  40                  45

Pro Val Val Phe Arg His Arg Glu His Met Gln Arg Leu His Asp Ser
    50                  55                  60

Ala Lys Ile Tyr Arg Phe Pro Val Ser Gln Ser Ile Asp Glu Leu Met
65                  70                  75                  80

Glu Ala Cys Arg Asp Val Ile Arg Lys Asn Asn Leu Thr Ser Ala Tyr
                85                  90                  95

Ile Arg Pro Leu Ile Phe Val Gly Asp Val Gly Met Gly Val Asn Pro
            100                 105                 110

Pro Ala Gly Tyr Ser Thr Asp Val Ile Ile Ala Ala Phe Pro Trp Gly
        115                 120                 125

Ala Tyr Leu Gly Ala Glu Ala Leu Glu Gln Gly Ile Asp Ala Met Val
    130                 135                 140

Ser Ser Trp Asn Arg Ala Ala Pro Asn Thr Ile Pro Thr Ala Ala Lys
145                 150                 155                 160

Ala Gly Gly Asn Tyr Leu Ser Ser Leu Leu Val Gly Ser Glu Ala Arg
                165                 170                 175

Arg His Gly Tyr Gln Glu Gly Ile Ala Leu Asp Val Asn Gly Tyr Ile
```

```
             180             185             190
Ser Glu Gly Ala Gly Glu Asn Leu Phe Glu Val Lys Asp Gly Val Leu
        195                 200                 205

Phe Thr Pro Pro Phe Thr Ser Ser Ala Leu Pro Gly Ile Thr Arg Asp
        210                 215                 220

Ala Ile Ile Lys Leu Ala Lys Glu Leu Gly Ile Glu Val Arg Glu Gln
225                 230                 235                 240

Val Leu Ser Arg Glu Ser Leu Tyr Leu Ala Asp Glu Val Phe Met Ser
                245                 250                 255

Gly Thr Ala Ala Glu Ile Thr Pro Val Arg Ser Val Asp Gly Ile Gln
            260                 265                 270

Val Gly Glu Gly Arg Cys Gly Pro Val Thr Lys Arg Ile Gln Gln Ala
        275                 280                 285

Phe Phe Gly Leu Phe Thr Gly Glu Thr Glu Asp Lys Trp Gly Trp Leu
        290                 295                 300

Asp Gln Val Asn Gln
305

<210> SEQ ID NO 237
<211> LENGTH: 1131
<212> TYPE: DNA
<213> ORGANISM: Saccharomyces cerevisiae

<400> SEQUENCE: 237
atgaccttgg cacccctaga cgcctccaaa gttaagataa ctaccacaca acatgcatct    60
aagccaaaac cgaacagtga gttagtgttt ggcaagagct tcacggacca catgttaact   120
gcggaatgga cagctgaaaa agggtggggt accccagaga ttaaaccta tcaaaatctg    180 tctttagacc cttccgcggt ggttttccat tatgcttttg agctattcga agggatgaag   240
gcttacagaa cggtggacaa caaaattaca atgtttcgtc agatatgaa tatgaagcgc    300 atgaataagt ctgctcagag aatctgtttg ccaacgttcg acccagaaga gttgattacc   360
ctaattggga aactgatcca gcaagataag tgcttagttc ctgaaggaaa aggttactct   420
ttatatatca ggcctacatt aatcggcact acggccggtt taggggtttc cacgcctgat   480
agagccttgc tatatgtcat ttgctgccct gtgggtcctt attacaaaac tggatttaag   540
gcggtcagac tggaagccac tgattatgcc acaagagctt ggccaggagg ctgtggtgac   600
aagaaactag gtgcaaacta cgcccctgc gtcctgccac aattgcaagc tgcttcaagg    660
ggttaccaac aaaatttatg gctatttggt ccaataaca acattactga agtcggcacc    720
atgaatgctt ttttcgtgtt taagatagt aaaacgggca agaaggaact agttactgct     780
ccactagacg gtaccatttt ggaaggtgtt actagggatt ccatttaaaa tcttgctaaa   840
gaaagactcg aaccaagtga atggaccatt agtgaacgct acttcactat aggcgaagtt   900
actgagagat ccaagaacgg tgaactactt gaagcctttg ttctggtac tgctgcgatt    960 gtttctccca ttaaggaaat cggctggaaa ggcgaacaaa ttaatattcc gttgttgccc  1020
ggcgaacaaa ccggtccatt ggccaaagaa gttgcacaat ggattaatgg aatccaatat  1080
ggcgagactg agcatggcaa ttggtcaagg gttgttactg atttgaactg a            1131

<210> SEQ ID NO 238
<211> LENGTH: 376
<212> TYPE: PRT
<213> ORGANISM: Saccharomyces cerevisiae

<400> SEQUENCE: 238
```

```
Met Thr Leu Ala Pro Leu Asp Ala Ser Lys Val Lys Ile Thr Thr Thr
1               5                   10                  15

Gln His Ala Ser Lys Pro Lys Pro Asn Ser Glu Leu Val Phe Gly Lys
                20                  25                  30

Ser Phe Thr Asp His Met Leu Thr Ala Glu Trp Thr Ala Glu Lys Gly
            35                  40                  45

Trp Gly Thr Pro Glu Ile Lys Pro Tyr Gln Asn Leu Ser Leu Asp Pro
        50                  55                  60

Ser Ala Val Val Phe His Tyr Ala Phe Glu Leu Phe Glu Gly Met Lys
65                  70                  75                  80

Ala Tyr Arg Thr Val Asp Asn Lys Ile Thr Met Phe Pro Asp Met
                85                  90                  95

Asn Met Lys Arg Met Asn Lys Ser Ala Gln Arg Ile Cys Leu Pro Thr
                100                 105                 110

Phe Asp Pro Glu Glu Leu Ile Thr Leu Ile Gly Lys Leu Ile Gln Gln
            115                 120                 125

Asp Lys Cys Leu Val Pro Glu Gly Lys Gly Tyr Ser Leu Tyr Ile Arg
130                 135                 140

Pro Thr Leu Ile Gly Thr Thr Ala Gly Leu Gly Val Ser Thr Pro Asp
145                 150                 155                 160

Arg Ala Leu Leu Tyr Val Ile Cys Cys Pro Val Gly Pro Tyr Tyr Lys
                165                 170                 175

Thr Gly Phe Lys Ala Val Arg Leu Glu Ala Thr Asp Tyr Ala Thr Arg
            180                 185                 190

Ala Trp Pro Gly Gly Cys Gly Asp Lys Lys Leu Gly Ala Asn Tyr Ala
                195                 200                 205

Pro Cys Val Leu Pro Gln Leu Gln Ala Ala Ser Arg Gly Tyr Gln Gln
210                 215                 220

Asn Leu Trp Leu Phe Gly Pro Asn Asn Ile Thr Glu Val Gly Thr
225                 230                 235                 240

Met Asn Ala Phe Phe Val Phe Lys Asp Ser Lys Thr Gly Lys Lys Glu
                245                 250                 255

Leu Val Thr Ala Pro Leu Asp Gly Thr Ile Leu Glu Gly Val Thr Arg
            260                 265                 270

Asp Ser Ile Leu Asn Leu Ala Lys Glu Arg Leu Glu Pro Ser Glu Trp
            275                 280                 285

Thr Ile Ser Glu Arg Tyr Phe Thr Ile Gly Glu Val Thr Glu Arg Ser
290                 295                 300

Lys Asn Gly Glu Leu Leu Glu Ala Phe Gly Ser Gly Thr Ala Ala Ile
305                 310                 315                 320

Val Ser Pro Ile Lys Glu Ile Gly Trp Lys Gly Glu Gln Ile Asn Ile
                325                 330                 335

Pro Leu Leu Pro Gly Glu Gln Thr Gly Pro Leu Ala Lys Glu Val Ala
            340                 345                 350

Gln Trp Ile Asn Gly Ile Gln Tyr Gly Glu Thr Glu His Gly Asn Trp
                355                 360                 365

Ser Arg Val Val Thr Asp Leu Asn
    370                 375

<210> SEQ ID NO 239
<211> LENGTH: 993
<212> TYPE: DNA
<213> ORGANISM: Methanobacterium thermoautotrophicum
```

<400> SEQUENCE: 239

```
tcagatgtag gtgagccatc cgaagctgtc ctctgtctct gccctgatta tcctgaagaa      60
ctcatcctgc agcagctttg taacgggacc ccttcgcccg gcacctatct ctataccatc     120
aactgatctg atgggtgtta tctctgcggc tgtacctgtg aagaaggcct catctgcgat     180
gtagagcatc tccctggtta tgggttcctc atgcacggta acaccctcgg tcctggctat     240
ctttattacg gagtcccttg ttatccccct cagaagggat gatgaaacag gggggtgta      300
aatttcaccc tcactgacga ggaatatgtt ctccccgcta ccctcactta tgtagccatg     360
gtagtccagc attatggcct catcatagcc gtgtctcaca gcctccatct tggcaagctg     420
tgagttgagg tagttaccgc cggcctttgc catgttgggc attgtgtttg gtgccatcct     480
ccgccaggtt gaaacaccag catcgacacc aacctcaagg gcctctgcac ccagataggc     540
cccccattcc caggcagcca cagcgacgtc cactgggcag ttaccgggt gaacacccat      600
ctcaccgtat cccctgaata ccacgggtct tatatagcac tcctcaagtc cgttctccct     660
gacggtctca actatggcat cacatatctg ctcctgggtg tagggtatgt ccatccggta     720
tatctttgca gaatcaaaaa ggcgtttaac atgctcccgc aaacggaaga tggctgaccc     780
cttactgttc ctgtagcacc ttattccctc aaagacagat gatccataat gcacaacatg     840
tgagagtacg tggacggtgg cttcttccca ttcaaccatt tcaccgttta accatatctt     900
tccactggct tcgcatgaca tgataataac ctcaggtgat ttactaggat aggttatggt     960
tggaggccta tataatgctc tccataaccg caa                                  993
```

<210> SEQ ID NO 240
<211> LENGTH: 330
<212> TYPE: PRT
<213> ORGANISM: Methanobacterium thermoautotrophicum

<400> SEQUENCE: 240

```
Met Arg Leu Trp Arg Ala Leu Tyr Arg Pro Pro Thr Ile Thr Tyr Pro
1               5                   10                  15
Ser Lys Ser Pro Glu Val Ile Ile Met Ser Cys Glu Ala Ser Gly Lys
            20                  25                  30
Ile Trp Leu Asn Gly Glu Met Val Glu Trp Glu Ala Thr Val His
        35                  40                  45
Val Leu Ser His Val Val His Tyr Gly Ser Ser Val Phe Glu Gly Ile
    50                  55                  60
Arg Cys Tyr Arg Asn Ser Lys Gly Ser Ala Ile Phe Arg Leu Arg Glu
65                  70                  75                  80
His Val Lys Arg Leu Phe Asp Ser Ala Lys Ile Tyr Arg Met Asp Ile
                85                  90                  95
Pro Tyr Thr Gln Glu Gln Ile Cys Asp Ala Ile Val Glu Thr Val Arg
            100                 105                 110
Glu Asn Gly Leu Glu Glu Cys Tyr Ile Arg Pro Val Val Phe Arg Gly
        115                 120                 125
Tyr Gly Glu Met Gly Val His Pro Val Asn Cys Pro Val Asp Val Ala
    130                 135                 140
Val Ala Ala Trp Glu Trp Gly Ala Tyr Leu Gly Ala Glu Ala Leu Glu
145                 150                 155                 160
Val Gly Val Asp Ala Gly Val Ser Thr Trp Arg Arg Met Ala Pro Asn
                165                 170                 175
Thr Met Pro Asn Met Ala Lys Ala Gly Gly Asn Tyr Leu Asn Ser Gln
            180                 185                 190
```

```
Leu Ala Lys Met Glu Ala Val Arg His Gly Tyr Asp Glu Ala Ile Met
        195                 200                 205

Leu Asp Tyr His Gly Tyr Ile Ser Glu Gly Ser Gly Glu Asn Ile Phe
    210                 215                 220

Leu Val Ser Glu Gly Glu Ile Tyr Thr Pro Pro Val Ser Ser Ser Leu
225                 230                 235                 240

Leu Arg Gly Ile Thr Arg Asp Ser Val Ile Lys Ile Ala Arg Thr Glu
                245                 250                 255

Gly Val Thr Val His Glu Glu Pro Ile Thr Arg Glu Met Leu Tyr Ile
                260                 265                 270

Ala Asp Glu Ala Phe Phe Thr Gly Thr Ala Ala Glu Ile Thr Pro Ile
            275                 280                 285

Arg Ser Val Asp Gly Ile Glu Ile Gly Ala Gly Arg Arg Gly Pro Val
        290                 295                 300

Thr Lys Leu Leu Gln Asp Glu Phe Phe Arg Ile Ile Arg Ala Glu Thr
305                 310                 315                 320

Glu Asp Ser Phe Gly Trp Leu Thr Tyr Ile
                325                 330

<210> SEQ ID NO 241
<211> LENGTH: 1095
<212> TYPE: DNA
<213> ORGANISM: Streptomyces coelicolor

<400> SEQUENCE: 241
tcacggccgg ggacgggcct ccgccatccg ctgctcggcg atccggtcgg ccgccgcggc      60
cggcggaata ccgtcctcct tcgcacgtgc gaatatggcc agcgtggtgt cgtagatctt     120
cgaggccttc gccttgcacc ggtcgaagtc gaacccgtgc agctcgtcgg cgacctggat     180
gacaccgccg gcgttcacca catagtccgg cgcgtagagg atcccgcggt cggcgaggtc     240
cttctcgacg cccgggtggg cgagctggtt gttggccgcg ccgcacacca ccttggcggt     300
cagcaccggc acggtgtcgt cgttcagcgc gccgccgagc gcgcagggcg cgtagatgtc     360
caggttctcc acccggatca gcgcgtcggt gtcggcgacg cgaccaccg acgggtgccg      420 ctccgtgatc ccgcgcacca cgtccttgcg cacgtccgtg acgacgacgt gggcgccctc     480
ggcgagcagg tgctcgacca ggtggtggcc gaccttgccg acgcccgcga tgccgacggt     540
gcggtcgcgc agcgtcgggt cgccccacag gtgctgggcg gcggcccgca tgccctggta     600
gacgccgaag gaggtgagca cggaggagtc gcccgcgccg ccgttctccg ggaacgccc      660 ggtcgtccag cggcactcgc gggccacgac gtccatgtcg gcgacgtagg tgccgacgtc     720
gcacgcggtg acgtagcggc cgcccagcga ggcgacgaac cggccgtagg cgaggagcag     780
ctcctcgctc ttgatctgct ccggatcgcc gatgatcacg gccttgccgc caccgtggtc     840
cagaccggcc atggcgttct tgtacgacat cccgcgggcg aggttcagcg cgtcggcgac     900
ggcctccgcc tcgctcgcgt acgggtagaa gcgggtaccg ccgagcgccg ggcccagggc     960
ggtggagtgg agggcgatca cggccttgag gccgctggca cggtcctggc agagcacgac    1020
ttgctcatgt cccccctgat ccgagtggaa cagggtgtgc agtacatcag caggtgcgcc    1080
gtttacgtcg gtcac                                                    1095

<210> SEQ ID NO 242
<211> LENGTH: 364
<212> TYPE: PRT
<213> ORGANISM: Streptomyces coelicolor
```

<400> SEQUENCE: 242

```
Met Thr Asp Val Asn Gly Ala Pro Ala Asp Val Leu His Thr Leu Phe
1               5                   10                  15

His Ser Asp Gln Gly Gly His Glu Gln Val Val Leu Cys Gln Asp Arg
            20                  25                  30

Ala Ser Gly Leu Lys Ala Val Ile Ala Leu His Ser Thr Ala Leu Gly
        35                  40                  45

Pro Ala Leu Gly Gly Thr Arg Phe Tyr Pro Tyr Ala Ser Glu Ala Glu
    50                  55                  60

Ala Val Ala Asp Ala Leu Asn Leu Ala Arg Gly Met Ser Tyr Lys Asn
65                  70                  75                  80

Ala Met Ala Gly Leu Asp His Gly Gly Lys Ala Val Ile Ile Gly
                85                  90                  95

Asp Pro Glu Gln Ile Lys Ser Glu Glu Leu Leu Ala Tyr Gly Arg
                100                 105                 110

Phe Val Ala Ser Leu Gly Gly Arg Tyr Val Thr Ala Cys Asp Val Gly
            115                 120                 125

Thr Tyr Val Ala Asp Met Asp Val Val Arg Glu Cys Arg Trp Thr
    130                 135                 140

Thr Gly Arg Ser Pro Glu Asn Gly Ala Gly Asp Ser Ser Val Leu
145                 150                 155                 160

Thr Ser Phe Gly Val Tyr Gln Gly Met Arg Ala Ala Gln His Leu
                165                 170                 175

Trp Gly Asp Pro Thr Leu Arg Asp Arg Thr Val Gly Ile Ala Gly Val
            180                 185                 190

Gly Lys Val Gly His His Leu Val Glu His Leu Leu Ala Glu Gly Ala
        195                 200                 205

His Val Val Thr Asp Val Arg Lys Asp Val Val Arg Gly Ile Thr
    210                 215                 220

Glu Arg His Pro Ser Val Val Ala Val Ala Asp Thr Asp Ala Leu Ile
225                 230                 235                 240

Arg Val Glu Asn Leu Asp Ile Tyr Ala Pro Cys Ala Leu Gly Gly Ala
                245                 250                 255

Leu Asn Asp Asp Thr Val Pro Val Leu Thr Ala Lys Val Val Cys Gly
                260                 265                 270

Ala Ala Asn Asn Gln Leu Ala His Pro Gly Val Glu Lys Asp Leu Ala
            275                 280                 285

Asp Arg Gly Ile Leu Tyr Ala Pro Asp Tyr Val Asn Ala Gly Gly
    290                 295                 300

Val Ile Gln Val Ala Asp Glu Leu His Gly Phe Asp Phe Asp Arg Cys
305                 310                 315                 320

Lys Ala Lys Ala Ser Lys Ile Tyr Asp Thr Thr Leu Ala Ile Phe Ala
                325                 330                 335

Arg Ala Lys Glu Asp Gly Ile Pro Ala Ala Ala Asp Arg Ile
            340                 345                 350

Ala Glu Gln Arg Met Ala Glu Ala Arg Pro Arg Pro
        355                 360
```

<210> SEQ ID NO 243
<211> LENGTH: 1095
<212> TYPE: DNA
<213> ORGANISM: Bacillus subtilis

<400> SEQUENCE: 243

```
atggaacttt ttaaatatat ggagaaatac gattacgaac aattggtatt ctgccaggat    60
gaacaatctg gattaaaagc gattatcgcc attcatgata caacgcttgg tccggcgctt   120
ggcggaacga gaatgtggac atatgaaaat gaagaagcgg caattgaaga tgcgctcaga   180
ttggcaagag gcatgaccta taagaacgcg gcggcaggct taaaccttgg cggcggaaaa   240
acagtcatta tcggcgatcc gcgcaaagac aaaaatgagg aaatgttccg cgcgtttggc   300
cgctatattc aaggactgaa tggcagatac atcacggctg aagatgtggg cacaacggtc   360
gaggatatgg atatcattca tgatgagaca gactatgtca cagggatttc tcctgctttc   420
ggctcttctg gaaatccgtc cccagtcaca gcgtacgggg tgtacagagg aatgaaggca   480
gcagctaaag ctgctttcgg aaccgattct cttgaaggaa aaaccattgc tgtacagggt   540
gttgggaacg tagcctataa cctttgccgc cacctgcatg aagaaggagc aaacttaatc   600
gttacggata tcaacaaaca atctgtacag cgtgcagttg aagattttgg cgcccgtgcg   660
gtagatcctg atgacattta ttcacaagac tgcgatattt atgcgccgtg tgcccttggt   720
gcgactatta cgacgacac  cattaaacag ctgaaggcga agtgatcgc aggtgcggct   780
aacaaccaat taaagagac  acgccatggt gatcaaattc acgaaatggg catcgtttat   840
gcaccggatt acgtgattaa cgcgggcggt gtcatcaacg tggcagatga gctttacggc   900
tataatgcag aacgtgcatt gaaaaaagtt gaaggcattt acggcaatat cgagcgtgta   960
cttgagattt ctcagcgtga cggcattcct gcatatttag cggctgaccg cttagcagag  1020
gaacggattg aacgcatgcg ccgctcaaga agccagtttt tgcaaaacgg ccacagtgta  1080
ttaagcagac gttaa                                                   1095
```

<210> SEQ ID NO 244
<211> LENGTH: 364
<212> TYPE: PRT
<213> ORGANISM: Bacillus subtilis

<400> SEQUENCE: 244

```
Met Glu Leu Phe Lys Tyr Met Glu Lys Tyr Asp Tyr Glu Gln Leu Val
1               5                   10                  15
Phe Cys Gln Asp Glu Gln Ser Gly Leu Lys Ala Ile Ile Ala Ile His
                20                  25                  30
Asp Thr Thr Leu Gly Pro Ala Leu Gly Gly Thr Arg Met Trp Thr Tyr
            35                  40                  45
Glu Asn Glu Glu Ala Ala Ile Glu Asp Ala Leu Arg Leu Ala Arg Gly
        50                  55                  60
Met Thr Tyr Lys Asn Ala Ala Ala Gly Leu Asn Leu Gly Gly Gly Lys
65                  70                  75                  80
Thr Val Ile Ile Gly Asp Pro Arg Lys Asp Lys Asn Glu Glu Met Phe
                85                  90                  95
Arg Ala Phe Gly Arg Tyr Ile Gln Gly Leu Asn Gly Arg Tyr Ile Thr
                100                 105                 110
Ala Glu Asp Val Gly Thr Thr Val Glu Asp Met Asp Ile Ile His Asp
        115                 120                 125
Glu Thr Asp Tyr Val Thr Gly Ile Ser Pro Ala Phe Gly Ser Ser Gly
    130                 135                 140
Asn Pro Ser Pro Val Thr Ala Tyr Gly Val Tyr Arg Gly Met Lys Ala
145                 150                 155                 160
Ala Ala Lys Ala Ala Phe Gly Thr Asp Ser Leu Glu Gly Lys Thr Ile
                165                 170                 175
```

```
Ala Val Gln Gly Val Gly Asn Val Ala Tyr Asn Leu Cys Arg His Leu
            180                 185                 190
His Glu Glu Gly Ala Asn Leu Ile Val Thr Asp Ile Asn Lys Gln Ser
        195                 200                 205
Val Gln Arg Ala Val Glu Asp Phe Gly Ala Arg Ala Val Asp Pro Asp
    210                 215                 220
Asp Ile Tyr Ser Gln Asp Cys Asp Ile Tyr Ala Pro Cys Ala Leu Gly
225                 230                 235                 240
Ala Thr Ile Asn Asp Asp Thr Ile Lys Gln Leu Lys Ala Lys Val Ile
                245                 250                 255
Ala Gly Ala Ala Asn Asn Gln Leu Lys Glu Thr Arg His Gly Asp Gln
            260                 265                 270
Ile His Glu Met Gly Ile Val Tyr Ala Pro Asp Tyr Val Ile Asn Ala
        275                 280                 285
Gly Gly Val Ile Asn Val Ala Asp Glu Leu Tyr Gly Tyr Asn Ala Glu
    290                 295                 300
Arg Ala Leu Lys Lys Val Glu Gly Ile Tyr Gly Asn Ile Glu Arg Val
305                 310                 315                 320
Leu Glu Ile Ser Gln Arg Asp Gly Ile Pro Ala Tyr Leu Ala Ala Asp
                325                 330                 335
Arg Leu Ala Glu Glu Arg Ile Glu Arg Met Arg Arg Ser Arg Ser Gln
            340                 345                 350
Phe Leu Gln Asn Gly His Ser Val Leu Ser Arg Arg
        355                 360

<210> SEQ ID NO 245
<211> LENGTH: 1785
<212> TYPE: DNA
<213> ORGANISM: Streptomyces viridifaciens

<400> SEQUENCE: 245
gtgtcaactt cctccgcttc ttccgggccg gacctcccct cgggcccga ggacacgcca      60 tggcagaagg ccttcagcag gctgcgggcg gtggatggcg tgccgcgcgt caccgcgccg     120
tccagtgatc cgcgtgaggt ctacatggac atcccggaga tcccccttctc caaggtccag     180 atcccccggg acggaatgga cgagcagcag tacgcagagg ccgagagcct cttccgccgc     240
tacgtagacg cccagacccg caacttcgcg ggataccagg tcaccagcga cctcgactac     300
cagcacctca gtcactatct caaccggcat ctgaacaacg tcggcgatcc ctatgagtcc     360
agctcctaca cgctgaactc caaggtcctt gagcgagccg ttctcgacta cttcgcctcc     420
ctgtggaacg ccaagtggcc ccatgacgca agcgatccgg aaacgtactg gggttacgtg     480
ctgaccatgg ctccagcgga aggcaacctg tacgggttgt ggaacgcacg ggactatctg     540
tcgggcaagc tgctgcggcg ccagcaccgg gaggccggcg gcgacaaggc ctcggtcgtc     600
tacacgcaag cgctgcgaca cgaagggcag agtccgcatg cctacgagcc ggtggcgttc     660
ttctcgcagg acacgcacta ctcgctcacg aaggccgtgc gggttctggg catcgacacc     720
ttccacagca tcggcagcag tcggtatccg gacgagaacc cgctgggccc cggcactccg     780
tggccgaccg aagtgccctc ggttgacggt gccatcgatg tcgacaaact cgcctcgttg     840
gtccgcttct tcgccagcaa gggctacccg atactggtca gcctcaacta cgggtcaacg     900
ttcaagggcg cctacgacga cgtcccggcc gtggcacagg ccgtgcggga catctgcacg     960
gaatacggtc tggatcggcg gcgggtatac cacgaccgca gtaaggacag tgacttcgac    1020
```

```
gagcgcagcg gcttctggat ccacatcgat gccgccctgg gggcgggcta cgctccctac    1080
ctgcagatgg cccgggatgc cggcatggtc gaggaggcgc cgcccgtttt cgacttccgg    1140 ctccccggagg tgcactcgct gaccatgagc ggccacaagt ggatgggaac accgtgggca   1200
tgcggtgtct acatgacacg gaccgggctg cagatgaccc cgccgaagtc gtccgagtac    1260
atcggggcgg ccgacaccac cttcgcgggc tcccgcaacg gcttctcgtc actgctgctg    1320
tgggactacc tgtcccggca ttcgtatgac gatctggtgc gcctggccgc cgactgcgac    1380
cggctggccg gctacgccca cgaccggttg ctgaccttgc aggacaaact cggcatggat    1440
ctgtgggtcg cccgcagccc gcagtccctc acggtgcgct tccgtcagcc atgtgcagac    1500
atcgtccgca agtactcgct gtcgtgtgag acggtctacg aagacaacga gcaacggacc    1560
tacgtacatc tctacgccgt tccccacctc actcgggaac tcgtggatga gctcgtgcgc    1620
gatctgcgcc agcccggagc cttcaccaac gctggtgcac tggaggggga ggcctgggcc    1680
ggggtgatcg atgccctcgg ccgcccggac cccgacggaa cctatgccgg cgccttgagc    1740
gctccggctt ccggccccccg ctccgaggac ggcggcggga gctga                  1785
```

<210> SEQ ID NO 246
<211> LENGTH: 594
<212> TYPE: PRT
<213> ORGANISM: Streptomyces viridifaciens

<400> SEQUENCE: 246

```
Met Ser Thr Ser Ser Ala Ser Ser Gly Pro Asp Leu Pro Phe Gly Pro
1               5                   10                  15

Glu Asp Thr Pro Trp Gln Lys Ala Phe Ser Arg Leu Arg Ala Val Asp
            20                  25                  30

Gly Val Pro Arg Val Thr Ala Pro Ser Ser Asp Pro Arg Glu Val Tyr
        35                  40                  45

Met Asp Ile Pro Glu Ile Pro Phe Ser Lys Val Gln Ile Pro Pro Asp
    50                  55                  60

Gly Met Asp Glu Gln Gln Tyr Ala Glu Ala Glu Ser Leu Phe Arg Arg
65                  70                  75                  80

Tyr Val Asp Ala Gln Thr Arg Asn Phe Ala Gly Tyr Gln Val Thr Ser
                85                  90                  95

Asp Leu Asp Tyr Gln His Leu Ser His Tyr Leu Asn Arg His Leu Asn
            100                 105                 110

Asn Val Gly Asp Pro Tyr Glu Ser Ser Ser Tyr Thr Leu Asn Ser Lys
        115                 120                 125

Val Leu Glu Arg Ala Val Leu Asp Tyr Phe Ala Ser Leu Trp Asn Ala
    130                 135                 140

Lys Trp Pro His Asp Ala Ser Asp Pro Glu Thr Tyr Trp Gly Tyr Val
145                 150                 155                 160

Leu Thr Met Gly Ser Ser Glu Gly Asn Leu Tyr Gly Leu Trp Asn Ala
                165                 170                 175

Arg Asp Tyr Leu Ser Gly Lys Leu Leu Arg Arg Gln His Arg Glu Ala
            180                 185                 190

Gly Gly Asp Lys Ala Ser Val Val Tyr Thr Gln Ala Leu Arg His Glu
        195                 200                 205

Gly Gln Ser Pro His Ala Tyr Glu Pro Val Ala Phe Phe Ser Gln Asp
    210                 215                 220

Thr His Tyr Ser Leu Thr Lys Ala Val Arg Val Leu Gly Ile Asp Thr
225                 230                 235                 240
```

```
Phe His Ser Ile Gly Ser Ser Arg Tyr Pro Asp Glu Asn Pro Leu Gly
                245                 250                 255

Pro Gly Thr Pro Trp Pro Thr Glu Val Pro Ser Val Asp Gly Ala Ile
            260                 265                 270

Asp Val Asp Lys Leu Ala Ser Leu Val Arg Phe Phe Ala Ser Lys Gly
        275                 280                 285

Tyr Pro Ile Leu Val Ser Leu Asn Tyr Gly Ser Thr Phe Lys Gly Ala
    290                 295                 300

Tyr Asp Asp Val Pro Ala Val Ala Gln Ala Val Arg Asp Ile Cys Thr
305                 310                 315                 320

Glu Tyr Gly Leu Asp Arg Arg Arg Val Tyr His Asp Arg Ser Lys Asp
                325                 330                 335

Ser Asp Phe Asp Glu Arg Ser Gly Phe Trp Ile His Ile Asp Ala Ala
            340                 345                 350

Leu Gly Ala Gly Tyr Ala Pro Tyr Leu Gln Met Ala Arg Asp Ala Gly
        355                 360                 365

Met Val Glu Glu Ala Pro Pro Val Phe Asp Phe Arg Leu Pro Glu Val
    370                 375                 380

His Ser Leu Thr Met Ser Gly His Lys Trp Met Gly Thr Pro Trp Ala
385                 390                 395                 400

Cys Gly Val Tyr Met Thr Arg Thr Gly Leu Gln Met Thr Pro Pro Lys
                405                 410                 415

Ser Ser Glu Tyr Ile Gly Ala Ala Asp Thr Thr Phe Ala Gly Ser Arg
            420                 425                 430

Asn Gly Phe Ser Ser Leu Leu Leu Trp Asp Tyr Leu Ser Arg His Ser
        435                 440                 445

Tyr Asp Asp Leu Val Arg Leu Ala Ala Asp Cys Asp Arg Leu Ala Gly
450                 455                 460

Tyr Ala His Asp Arg Leu Leu Thr Leu Gln Asp Lys Leu Gly Met Asp
465                 470                 475                 480

Leu Trp Val Ala Arg Ser Pro Gln Ser Leu Thr Val Arg Phe Arg Gln
                485                 490                 495

Pro Cys Ala Asp Ile Val Arg Lys Tyr Ser Leu Ser Cys Glu Thr Val
            500                 505                 510

Tyr Glu Asp Asn Glu Gln Arg Thr Tyr Val His Leu Tyr Ala Val Pro
        515                 520                 525

His Leu Thr Arg Glu Leu Val Asp Glu Leu Val Arg Asp Leu Arg Gln
    530                 535                 540

Pro Gly Ala Phe Thr Asn Ala Gly Ala Leu Glu Gly Glu Ala Trp Ala
545                 550                 555                 560

Gly Val Ile Asp Ala Leu Gly Arg Pro Asp Pro Asp Gly Thr Tyr Ala
                565                 570                 575

Gly Ala Leu Ser Ala Pro Ala Ser Gly Pro Arg Ser Glu Asp Gly Gly
            580                 585                 590

Gly Ser

<210> SEQ ID NO 247
<211> LENGTH: 1323
<212> TYPE: DNA
<213> ORGANISM: Alcaligenes denitrificans

<400> SEQUENCE: 247
atgagcgctg ccaaactgcc cgacctgtcc cacctctgga tgcccttttac cgccaaccgg      60 cagttcaagg cgaaccccg cctgctggcc tcggccaagg gcatgtacta cacgtctttc     120
```

```
gacggccgcc agatcctgga cggcacggcc ggcctgtggt gcgtgaacgc cggccactgc    180
cgcgaagaaa tcgtctccgc catcgccagc caggccggcg tcatggacta cgcgccgggg    240
ttccagctcg gccacccgct ggccttcgag gccgccaccg ccgtggccgg cctgatgccg    300
cagggcctgg accgcgtgtt cttcaccaat tcgggctccg aatcggtgga caccgcgctg    360
aagatcgccc tggcctacca ccgcgcgcgc ggcgaggcgc agcgcacccg cctcatcggg    420
cgcgagcgcg gctaccacgg cgtgggcttc ggcggcattt ccgtgggcgg catctcgccc    480
aaccgcaaga ccttctccgg cgcgctgctg ccggccgtgg accacctgcc gcacacccac    540
agcctggaac acaacgcctt cacgcgcggc cagcccgagt ggggcgcgca cctggccgac    600
gagttggaac gcatcatcgc cctgcacgac gcctccacca tcgcggccgt gatcgtcgag    660
cccatggccg gctccaccgg cgtgctcgtc ccgcccaagg gctatctcga aaaactgcgc    720
gaaatcaccg cccgccacgg cattctgctg atcttcgacg aagtcatcac cgcgtacggc    780
cgcctgggcg aggccaccgc cgcggcctat ttcggcgtaa cgcccgacct catcaccatg    840
gccaagggcg tgagcaacgc cgccgttccg gccgcgccg tcgcggtgcg ccgcgaagtg    900
catgacgcca tcgtcaacgg accgcaaggc ggcatcgagt tcttccacgg ctacacctac    960
tcggcccacc cgctggccgc cgccgccgtg ctcgccacgc tggacatcta ccgccgcgaa   1020
gacctgttcg cccgcgcccg caagctgtcg gccgcgttcg aggaagccgc ccacagcctc   1080
aagggcgcgc cgcacgtcat cgacgtgcgc aacatcggcc tggtggccgg catcgagctg   1140
tcgccgcgcg aaggcgcccc gggcgcgcgc ccgccgaag ccttccagaa atgcttcgac   1200
accggcctca tggtgcgcta cacgggcgac atcctcgcgg tgtcgcctcc gctcatcgtc   1260
gacgaaaacc agatcggcca gatcttcgag ggcatcggca aggtgctcaa ggaagtggct   1320
tag                                                                 1323
```

<210> SEQ ID NO 248
<211> LENGTH: 440
<212> TYPE: PRT
<213> ORGANISM: Alcaligenes denitrificans

<400> SEQUENCE: 248

```
Met Ser Ala Ala Lys Leu Pro Asp Leu Ser His Leu Trp Met Pro Phe
1               5                   10                  15

Thr Ala Asn Arg Gln Phe Lys Ala Asn Pro Arg Leu Leu Ala Ser Ala
            20                  25                  30

Lys Gly Met Tyr Tyr Thr Ser Phe Asp Gly Arg Gln Ile Leu Asp Gly
        35                  40                  45

Thr Ala Gly Leu Trp Cys Val Asn Ala Gly His Cys Arg Glu Glu Ile
    50                  55                  60

Val Ser Ala Ile Ala Ser Gln Ala Gly Val Met Asp Tyr Ala Pro Gly
65                  70                  75                  80

Phe Gln Leu Gly His Pro Leu Ala Phe Glu Ala Thr Ala Val Ala
            85                  90                  95

Gly Leu Met Pro Gln Gly Leu Asp Arg Val Phe Phe Thr Asn Ser Gly
            100                 105                 110

Ser Glu Ser Val Asp Thr Ala Leu Lys Ile Ala Leu Ala Tyr His Arg
        115                 120                 125

Ala Arg Gly Glu Ala Gln Arg Thr Arg Leu Ile Gly Arg Glu Arg Gly
    130                 135                 140

Tyr His Gly Val Gly Phe Gly Gly Ile Ser Val Gly Gly Ile Ser Pro
```

|   |   |   |   |   |   |   |   |   |   |   |   |   |   |   |
|---|---|---|---|---|---|---|---|---|---|---|---|---|---|---|
| 145 | | | | | 150 | | | | | 155 | | | | 160 |
| Asn | Arg | Lys | Thr | Phe | Ser | Gly | Ala | Leu | Leu | Pro | Ala | Val | Asp | His | Leu |

Asn Arg Lys Thr Phe Ser Gly Ala Leu Leu Pro Ala Val Asp His Leu
145                 150                 155                 160

Pro His Thr His Ser Leu Glu His Asn Ala Phe Thr Arg Gly Gln Pro
            165                 170                 175

Glu Trp Gly Ala His Leu Ala Asp Glu Leu Glu Arg Ile Ile Ala Leu
        180                 185                 190

His Asp Ala Ser Thr Ile Ala Ala Val Ile Val Glu Pro Met Ala Gly
    195                 200                 205

Ser Thr Gly Val Leu Val Pro Pro Lys Gly Tyr Leu Glu Lys Leu Arg
210                 215                 220

Glu Ile Thr Ala Arg His Gly Ile Leu Leu Ile Phe Asp Glu Val Ile
225                 230                 235                 240

Thr Ala Tyr Gly Arg Leu Gly Glu Ala Thr Ala Ala Tyr Phe Gly
        245                 250                 255

Val Thr Pro Asp Leu Ile Thr Met Ala Lys Gly Val Ser Asn Ala Ala
    260                 265                 270

Val Pro Ala Gly Ala Val Ala Val Arg Arg Glu Val His Asp Ala Ile
275                 280                 285

Val Asn Gly Pro Gln Gly Gly Ile Glu Phe Phe His Gly Tyr Thr Tyr
290                 295                 300

Ser Ala His Pro Leu Ala Ala Ala Ala Val Leu Ala Thr Leu Asp Ile
305                 310                 315                 320

Tyr Arg Arg Glu Asp Leu Phe Ala Arg Ala Arg Lys Leu Ser Ala Ala
        325                 330                 335

Phe Glu Glu Ala Ala His Ser Leu Lys Gly Ala Pro His Val Ile Asp
    340                 345                 350

Val Arg Asn Ile Gly Leu Val Ala Gly Ile Glu Leu Ser Pro Arg Glu
355                 360                 365

Gly Ala Pro Gly Ala Arg Ala Ala Glu Ala Phe Gln Lys Cys Phe Asp
370                 375                 380

Thr Gly Leu Met Val Arg Tyr Thr Gly Asp Ile Leu Ala Val Ser Pro
385                 390                 395                 400

Pro Leu Ile Val Asp Glu Asn Gln Ile Gly Gln Ile Phe Glu Gly Ile
        405                 410                 415

Gly Lys Val Leu Lys Glu Val Ala
    420                 425

<210> SEQ ID NO 249
<211> LENGTH: 1332
<212> TYPE: DNA
<213> ORGANISM: Ralstonia eutropha

<400> SEQUENCE: 249
atggacgccg cgaagaccgt gattcccgat ctcgatgccc tgtggatgcc ctttaccgcg      60
aaccgccagt acaaggcggc gccgcgcctg ctggcctcgg ccagcggcat gtactacacc     120
acccacgacg acgccagat cctcgacggt tgcgcgggcc tctggtgcgt agcggccggc     180
cactgccgca aggagattgc cgaggccgtg gcccgccagg ccgccacgct cgactacgcg     240
ccgccgttcc agatgggcca tccgctgtcg ttcgaagccg ccaccaaggt ggccgcgatc     300
atgccgcagg gactggaccg catcttcttc acgaattccg gttcggaatc ggtggacacc     360
gcgctgaaga ttgcgctggc ctaccaccgt gcgcgcggcc agggccagcg cacccgcttc     420
atcgggcgcg aacgcggtta ccacggcgtg ggctttggcg gcatggctgt cggtggcatc     480

```
gggccgaacc gcaaggcgtt ctcggccaac ctgatgccgg gcaccgacca tctgccggcg    540
acgctgaata tcgccgaagc ggcgttctcc aagggtcagc cgacatgggg cgcgcacctt    600
gccgacgaac tcgagcgcat cgtcgcgctg catgatccgt ccacgattgc cgccgtcatc    660
gtggaaccgc tggcgggctc cgccggggtg ctggtgccgc cggtcggcta cctcgacaag    720
ctgcgcgaga tcacgaccaa gcacggcatc ctgctgatct tcgacgaggt catcacggcc    780
tttggtcgcc tgggtaccgc caccgcggcg gaacgcttca aggtcacgcc ggacctgatc    840
accatggcca aggccatcaa caacgccgcc gtgccgatgg gtgccgtggc cgtgcgccgc    900
gaagtccatg acaccgtggt caactcggcc gcgccgggcg cgatcgaact cgcgcatggc    960
tacacctact cgggccaccc gctggccgcc gccgctgcca tcgccacgct ggacctgtat   1020
cagcgcgaga acctgttcgg ccgtgccgcg gagctgtcgc cggtgttcga agcggccgtt   1080
cacagcgtac gcagcgcgcc gcatgtgaag gacatccgca acctcggcat ggtggccggc   1140
atcgagctgg agccgcgtcc gggccagccc ggcgcacgcg cctacgaagc cttcctcaaa   1200
tgccttgagc gtggcgtgct ggtgcgctac accggcgata tcctcgcgtt ctcgccgccg   1260
ctgatcatca gcgaggcgca gattgccgag ctgttcgata cggtcaagca ggccttgcag   1320
gaagtgcagt aa                                                       1332
```

<210> SEQ ID NO 250
<211> LENGTH: 443
<212> TYPE: PRT
<213> ORGANISM: Ralstonia eutropha

<400> SEQUENCE: 250

Met Asp Ala Ala Lys Thr Val Ile Pro Asp Leu Asp Ala Leu Trp Met
1               5                   10                  15

Pro Phe Thr Ala Asn Arg Gln Tyr Lys Ala Ala Pro Arg Leu Leu Ala
            20                  25                  30

Ser Ala Ser Gly Met Tyr Tyr Thr Thr His Asp Gly Arg Gln Ile Leu
        35                  40                  45

Asp Gly Cys Ala Gly Leu Trp Cys Val Ala Ala Gly His Cys Arg Lys
    50                  55                  60

Glu Ile Ala Glu Ala Val Ala Arg Gln Ala Ala Thr Leu Asp Tyr Ala
65                  70                  75                  80

Pro Pro Phe Gln Met Gly His Pro Leu Ser Phe Glu Ala Ala Thr Lys
                85                  90                  95

Val Ala Ala Ile Met Pro Gln Gly Leu Asp Arg Ile Phe Phe Thr Asn
            100                 105                 110

Ser Gly Ser Glu Ser Val Asp Thr Ala Leu Lys Ile Ala Leu Ala Tyr
        115                 120                 125

His Arg Ala Arg Gly Glu Gly Gln Arg Thr Arg Phe Ile Gly Arg Glu
    130                 135                 140

Arg Gly Tyr His Gly Val Gly Phe Gly Gly Met Ala Val Gly Gly Ile
145                 150                 155                 160

Gly Pro Asn Arg Lys Ala Phe Ser Ala Asn Leu Met Pro Gly Thr Asp
                165                 170                 175

His Leu Pro Ala Thr Leu Asn Ile Ala Glu Ala Phe Ser Lys Gly
            180                 185                 190

Gln Pro Thr Trp Gly Ala His Leu Ala Asp Glu Leu Glu Arg Ile Val
        195                 200                 205

Ala Leu His Asp Pro Ser Thr Ile Ala Ala Val Ile Val Glu Pro Leu

```
                210                 215                 220
Ala Gly Ser Ala Gly Val Leu Val Pro Pro Val Gly Tyr Leu Asp Lys
225                 230                 235                 240

Leu Arg Glu Ile Thr Thr Lys His Gly Ile Leu Leu Ile Phe Asp Glu
                245                 250                 255

Val Ile Thr Ala Phe Gly Arg Leu Gly Thr Ala Thr Ala Ala Glu Arg
            260                 265                 270

Phe Lys Val Thr Pro Asp Leu Ile Thr Met Ala Lys Ala Ile Asn Asn
        275                 280                 285

Ala Ala Val Pro Met Gly Ala Val Ala Arg Arg Glu Val His Asp
290                 295                 300

Thr Val Val Asn Ser Ala Ala Pro Gly Ala Ile Glu Leu Ala His Gly
305                 310                 315                 320

Tyr Thr Tyr Ser Gly His Pro Leu Ala Ala Ala Ala Ile Ala Thr
                325                 330                 335

Leu Asp Leu Tyr Gln Arg Glu Asn Leu Phe Gly Arg Ala Ala Glu Leu
                340                 345                 350

Ser Pro Val Phe Glu Ala Ala Val His Ser Val Arg Ser Ala Pro His
                355                 360                 365

Val Lys Asp Ile Arg Asn Leu Gly Met Val Ala Gly Ile Glu Leu Glu
        370                 375                 380

Pro Arg Pro Gly Gln Pro Gly Ala Arg Ala Tyr Glu Ala Phe Leu Lys
385                 390                 395                 400

Cys Leu Glu Arg Gly Val Leu Val Arg Tyr Thr Gly Asp Ile Leu Ala
                405                 410                 415

Phe Ser Pro Pro Leu Ile Ile Ser Glu Ala Gln Ile Ala Glu Leu Phe
                420                 425                 430

Asp Thr Val Lys Gln Ala Leu Gln Glu Val Gln
                435                 440

<210> SEQ ID NO 251
<211> LENGTH: 1341
<212> TYPE: DNA
<213> ORGANISM: Shewanella oneidensis

<400> SEQUENCE: 251
atggccgact cacccaacaa cctcgctcac gaacatcctt cacttgaaca ctattggatg      60
ccttttaccg ccaatcgcca attcaaagcg agccctcgtt tactcgccca agctgaaggt     120
atgtattaca cagatatcaa tggcaacaag gtattagact ctacagcggg cttatggtgt     180
tgtaatgctg gccatggtcg ccgtgagatc agtgaagccg tcagcaaaca aattcggcag     240
atggattacg ctccctcctt ccaaatgggc catcccatcg cttttgaact ggccgaacgt     300
ttaaccgaac tcagcccaga aggactcaac aaagtattct ttaccaactc aggctctgag     360
tcggttgata ccgcgctaaa aatggctctt tgctaccata gagccaatgg ccaagcgtca     420
cgcacccgct ttattggccg tgaaatgggt taccatggcg taggatttgg tgggatctcg     480
gtgggtggtt taagcaataa ccgtaaagcc ttcgcggcc agctattgca aggcgtggat     540
cacctgcccc acaccttaga cattcaacat gccgccttta gtcgtggctt accgagcctc     600
ggtgctgaaa aagctgaggt attagaacaa ttagtcacac tccatggcgc cgaaaatatt     660
gccgccgtta ttgttgaacc catgtcaggt tctgcagggg taattttacc acctcaaggc     720
tacttaaaac gcttacgtga atcactaaa aaacacggca tcttattgat tttcgatgaa     780
gtcattaccg catttggccg tgtaggtgca gcattcgcca gccaacgttg ggcgttatt     840
```

```
ccagacataa tcaccacggc taaagccatt aataatggcg ccatccccat gggcgcagtg      900
tttgtacagg attatatcca cgatacttgc atgcaagggc caaccgaact gattgaattt      960
ttccacggtt atacctattc gggccaccca gtcgccgcag cagcagcact cgccacgctc     1020
tccatctacc aaaacgagca actgtttgag cgcagttttg agcttgagcg gtatttcgaa     1080
gaagccgttc atagcctcaa agggttaccg aatgtgattg atattcgcaa caccggatta     1140
gtcgcgggtt ccagctagc accgaatagc caaggtgttg gtaaacgcgg atacagcgtg      1200
ttcgagcatt gtttccatca aggcacactc gtgcgggcaa cgggcgatat tatcgccatg     1260
tccccaccac tcattgttga aaacatcag attgaccaaa tggtaaatag ccttagcgat      1320
gcaattcacg ccgttggatg a                                               1341
```

<210> SEQ ID NO 252
<211> LENGTH: 446
<212> TYPE: PRT
<213> ORGANISM: Shewanella oneidensis

<400> SEQUENCE: 252

Met Ala Asp Ser Pro Asn Asn Leu Ala His Glu His Pro Ser Leu Glu
1               5                   10                  15

His Tyr Trp Met Pro Phe Thr Ala Asn Arg Gln Phe Lys Ala Ser Pro
            20                  25                  30

Arg Leu Leu Ala Gln Ala Glu Gly Met Tyr Tyr Thr Asp Ile Asn Gly
        35                  40                  45

Asn Lys Val Leu Asp Ser Thr Ala Gly Leu Trp Cys Cys Asn Ala Gly
    50                  55                  60

His Gly Arg Arg Glu Ile Ser Glu Ala Val Ser Lys Gln Ile Arg Gln
65                  70                  75                  80

Met Asp Tyr Ala Pro Ser Phe Gln Met Gly His Pro Ile Ala Phe Glu
                85                  90                  95

Leu Ala Glu Arg Leu Thr Glu Leu Ser Pro Glu Gly Leu Asn Lys Val
            100                 105                 110

Phe Phe Thr Asn Ser Gly Ser Glu Ser Val Asp Thr Ala Leu Lys Met
        115                 120                 125

Ala Leu Cys Tyr His Arg Ala Asn Gly Gln Ala Ser Arg Thr Arg Phe
    130                 135                 140

Ile Gly Arg Glu Met Gly Tyr His Gly Val Gly Phe Gly Gly Ile Ser
145                 150                 155                 160

Val Gly Gly Leu Ser Asn Asn Arg Lys Ala Phe Ser Gly Gln Leu Leu
                165                 170                 175

Gln Gly Val Asp His Leu Pro His Thr Leu Asp Ile Gln His Ala Ala
            180                 185                 190

Phe Ser Arg Gly Leu Pro Ser Leu Gly Ala Glu Lys Ala Glu Val Leu
        195                 200                 205

Glu Gln Leu Val Thr Leu His Gly Ala Glu Asn Ile Ala Ala Val Ile
    210                 215                 220

Val Glu Pro Met Ser Gly Ser Ala Gly Val Ile Leu Pro Pro Gln Gly
225                 230                 235                 240

Tyr Leu Lys Arg Leu Arg Glu Ile Thr Lys Lys His Gly Ile Leu Leu
                245                 250                 255

Ile Phe Asp Glu Val Ile Thr Ala Phe Gly Arg Val Gly Ala Ala Phe
            260                 265                 270

Ala Ser Gln Arg Trp Gly Val Ile Pro Asp Ile Ile Thr Thr Ala Lys

|     |     |     |     | 275 |     |     |     | 280 |     |     |     | 285 |     |     |
| --- | --- | --- | --- | --- | --- | --- | --- | --- | --- | --- | --- | --- | --- | --- |
| Ala | Ile | Asn | Asn | Gly | Ala | Ile | Pro | Met | Gly | Ala | Val | Phe | Val | Gln | Asp |
|     |     |     |     | 290 |     |     |     |     | 295 |     |     |     | 300 |     |     |

Tyr Ile His Asp Thr Cys Met Gln Gly Pro Thr Glu Leu Ile Glu Phe
305                 310                 315                 320

Phe His Gly Tyr Thr Tyr Ser Gly His Pro Val Ala Ala Ala Ala Ala
                    325                 330                 335

Leu Ala Thr Leu Ser Ile Tyr Gln Asn Glu Gln Leu Phe Glu Arg Ser
                340                 345                 350

Phe Glu Leu Glu Arg Tyr Phe Glu Glu Ala Val His Ser Leu Lys Gly
            355                 360                 365

Leu Pro Asn Val Ile Asp Ile Arg Asn Thr Gly Leu Val Ala Gly Phe
370                 375                 380

Gln Leu Ala Pro Asn Ser Gln Gly Val Gly Lys Arg Gly Tyr Ser Val
385                 390                 395                 400

Phe Glu His Cys Phe His Gln Gly Thr Leu Val Arg Ala Thr Gly Asp
                405                 410                 415

Ile Ile Ala Met Ser Pro Pro Leu Ile Val Glu Lys His Gln Ile Asp
                420                 425                 430

Gln Met Val Asn Ser Leu Ser Asp Ala Ile His Ala Val Gly
                435                 440                 445

```
<210> SEQ ID NO 253
<211> LENGTH: 1347
<212> TYPE: DNA
<213> ORGANISM: Pseudomonas putida

<400> SEQUENCE: 253
atgaacatgc cgaaactgg tcctgccggt atcgccagcc agctcaagct ggacgcccac      60
tggatgccct acaccgccaa ccgcaacttc agcgcgacc acgcctgat cgtggcggcc     120
gaaggcaact acctggtcga tgaccacggg cgcaagatct cgacgccct gtccggcctg     180
tggacctgcg gcgcagggca cactcgcaag gaaatcgctg acgcggtgac ccgtcaactg     240
agtacgctgg actactcccc agcgttccag ttcggccacc cgctgtcgtt ccagctggcg     300
gaaaagatcg ccgagctggt tccgggcaat ctgaatcacg tcttctatac caactccggt     360
tccgagtgcg ccgataccgc actgaagatg gtgcgtgcct actggcgcct gaaaggccag     420
gcaaccaaga ccaagatcat cggccgtgcc cgtggttacc atggcgtgaa catcgccggt     480
accagcctgg gtggcgtcaa cggtaaccgc aagatgtttg ccagctgct ggacgtcgac     540
cacctgcctc acactgtatt gccggtgaac gccttctcga aaggcttgcc ggaagagggc     600
ggtatcgcgc tggctgacga atgctcaag ctgatcgagc tgcacgatgc ctccaacatc     660
gcagcagtca tcgtcgagcc gctggccggt tcggccggtg tgctgccgcc gccaaagggt     720
tacctgaagc gcctgcgtga atctgcacc cagcacaaca ttctgctgat cttcgacgaa     780
gtgatcacag gcttcggccg catgggcgcg atgaccggct cggaagcctt cggcgttacc     840
ccggacctga tgtgcatcgc caagcaggtg accaacggcg ccatcccgat gggcgcagtg     900
attgccagca gcgagatcta ccagaccttc atgaaccagc gaccccgga atacgccgtg     960
gaattcccac acggctacac ctattcggcg cacccggtag cctgtgccgc cggtctcgcc    1020
gcgctggacc tgctgcagaa ggaaaacctg gtgcagtccg cggctgaact ggcgccgcat    1080
ttcgagaagc tgctgcacgg cgtgaagggc accaagaata tcgtcgatat ccgcaactac    1140
ggcctggccg gcgccatcca gatcgccgcc cgtgacggtg atgccatcgt tcgcccttac    1200
```

```
gaagcggcca tgaagctgtg gaaagcgggc ttctatgtac gctttggtgg cgacaccctg   1260
cagttcggcc aaccttcaa taccaagccg caggaactgg accgcttgtt cgatgctgtt   1320
ggcgaaaccc tgaacctgat cgactga                                      1347
```

<210> SEQ ID NO 254
<211> LENGTH: 448
<212> TYPE: PRT
<213> ORGANISM: Pseudomonas putida

<400> SEQUENCE: 254

```
Met Asn Met Pro Glu Thr Gly Pro Ala Gly Ile Ala Ser Gln Leu Lys
1               5                   10                  15

Leu Asp Ala His Trp Met Pro Tyr Thr Ala Asn Arg Asn Phe Gln Arg
            20                  25                  30

Asp Pro Arg Leu Ile Val Ala Ala Glu Gly Asn Tyr Leu Val Asp Asp
        35                  40                  45

His Gly Arg Lys Ile Phe Asp Ala Leu Ser Gly Leu Trp Thr Cys Gly
    50                  55                  60

Ala Gly His Thr Arg Lys Glu Ile Ala Asp Ala Val Thr Arg Gln Leu
65                  70                  75                  80

Ser Thr Leu Asp Tyr Ser Pro Ala Phe Gln Phe Gly His Pro Leu Ser
                85                  90                  95

Phe Gln Leu Ala Glu Lys Ile Ala Glu Leu Val Pro Gly Asn Leu Asn
            100                 105                 110

His Val Phe Tyr Thr Asn Ser Gly Ser Glu Cys Ala Asp Thr Ala Leu
        115                 120                 125

Lys Met Val Arg Ala Tyr Trp Arg Leu Lys Gly Gln Ala Thr Lys Thr
    130                 135                 140

Lys Ile Ile Gly Arg Ala Arg Gly Tyr His Gly Val Asn Ile Ala Gly
145                 150                 155                 160

Thr Ser Leu Gly Gly Val Asn Gly Asn Arg Lys Met Phe Gly Gln Leu
                165                 170                 175

Leu Asp Val Asp His Leu Pro His Thr Val Leu Pro Val Asn Ala Phe
            180                 185                 190

Ser Lys Gly Leu Pro Glu Glu Gly Ile Ala Leu Ala Asp Glu Met
            195                 200                 205

Leu Lys Leu Ile Glu Leu His Asp Ala Ser Asn Ile Ala Ala Val Ile
    210                 215                 220

Val Glu Pro Leu Ala Gly Ser Ala Gly Val Leu Pro Pro Lys Gly
225                 230                 235                 240

Tyr Leu Lys Arg Leu Arg Glu Ile Cys Thr Gln His Asn Ile Leu Leu
                245                 250                 255

Ile Phe Asp Glu Val Ile Thr Gly Phe Gly Arg Met Gly Ala Met Thr
            260                 265                 270

Gly Ser Glu Ala Phe Gly Val Thr Pro Asp Leu Met Cys Ile Ala Lys
        275                 280                 285

Gln Val Thr Asn Gly Ala Ile Pro Met Gly Ala Val Ile Ala Ser Ser
    290                 295                 300

Glu Ile Tyr Gln Thr Phe Met Asn Gln Pro Thr Pro Glu Tyr Ala Val
305                 310                 315                 320

Glu Phe Pro His Gly Tyr Thr Tyr Ser Ala His Pro Val Ala Cys Ala
                325                 330                 335

Ala Gly Leu Ala Ala Leu Asp Leu Leu Gln Lys Glu Asn Leu Val Gln
```

```
              340             345             350
Ser Ala Ala Glu Leu Ala Pro His Phe Glu Lys Leu Leu His Gly Val
            355             360             365

Lys Gly Thr Lys Asn Ile Val Asp Ile Arg Asn Tyr Gly Leu Ala Gly
            370             375             380

Ala Ile Gln Ile Ala Ala Arg Asp Gly Asp Ala Ile Val Arg Pro Tyr
385             390             395             400

Glu Ala Ala Met Lys Leu Trp Lys Ala Gly Phe Tyr Val Arg Phe Gly
            405             410             415

Gly Asp Thr Leu Gln Phe Gly Pro Thr Phe Asn Thr Lys Pro Gln Glu
            420             425             430

Leu Asp Arg Leu Phe Asp Ala Val Gly Glu Thr Leu Asn Leu Ile Asp
            435             440             445

<210> SEQ ID NO 255
<211> LENGTH: 1701
<212> TYPE: DNA
<213> ORGANISM: Streptomyces cinnamonensis

<400> SEQUENCE: 255
atggacgctg acgcgatcga ggaaggccgc cgacgctggc aggcccgtta cgacaaggcc    60
cgcaagcgcg acgcggactt caccacgctc tccggggacc ccgtcgaccc cgtctacggc   120
ccccggcccg ggacacgta cgacgggttc gagcggatcg gctggccggg ggagtacccc   180
ttcacccgcg ggctctacgc caccgggtac cgcggccgca cctggaccat ccgccagttc   240
gccggcttcg gcaacgccga gcagacgaac gagcgctaca gatgatcct ggccaacggc    300 ggcggcggcc tctccgtcgc cttcgacatg ccgaccctca tgggccgcga ctccgacgac   360
ccgcgctcgc tcgcgaggt cggccactgc ggtgtcgcca tcgactccgc cgccgacatg    420
gaggtcctct tcaaggacat cccgctcggc gacgtcacga cgtccatgac catcagcggg   480
cccgccgtgc ccgtcttctg catgtacctc gtcgcggccg agcgccaggg cgtcgacccg   540
gccgtcctca acggcacgct gcagaccgac atcttcaagg agtacatcgc ccagaaggag   600
tggctcttcc agcccgagcc gcacctgcgc ctcatcggcg acctgatgga gcactgcgcg   660
cgcgacatcc ccgcgtacaa gccgctctcg gtctccggct accacatccg cgaggccggg   720
gcgacggccg cgcaggagct cgcgtacacc ctcgcggacg gcttcgggta cgtggaactg   780
ggcctctcgc gcggcctgga cgtggacgtc ttcgcgcccg gcctctcctt cttcttcgac   840
gcgcacgtcg acttcttcga ggagatcgcg aagttccgcg ccgcacgccg catctgggcg   900
cgctggctcc gggacgagta cggagcgaag accgagaagg cacagtggct gcgcttccac   960
acgcagaccg cggggtctc gctcacggcc cagcagccgt acaacaacgt ggtgcggacg  1020
gcggtggagg ccctcgccgc ggtgctcggc ggcacgaact ccctgcacac caacgctctc  1080
gacgagaccc ttgccctccc cagcgagcag gccgcggaga tcgcgctgcg cacccagcag  1140
gtgctgatgg aggagaccgg cgtcgccaac gtcgcggacc cgctgggcgg ctcctggtac  1200
atcgagcagc tcaccgaccg catcgaggcc gacgccgaga agatcttcga gcagatcagg  1260
gagcgggggc ggcgggcctg ccccgacggg cagcacccga tcgggccgat cacctccggc  1320
atcctgcgcg gcatcgagga cggctggttc accggcgaga tcgccgagtc cgccttccag  1380
taccagcggt ccctggagaa gggcgacaag cgggtcgtcg cgtcaactg cctcgaaggc  1440 tccgtcaccg cgacctgga gatcctgcgc gtcagccacg aggtcgagcg cgagcaggtg  1500
cgggagcttg cggggcgcaa ggggcggcgt gacgatgcgc gggtgcgggc ctcgctcgac  1560
```

-continued

```
gcgatgctcg ccgctgcgcg ggacgggtcg aacatgattg cccccatgct ggaggcggtg    1620
cgggccgagg cgaccctcgg ggagatctgc ggggtgcttc gcgatgagtg gggggtctac    1680
gtggagccgc ccgggttctg a                                              1701
```

<210> SEQ ID NO 256
<211> LENGTH: 566
<212> TYPE: PRT
<213> ORGANISM: Streptomyces cinnamonensis

<400> SEQUENCE: 256

```
Met Asp Ala Asp Ala Ile Glu Glu Gly Arg Arg Arg Trp Gln Ala Arg
1               5                   10                  15

Tyr Asp Lys Ala Arg Lys Arg Asp Ala Asp Phe Thr Thr Leu Ser Gly
                20                  25                  30

Asp Pro Val Asp Pro Val Tyr Gly Pro Arg Pro Gly Asp Thr Tyr Asp
            35                  40                  45

Gly Phe Glu Arg Ile Gly Trp Pro Gly Glu Tyr Pro Phe Thr Arg Gly
    50                  55                  60

Leu Tyr Ala Thr Gly Tyr Arg Gly Arg Thr Trp Thr Ile Arg Gln Phe
65                  70                  75                  80

Ala Gly Phe Gly Asn Ala Glu Gln Thr Asn Glu Arg Tyr Lys Met Ile
                85                  90                  95

Leu Ala Asn Gly Gly Gly Leu Ser Val Ala Phe Asp Met Pro Thr
            100                 105                 110

Leu Met Gly Arg Asp Ser Asp Asp Pro Arg Ser Leu Gly Glu Val Gly
        115                 120                 125

His Cys Gly Val Ala Ile Asp Ser Ala Ala Asp Met Glu Val Leu Phe
    130                 135                 140

Lys Asp Ile Pro Leu Gly Asp Val Thr Thr Ser Met Thr Ile Ser Gly
145                 150                 155                 160

Pro Ala Val Pro Val Phe Cys Met Tyr Leu Val Ala Ala Glu Arg Gln
                165                 170                 175

Gly Val Asp Pro Ala Val Leu Asn Gly Thr Leu Gln Thr Asp Ile Phe
            180                 185                 190

Lys Glu Tyr Ile Ala Gln Lys Glu Trp Leu Phe Gln Pro Glu Pro His
        195                 200                 205

Leu Arg Leu Ile Gly Asp Leu Met Glu His Cys Ala Arg Asp Ile Pro
    210                 215                 220

Ala Tyr Lys Pro Leu Ser Val Ser Gly Tyr His Ile Arg Glu Ala Gly
225                 230                 235                 240

Ala Thr Ala Ala Gln Glu Leu Ala Tyr Thr Leu Ala Asp Gly Phe Gly
                245                 250                 255

Tyr Val Glu Leu Gly Leu Ser Arg Gly Leu Asp Val Asp Val Phe Ala
            260                 265                 270

Pro Gly Leu Ser Phe Phe Phe Asp Ala His Val Asp Phe Phe Glu Glu
        275                 280                 285

Ile Ala Lys Phe Arg Ala Ala Arg Ile Trp Ala Arg Trp Leu Arg
    290                 295                 300

Asp Glu Tyr Gly Ala Lys Thr Glu Lys Ala Gln Trp Leu Arg Phe His
305                 310                 315                 320

Thr Gln Thr Ala Gly Val Ser Leu Thr Ala Gln Gln Pro Tyr Asn Asn
                325                 330                 335

Val Val Arg Thr Ala Val Glu Ala Leu Ala Ala Val Leu Gly Gly Thr
```

```
                340                 345                 350
Asn Ser Leu His Thr Asn Ala Leu Asp Glu Thr Leu Ala Leu Pro Ser
            355                 360                 365

Glu Gln Ala Ala Glu Ile Ala Leu Arg Thr Gln Gln Val Leu Met Glu
        370                 375                 380

Glu Thr Gly Val Ala Asn Val Ala Asp Pro Leu Gly Gly Ser Trp Tyr
385                 390                 395                 400

Ile Glu Gln Leu Thr Asp Arg Ile Glu Ala Asp Ala Glu Lys Ile Phe
                405                 410                 415

Glu Gln Ile Arg Glu Arg Gly Arg Arg Ala Cys Pro Asp Gly Gln His
            420                 425                 430

Pro Ile Gly Pro Ile Thr Ser Gly Ile Leu Arg Gly Ile Glu Asp Gly
        435                 440                 445

Trp Phe Thr Gly Glu Ile Ala Glu Ser Ala Phe Gln Tyr Gln Arg Ser
    450                 455                 460

Leu Glu Lys Gly Asp Lys Arg Val Val Gly Val Asn Cys Leu Glu Gly
465                 470                 475                 480

Ser Val Thr Gly Asp Leu Glu Ile Leu Arg Val Ser His Glu Val Glu
                485                 490                 495

Arg Glu Gln Val Arg Glu Leu Ala Gly Arg Lys Gly Arg Arg Asp Asp
            500                 505                 510

Ala Arg Val Arg Ala Ser Leu Asp Ala Met Leu Ala Ala Arg Asp
        515                 520                 525

Gly Ser Asn Met Ile Ala Pro Met Leu Glu Ala Val Arg Ala Glu Ala
    530                 535                 540

Thr Leu Gly Glu Ile Cys Gly Val Leu Arg Asp Glu Trp Gly Val Tyr
545                 550                 555                 560

Val Glu Pro Pro Gly Phe
                565

<210> SEQ ID NO 257
<211> LENGTH: 411
<212> TYPE: DNA
<213> ORGANISM: Streptomyces cinnamonensis

<400> SEQUENCE: 257
atgggtgtgg cagccgggcc gatccgcgtg gtggtcgcca agccggggct cgacgggcac      60
gatcgcgggg ccaaggtgat cgcgcgggcg ttgcgtgacg cgggtatgga ggtcatctac     120
accgggctgc accagacgcc cgagcaggtg gtggacaccg cgatccagga ggacgccgac     180
gcgatcggcc tctccatcct ctccggagcg cacaacacgc tgttcgcgcg cgtgttggag     240
ctcttgaagg gcgggacgc ggaggacatc aaggtgtttg gtggcggcat catcccggag     300
gcggacatcg cgccgctgaa ggagaagggc gtcgcggaga tcttcacgcc cggggccacc     360
accacgtcga tcgtggagtg ggttcggggg aacgtgcgac aggccgtctg a             411

<210> SEQ ID NO 258
<211> LENGTH: 136
<212> TYPE: PRT
<213> ORGANISM: Streptomyces cinnamonensis

<400> SEQUENCE: 258

Met Gly Val Ala Ala Gly Pro Ile Arg Val Val Ala Lys Pro Gly
1               5                   10                  15

Leu Asp Gly His Asp Arg Gly Ala Lys Val Ile Ala Arg Ala Leu Arg
            20                  25                  30
```

Asp Ala Gly Met Glu Val Ile Tyr Thr Gly Leu His Gln Thr Pro Glu
         35                  40                  45

Gln Val Val Asp Thr Ala Ile Gln Glu Asp Ala Asp Ala Ile Gly Leu
     50                  55                  60

Ser Ile Leu Ser Gly Ala His Asn Thr Leu Phe Ala Arg Val Leu Glu
 65                  70                  75                  80

Leu Leu Lys Glu Arg Asp Ala Glu Asp Ile Lys Val Phe Gly Gly Gly
                 85                  90                  95

Ile Ile Pro Glu Ala Asp Ile Ala Pro Leu Lys Glu Lys Gly Val Ala
             100                 105                 110

Glu Ile Phe Thr Pro Gly Ala Thr Thr Ser Ile Val Glu Trp Val
             115                 120                 125

Arg Gly Asn Val Arg Gln Ala Val
    130                 135

<210> SEQ ID NO 259
<211> LENGTH: 1701
<212> TYPE: DNA
<213> ORGANISM: Streptomyces coelicolor

<400> SEQUENCE: 259

| | | | | | |
|---|---|---|---|---|---|
| atggacgctc | atgccataga | ggagggccgc | cttcgctggc | aggcccggta | cgacgcggcg | 60 |
| cgcaagcgcg | acgcggactt | caccacgctc | tccggagacc | ccgtggagcc | ggtgtacggg | 120 |
| ccccgccccg | ggacgagta | cgagggcttc | gagcggatcg | gctggccggg | cgagtacccc | 180 |
| ttcacccgcg | gcctgtatcc | gaccgggtac | cgggggcgta | cgtggaccat | ccggcagttc | 240 |
| gccgggttcg | gcaacgccga | gcagaccaac | gagcgctaca | agatgatcct | ccgcaacggc | 300 |
| ggcggcgggc | tctcggtcgc | cttcgacatg | ccgaccctga | tgggccgcga | ctccgacgac | 360 |
| ccgcgctcgc | tgggcgaggt | cgggcactgc | ggggtggcca | tcgactcggc | cgccgacatg | 420 |
| gaagtgctgt | tcaaggacat | cccgctcggg | gacgtgacga | cctccatgac | gatcagcggg | 480 |
| cccgccgtgc | ccgtgttctg | catgtacctc | gtcgccgccg | agcgccaggg | cgtcgacgca | 540 |
| tccgtgctca | acggcacgct | gcagaccgac | atcttcaagg | agtacatcgc | ccagaaggag | 600 |
| tggctcttcc | agcccgagcc | ccacctccgg | ctcatcggcg | acctcatgga | gtactgcgcg | 660 |
| gccggcatcc | ccgcctacaa | gccgctctcc | gtctccggct | accacatccg | cgaggcgggc | 720 |
| gcgacggccg | cgcaggagct | ggcgtacacg | ctcgccgacg | gcttcggata | cgtggagctg | 780 |
| ggcctcagcc | gcgggctcga | cgtggacgtc | ttcgcgcccg | cctctccctt | cttcttcgac | 840 |
| gcgcacctcg | acttcttcga | ggagatcgcc | aagttccgcg | cggcccgcag | gatctgggcc | 900 |
| cgctggatgc | gcgacgtgta | cggcgcgcgg | accgacaagg | cccagtggct | gcggttccac | 960 |
| acccagaccg | ccggagtctc | gctcaccgcg | cagcagccgt | acaacaacgt | cgtacgcacc | 1020 |
| gcggtggagg | cgctggcggc | cgtgctcggc | ggcaccaact | ccctgcacac | caacgcgctc | 1080 |
| gacgagaccc | tcgccctgcc | cagcgagcag | gccgccgaga | tcgccctgcg | cacccagcag | 1140 |
| gtgctgatgg | aggagaccgg | cgtcgccaac | gtcgccgacc | cgctgggcgg | ttcctggttc | 1200 |
| atcgagcagc | tgaccgaccg | catcgaggcc | gacgccgaga | gatcttcga | gcagatcaag | 1260 |
| gagcgggggc | tgcgcgccca | ccccgacggg | cagcaccccg | tcggaccgat | cacctccggc | 1320 |
| ctgctgcgcg | gcatcgagga | cggctggttc | accggcgaga | tcgccgagtc | cgccttccgc | 1380 |
| taccagcagt | ccttggagaa | ggacgacaag | aaggtggtcg | gcgtcaacgt | ccacaccggc | 1440 |
| tccgtcaccg | gcgacctgga | gatcctgcgg | gtcagccacg | aggtcgagcg | cgagcaggtg | 1500 |

```
cgggtcctgg gcgagcgcaa ggacgcccgg gacgacgccg ccgtgcgcgg cgccctggac    1560
gccatgctgg ccgcggcccg ctccggcggc aacatgatcg ggccgatgct ggacgcggtg    1620
cgcgcggagg cgacgctggg cgagatctgc ggtgtgctgc gcgacgagtg ggggtgtac     1680 acggaaccgg cggggttctg a                                              1701
```

<210> SEQ ID NO 260
<211> LENGTH: 566
<212> TYPE: PRT
<213> ORGANISM: Streptomyces coelicolor

<400> SEQUENCE: 260

```
Met Asp Ala His Ala Ile Glu Glu Gly Arg Leu Arg Trp Gln Ala Arg
1               5                   10                  15

Tyr Asp Ala Ala Arg Lys Arg Asp Ala Asp Phe Thr Thr Leu Ser Gly
            20                  25                  30

Asp Pro Val Glu Pro Val Tyr Gly Pro Arg Pro Gly Asp Glu Tyr Glu
        35                  40                  45

Gly Phe Glu Arg Ile Gly Trp Pro Gly Glu Tyr Pro Phe Thr Arg Gly
    50                  55                  60

Leu Tyr Pro Thr Gly Tyr Arg Gly Arg Thr Trp Thr Ile Arg Gln Phe
65                  70                  75                  80

Ala Gly Phe Gly Asn Ala Glu Gln Thr Asn Glu Arg Tyr Lys Met Ile
                85                  90                  95

Leu Arg Asn Gly Gly Gly Gly Leu Ser Val Ala Phe Asp Met Pro Thr
            100                 105                 110

Leu Met Gly Arg Asp Ser Asp Pro Arg Ser Leu Gly Glu Val Gly
        115                 120                 125

His Cys Gly Val Ala Ile Asp Ser Ala Ala Asp Met Glu Val Leu Phe
    130                 135                 140

Lys Asp Ile Pro Leu Gly Asp Val Thr Thr Ser Met Thr Ile Ser Gly
145                 150                 155                 160

Pro Ala Val Pro Val Phe Cys Met Tyr Leu Val Ala Ala Glu Arg Gln
                165                 170                 175

Gly Val Asp Ala Ser Val Leu Asn Gly Thr Leu Gln Thr Asp Ile Phe
            180                 185                 190

Lys Glu Tyr Ile Ala Gln Lys Glu Trp Leu Phe Gln Pro Glu Pro His
        195                 200                 205

Leu Arg Leu Ile Gly Asp Leu Met Glu Tyr Cys Ala Ala Gly Ile Pro
    210                 215                 220

Ala Tyr Lys Pro Leu Ser Val Ser Gly Tyr His Ile Arg Glu Ala Gly
225                 230                 235                 240

Ala Thr Ala Ala Gln Glu Leu Ala Tyr Thr Leu Ala Asp Gly Phe Gly
                245                 250                 255

Tyr Val Glu Leu Gly Leu Ser Arg Gly Leu Asp Val Asp Val Phe Ala
            260                 265                 270

Pro Gly Leu Ser Phe Phe Phe Asp Ala His Leu Asp Phe Glu Glu
        275                 280                 285

Ile Ala Lys Phe Arg Ala Ala Arg Ile Trp Ala Arg Trp Met Arg
    290                 295                 300

Asp Val Tyr Gly Ala Arg Thr Asp Lys Ala Gln Trp Leu Arg Phe His
305                 310                 315                 320

Thr Gln Thr Ala Gly Val Ser Leu Thr Ala Gln Gln Pro Tyr Asn Asn
                325                 330                 335
```

Val Val Arg Thr Ala Val Glu Ala Leu Ala Ala Val Leu Gly Gly Thr
            340                 345                 350

Asn Ser Leu His Thr Asn Ala Leu Asp Glu Thr Leu Ala Leu Pro Ser
        355                 360                 365

Glu Gln Ala Ala Glu Ile Ala Leu Arg Thr Gln Val Leu Met Glu
    370                 375                 380

Glu Thr Gly Val Ala Asn Val Ala Asp Pro Leu Gly Gly Ser Trp Phe
385                 390                 395                 400

Ile Glu Gln Leu Thr Asp Arg Ile Glu Ala Asp Ala Glu Lys Ile Phe
                405                 410                 415

Glu Gln Ile Lys Glu Arg Gly Leu Arg Ala His Pro Asp Gly Gln His
            420                 425                 430

Pro Val Gly Pro Ile Thr Ser Gly Leu Leu Arg Gly Ile Glu Asp Gly
            435                 440                 445

Trp Phe Thr Gly Glu Ile Ala Glu Ser Ala Phe Arg Tyr Gln Gln Ser
    450                 455                 460

Leu Glu Lys Asp Asp Lys Lys Val Val Gly Val Asn Val His Thr Gly
465                 470                 475                 480

Ser Val Thr Gly Asp Leu Glu Ile Leu Arg Val Ser His Glu Val Glu
                485                 490                 495

Arg Glu Gln Val Arg Val Leu Gly Glu Arg Lys Asp Ala Arg Asp Asp
            500                 505                 510

Ala Ala Val Arg Gly Ala Leu Asp Ala Met Leu Ala Ala Ala Arg Ser
            515                 520                 525

Gly Gly Asn Met Ile Gly Pro Met Leu Asp Ala Val Arg Ala Glu Ala
    530                 535                 540

Thr Leu Gly Glu Ile Cys Gly Val Leu Arg Asp Glu Trp Gly Val Tyr
545                 550                 555                 560

Thr Glu Pro Ala Gly Phe
                565

<210> SEQ ID NO 261
<211> LENGTH: 417
<212> TYPE: DNA
<213> ORGANISM: Streptomyces coelicolor

<400> SEQUENCE: 261
atgggtgtgg cagccggtcc gatccgcgtg gtggtggcca agccggggct cgacggccac    60
gatcgcgggg ccaaggtgat cgcgagggcc ctgcgtgacg ccggtatgga ggtgatctac   120
accgggctcc accagacgcc cgagcagatc gtcgacaccg cgatccagga ggacgccgac   180
gcgatcgggc tgtccatcct ctccggtgcg cacaacacgc tcttcgccgc cgtgatcgag   240
ctgctccggg agcgggacgc cgcggacatc ctggtcttcg gcggcgggat catccccgag   300
gcggacatcg ccccgctgaa ggagaagggc gtcgcggaga tcttcacgcc cggcgccacc   360
acggcgtcca tcgtggactg ggtccgggcg aacgtgcggg agcccgcggg agcatag     417

<210> SEQ ID NO 262
<211> LENGTH: 138
<212> TYPE: PRT
<213> ORGANISM: Streptomyces coelicolor

<400> SEQUENCE: 262

Met Gly Val Ala Ala Gly Pro Ile Arg Val Val Ala Lys Pro Gly
1               5                  10                  15

| | | | | | | | | | | | |
|---|---|---|---|---|---|---|---|---|---|---|---|
|Leu|Asp|Gly|His|Asp|Arg|Gly|Ala|Lys|Val|Ile|Ala|Arg|Ala|Leu|Arg|
| | | |20| | | |25| | | |30| | | | |

Leu Asp Gly His Asp Arg Gly Ala Lys Val Ile Ala Arg Ala Leu Arg
               20                   25                30

Asp Ala Gly Met Glu Val Ile Tyr Thr Gly Leu His Gln Thr Pro Glu
               35                   40                   45

Gln Ile Val Asp Thr Ala Ile Gln Glu Asp Ala Asp Ala Ile Gly Leu
               50                   55                   60

Ser Ile Leu Ser Gly Ala His Asn Thr Leu Phe Ala Ala Val Ile Glu
65                   70                   75                      80

Leu Leu Arg Glu Arg Asp Ala Ala Asp Ile Leu Val Phe Gly Gly Gly
               85                   90                   95

Ile Ile Pro Glu Ala Asp Ile Ala Pro Leu Lys Glu Lys Gly Val Ala
              100                  105               110

Glu Ile Phe Thr Pro Gly Ala Thr Thr Ala Ser Ile Val Asp Trp Val
              115                  120               125

Arg Ala Asn Val Arg Glu Pro Ala Gly Ala
              130                  135

<210> SEQ ID NO 263
<211> LENGTH: 1701
<212> TYPE: DNA
<213> ORGANISM: Streptomyces avermitilis

<400> SEQUENCE: 263

```
tcagaaaccg gcgggctccg tgtagacccc ccactcctcc cggaggacat cgcagatctc      60
gcccagcgtg gcctccgcgc ggaccgcgtc cagcatcggg gcgatcatgt tcgacccgtc     120
gcgcgcggcg gcgagcatcg cgtccagggc cgcggttacg gccgtgtcgt cgcgcccga     180
cttccgctcg cccagcaccc gcacctgctc gcgctccacc tcgtggctga cgcgcaggat     240
ctccaggtcg cccgtcacgg acccgtggtg gacgttgacg ccgacgaccc gcttgtcgcc     300
cttctccagc gcctgctggt actggaaggc cgactcggcg atctccccgg tgaaccagcc     360
gtcctcgatg ccgcgcagga tgccggaggt gatgggcccg atcgggtgcc gcccgtccgg     420
gtgggcccgc agcccgcgct ccctgatctg ttcgaagatc ttctcggcgt cggcctcgat     480
ccggtcggtc agctgctcca cgtaccagga accgcccagc ggatcggcca cgttggcgac     540
gcccgtctcc tccatcagca cctgctgggt gcgcagggcg atctcggccg cctgctcgga     600
cggcagggcg agggtctcgt cgagggcgtt ggtgtgcagc gagttcgtcc cgccgagcac     660
cgcggcgagg gcctccacgg ccgtccgtac gacgttgttg tacggctgct gcgcggtgag     720
cgagacgccc gcggtctggg tgtggaagcg cagccactgc gccttctccg acttcgcccc     780
gtacacgtcc cgcagccagc gcgcccagat gcgccgcgcc gcacggaact tggcgatctc     840
ctcgaagaag tcgacgtgcg cgtcgaagaa gaaggagagc ccgggcgcga acacgtccac     900
gtccaggccg cggctcagcc ccagctccac gtatccgaaa ccgtcggcga gggtgtacgc     960
cagctcctgg gcggccgtgg caccggcctc ccggatgtgg tacccggaga cggacagcgg    1020
cttgtacgcg gggatcttcg aggcgcagtg ctccatcagg tcgccgatga ccgcagatg     1080
gggctcgggc tggaagagcc actccttctg cgcgatgtac tccttgaaga tgtcggtctg    1140
gagggtgccg ttgaggacgg aggggtcgac gccctgccgc tcggccgcga ccaggtacat    1200
gcagaagacg ggcacggcgg gccgctgat cgtcatcgac gtcgtcacgt cacccagcgg    1260
gatgtccttg aacaggacct ccatgtcggc cgccgagtcg atcgcgaccc cgcagtgccc    1320
gacctcgccg agcgcgcggc ggtcgtcgga gtcgcgcccc atgagcgtcg gcatgtcgaa    1380
ggccacggac agcccaccgc cgccgttggc gaggatcttc ttgtagcgct cgttggtctg    1440
```

```
ctcggcgttg ccgaacccgg cgaactgccg gatggtccag gtccggcccc ggtagccggt    1500
cggatacaga ccgcgcgtga aggggtactc acccggccag ccgatccgct cgaaaccctc    1560
gtacgcgtcc ccgggccggg gcccgtacgc cggctccacg ggatcgccgg agagcgtggt    1620
gaaatcggcc tcgcgcttgc gtgaggcgtc gtagcgggcc tgccagcgtc ggcggccttc    1680
ctcgatggcg tcagcgtcca t                                              1701
```

<210> SEQ ID NO 264
<211> LENGTH: 566
<212> TYPE: PRT
<213> ORGANISM: Streptomyces avermitilis

<400> SEQUENCE: 264

```
Met Asp Ala Asp Ala Ile Glu Glu Gly Arg Arg Trp Gln Ala Arg
1               5                   10                  15

Tyr Asp Ala Ser Arg Lys Arg Glu Ala Asp Phe Thr Thr Leu Ser Gly
            20                  25                  30

Asp Pro Val Glu Pro Ala Tyr Gly Pro Arg Pro Gly Asp Ala Tyr Glu
        35                  40                  45

Gly Phe Glu Arg Ile Gly Trp Pro Gly Glu Tyr Pro Phe Thr Arg Gly
    50                  55                  60

Leu Tyr Pro Thr Gly Tyr Arg Gly Arg Thr Trp Thr Ile Arg Gln Phe
65                  70                  75                  80

Ala Gly Phe Gly Asn Ala Glu Gln Thr Asn Glu Arg Tyr Lys Lys Ile
                85                  90                  95

Leu Ala Asn Gly Gly Gly Leu Ser Val Ala Phe Asp Met Pro Thr
            100                 105                 110

Leu Met Gly Arg Asp Ser Asp Arg Arg Ala Leu Gly Glu Val Gly
        115                 120                 125

His Cys Gly Val Ala Ile Asp Ser Ala Ala Asp Met Glu Val Leu Phe
    130                 135                 140

Lys Asp Ile Pro Leu Gly Asp Val Thr Thr Ser Met Thr Ile Ser Gly
145                 150                 155                 160

Pro Ala Val Pro Val Phe Cys Met Tyr Leu Val Ala Ala Glu Arg Gln
                165                 170                 175

Gly Val Asp Pro Ser Val Leu Asn Gly Thr Leu Gln Thr Asp Ile Phe
            180                 185                 190

Lys Glu Tyr Ile Ala Gln Lys Glu Trp Leu Phe Gln Pro Glu Pro His
        195                 200                 205

Leu Arg Leu Ile Gly Asp Leu Met Glu His Cys Ala Ser Lys Ile Pro
    210                 215                 220

Ala Tyr Lys Pro Leu Ser Val Ser Gly Tyr His Ile Arg Glu Ala Gly
225                 230                 235                 240

Ala Thr Ala Ala Gln Glu Leu Ala Tyr Thr Leu Ala Asp Gly Phe Gly
                245                 250                 255

Tyr Val Glu Leu Gly Leu Ser Arg Gly Leu Asp Val Asp Val Phe Ala
            260                 265                 270

Pro Gly Leu Ser Phe Phe Phe Asp Ala His Val Asp Phe Phe Glu Glu
        275                 280                 285

Ile Ala Lys Phe Arg Ala Ala Arg Ile Trp Ala Arg Trp Leu Arg
    290                 295                 300

Asp Val Tyr Gly Ala Lys Ser Glu Lys Ala Gln Trp Leu Arg Phe His
305                 310                 315                 320
```

```
Thr Gln Thr Ala Gly Val Ser Leu Thr Ala Gln Gln Pro Tyr Asn Asn
            325                 330                 335

Val Val Arg Thr Ala Val Glu Ala Leu Ala Ala Val Leu Gly Gly Thr
        340                 345                 350

Asn Ser Leu His Thr Asn Ala Leu Asp Glu Thr Leu Ala Leu Pro Ser
    355                 360                 365

Glu Gln Ala Ala Glu Ile Ala Leu Arg Thr Gln Gln Val Leu Met Glu
370                 375                 380

Glu Thr Gly Val Ala Asn Val Ala Asp Pro Leu Gly Gly Ser Trp Tyr
385                 390                 395                 400

Val Glu Gln Leu Thr Asp Arg Ile Glu Ala Asp Ala Glu Lys Ile Phe
                405                 410                 415

Glu Gln Ile Arg Glu Arg Gly Leu Arg Ala His Pro Asp Gly Arg His
            420                 425                 430

Pro Ile Gly Pro Ile Thr Ser Gly Ile Leu Arg Gly Ile Glu Asp Gly
        435                 440                 445

Trp Phe Thr Gly Glu Ile Ala Glu Ser Ala Phe Gln Tyr Gln Gln Ala
    450                 455                 460

Leu Glu Lys Gly Asp Lys Arg Val Val Gly Val Asn Val His His Gly
465                 470                 475                 480

Ser Val Thr Gly Asp Leu Glu Ile Leu Arg Val Ser His Glu Val Glu
                485                 490                 495

Arg Glu Gln Val Arg Val Leu Gly Glu Arg Lys Ser Gly Arg Asp Asp
            500                 505                 510

Thr Ala Val Thr Ala Ala Leu Asp Ala Met Leu Ala Ala Ala Arg Asp
        515                 520                 525

Gly Ser Asn Met Ile Ala Pro Met Leu Asp Ala Val Arg Ala Glu Ala
    530                 535                 540

Thr Leu Gly Glu Ile Cys Asp Val Leu Arg Glu Glu Trp Gly Val Tyr
545                 550                 555                 560

Thr Glu Pro Ala Gly Phe
                565

<210> SEQ ID NO 265
<211> LENGTH: 417
<212> TYPE: DNA
<213> ORGANISM: Streptomyces avermitilis

<400> SEQUENCE: 265
ctacgccccg gcaggctgcc gcacgttcgc ccgcacccac tccacgatcg acgccgtggt    60
cgccccgga gtgaagatct ccgcgacacc cttctccttc agcggcgcga tgtccgcctc   120
ggggatgatg ccgccaccga acaccttgat gtcctcggca tcgcgctcct tgagcagatc   180
gatgaccgcc gcgaacaacg tgttgtgcgc cccggacagg atcgacagcc cgatcgcgtc   240
ggcgtcctcc tggatggccg tgcccacgat ctgctccggc gtctggtgca gcccgtgta   300
aatgacctcc ataccggcat cgcgcagcgc ccgcgcgatc accttggccc cgcgatcgtg   360
gccatcgagc cccggcttgg ccaccaccac gcggatcgga ccggctgcca cacccat      417

<210> SEQ ID NO 266
<211> LENGTH: 138
<212> TYPE: PRT
<213> ORGANISM: Streptomyces avermitilis

<400> SEQUENCE: 266

Met Gly Val Ala Ala Gly Pro Ile Arg Val Val Val Ala Lys Pro Gly
```

```
  1               5                  10                 15
Leu Asp Gly His Asp Arg Gly Ala Lys Val Ile Ala Arg Ala Leu Arg
              20                 25                 30
Asp Ala Gly Met Glu Val Ile Tyr Thr Gly Leu His Gln Thr Pro Glu
              35                 40                 45
Gln Ile Val Gly Thr Ala Ile Gln Glu Asp Ala Asp Ala Ile Gly Leu
          50                 55                 60
Ser Ile Leu Ser Gly Ala His Asn Thr Leu Phe Ala Val Ile Asp
 65                 70                 75                 80
Leu Leu Lys Glu Arg Asp Ala Glu Asp Ile Lys Val Phe Gly Gly Gly
                  85                 90                 95
Ile Ile Pro Glu Ala Asp Ile Ala Pro Leu Lys Glu Lys Gly Val Ala
              100                105                110
Glu Ile Phe Thr Pro Gly Ala Thr Ala Ser Ile Val Glu Trp Val
              115                120                125
Arg Ala Asn Val Arg Gln Pro Ala Gly Ala
              130                135
```

<210> SEQ ID NO 267
<211> LENGTH: 2910
<212> TYPE: DNA
<213> ORGANISM: Staphylococcus aureus

<400> SEQUENCE: 267

```
gatcaatttc ttttaagtaa tctaaatccc catttttaa tttcttttta gcctctttaa    60
ataatcctga ataaactaat acctgtttac ctttaagtga tttataaaat gcatcaaga   120
cttttttgatt tatttattaa ataatcacta tctttaccag aatacttagc catttcatat   180
aattctttat tattatttg tcttattttt tgaacttgaa cttgtgttat ttctgaaatg   240
cccgttacat cacgccataa atctaaccat tcttgttggc taatataata tcttttatct   300
gtgaaatacg atttatttac tgcaattaac acatgaaaat gaggattata atcatctctt   360
tttttattat atgtaatctc taacttacga acatatccct ttataacact acctactttt   420
tttctcttta taagttttct aaaagaatta ttataacgtt ttatttcatt ttctaattca   480
tcactcatta cattaggtgt agtcaaagtt aaaaagataa actccttttt ctcttgctgc   540
ttaatatatt gcatcatcaa agataaaccc aatgcatctt ttctagcttt tctccaagca   600
cagacaggac aaaatcgatt tttacaagaa ttagctttat ataatttctg ttttttctaaa   660
gttttatcag ctacaaaaga cagaaatgta ttgcaatctt caactaaatc catttgattc   720
tctccaatat gacgtttaat aaatttctga atacttgat ttctttgttt tttctcagta   780
tacttttcca tgttataaca cataaaaaca acttagtttt cacaaactat gacaataaaa   840
aaagttgctt tttccccttt ctatgtatgt ttttactag tcatttaaaa cgatacatta   900
ataggtacga aaaagcaact ttttttgcgc ttaaaaccag tcataccaat aacttaaggg   960
taactagcct cgccggcaat agttacccctt attatcaaga taagaagaa aaggattttt  1020
cgctacgctc aaatccttta aaaaaacaca aaagaccaca ttttttaatg tggtctttat  1080
tcttcaacta aagcacccat tagttcaaca aacgaaaatt ggataaagtg ggatattttt  1140
aaaatatata tttatgttac agtaatattg acttttaaaa aaggattgat tctaatgaag  1200
aaagcagaca gtaagcctc ctaaattcac tttagataaa aatttaggag gcatatcaaa  1260
tgaactttaa taaaattgat ttagacaatt ggaagagaaa agagatatt aatcattatt  1320
tgaaccaaca aacgactttt agtataacca cagaaattga tattagtgtt ttataccgaa  1380
```

```
acataaaaca agaaggatat aaattttacc ctgcatttat tttcttagtg acaagggtga    1440
taaactcaaa tacagctttt agaactggtt acaatagcga cggagagtta ggttattggg    1500
ataagttaga gccactttat acaatttttg atggtgtatc taaaacattc tctggtattt    1560
ggactcctgt aaagaatgac ttcaaagagt tttatgattt atacctttct gatgtagaga    1620
aatataatgg ttcggggaaa ttgtttccca aaacacctat acctgaaaat gcttttctc     1680 tttctattat tccatggact tcatttactg ggtttaactt aaatatcaat aataatagta    1740
attaccttct acccattatt acagcaggaa aattcattaa taaaggtaat tcaatatatt    1800
taccgctatc tttacaggta catcattctg tttgtgatgg ttatcatgca ggattgttta    1860
tgaactctat tcaggaattg tcagataggc ctaatgactg gcttttataa tatgagataa    1920
tgccgactgt acttttaca gtcggttttc taatgtcact aacctgcccc gttagttgaa     1980
gaaggttttt atattacagc tccagatcca tatccttctt tttctgaacc gacttctcct    2040
ttttcgcttc tttattccaa ttgctttatt gacgttgagc ctcggaaccc ttaacaatcc    2100
caaaacttgt cgaatggtcg gcttaatagc tcacgctatg ccgacattcg tctgcaagtt    2160
tagttaaggg ttcttctcaa cgcacaataa attttctcgg cataaatgcg tggtctaatt    2220
tttattttta ataaccttga tagcaaaaaa tgccattcca atacaaaacc atacctat     2280 aatcgataac cacataacag tcataaaacc actccttttt aacaaacttt atcacaagaa    2340
atatttaaat tttaaatgcc tttattttga attttaaggg gcattttaaa gatttagggg    2400
taaatcatat agttttatgc ctaaaaacct acagaagctt ttaaaaagca aatatgagcc    2460
aaataaatat attctaattc tacaaacaaa aatttgagca aattcagtgt cgattttta    2520 agacactgcc cagttacatg caaattaaaa ttttcatgat tttttatagt tcctaacagg    2580
gttaaaattt gtataacgaa agtataatgt ttatataacg ttagtataat aaagcatttt    2640
aacattatac ttttgataat cgtttatcgt cgtcatcaca ataacttta aaatactcgt     2700 gcataattca cgctgacctc ccaataacta catggtgtta tcgggaggtc agctgttagc    2760
acttatattt tgttattgtt cttcctcgat ttcgtctatc attttgtgat taatttctct    2820
tttttcttgt tctgttaagt cataaagttc actagctaaa tactcttttt gtttccaaat    2880
ataaaaaatt tgatagatat attacggttg                                     2910
```